(12) United States Patent
Quattropani et al.

(10) Patent No.: US 8,791,142 B2
(45) Date of Patent: Jul. 29, 2014

(54) OXAZOLE PYRIDINE DERIVATIVES USEFUL AS S1P1 RECEPTOR AGONISTS

(75) Inventors: Anna Quattropani, Geneva (CH); Patrick Gerber, Etoy (CH); Jerome Dorbais, Annecy (FR)

(73) Assignee: Merck Serono S.A., Coinsins, Vaud (CH)

( * ) Notice: Subject to any disclaimer, the term of this patent is extended or adjusted under 35 U.S.C. 154(b) by 135 days.

(21) Appl. No.: 13/203,044

(22) PCT Filed: Mar. 2, 2010

(86) PCT No.: PCT/EP2010/052613
§ 371 (c)(1),
(2), (4) Date: Aug. 24, 2011

(87) PCT Pub. No.: WO2010/100142
PCT Pub. Date: Sep. 10, 2010

(65) Prior Publication Data
US 2011/0306636 A1    Dec. 15, 2011

Related U.S. Application Data

(60) Provisional application No. 61/156,985, filed on Mar. 3, 2009.

(30) Foreign Application Priority Data

Mar. 3, 2009   (EP) .................... 09154174

(51) Int. Cl.
*A61K 31/443*        (2006.01)
*C07D 413/04*        (2006.01)

(52) U.S. Cl.
USPC ........................................ 514/340; 546/269.4

(58) Field of Classification Search
USPC ........................................ 546/269.4; 514/340
See application file for complete search history.

(56) References Cited

U.S. PATENT DOCUMENTS

| 7,947,707 B2 | 5/2011 | Toyoshima et al. |
| 2008/0200535 A1 | 8/2008 | Ohmori et al. |

FOREIGN PATENT DOCUMENTS

| WO | WO 2004/103279 | 12/2001 |
| WO | WO 2005/058848 | 6/2005 |
| WO | WO 2006/131336 | 12/2006 |
| WO | WO 2007/043400 | 4/2007 |
| WO | WO 2008/023783 | 2/2008 |

OTHER PUBLICATIONS

Database CA [Online] Chemical Abstracts Service, Accession No. 2007:438168, Toyoshima, T. et al. "Preparation of nitrogenated aromatic heterocyclic compounds as xanthine oxidase inhibitors and pharmaceutical composition comprising the same" Apr. 20, 2007, pp. 1-27, XP-002539400.
Written Opinion in International Application No. PCT/EP2010/052613, Aug. 10, 2010, pp. 1-7.

*Primary Examiner* — Patricia L Morris
(74) *Attorney, Agent, or Firm* — Saliwanchik, Lloyd & Eisenschenk

(57) ABSTRACT

The present invention provides oxadiazole pyridine derivatives of Formula (I), their use as medicaments and their use for treating multiple sclerosis and other diseases.

7 Claims, No Drawings

OXAZOLE PYRIDINE DERIVATIVES USEFUL AS S1P1 RECEPTOR AGONISTS

CROSS-REFERENCE TO RELATED APPLICATIONS

This application is the U.S. national stage application of International Patent Application No. PCT/EP2010/052613, filed Mar. 2, 2010, which claims the benefit of U.S. Provisional Patent Application No. 61/156,985, filed Mar. 3, 2009, the disclosures of which are hereby incorporated by reference in their entireties, including all figures, tables and amino acid or nucleic acid sequences.

The present invention relates to oxadiazoles pyridine and pyrimidine derivatives, their use as medicaments and their use for treating multiple sclerosis and other diseases.

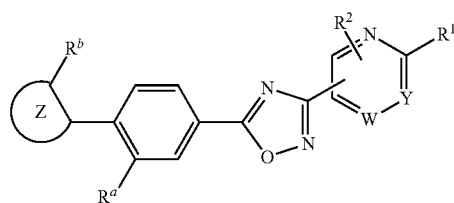

(I)

wherein
$R^1$ denotes —$CO_2R^3$, —$CON(H)_{2-p}(A)_p$, —$N(H)(CH_2)_n CO_2R^3$, —$N(R^3)(CH_2)_n CO_2R^3$, —NH—CO-A, Hal, —$CF_3$, —$OCF_3$, —OH, —OA, —CN, or —$NO_2$, —$(CH_2)_n$ Het, —$(CH_2)_s N(H)_{2-p}(A)_p$, —$CH(CH_3)(CH_2)_n N(H)_{2-p}(A)_p$, —$CH(R^3)(CH_2)_n N(H)_{2-p}(A)_p$, —$(CH_2)_s (R^3)(CH_2)_n CO_2R^3$, —$(CH_2)_s NH$—CO-A, —$(CH_2)_n N(R^3)_2$, —$CH(CH_3)(CH_2)_n N(R^3)CH(CH_3)(CH_2)_n CO_2R^3$, —$CH(R^3)(CH_2)_n N(R^3)CH(R^3)(CH_2)_n CO_2R^3$,
or when in position meta or para to the oxadiazole ring, $R^1$ also denotes —$N(H)_{2-p}(A)_p$ or A,
$R^2$ is H, Hal, —CN, —$NO_2$, —OH, OA, —$CO_2R^3$, —$CON(H)_{2-p}(A)_p$, —$N(H)(CH_2)_n CO_2R^3$, —NH—CO-A, —$CF_3$, —$OCF_3$, or when in position meta or para to the oxadiazole ring, $R^2$ also denotes —$N(H)_{2-p}(A)_p$ or A,
$R^a$, $R^b$ are independently from each other A, —$CF_3$, Hal, —$CH_2$—$OR^3$, $OR^3$, —$OCF_3$, $(C_1-C_7)$alkyl, —$(CH_2)_n$—O—$(CH_2)_n$OMe or $CH(CH_3)OCH_3$.
W, Y are independently from each other CH or N,
Z denotes Ar or Het,
A is branched or linear alkyl having 1 to 12 C-atoms, wherein one or more, preferably 1 to 7 H-atoms may be replaced by Hal, $OR^3$, CN, $CO_2R^3$ or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms
Ar denotes a monocyclic or bicyclic, aromatic carbocyclic ring having 6 to 14 carbon atoms, which is unsubstituted or monosubstituted, disubstituted or trisubstituted by, Hal, —$CF_3$, —$OCF_3$, —$NO_2$, —CN, perfluoroalkyl, A, OA, —OH, —$NH_2$, —COH, —$COOR^3$, —$CONH_2$, —$CON(H)_{2-q}A_q$, —$NR^3(CH_2)_n COA$, —$NR^3(CH_2)_n COOA$, —$NR^3(CH_2)_n COR^3$, —$N(H)_{2-q}A_q$, —$NHSO_2A$, —$NHSO_2$—$N(H)_{2-m}(A)_m$, —$N(H)_{1-q}A_q COA$, —$N(H)_{1-q}A_q SO_2$—$N(H)_{2-m}(A)_m$, —$N(H)_{1-q}A_q CON(H)_{2-m}(A)_m$, —COOA, —$SO_2A$, —$SO_2N(H)_{2-m}(A)_m$, —$SO_2$Het, —$(CH_2)_n OR^3$.

Het denotes a monocyclic or bicyclic saturated, unsaturated or aromatic heterocyclic ring having 1 to 4 N, O and/or S atoms which is unsubstituted or monosubstituted, disubstituted or trisubstituted by alkyl having 1 to 8 carbon atoms, alkoxy having 1 to 8 carbon atoms, Hal, —$CF_3$, —$OCF_3$, —$NO_2$, —CN, perfluoroalkyl, A, OA, —OH, —$NH_2$, —COH, —$COOR^3$, —$CONH_2$, —$CON(H)_{2-q}A_q$, —$NR^3(CH_2)_n COA$, —$NR^3(CH_2)_n COOA$, —$NR^3(CH_2)_n COR^3$, —$N(H)_{2-q}A_q$, —$NHSO_2A$, —$NHSO_2$—$N(H)_{2-m}(A)_m$, —$N(H)_{1-q}A_q COA$, —$N(H)_{1-q}A_q SO_2$—$N(H)_{2-m}(A)_m$, —$N(H)_{1-q}A_q CON(H)_{2-m}(A)_m$, —COOA, —$SO_2A$, —$SO_2N(H)_{2-m}(A)_m$, —$SO_2$Het, —$(CH_2)_n OR^3$.
Hal is F, Cl, Br or I,
$R^3$ is H or A,
m is 0, 1 or 2,
p is 0, 1 or 2,
q is 0 or 1,
s is 1, 2, 3, 4 or 5, and
n is 0, 1, 2, 3, 4 or 5,
and pharmaceutically acceptable derivatives, solvates, tautomers, salts and stereoisomers thereof, including mixtures thereof in all ratios.

The compounds of formula (I) and related formulae are preferably binding on receptors for sphingosine 1-phosphate ($S_1P$). $S_1P$ is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S_1P_1$, $S_1P_2$, $S_1P_3$, $S_1P_4$, and $S_1P_5$, also known as endothelial differentiation genes, which are Edg1, Edg5, Edg3, Edg6 and Edg8 respectively), that have widespread cellular and tissue distribution and are well conserved in human and rodent species.

$S_1P$ is involved in a number of cellular functions such as survival, proliferation and immunological responses. The compounds of the present invention are preferably acting as $S_1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective $S_1P_1$ agonist, exerts immunosuppressive activity and shows therapeutic effects in the treatment of relapsing-remitting multiple sclerosis. Numerous publications have been already published using this compound: Oyster J G Annu Rev Immunol 23:127-59, 2005, Rosen H Nat Rev Immunol 5:560-570, 2005, Rosen H Trends Immunol 28:102-107, 2007, Yopp A C Clin Transplant 20:788-795, 2006, Kappos L N Engl J Med 355:1124-1140, 2006, Massberg S N Engl J Med 355:1088-1089, 2006.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They are also useful as part of chemotherapeutic regimens for the treatment of cancers, lymphomas and leukemias.

Compounds used as S1P1 agonists and similar to those of the present application are disclosed in the application WO2004/103279. These compounds are characterized in that the heterocyclic moiety linked to the oxadiazole is substituted with an amino group in ortho position with respect to the oxadiazole.

It has been found that the compounds of the present invention are selective S1P1 agonists with improved pharmacological and/or other properties.

Thus, the present invention preferably comprises compounds which are agonists of the S1P1/Edg1 receptor, especially having selectivity over the S1P3/Edg3 receptor. An S1P1/Edg1 receptor selective agonist has advantages over current therapies and extends the therapeutic window of lymphocyte sequestration agents, allowing better tolerability with higher dosing and thus improving efficacy.

Preferred compounds of the present invention exhibit pronounced ability to cross the blood/brain barrier.

The invention further relates to the manufacture of a medicament for the improvement of vascular function, either alone or in combination with other active compounds or therapies.

The inventions further relates to the use of compounds according to formula (I) in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA4Ig, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod.

The invention further relates to a kit or a set comprising at least one compound of Formula (I), preferably in combination with immunomodulating agents. Alternatively, the kit consists of separate packs of:
(a) an effective amount of a compound of the formula (I) and/or pharmaceutically usable derivatives, solvates and stereoisomers thereof, including mixtures thereof in all ratios, and
(b) an effective amount of a further medicament active ingredient.

In general, the oxadiazole compounds according to Formula (I) of this invention may be prepared from readily available starting materials. If such starting materials are not commercially available, they may be prepared by standard synthetic techniques. In general, the synthesis pathways for any individual compound of Formula (I) will depend on the specific substituents of each molecule, such factors being appreciated by those of ordinary skill in the art. The following general methods and procedures described hereinafter in the examples may be employed to prepare compounds of Formula (I). Reaction conditions depicted in the following schemes, such as temperatures, solvent, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, $3^{rd}$ Edition 1999.

Depending on the nature of $R^1$, $R^2$, $R^a$, $R^b$, Y, W and Z, different synthetic strategies may be selected for the synthesis of compounds of Formula (I). In the process illustrated in the following schemes $R^1$, $R^2$, $R^a$, $R^b$, Y, W and Z, are as above-defined in the description unless otherwise mentioned.

According to a preferred synthetic pathway, the compounds of Formula (I), wherein $R^1$, $R^2$, $R^a$, $R^b$, Y, W and Z are defined as above, can be obtained in a 2-step protocol as outlined in Scheme 1. The first step consists in the coupling of a carboxylic acid of Formula (III) wherein $R^a$, $R^b$ and Z are as above defined, with an amidoxime of Formula (II), wherein $R^1$, $R^2$, Y, and W are defined as above. General protocols for such coupling are given below in the examples, using conditions and methods well known to those skilled in the art. Standard coupling agent, such as HATU, EDC or isobutyl chloroformate can be used in the presence or not of a base such as DIEA, TEA or NMM in a suitable solvent such as DMF, ACN, THF or iPrOAc at a temperature rising from about 0° C. to RT, preferably at 0° C. for a time of 30 minutes to a few hours. Alternatively, a carboxylic acid derivative (e.g. acyl chloride) may be coupled with the amidoxime (II), using conditions and methods well known to those skilled in the art, in the presence of a base such as pyridine or DIEA in a suitable solvent such as toluene, DCM, THF or DMF, at a temperature rising from about 0° C. to RT, preferably at RT, for a few hours. The second step consists of the cyclization and dehydration of the O-substituted amidoximes (IV) to form oxadiazole (I). Conditions are given below in the examples, using methods well known to those skilled in the art to prepare oxadiazole, such as thermolysis at temperature rising from 80° C. to about 120° C., typically 90° C., for a time comprised between 12 and 72 hours, preferably for 15 hours, in a suitable solvent or mixture of solvents, such as toluene, pyridine, ACN, THF, DMF or iPrOAc in the presence or not of a base such as DIEA, TEA or NMM.

Scheme 1

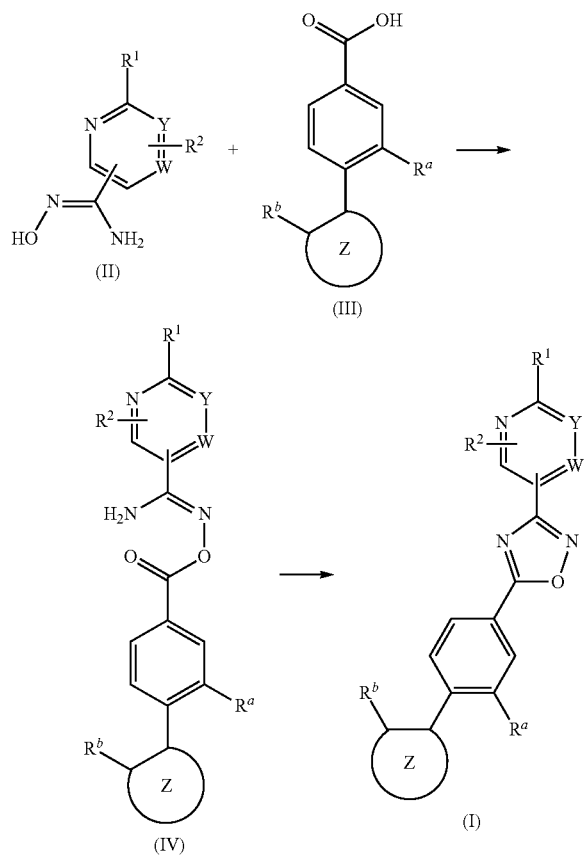

Compounds of Formula (I) wherein $R^1$, $R^2$, $R^a$, $R^b$, Y, W and Z are as above defined, may be converted to alternative compounds of Formula (I), using suitable interconversion procedures such as those described hereinafter in the examples, or conventional interconversion procedures well known by one skilled in the art. In particular, but not limited to, ester derivatives of Formula (I), and preferably methyl or tert-butyl ester derivatives, may be converted into the corresponding carboxylic acid derivatives of Formula (I), using conditions well known to those skilled in the art, such as a metal hydroxide (e.g. lithium hydroxide, sodium hydroxide or potassium hydroxide), in a suitable solvent such as THF, methanol, ethanol or water or mixtures thereof, or using an acid (e.g. HCl or TFA), in a suitable solvent such as dioxane, DCM, at a temperature between about 20° C. to about 50° C., preferably at RT, for a few hours.

The method for preparing ester derivatives of Formula (I) selected below:

tert-butyl N-(5-{5-[2-(methoxymethyl)-2'-methylbiphenyl-4-yl]-1,2,4-oxadiazol-3-yl}pyridin-2-yl)-beta-alaninate
tert-butyl N-(5-{5-[2-(methoxymethyl)-2'-methylbiphenyl-4-yl]-1,2,4-oxadiazol-3-yl}pyridin-2-yl)glycinate
tert-butyl N-(4-{5-[2-(methoxymethyl)-2'-methylbiphenyl-4-yl]-1,2,4-oxadiazol-3-yl}pyridin-2-yl)-beta-alaninate
tert-butyl 4-[(5-{5-[2-(methoxymethyl)-2'-methylbiphenyl-4-yl]-1,2,4-oxadiazol-3-yl}pyridin-2-yl)amino]butanoate
tert-butyl N-(4-{5-[2-(methoxymethyl)-2'-methylbiphenyl-4-yl]-1,2,4-oxadiazol-3-yl}pyridin-2-yl)glycinate
methyl 5-{5-[2-(methoxymethyl)-2'-methylbiphenyl-4-yl]-1,2,4-oxadiazol-3-yl}pyridine-2-carboxylate
tert-butyl N-(3-chloro-5-{5-[2-(methoxymethyl)-2'-methylbiphenyl-4-yl]-1,2,4-oxadiazol-3-yl}pyridin-2-yl)-beta-alaninate
tert-butyl N-(3-chloro-5-{5-[2-(methoxymethyl)-2'-methylbiphenyl-4-yl]-1,2,4-oxadiazol-3-yl}pyridin-2-yl)glycinate
tert-butyl N-(3-chloro-5-{5-[2'-fluoro-2-(methoxymethyl)biphenyl-4-yl]-1,2,4-oxadiazol-3-yl}pyridin-2-yl)-beta-alaninate
tert-butyl N-(3-chloro-5-{5-[2'-chloro-2-(methoxymethyl)biphenyl-4-yl]-1,2,4-oxadiazol-3-yl}pyridin-2-yl)-beta-alaninate
tert-butyl N-(5-{5-[2'-fluoro-2-(methoxymethyl)biphenyl-4-yl]-1,2,4-oxadiazol-3-yl}-3-methylpyridin-2-yl)-beta-alaninate
tert-butyl 4-[(3-chloro-5-{5-[2'-fluoro-2-(methoxymethyl)biphenyl-4-yl]-1,2,4-oxadiazol-3-yl}pyridin-2-yl)amino]butanoate
tert-butyl 4-[(5-{5-[2'-fluoro-2-(methoxymethyl)biphenyl-4-yl]-1,2,4-oxadiazol-3-yl}-3-methylpyridin-2-yl)amino]butanoate
tert-butyl 4-[(3-chloro-5-{5-[2-(methoxymethyl)-2'-methylbiphenyl-4-yl]-1,2,4-oxadiazol-3-yl}pyridin-2-yl)amino]butanoate
tert-butyl 4-[(5-{5-[2-(methoxymethyl)-2'-methylbiphenyl-4-yl]-1,2,4-oxadiazol-3-yl}-3-methylpyridin-2-yl)amino]butanoate
tert-butyl N-(5-{5-[2-(methoxymethyl)-2'-methylbiphenyl-4-yl]-1,2,4-oxadiazol-3-yl}-3-methylpyridin-2-yl)-beta-alaninate
tert-butyl N-(3-methyl-5-{5-[2'-methyl-2-(trifluoromethyl)biphenyl-4-yl]-1,2,4-oxadiazol-3-yl}pyridin-2-yl)-beta-alaninate
tert-butyl N-(3-chloro-5-{5-[2'-methyl-2-(trifluoromethyl)biphenyl-4-yl]-1,2,4-oxadiazol-3-yl}pyridin-2-yl)-beta-alaninate
tert-butyl N-(3-chloro-5-{5-[2'-fluoro-2-(trifluoromethyl)biphenyl-4-yl]-1,2,4-oxadiazol-3-yl}pyridin-2-yl)-beta-alaninate
tert-butyl N-(5-{5-[2'-fluoro-2-(trifluoromethyl)biphenyl-4-yl]-1,2,4-oxadiazol-3-yl}-3-methylpyridin-2-yl)-beta-alaninate
tert-butyl N-{3-chloro-5-[5-(2-ethoxy-2'-methylbiphenyl-4-yl)-1,2,4-oxadiazol-3-yl]pyridin-2-yl}-beta-alaninate
tert-butyl N-(3-chloro-5-{5-[2-methyl-2'-(trifluoromethyl)biphenyl-4-yl]-1,2,4-oxadiazol-3-yl}pyridin-2-yl)-beta-alaninate
tert-butyl N-(3-chloro-5-{5-[2-ethoxy-2'-(trifluoromethyl)biphenyl-4-yl]-1,2,4-oxadiazol-3-yl}pyridin-2-yl)-beta-alaninate
tert-butyl N-(3-chloro-5-{5-[3'-fluoro-2-(methoxymethyl)-2'-methylbiphenyl-4-yl]-1,2,4-oxadiazol-3-yl}pyridin-2-yl)-beta-alaninate
tert-butyl N-{3-chloro-5-[5-(2,2'-dimethylbiphenyl-4-yl)-1,2,4-oxadiazol-3-yl]pyridin-2-yl}-beta-alaninate
tert-butyl 2-(methyl((4-(5-(4-(2-methylpiperidin-1-yl)-3-(trifluoromethyl)phenyl)-1,2,4-oxadiazol-3-yl)pyridin-2-yl)methyl)amino)acetate
tert-butyl N-[(5-{5-[2-(methoxymethyl)-2'-methylbiphenyl-4-yl]-1,2,4-oxadiazol-3-yl}pyridin-2-yl)methyl]-N-methylglycinate
tert-butyl 2-(methyl((5-(5-(2-methyl-2'-(trifluoromethyl)biphenyl-4-yl)-1,2,4-oxadiazol-3-yl)pyridin-2-yl)methyl)amino)acetate
methyl cis-2-(3-chloro-5-(5-(2-(methoxymethyl)-2'-methylbiphenyl-4-yl)-1,2,4-oxadiazol-3-yl)pyridin-2-ylamino)cyclopentanecarboxylate (2S,4R)-methyl 1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylate is more particularly described in the examples.

Alternatively, alcohol derivatives of Formula (XII) may be converted into the corresponding amine derivatives of Formula (I), wherein $R^1$=—$(CH_2)_nN(R^3)_2$ with n being 1 to 5, as outlined in Scheme 1a. Alcohol functionality of compound of Formula (XII) may be transformed first into a leaving group, such as a chloride or a sulfonate, using conditions well known to those skilled in the art. As an illustration, alcohol derivatives of Formula (XII) may react with methanesulfonyl chloride, in the presence of a base, such as but not limited to a tertiary amine (e.g. TEA or DIEA), in a suitable solvent such as DCM, at a temperature between about 20° C. to about 50° C., preferably at RT, for a few hours. The resulting compound may be then reacted with a suitable amine of Formula $HN(R^3)_2$, affording compound of Formula (I), wherein $R^1$=—$(CH_2)_nN(R^3)_2$.

Scheme 1a

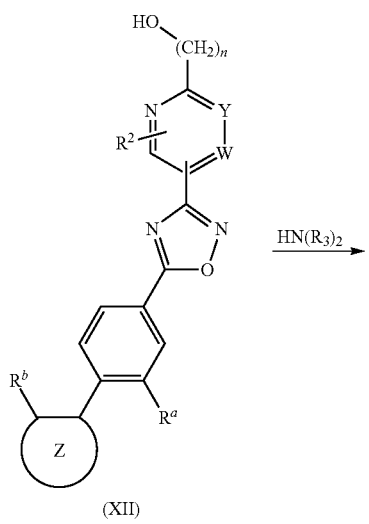

(XII)

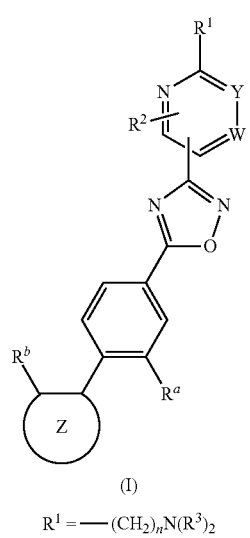

(I)

$R^1 = —(CH_2)_nN(R^3)_2$

Alcohol derivatives of Formula (XII) may be prepared starting from a carboxylic acid of Formula (III) wherein $R^a$, $R^b$ and Z are as above defined, with a suitable amidoxime of Formula (II), wherein $R^2$, Y, and W are defined as above and wherein $R^1$ is —$(CH_2)_nOH$ or —$(CH_2)_nOPG$ wherein PG is an hydroxyl-protecting group and wherein n is 1, 2, 3, 4 or 5, preferably 1 or 2

The method for preparing alcohol derivatives of Formula (XII) selected below:
(4-(5-(4-(2-methylpiperidin-1-yl)-3-(trifluoromethyl)phenyl)-1,2,4-oxadiazol-3-yl)pyridin-2-yl)methanol
(4-(5-(2-(methoxymethyl)-2'-methylbiphenyl-4-yl)-1,2,4-oxadiazol-3-yl)pyridin-2-yl)methanol
(5-(5-(2'-methyl-2-(trifluoromethyl)biphenyl-4-yl)-1,2,4-oxadiazol-3-yl)pyridin-2-yl)methanol
(4-(5-(2'-methyl-2-(trifluoromethyl)biphenyl-4-yl)-1,2,4-oxadiazol-3-yl)pyridin-2-yl)methanol
(5-(5-(2-methyl-2'-(trifluoromethyl)biphenyl-4-yl)-1,2,4-oxadiazol-3-yl)pyridin-2-yl)methanol is more particularly described in the examples.

Compounds of Formula (II) wherein $R^1$, $R^2$, Y and W are as above defined are either commercially available or may be prepared according to Scheme 2 by addition of aqueous hydroxylamine or hydroxylamine hydrochloride to the corresponding substituted benzonitrile of Formula (V) in a suitable solvent, such as EtOH, in presence or not of a base, such as TEA, at a temperature ranging from RT to about 80° C., preferably at RT, for a few hours.

Scheme 2

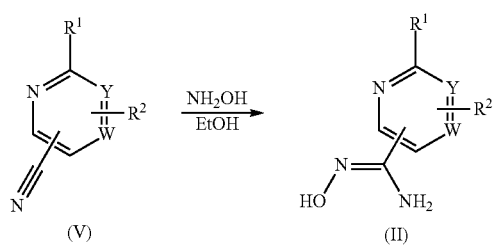

The method for preparing compounds of formula (II) selected below:
tert-butyl N-{5-[amino(hydroxyimino)methyl]pyridin-2-yl}-beta-alaninate
tert-butyl N-{5-[amino(hydroxyimino)methyl]pyridin-2-yl}glycinate
tert-butyl N-{4-[amino(hydroxyimino)methyl]pyridin-2-yl}-beta-alaninate
tert-butyl 4-({5-[amino(hydroxyimino)methyl]pyridin-2-yl}amino)butanoate
tert-butyl N-{4-[amino(hydroxyimino)methyl]pyridin-2-yl}glycinate
6-amino-5-chloro-N'-hydroxypyridine-3-carboximidamide
2-amino-N'-hydroxypyridine-4-carboximidamide
5-amino-N'-hydroxypyrazine-2-carboximidamide
2-amino-N'-hydroxypyrimidine-5-carboximidamide
6-amino-N'-hydroxy-5-methylpyridine-3-carboximidamide
N',6-dihydroxypyridine-3-carboximidamide
methyl 5-[amino(hydroxyimino)methyl]pyridine-2-carboxylate
N'-hydroxy-6-[(2-hydroxyethyl)amino]pyridine-3-carboximidamide
N'-hydroxy-6-(methylamino)pyridine-3-carboximidamide
5-Chloro-N'-hydroxy-6-[(2-methoxyethyl)amino]pyridine-3-carboximidamide
tert-butyl 3-({5-[amino(hydroxyimino)methyl]-3-chloropyridin-2-yl}amino)propanoate
tert-butyl ({5-[amino(hydroxyimino)methyl]-3-chloropyridin-2-yl}amino)acetate
N'-hydroxy-6-[(3-hydroxypropyl)amino]pyridine-3-carboximidamide N'-hydroxy-6-[(2-hydroxypropyl)amino]pyridine-3-carboximidamide
6-[(2,3-dihydroxypropyl)amino]-N'-hydroxypyridine-3-carboximidamide
tert-butyl 3-({5-[amino(hydroxyimino)methyl]-3-methylpyridin-2-yl}amino)propanoate
tert-butyl 4-({5-[amino(hydroxyimino)methyl]-3-chloropyridin-2-yl}amino)butanoate
tert-butyl 4-({5-[amino(hydroxyimino) methyl]-3-methylpyridin-2-yl}amino)butanoate
6-chloro-5-fluoro-N'-hydroxypyridine-3-carboximidamide
5-chloro-N'-hydroxy-6-[(2-hydroxyethyl)amino]pyridine-3-carboximidamide
is more particularly described in the examples.

Compounds of Formula (V), wherein $R^1$, $R^2$, Y and W are as above defined, are either commercially available or may be prepared from alternative compounds of Formula (V), using suitable interconversion procedures such as those described hereinafter in the examples, or conventional interconversion procedures well known by one skilled in the art. In particular, but not limited to, compounds of Formula (V), wherein $R^1$=N(H)$_{2-p}$(A)$_p$ with p=1 or 2 and $R^2$, Y and W are as above defined, may be prepared by treatment of a compound of Formula (V), wherein $R^1$=Cl and $R^2$, Y and W are as above defined, with an amine derivative N(H)$_{3-p}$(A)$_p$ in a suitable solvent, such as dioxane, DMSO or DMA, in the presence or not of a base, such as DIEA, at a temperature ranging from RT to reflux.

The method for preparing compounds of formula (V) selected below:
tert-butyl N-(5-cyanopyridin-2-yl)-beta-alaninate
tert-butyl N-(5-cyanopyridin-2-yl)glycinate
tert-butyl N-(4-cyanopyridin-2-yl)-beta-alaninate
tert-butyl 4-[(5-cyanopyridin-2-yl)amino]butanoate
tert-butyl N-(4-cyanopyridin-2-yl)glycinate 5-chloro-6-[(2-methoxyethyl)amino]nicotinonitrile
tert-butyl 3-[(3-chloro-5-cyanopyridin-2-yl)amino]propanoate
tert-butyl[(3-chloro-5-cyanopyridin-2-yl)amino]acetate
6-[(2,3-dihydroxypropyl)amino]nicotinonitrile
tert-butyl 3-[(5-cyano-3-methylpyridin-2-yl)amino]propanoate
tert-butyl 4-[(3-chloro-5-cyanopyridin-2-yl)amino]butanoate
tert-butyl 4-[(5-cyano-3-methylpyridin-2-yl)amino]butanoate
5-chloro-6-[(2-hydroxyethyl)amino]nicotinonitrile
is more particularly described in the examples.

Compounds of Formula (III), wherein $R^a$, $R^b$ and Z are defined as above, may be prepared by standard synthetic techniques, as hereinafter described in the examples, using conditions and methods well known to those skilled in the art (Scheme 3). In a first synthetic pathway, compounds of Formula (III), wherein $R^a$, $R^b$ and Z are defined as above, may be obtained by metal catalyzed cross-coupling reaction, followed by hydrolysis of the resulting ester (VI). More particularly, they may be obtained by Suzuki-Miyura coupling reaction between an alkyl benzoate (VII), where LG$_1$ may preferably be Br, I or a sulfonate ester such as triflate, and a boronic acid or ester of Formula (XII) (Miyaura, N.; Suzuki, A. Chem. Rev. 1995, 95, 2457; Takahiro I. and Toshiaki M., Tetrahedron Lett. 2005, 46, 3573-3577). In a typical procedure, alkyl benzoate (VII) and boronic acid (XII) are heated in a suitable solvent, such as a mixture of toluene and water, in the presence of a base, such as K$_2$CO$_3$, and a catalytic amount of a palladium catalyst, such as Pd(PPh$_3$)$_4$, with the possible addition of a phosphine ligand, such as PPh$_3$. The resulting ester (VI) may be hydrolyzed using a metal hydroxide, such as NaOH, in a suitable solvent, such as MeOH, EtOH, water or mixtures thereof, at a temperature rising from about 20° C. to 60° C., preferably at RT, for a few hours.

Scheme 3

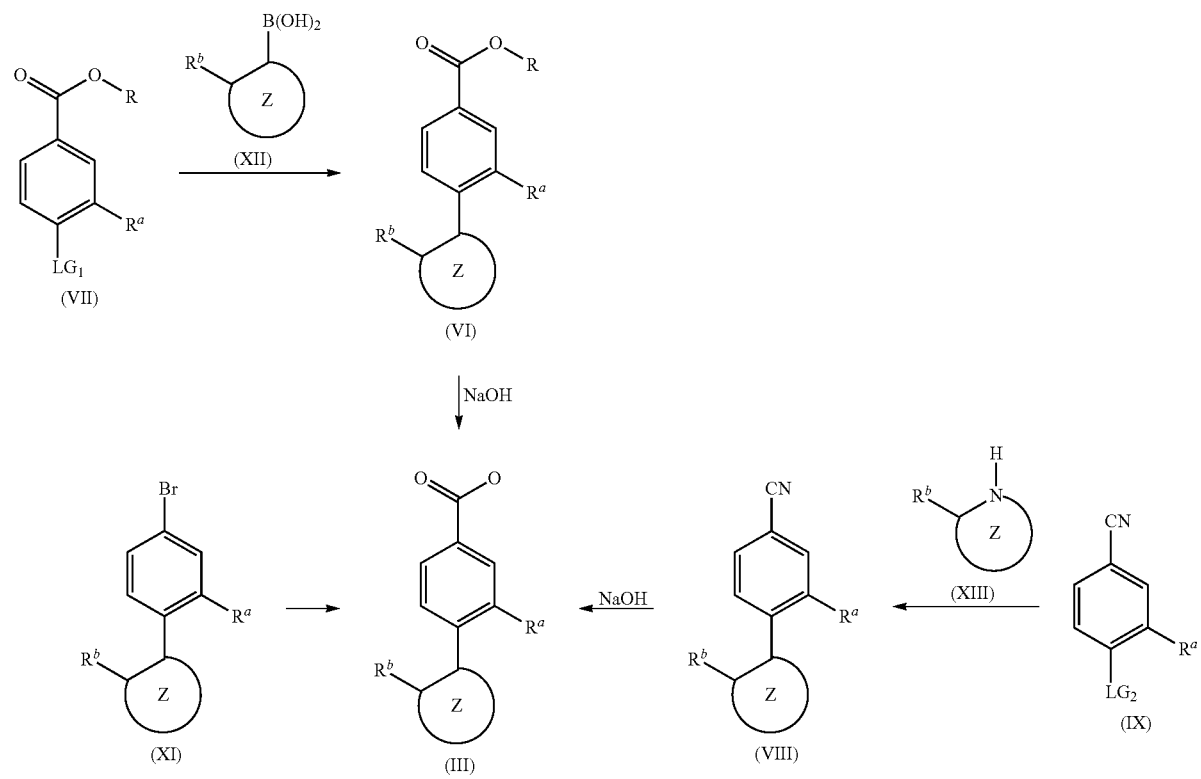

In a second synthetic pathway, compounds of Formula (III), wherein $R^a$, $R^b$ and Z are defined as above, may be obtained by a coupling reaction, followed by hydrolysis of the resulting nitrile (VIII). More particularly, according to Scheme 3, compounds of Formula (VIII), wherein $R^a$ and $R^b$ are defined as above and Z is Het including a nitrogen atom at the position adjacent to $R^b$ making a bond with the aryl moiety, may be prepared by a $SN_{Ar}$ reaction between a compound of Formula (XIII), wherein $R^b$ is defined as above and Z is Het including a secondary amine at the position adjacent to $R^b$, and a benzonitrile of Formula (IX), wherein $R^a$ is defined as above and $LG_2$ is a suitable leaving group. Preferably, $LG_2$ is a fluorine atom. The reaction is preferably carried out in a suitable solvent, such as DMSO, in the presence or not of an additional base, such as DIEA or DBU. the reaction may be performed at a temperature rising from RT to 120° C., preferably at 100° C. The resulting benzonitrile of Formula (VIII) may be hydrolyzed into the corresponding carboxylic acid (III) by treatment with an aqueous solution of metal hydroxide, such as NaOH, in a suitable solvent, such as MeOH or EtOH, at a temperature rising from RT to reflux, preferably at reflux, for a few hours e.g. from 1 to 24 hours In a third synthetic pathway, according to Scheme 3, compounds of Formula (III), wherein $R^a$, $R^b$ and Z are defined as above, may be prepared from arylbromide of Formula (XI) in a two steps process. The first step is a halogen-metal exchange with a lithiated alkyl, such as nBuLi or tBuLi, in a suitable solvent, such as $Et_2O$, at low temperature, preferably at −78° C. The second step is the quench of the organolithiated derivative by addition of $CO_2$, as gas or in solid state, as electrophile.

The method for preparing compounds of formula (III) selected below:
2-(methoxymethyl)-2'-methylbiphenyl-4-carboxylic acid
3-(methoxymethyl)-4-(2-methylpiperidin-1-yl)benzoic acid
2'-ethyl-2-(methoxymethyl)-1,1'-biphenyl-4-carboxylic acid
2'-methyl-2-(trifluoromethyl)biphenyl-4-carboxylic acid
4-(2-methylpiperidin-1-yl)-3-(trifluoromethyl)benzoic acid
4-(2-ethylpiperidin-1-yl)-3-(methoxymethyl)benzoic acid
2'-Chloro-2-(methoxymethyl)biphenyl-4-carboxylic acid
3-(methoxymethyl)-4-(2-methylpyrrolidin-1-yl)benzoic acid
2'-fluoro-2-(methoxymethyl)biphenyl-4-carboxylic acid
2'-fluoro-2-(trifluoromethyl)biphenyl-4-carboxylic acid
2-ethoxy-2'-methyl-1,1'-biphenyl-4-carboxylic acid
2-methyl-2'-(trifluoromethyl)biphenyl-4-carboxylic acid
2-ethoxy-2'-(trifluoromethyl)biphenyl-4-carboxylic acid
3'-fluoro-2-(methoxymethyl)-2'-methylbiphenyl-4-carboxylic acid
2,2'-dimethyl-1,1'-biphenyl-4-carboxylic acid
is more particularly described in the examples.

Compounds of Formulae (V), (VII), (IX), (XI), (XII) and (XIII) may be obtained either from commercial sources or they may be prepared from known compounds using procedures such as those described hereinafter in the examples, or conventional procedures, well known by one skilled in the art.

Compounds of Formulae (III), (V), (VI), (VII), (VIII), (IX), (XI), (XII) and (XIII), wherein $R^1$, $R^2$, $R^a$, $R^b$, Y, W, Z, $LG_1$ and $LG_2$ are as above defined, may be converted to alternative compounds of Formulae (III), (V), (VI), (VII), (VIII), (IX), (XI), (XII) and (XIII) respectively, using suitable interconversion procedures such as those described hereinafter in the examples, or conventional interconversion procedures well known by one skilled in the art.

If the above set of general synthetic methods is not applicable to obtain compounds according to Formula (I) and/or necessary intermediates for the synthesis of compounds of Formula (I), suitable methods of preparation known by a person skilled in the art should be used.

Compounds of this invention can be isolated in association with solvent molecules by crystallization from an appropriate solvent or by evaporation of an appropriate solvent.

The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

Both types of salts may be formed or interconverted using ion-exchange resin techniques.

The compounds of invention have been named according the standards used in the program "ACD/Name Batch" from Advanced Chemistry Development Inc., ACD/Labs (7.00 Release). Product version: 7.10, build: 15 Sep. 2003.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I) and related formulae, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group"

is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula (I) and related formulae are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using LiOH, NaOH or KOH in water, water/THF, water/THF/ethanol or water/dioxane, at temperatures between 0 and 100° C.

Free amino groups can furthermore be acylated in a conventional manner using an acid chloride or anhydride or alkylated using an unsubstituted or substituted alkyl halide or reacted with $CH_3—C(=NH)—OEt$, advantageously in an inert solvent, such as dichloromethane or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula (I) and so-called prodrug compounds.

The term "prodrug derivatives" or "prodrug" is taken to mean compounds of the formula (I) which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Preferably, the invention relates to compounds of Formula (Ia) to (Ii):

(Ia)
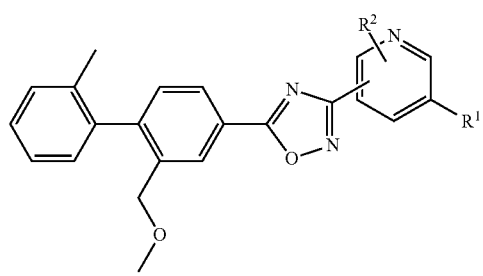

(Ib)
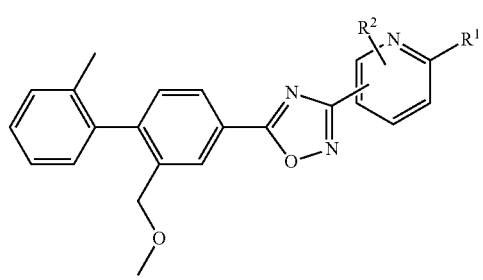

wherein $R^1$ and $R^2$ are as above defined (Ic)
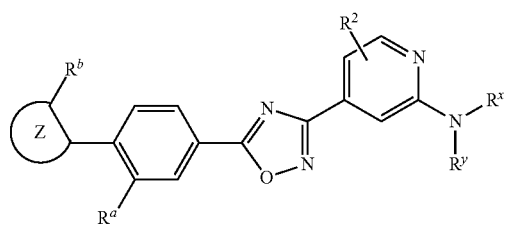

(Id)
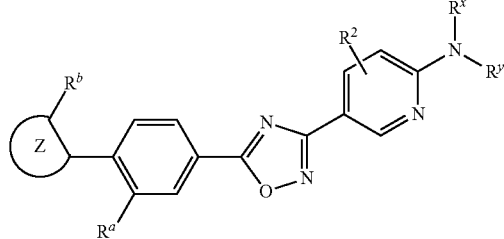

wherein Z, $R^a$, $R^b$, and $R^2$ are as above defined and wherein $R^x$ and $R^y$ are independently from one another H, $(CH_2)_nCO_2R^3$, A or, $C_1$-$C_7$ alkyl, wherein n and $R^3$ are as defined above. $R^x$ and $R^y$ together may form a ring being a Het group, preferably a 5 to 6 membered heterocyclic ring optionally substituted with $CO_2R^3$ and/or $OR^3$.

(Ie)
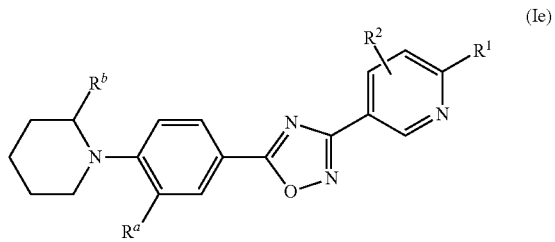

(If)
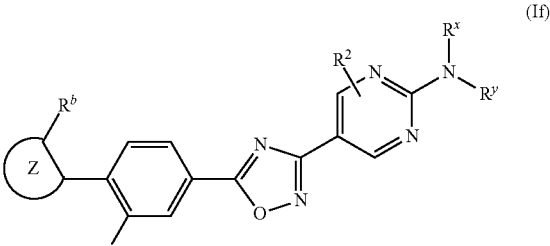

(Ig)
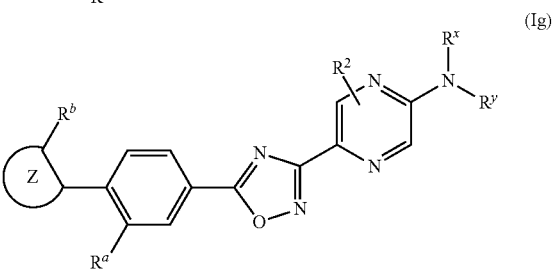

wherein Z, $R^a$, $R^b$, $R^1$, $R^2$, $R^x$ and $R^y$ are as above defined.

(Ih)
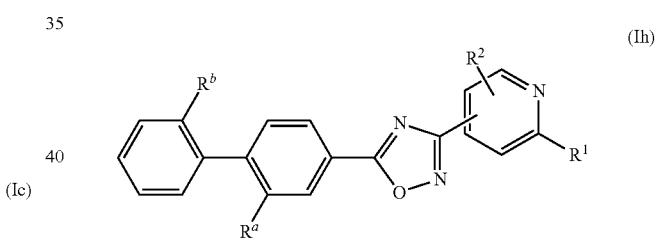

(Ii)
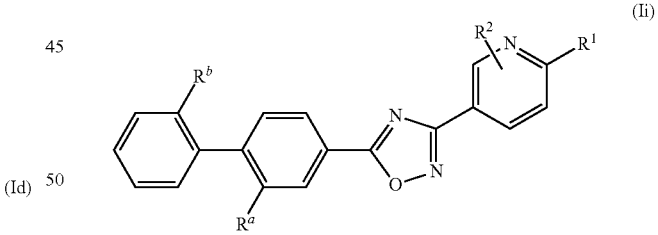

Wherein $R^a$, $R^b$, $R^1$ and $R^2$ are as above defined. and pharmaceutically acceptable derivatives, solvates, tautomers, salts and stereoisomers thereof, including mixtures thereof in all ratios.

The term "alkyl" refers to a linear or branched saturated hydrocarbon chain; this term is exemplified by groups such as methyl; ethyl; n-propyl; isopropyl; n-butyl; isobutyl; tertbutyl; n-hexyl. The term "$C_1$-$C_6$-alkyl" refers to alkyl groups having 1 to 6 carbon atoms. "$C_1$-$C_7$ alkyl" refers to alkyl groups having 1 to 7 carbon atoms.

The term "alkenyl" refers to unsaturated alkyl groups having at least one double bond and includes both linear- and branched alkenyl groups; this term is exemplified by groups such as propenyl, but-3-enyl, pent-4-enyl.

The term "$C_2$-$C_6$ alkenyl" refers to alkenyl groups having from 2 to 6 carbon atoms. ($C_1$-$C_7$)alkyl denotes a linear or branched alkyl having 1 to 6 carbon atom.

The term "cycloalkyl" refers to alkyl groups having a monocyclic ring, bicyclic or multiple fused alkyl rings; such cycloalkyl rings include e.g. cyclopropyl, cyclobutyl, cyclopentyl; cyclohexyl, cycloheptyl, cyclooctyl; and the like; such multiple ring structures include e.g. adamantanyl; and bicyclo[2.2.1]heptane. "$C_3$-$C_8$", "$C_3$-$C_{10}$" etc. refers to the cycle size of the corresponding cycloalkyl.

The term "perfluoroalkyl" refers to an alkyl group wherein each hydrogen atom has been replaced by a fluoro atom. Perfluoroalkyl preferably denotes $CF_3$.

The term "amino" or "amino-group" refers to a group —$N(H)_{2-p}(A)_p$, —$N(H)(CH_2)_nCO_2R^3$, wherein p, n, A and $R^3$ are as defined under the Formula (I).

The term "hydroxyl" or "hydroxyl group" refers to —OH group.

The term "cycloalkylalkylene" preferably denotes cyclopropylmethylene, cyclobutylmethylene, cyclopentylmethylene, cyclohexylmethylene or cycloheptylmethylene.

The term "alkylene" preferably denotes methylene, ethylene, propylene, butylene, pentylene or hexylene, furthermore branched alkylene.

The term "alkyloxy" or "alkoxy" refers to the group —O-alkyl or —O-cycloalkyl. Preferred alkoxy are methoxy, ethoxy group.

The term "substituent" is to be understood as an atom or group of atoms substituted in place of a hydrogen atom on the parent chain or ring. The variables of Formula (I) and related formulae such as for examples $R^a$, $R^b$, $R^1$ and $R^2$, are substituents of the core structure and take the place of a hydrogen atom. When in a ring, the substituent is not specifically localised, it can take the place of a H atom linked to any H-bearing atom of the ring. The same is true for the connexion of 2 moieties of the chemical structure. As an example, the meaning that W and Y denote CH in Formula (I) also means that when W and Y are linked to the oxadiazole group or to the $R^2$ group, W and Y denote C.

Ar preferably denotes a monocyclic aromatic carbocyclic ring having 6 carbon atoms, which is monosubstituted, disubstituted or trisubstituted by Hal, A, $OR^3$, $N(R^3)_2$, $NO_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$.

If Z is Ar, the group

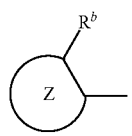

is preferably one of the following groups:

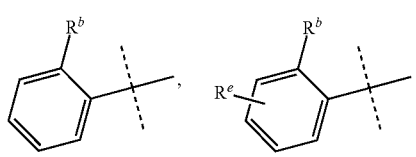

wherein $R^b$ and $R^e$ independently from one another denote A, OA, $OR^3$, $CF_3$, $OCF_3$. More preferably, Z is ortho-methylphenyl.

Het preferably denotes a monocyclic or bicyclic, saturated, unsaturated or aromatic heterocyclic ring having 1 or 2 N atoms, 1 or 2 O atom, or 1 or 2 S atom, and which is monosubstituted, disubstituted or trisubstituted by Hal, A, —[C$(R^3)_2]_n$—Ar, —[C$(R^3)_2]_n$-cycloalkyl, $OR^3$, $CF_3$, $OCF_3$, $N(R^3)_2$, $NR^3CON(R^3)_2$, $NO_2$, CN, —[C$(R^3)_2]_n$—$COOR^3$, —[C$(R^3)_2]_n$—CON$(R^3)_2$, $NR^3COA$, $NR^3SO_2A$, $COR^3$, $SO_2N(R^3)_2$, SOA, and/or $SO_2A$.

Het preferably denotes monocyclic, saturated, unsaturated or aromatic heterocyclic ring having 1 N atom, and which is monosubstituted, disubstituted or trisubstituted by Hal, ($C_1$-$C_6$)alkyl, —$CF_3$, —$OCF_3$, $OCH_3$, —$CH_2OCH_3$. Het is preferably saturated.

When it contains 1 or more nitrogen atoms, Het is preferably linked to the rest of the molecule through the N atom.

If Z is Het the group

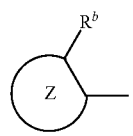

is preferably

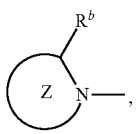

and more preferably one of the following groups:

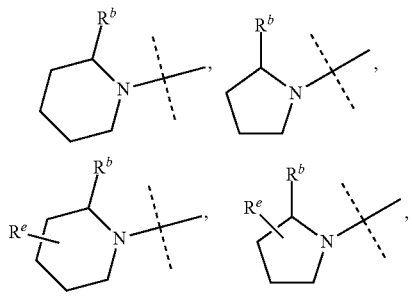

wherein $R^b$ and $R^e$ independently from one another denote A, Hal, OA, $OR^3$, $CF_3$, $OCF_3$. Particularly, $R^b$ and $R^e$ independently from one another denote Hal, or alkyl having 1 to 7 carbon atoms.

If Z is Het, the group

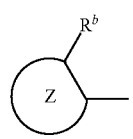

also denotes one of the following groups:

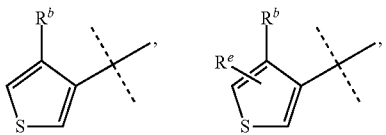

wherein $R^b$ and $R^e$ independently from one another denote A, OA, $OR^3$, $CF_3$, $OCF_3$.

Most preferably Het denotes methylpiperidine, $R^1$ is preferably in position meta or para to the oxadiazole group and preferably denotes a group selected from $(T)_tCO_2R^3$, $(T)_tN(R^3)_2$, $(T)_tCON(R^3)_2$, $(T)_tOR^3$, or $(T)_tHet$, wherein t is 0 or 1, preferably 1, and wherein T denotes an alkyl chain having 1 to 5, preferably 1 to 4 carbon atoms, more preferably 3 carbon atoms, wherein 1 $CH_2$ group is replaced by a group $(NR^3)$, and wherein 1 or 2 H may be replaced by an alkyl group having 1 to 3 carbon atoms.

Most preferably $R^1$ denotes $NH_2$, $NH(CH_3)$, $N(CH_3)_2$, Hal, OH, $OCH_3$, COOH, $COOCH_3$, $CONH_2$, or one of the following groups:

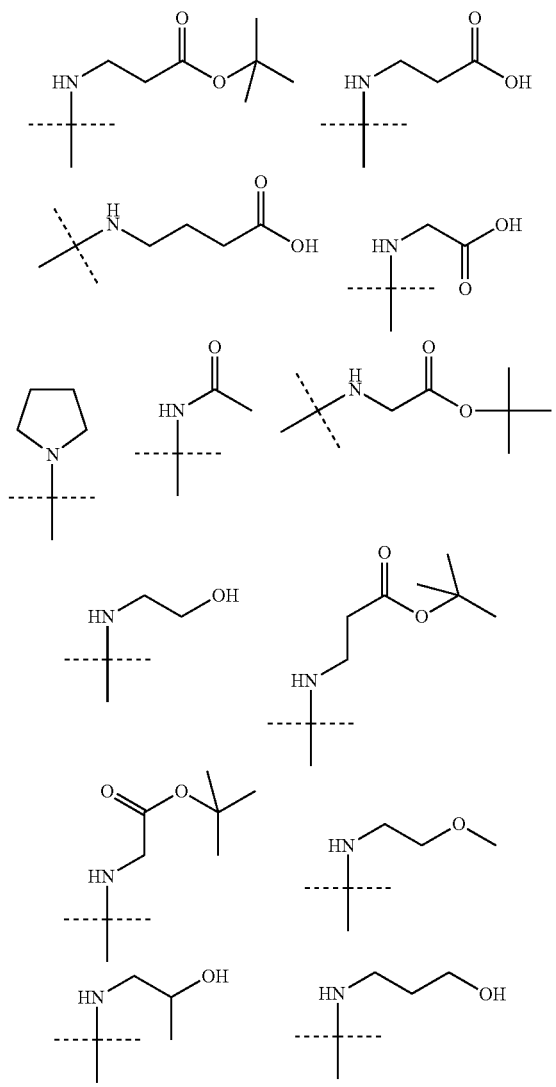

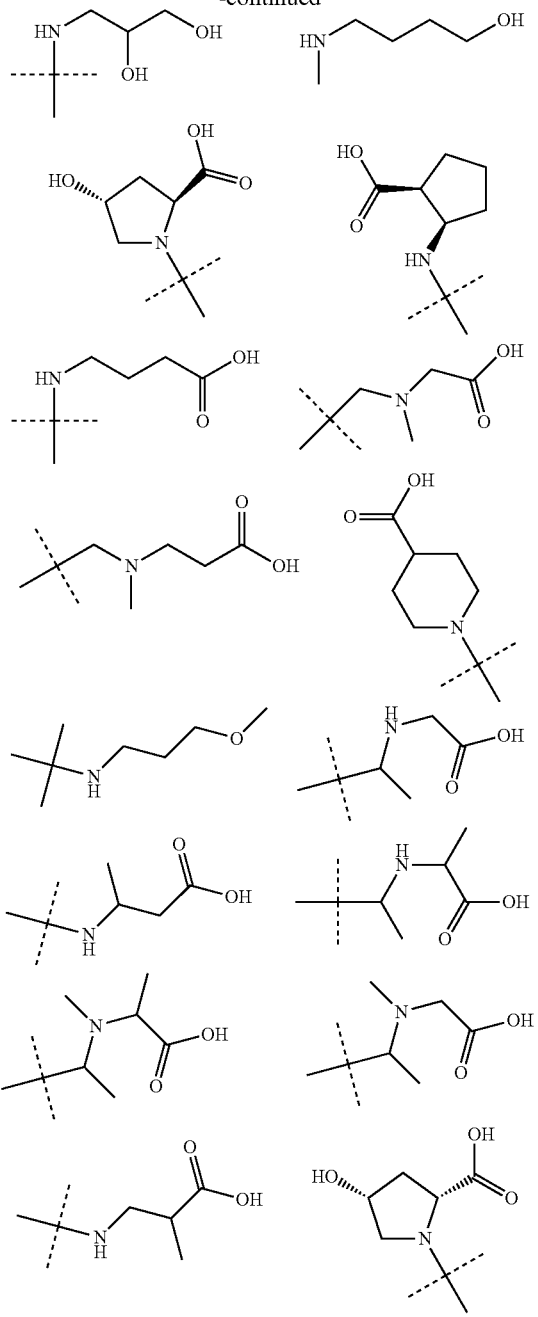

$R^a$ more preferably denotes A, $-CF_3$, Hal, $-CH_2-OR^3$, $OR^3$, $-OCF_3$, $(C_1-C_7)$alkyl wherein A denotes a branched or linear alkyl having 1 to 12 C-atoms, wherein one or more, preferably 1 to 7 H-atoms may be replaced by Hal, $OR^3$, or $N(R^3)_2$ and wherein one or more, preferably 1 to 7 non-adjacent $CH_2$-groups may be replaced by O or $NR^3$.

In a specific embodiment, $R^1$ and $R^2$ also denote A or $N(H)_{2-p}(A)_p$.

$R^a$ most preferably denotes $-CF_3$, $-CN$, $-CH_3$, $-CH_2OCH_3$, $-CH_2N(CH_3)_2$, $-NHSO_2CH_3$, $-NO_2$, $-OCH_3$, $-CH_2-CH_3$, $-CH_2-CH(CH_3)_2$, $-CF_3$, $-CH_2-CF_3$, $-CH_2OCH_2CH_3$, $-OCH_2CH_3$, $-CH_2OCF_3$, $-CH_2-N(CH_3)-CH_2CH_3$, $-CH(CH_3)OCH_3$, $R^b$ most preferably denotes a $C_1-C_6$ alkyl or $C_1-C_6$ alkyl wherein one $-CH_2-$ group is replaced by oxygen. More preferably $R^b$ denotes —CH$_3$, —CH$_2$—CH$_3$, —CH$_2$—CH(CH$_3$)$_2$, —CF$_3$, —CH$_2$—CF$_3$, —CH$_2$OCH$_3$, —CH$_2$OCH$_2$CH$_3$, F, Cl, —CH$_2$F, —OCF$_2$CH$_3$, —CH$_2$OCF$_3$, —CH$_2$—N(CH$_3$)$_2$, —CH$_2$—N(CH$_3$)—CH$_2$CH$_3$.

In the preferred compounds of the invention, when $R^2$ is in ortho position with respect to the oxadiazole ring, $R^2$ is not —N(R$^3$)$_2$.

In the preferred compounds of the invention, the pyridine or pirimidine moiety is not substituted in position ortho with respect to the oxadiazole ring.

In a preferred embodiment, the invention provides compounds of Formula (I) wherein Z, $R^a$, $R^b$ are as defined under Formula (I), wherein $R^2$ is Hal, A or H, wherein W and Y denote —CH— and wherein $R^1$ denotes N(H)$_{2-p}$(A)$_p$ or N(H)(CH$_2$)$_n$CO$_2$R$^3$, wherein p, n and R$^3$ are as above defined.

In a second preferred embodiment, the invention provides compounds of Formula (I) wherein Z, $R^a$, $R^b$ are as defined under Formula (I), wherein $R^2$ is H, wherein W and Y denote —CH— and wherein $R^1$ denotes NH$_2$ or N(CH$_3$)$_2$.

In a third preferred embodiment, the invention provides compounds of Formula (I) wherein Z, $R^a$, $R^b$ are as defined under Formula (I), wherein $R^2$ is Hal, A or H, wherein W and Y denote —CH— and wherein $R^1$ denotes NH(CH$_2$)$_n$CO$_2$R$^3$, wherein n is 1, 2 or 3, preferably 1 or 2, and R$^3$ is H or (C$_1$-C$_6$)alkyl, preferably H.

In a fourth preferred embodiment, the invention provides compounds of Formula (I) wherein Z, $R^a$, $R^b$ are as defined under Formula (I), wherein $R^2$ is Hal, A or H, wherein W and Y denote —CH— and wherein $R^1$ denotes —OH or —OA.

In a fifth preferred embodiment, the invention provides compounds of Formula (I) wherein $R^a$, $R^b$ are as defined under Formula (I), wherein Z is phenyl or piperidine, wherein $R^2$ is H, wherein W and Y denote —CH— and wherein $R^1$ denotes —OH or —OCH$_3$.

In a sixth preferred embodiment, the invention provides compounds of Formula (I) wherein Z, $R^a$, $R^b$ are as defined under Formula (I), wherein $R^2$ is Hal, A or H, wherein W and Y denote —CH— and wherein $R^1$ denotes —CO$_2$R$^3$, —CON(H)$_{2-p}$(A)$_p$, wherein R$^3$, A and p are as defined under Formula (I).

In a seventh preferred embodiment, the invention provides compounds of Formula (I) wherein $R^a$, $R^b$ are as defined under Formula (I), wherein Z is phenyl or piperidine, wherein $R^2$ is H, wherein W and Y denote —CH— and wherein $R^1$ denotes —COOH, —COO(C$_1$-C$_6$)alkyl, CONH$_2$, CONH(C$_1$-C$_6$)alkyl.

In a eighth preferred embodiment, the invention provides compounds of Formula (I) wherein Z is a phenyl or piperidine, wherein $R^a$, $R^b$, W and Y are as defined under Formula (I), wherein $R^2$ is H or Hal, and wherein $R^1$ denotes N(H)$_{2-p}$(A)$_p$ or N(H)(CH$_2$)$_n$CO$_2$R$^3$, wherein p, n and R$^3$ are as defined under Formula (I).

Preferred compounds are selected from the following examples 1 to 97.

| Ex | Formula |
|---|---|
| 1 | |
| 2 | |
| 3 | |

-continued

| Ex | Formula |
|---|---|
| 4 | |
| 5 | |
| 6 | |
| 7 | |
| 8 | |

-continued
| Ex | Formula |
|---|---|
| 9 | 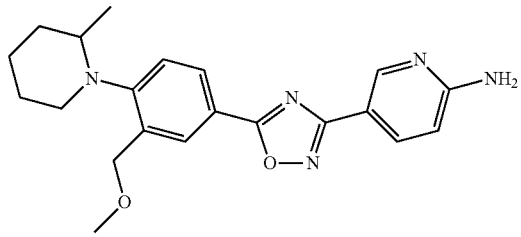 [SMILES: COCc1cc(-c2nc(-c3ccc(N)nc3)no2)ccc1N1CCCCC1C] |
| 10 | 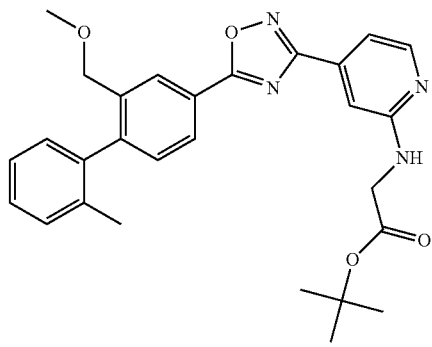 [SMILES: COCc1cc(-c2nc(-c3ccnc(NCC(=O)OC(C)(C)C)c3)no2)ccc1-c1ccccc1C] |
| 11 | 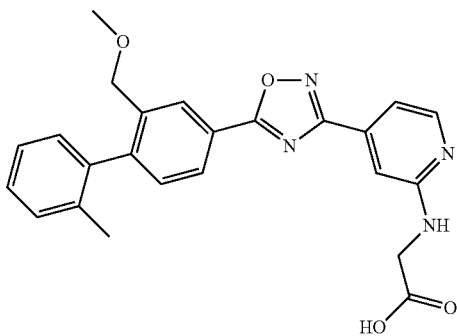 [SMILES: COCc1cc(-c2nc(-c3ccnc(NCC(=O)O)c3)no2)ccc1-c1ccccc1C] |
| 12 | 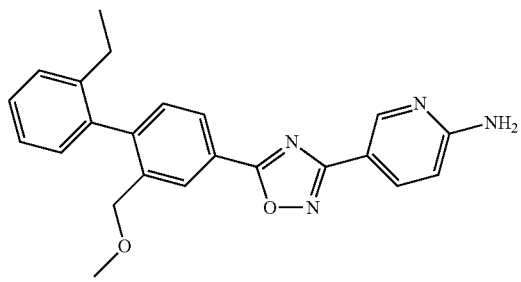 [SMILES: CCc1ccccc1-c1ccc(-c2nc(-c3ccc(N)nc3)no2)cc1COC] |
| 13 | 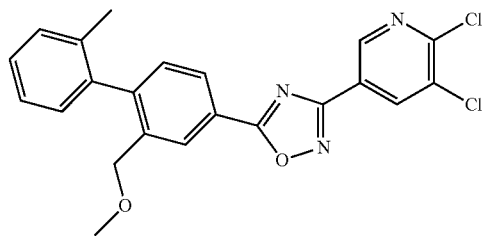 [SMILES: COCc1cc(-c2nc(-c3cnc(Cl)c(Cl)c3)no2)ccc1-c1ccccc1C] |

-continued
| Ex | Formula |
|---|---|
| 14 | 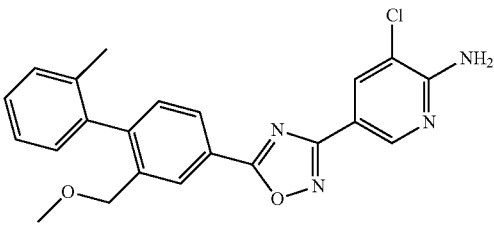 [SMILES: COCc1cc(-c2nc(-c3cnc(N)c(Cl)c3)no2)ccc1-c1ccccc1C] |
| 15 | 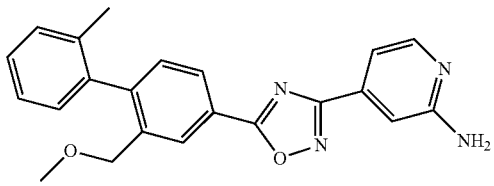 [SMILES: COCc1cc(-c2nc(-c3ccnc(N)c3)no2)ccc1-c1ccccc1C] |
| 16 | 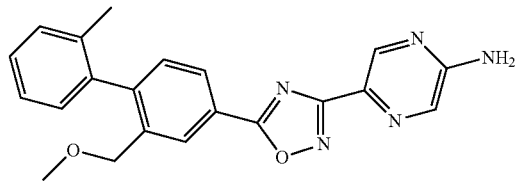 [SMILES: COCc1cc(-c2nc(-c3cnc(N)cn3)no2)ccc1-c1ccccc1C] |
| 17 | 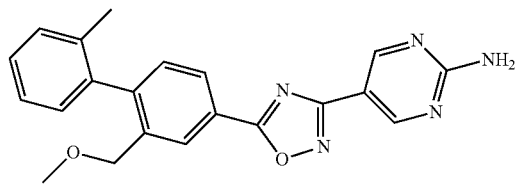 [SMILES: COCc1cc(-c2nc(-c3cnc(N)nc3)no2)ccc1-c1ccccc1C] |
| 18 | 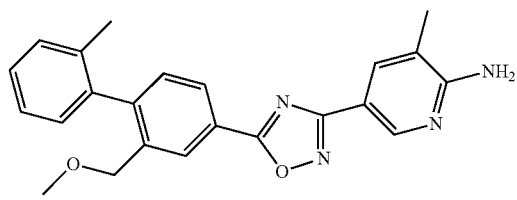 [SMILES: COCc1cc(-c2nc(-c3cnc(N)c(C)c3)no2)ccc1-c1ccccc1C] |
| 19 | 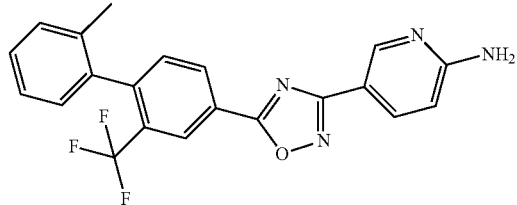 [SMILES: Cc1ccccc1-c1ccc(-c2nc(-c3ccc(N)nc3)no2)cc1C(F)(F)F] |
| 20 | 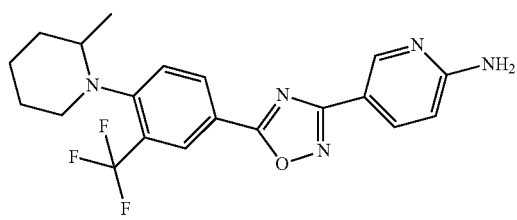 [SMILES: CC1CCCCN1c1ccc(-c2nc(-c3ccc(N)nc3)no2)cc1C(F)(F)F] |

-continued

| Ex | Formula |
|---|---|
| 21 | 5-[2'-methyl-2-(methoxymethyl)biphenyl-4-yl]-3-(6-hydroxypyridin-3-yl)-1,2,4-oxadiazole |
| 22 | 5-[3-(methoxymethyl)-4-(2-methylpiperidin-1-yl)phenyl]-3-(6-hydroxypyridin-3-yl)-1,2,4-oxadiazole |
| 23 | 5-[2'-methyl-2-(methoxymethyl)biphenyl-4-yl]-3-(6-methoxypyridin-3-yl)-1,2,4-oxadiazole |
| 24 | methyl 5-{5-[2'-methyl-2-(methoxymethyl)biphenyl-4-yl]-1,2,4-oxadiazol-3-yl}pyridine-2-carboxylate |
| 25 | 5-{5-[2'-methyl-2-(methoxymethyl)biphenyl-4-yl]-1,2,4-oxadiazol-3-yl}pyridine-2-carboxylic acid |
| 26 | 5-{5-[2'-methyl-2-(methoxymethyl)biphenyl-4-yl]-1,2,4-oxadiazol-3-yl}pyridine-2-carboxamide |
| 27 | 5-[5-[3-(methoxymethyl)-4-(2-ethylpiperidin-1-yl)phenyl]-1,2,4-oxadiazol-3-yl]pyridin-2-amine |

-continued
| Ex | Formula |
|---|---|
| 28 | 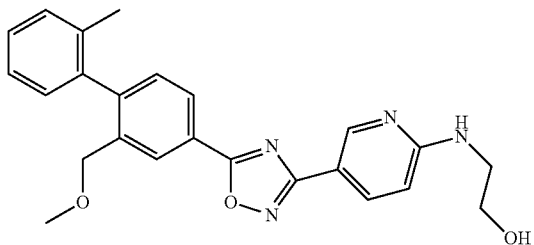 [SMILES: COCc1cc(-c2nc(-c3ccc(NCCO)nc3)no2)ccc1-c1ccccc1C] |
| 29 | 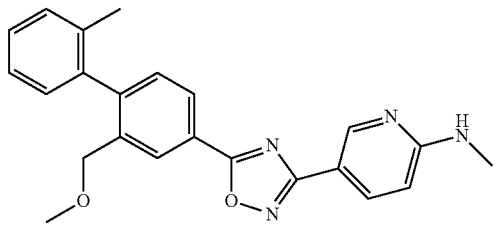 [SMILES: CNc1ccc(-c2noc(-c3ccc(-c4ccccc4C)c(COC)c3)n2)cn1] |
| 30 | 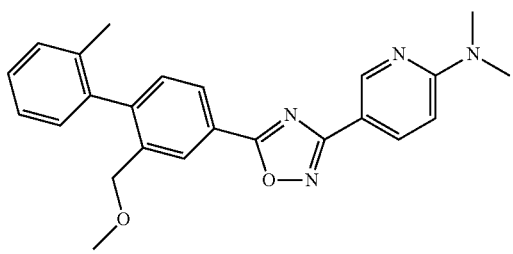 [SMILES: COCc1cc(-c2nc(-c3ccc(N(C)C)nc3)no2)ccc1-c1ccccc1C] |
| 31 | 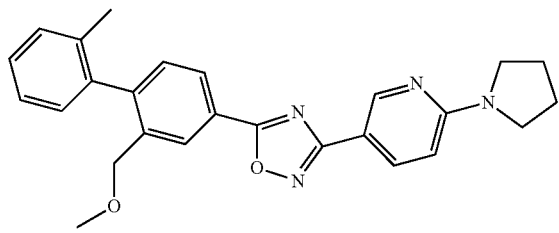 [SMILES: COCc1cc(-c2nc(-c3ccc(N4CCCC4)nc3)no2)ccc1-c1ccccc1C] |
| 32 | 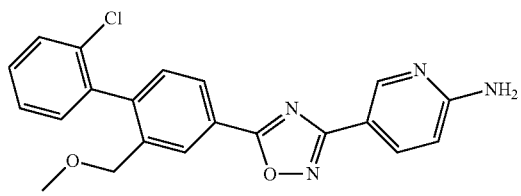 |
| 33 | 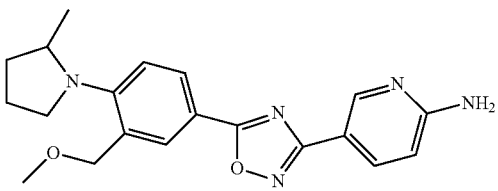 [SMILES: COCc1cc(-c2nc(-c3ccc(N)nc3)no2)ccc1N1CCCC1C] |

-continued
| Ex | Formula |
|---|---|
| 34 | 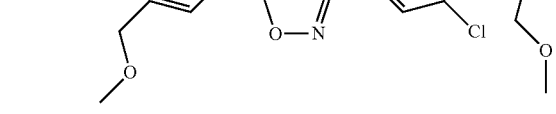 |
| 35 |  |
| 36 | 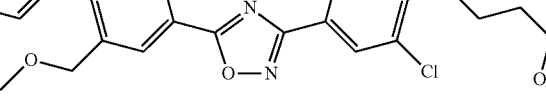 |
| 37 |  |
| 38 | 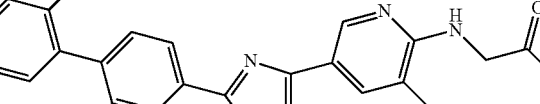 |
| 39 | 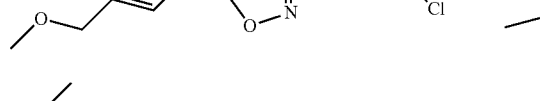 |
| 40 | 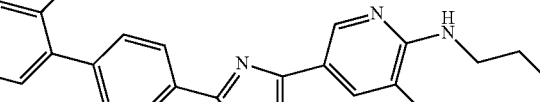 |

-continued

| Ex | Formula |
|---|---|
| 41 | |
| 42 | |
| 43 | |
| 44 | |
| 45 | |
| 46 | |

-continued
| Ex | Formula |
|----|---------|
| 47 | 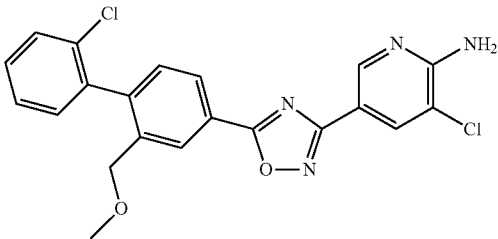 [SMILES: COCc1cc(-c2nc(-c3cnc(N)c(Cl)c3)no2)ccc1-c1ccccc1Cl] |
| 48 | 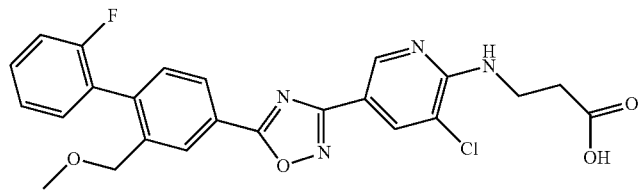 [SMILES: COCc1cc(-c2nc(-c3cnc(NCCC(=O)O)c(Cl)c3)no2)ccc1-c1ccccc1F] |
| 49 | 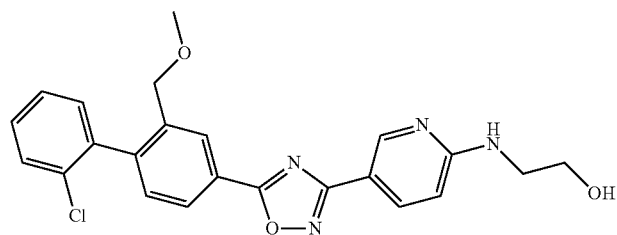 [SMILES: COCc1cc(-c2nc(-c3ccc(NCCO)nc3)no2)ccc1-c1ccccc1Cl] |
| 50 | 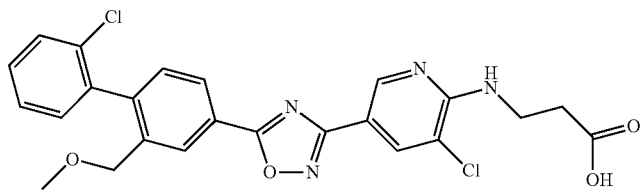 [SMILES: COCc1cc(-c2nc(-c3cnc(NCCC(=O)O)c(Cl)c3)no2)ccc1-c1ccccc1Cl] |
| 51 | 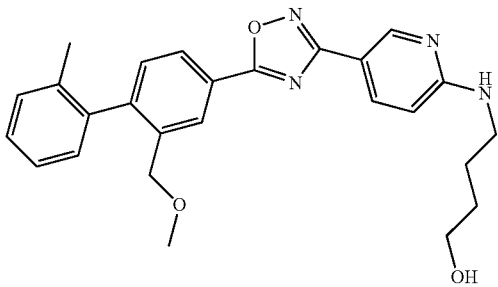 [SMILES: COCc1cc(-c2nc(-c3ccc(NCCCCO)nc3)no2)ccc1-c1ccccc1C] |
| 52 | 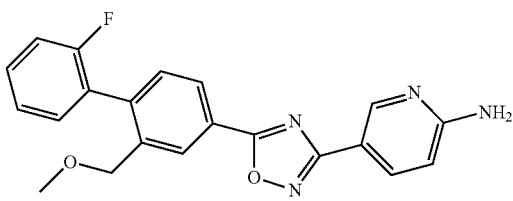 [SMILES: COCc1cc(-c2nc(-c3ccc(N)nc3)no2)ccc1-c1ccccc1F] |

| Ex | Formula |
|---|---|
| 53 | 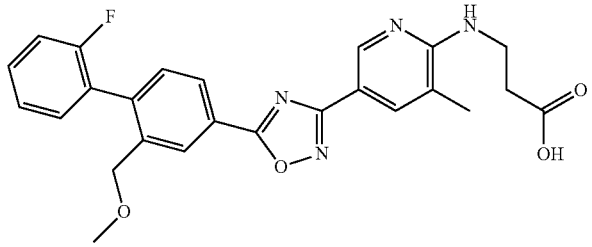 |
| 54 | 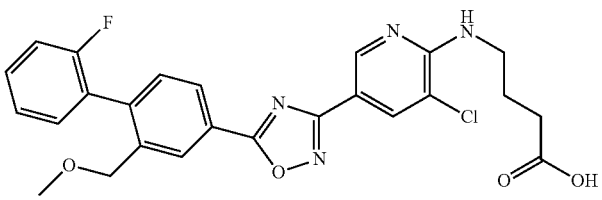 |
| 55 | 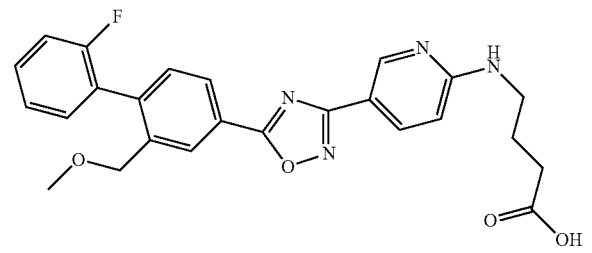 [SMILES: COCc1cc(-c2nc(-c3ccc(NCCCC(=O)O)nc3)no2)ccc1-c1ccccc1F] |
| 56 | 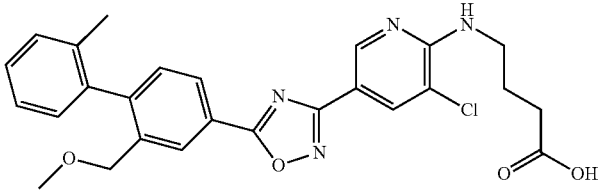 |
| 57 | 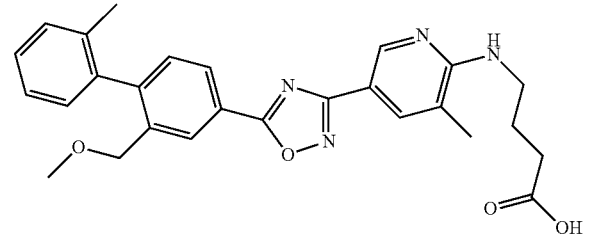 [SMILES: COCc1cc(-c2nc(-c3cnc(NCCCC(=O)O)c(C)c3)no2)ccc1-c1ccccc1C] |
| 58 | 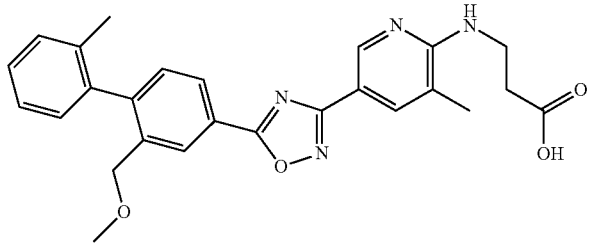 [SMILES: COCc1cc(-c2nc(-c3cnc(NCCC(=O)O)c(C)c3)no2)ccc1-c1ccccc1C] |

-continued
| Ex | Formula |
|---|---|
| 59 | 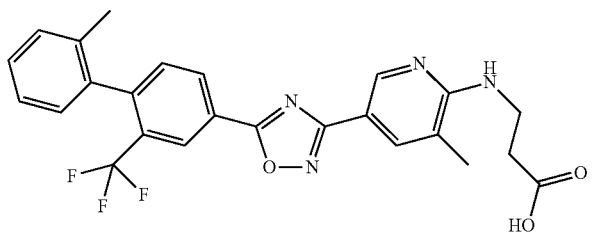 [SMILES: Cc1ccccc1-c1ccc(-c2nc(-c3cnc(NCCC(=O)O)c(C)c3)no2)cc1C(F)(F)F] |
| 60 | 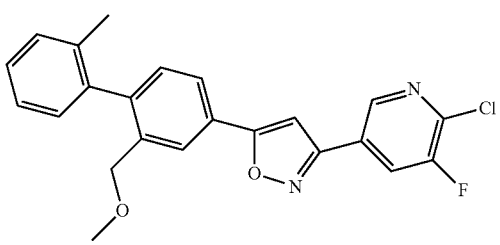 [SMILES: COCc1cc(-c2cc(-c3cnc(Cl)c(F)c3)no2)ccc1-c1ccccc1C] |
| 61 | 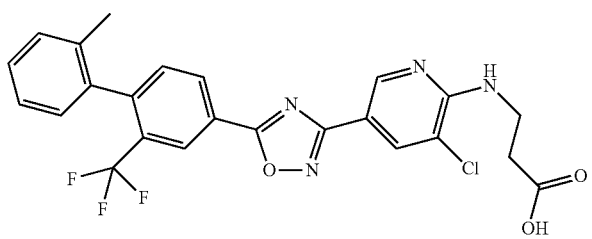 [SMILES: Cc1ccccc1-c1ccc(-c2nc(-c3cnc(NCCC(=O)O)c(Cl)c3)no2)cc1C(F)(F)F] |
| 62 | 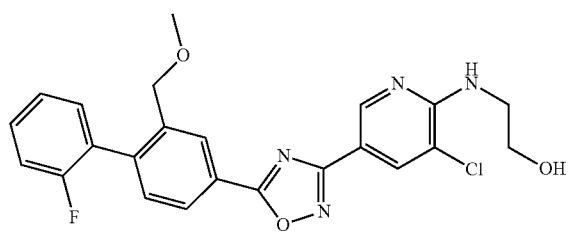 [SMILES: COCc1cc(-c2nc(-c3cnc(NCCO)c(Cl)c3)no2)ccc1-c1ccccc1F] |
| 63 | 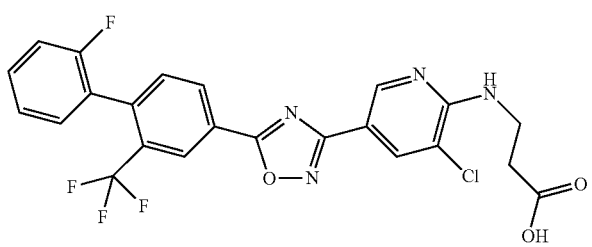 [SMILES: O=C(O)CCNc1ncc(-c2noc(-c3ccc(-c4ccccc4F)c(C(F)(F)F)c3)n2)cc1Cl] |
| 64 | 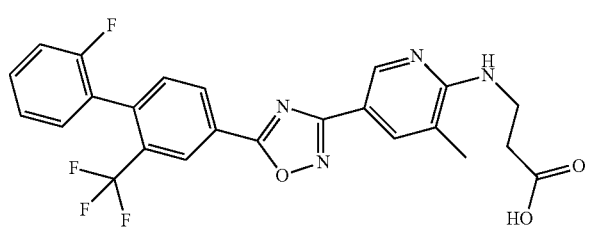 [SMILES: Cc1cc(-c2noc(-c3ccc(-c4ccccc4F)c(C(F)(F)F)c3)n2)cnc1NCCC(=O)O] |

-continued
| Ex | Formula |
|---|---|
| 65 | 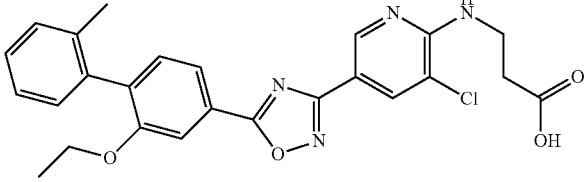 |
| 66 | 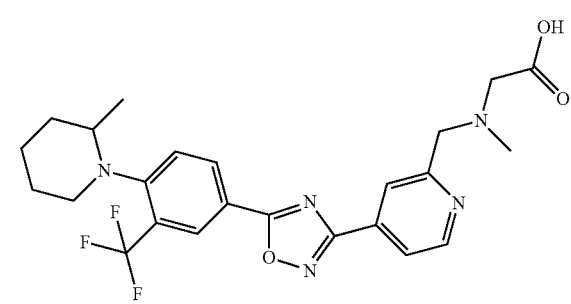 [SMILES: CC1CCCCN1c1ccc(-c2nc(-c3ccnc(CN(C)CC(=O)O)c3)no2)cc1C(F)(F)F] |
| 67 | 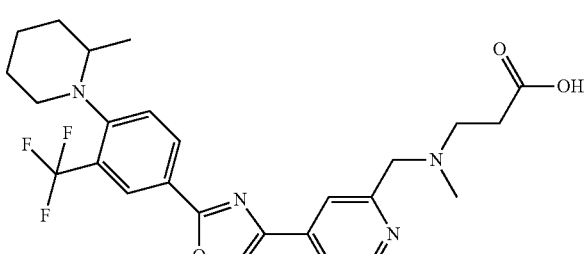 |
| 68 | 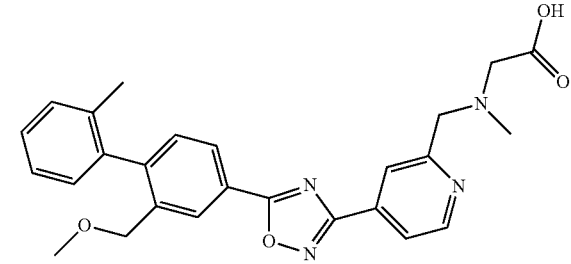 [SMILES: COCc1cc(-c2nc(-c3ccnc(CN(C)CC(=O)O)c3)no2)ccc1-c1ccccc1C] |
| 69 | 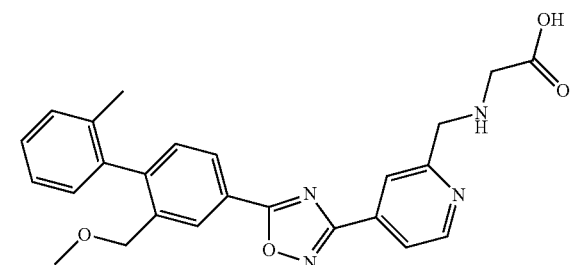 |
| 70 | 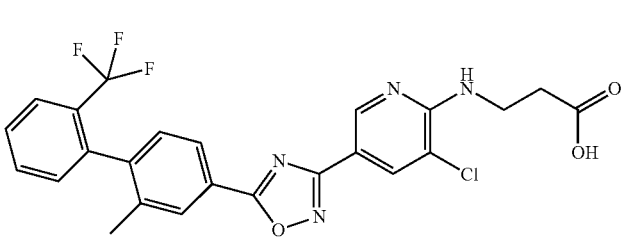 [SMILES: Cc1cc(-c2nc(-c3cnc(NCCC(=O)O)c(Cl)c3)no2)ccc1-c1ccccc1C(F)(F)F] |

-continued
| Ex | Formula |
|---|---|
| 71 | 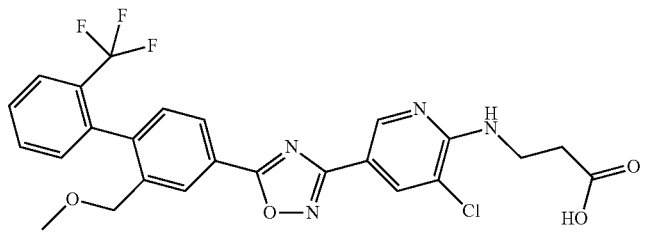 [SMILES: COCc1cc(-c2nc(-c3cnc(NCCC(=O)O)c(Cl)c3)no2)ccc1-c1ccccc1C(F)(F)F] |
| 72 | 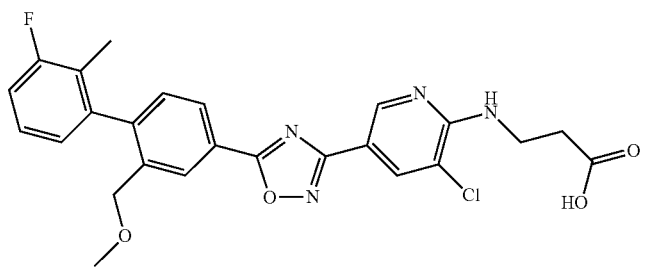 [SMILES: COCc1cc(-c2nc(-c3cnc(NCCC(=O)O)c(Cl)c3)no2)ccc1-c1cccc(F)c1C] |
| 73 | 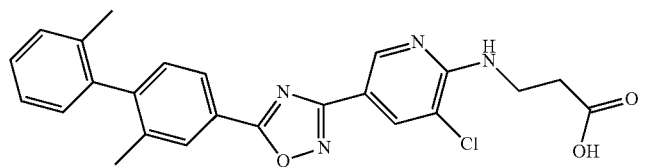 [SMILES: Cc1ccccc1-c1ccc(-c2nc(-c3cnc(NCCC(=O)O)c(Cl)c3)no2)cc1C] |
| 74 | 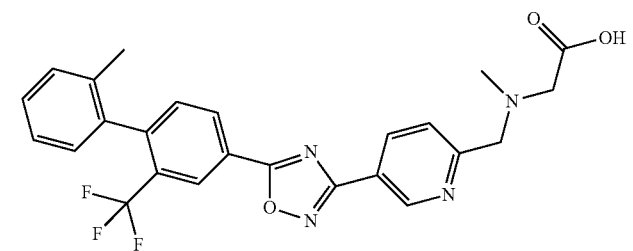 [SMILES: Cc1ccccc1-c1ccc(-c2nc(-c3ccc(CN(C)CC(=O)O)nc3)no2)cc1C(F)(F)F] |
| 75 | 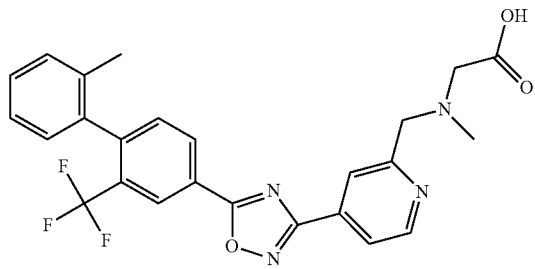 [SMILES: Cc1ccccc1-c1ccc(-c2nc(-c3ccnc(CN(C)CC(=O)O)c3)no2)cc1C(F)(F)F] |
| 76 | 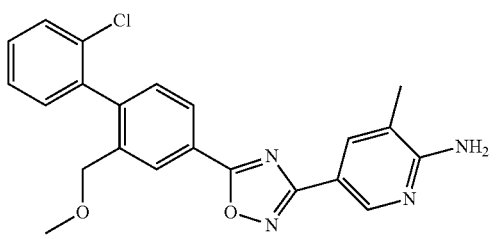 [SMILES: COCc1cc(-c2nc(-c3cnc(N)c(C)c3)no2)ccc1-c1ccccc1Cl] |

-continued

| Ex | Formula |
|---|---|
| 77 | |
| 78 | |
| 79 | |
| 80 | |
| 81 | |
| 82 | |

-continued
| Ex | Formula |
|---|---|
| 83 | 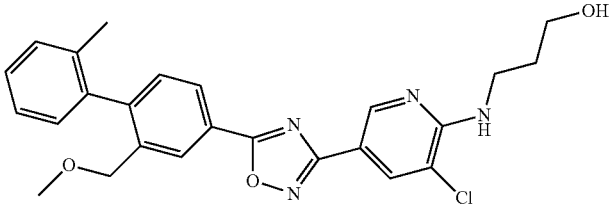 [SMILES: COCc1cc(-c2nc(-c3cnc(NCCCO)c(Cl)c3)no2)ccc1-c1ccccc1C] |
| 84 | 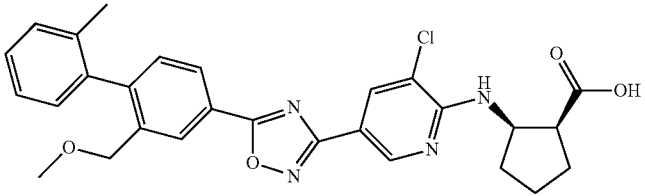 [SMILES: COCc1cc(-c2nc(-c3cnc(N[C@@H]4CCC[C@@H]4C(=O)O)c(Cl)c3)no2)ccc1-c1ccccc1C] |
| 85 | 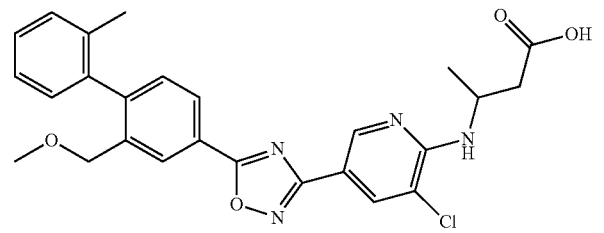 [SMILES: COCc1cc(-c2nc(-c3cnc(NC(C)CC(=O)O)c(Cl)c3)no2)ccc1-c1ccccc1C] |
| 86 | 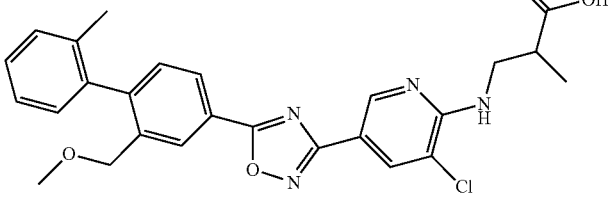 |
| 87 | 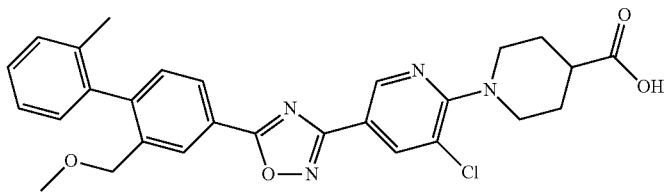 [SMILES: COCc1cc(-c2nc(-c3cnc(N4CCC(C(=O)O)CC4)c(Cl)c3)no2)ccc1-c1ccccc1C] |
| 88 | 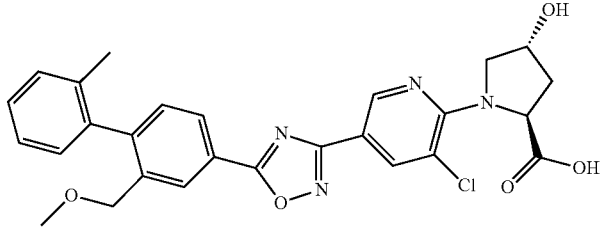 [SMILES: COCc1cc(-c2nc(-c3cnc(N4C[C@H](O)C[C@H]4C(=O)O)c(Cl)c3)no2)ccc1-c1ccccc1C] |
| 89 | 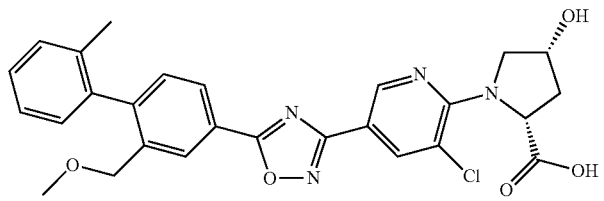 [SMILES: COCc1cc(-c2nc(-c3cnc(N4C[C@H](O)C[C@@H]4C(=O)O)c(Cl)c3)no2)ccc1-c1ccccc1C] |

| Ex | Formula |
|---|---|
| 90 | 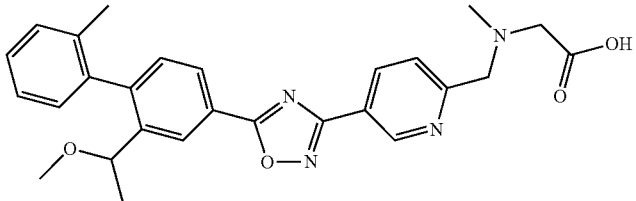 [SMILES: COC(C)c1cc(-c2nc(-c3ccc(CN(C)CC(=O)O)nc3)no2)ccc1-c1ccccc1C] |
| 91 | 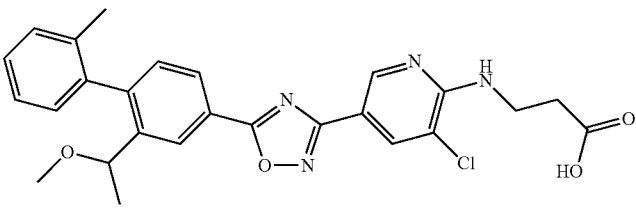 [SMILES: COC(C)c1cc(-c2nc(-c3cnc(NCCC(=O)O)c(Cl)c3)no2)ccc1-c1ccccc1C] |
| 92 | 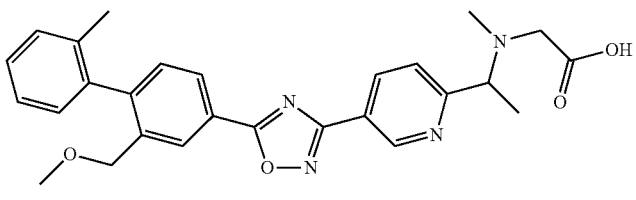 [SMILES: COCc1cc(-c2nc(-c3ccc(C(C)N(C)CC(=O)O)nc3)no2)ccc1-c1ccccc1C] |
| 93 | 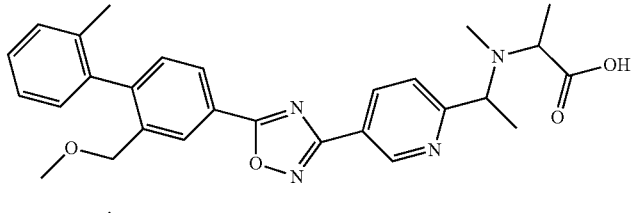 |
| 94 | 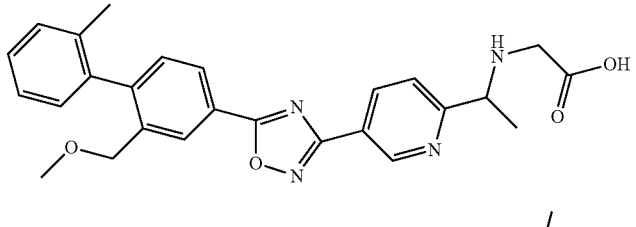 |
| 95 | 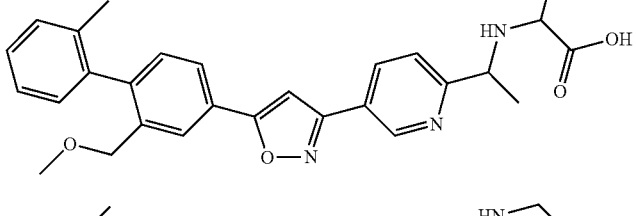 |
| 96 | 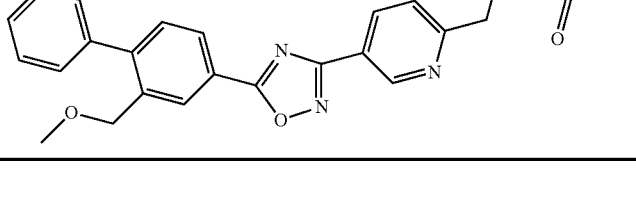 |

Pharmaceutical Salts and Other Forms

The said compounds of the formula I can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassiumethoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula I are likewise included. In the case of certain compounds of the formula I, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzene-sulfonate (besylate), bisulfate, bisulfite, bromide, butyrate, camphorate, camphorsulfonate, caprylate, chloride, chlorobenzoate, citrate, cyclopentane-propionate, digluconate, dihydrogen-phosphate, dinitrobenzoate, dodecyl-sulfate, ethanesulfonate, fumarate, galacterate (from mucic acid), galacturonate, glucoheptanoate, gluco-nate, glutamate, glycerophosphate, hemi-succinate, hemisulfate, heptanoate, hexanoate, hippurate, hydrochloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminium, ammonium, calcium, copper, iron (III), iron(II), lithium, magne-sium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethylamine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lido-caine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula (I) of the present invention which contain basic N-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula (I) are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula I contains more than one group which is capable of forming pharmaceutically acceptable salts of this type, the formula (I) also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula I can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula (I), in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I) and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compounds of formula (I). The present invention preferably relates to a method, wherein the sphingosine 1-phosphate-1 associated disorder is an autoimmune disorder or condition associated with an overactive immune response.

The present invention furthermore relates to a method of treating a subject suffering from an immunerogulatory abnomality, comprising administering to said subject a compounds of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Preferred compounds of formula (I) exhibit a EC50 in GTPγS for the binding to the $S_1P_1$ receptor of less than about 20 nM, preferably less than about 10 nM, more preferably less than about 5 nM.

Preferred compounds of Formula (I) exhibit a selectivity on S1P1 receptor over the S1P3 receptor of a magnitude of more than about 20. More preferably, compounds of formula (I) are 50 fold selective for S1P1 compare to S1P3, more preferably, 100 fold, even more preferably 1000 fold.

In the following the present invention shall be illustrated by means of some examples, which are not construed to be viewed as limiting the scope of the invention.

EXAMPLES

Ac (acetyl), ACN (acetonitrile), AIBN (A, A'-azoisobutyronitrile), cHex (cyclohexane), DCM (dichloromethane), DIEA (diisopropylethylamine), DMA (dimethylacetamide), DMF (dimethylformamide), DMSO (dimethylsulfoxide), eq (equivalent), Et (ethyl), EDC (1-(3-dimethyl-amino-propyl)-3-ethylcarbodiimide), ESI (electro-spray ionization), HATU (O-(7-azabenzotriazol-1-yl)-N,N,N',N'-tetramethyluronium hexafluorophosphate), HPLC (high performance liquid chromatography), iPr (isopropyl), L (liter), LC (liquid chromatography), Me (methyl), mg (milligram), min (minute), mL (milliliter), μL (microliter), mmol (millimole), M (molar), MHz (megaherz), MS (mass spectrometry), MTBE (methyl tert-butyl ether), NBS (N-bromosuccinimide), NMM (N-methyl morpholine), NMR (nuclear magnetic resonance), OAc (acetate), pet ether (petroleum ether), Ph (phenyl), Rt (retention time), RT (room temperature), SPE (solid phase extraction), tBu (tert-butyl), THF (tetrahydrofuran), UPLC (ultra performance liquid chromatography), UV (ultraviolet).

The commercially available starting materials used in the following experimental description were purchased from Merck or Sigma-Aldrich-Fluka unless otherwise reported.

NMR, HPLC and MS data provided in the examples described below are registered on: NMR Bruker DPX-300 or Bruker AV 400, using residual signal of deuterated solvent as internal reference.

HPLC: The HPLC data provided in the examples described below were obtained as follows:

Method A: Waters Alliance 2695, column Waters XBridge C8 3.5 µm 4.6×50 mm, conditions: solvent A ($H_2O$ with 0.1% TFA), solvent B (ACN with 0.05% TFA), gradient 5% B to 100% B over 8 min, UV detection with PDA Water 996 (230-400 nm).

Method B: HPLC columns: Phenomenex Luna 5 µm C18 (2), 100×4.6 mm (plus guard cartridge) at a flow of 2 ml/min; 3.5 min gradient from 95:5 ([0.1% (V/V) formic acid in $H_2O$]:[0.1% (V/V) formic acid in MeCN]) to 5:95% ([0.1% (V/V) formic acid in $H_2O$]:[0.1% (V/V) formic acid in MeCN]) then held for 2 minutes at 5:95 ([0.1% (V/V) formic acid in $H_2O$]:[0.1% (V/V) formic acid in MeCN]).

Method C: HPLC columns: Waters Xterra MS 5 µm C18, 100×4.6 mm (plus guard cartridge) at a flow of 2 ml/min; 3.5 min gradient from 95:5 ([10 mM ammonium bicarbonate in $H_2O$]:MeCN) to 5:95 ([10 mM ammonium bicarbonate in $H_2O$]:MeCN) then held for 1.5 minutes at 5:95 ([10 mM ammonium bicarbonate in $H_2O$]:MeCN).

Method D: Method B using HPLC columns: Supelco, Ascentis® Express C18 or Hichrom Halo C18, 2.7 µm C18, 100×4.6 mm.

Method E: HPLC columns: Phenomenex Luna 5 µm C18 (2), 100×4.6 mm (plus guard cartridge) at a flow of 2 ml/min; 3.5 min gradient from 95:5 ([0.1% (V/V) formic acid in $H_2O$]:[0.1% (V/V) formic acid in MeCN]) to 5:95% ([0.1% (V/V) formic acid in $H_2O$]:[0.1% (V/V) formic acid in MeCN]) then held for 4 minutes at 5:95 ([0.1% (V/V) formic acid in $H_2O$]:[0.1% (V/V) formic acid in MeCN]).

Method F: HPLC columns: Hichrom, Kromasil Eternity, 2.5 µm C18, 150×4.6 mm at a flow of 1 ml/min; 6.0 min gradient from 95:5 ([10 mM ammonium bicarbonate in $H_2O$]:MeCN) to 5:95 ([10 mM ammonium bicarbonate in $H_2O$]:MeCN) then held for 4.6 minutes at 5:95 ([10 mM ammonium bicarbonate in $H_2O$]:MeCN).

Method G: Method C using HPLC columns: Phenomenex, Gemini NX, 3 µm C18, 100×4.6 mm.

All Methods: Typical Injections 2-7 µl, UV detection via HP or Waters DAD, Start Range (nm); 210, End Range (nm); 400, Range interval (nm); 4.0. Other wavelength traces are extracted from the DAD data.

Optional ELS detection using Polymer Labs ELS-1000. MS detection: MicromassZQ, single quadrapole LC-MS instrument.

Ionisation is either electrospray (ESI) or APCI dependent on compound types.

UPLC/MS: Waters Acquity, column Waters Acquity UPLC BEH C18 1.7 µm 2.1×50 mm, conditions: solvent A (10 mM ammonium acetate in water+5% ACN), solvent B (ACN), gradient 5% B to 100% B over 2 or 3 min, UV detection (PDA, 230-400 nm) and MS detection (SQ detector, positive and negative ESI modes, cone voltage 30V).

The microwave chemistry is performed on a single mode microwave reactor Emrys™ Optimiser from Personal Chemistry.

Method A: General Procedure for the Amidoxime Moiety Formation

To a solution of nitrile derivative (1 eq) in EtOH or THF (1-5 mL/mmol of nitrile derivative) was added a 50% aqueous solution of $NH_2OH$ (5 eq). The resulting mixture was stirred at a temperature comprised between RT and 80° C. for 1 to 72 hours. In case of precipitation of the expected compound, the precipitate was filtered off and washed with an adequate solvent, such as EtOH, iPrOH or water, and then dried under reduced pressure to give the expected amidoxime derivative. In all other cases, the reaction mixture was concentrated under reduced pressure, diluted with an adequate solvent, such as water or iPrOH, until precipitation. The precipitate was filtered off and washed with an adequate solvent, such as iPrOH or water, and then dried under reduced pressure to give the expected amidoxime derivative.

Method B: General Procedure for the Oxadiazole Ring Formation

DIEA (2.0 to 2.2 eq) and HATU (1.0 to 1.1 eq) were added into a solution of the carboxylic acid derivative (1 eq) in anhydrous DMF (4 mL/mmol of carboxylic acid derivative) cooled at 0° C. The resulting mixture was stirred at 0° C. for a period of 5 to 30 minutes. Then the amidoxime derivative (1.0 to 1.2 eq) was added neat or as a DMF solution. The resulting mixture was stirred at 0° C. or RT for a period of 30 minutes to 2 hours. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were removed under reduced pressure. The residue was taken up with toluene (6 mL/mmol of carboxylic acid derivative) and pyridine (2 mL/mmol of carboxylic acid derivative). The resulting mixture was heated at a temperature between 80° C. to reflux for a period of 12 to 72 hours. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were evaporated under reduced pressure. Purification by flash chromatography or precipitation gave the expected oxadiazole derivative.

Method C: General Procedure for the Oxadiazole Ring Formation Using Isobutyl Chloroformate NMM (3 to 5 eq) and isobutyl chloroformate (1.0 to 1.1 eq) were added into a solution of the carboxylic acid derivative (1.0 eq) in a suitable solvent, such as dioxane or isopropyl acetate and stirred at a temperature comprised between 0° C. and RT for 10 minutes to a few hours. Then the amidoxime derivative (1.0 to 1.2 eq) was added in one portion and the reaction mixture was stirred at a temperature comprised between 0° C. and RT for 20 min to a few hours, and then heated at a temperature comprised between 80° C. to reflux for a period of 12 to 24 hours. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were evaporated under reduced pressure. Purification by flash chromatography or precipitation gave the expected oxadiazole derivative.

Method D: General Procedure for the Tert-Butyl Ester Hydrolysis

A solution of the tert-butyl ester derivative (1.0 eq) was prepared in a 4N solution of HCl in dioxane (5-30 mL/mmol of tert-butyl ester) and stirred at RT for a period of 2 to 48 hours, in presence or not of a few drops of water. In case of a significant precipitation of the carboxylic acid, the precipitate was filtered off. In all other cases, the reaction mixture was concentrated under reduced pressure. Then the expected compound was crystallized or precipitated from an adequate solvent or a mixture of them, such as ACN, water, MTBE or EtOAc, and then dried under reduced pressure.

Method E: General Procedure for the Amidoxime Moiety Formation Using Hydroxylamine Hydrochloride To a solution of nitrile derivative (1 eq) in EtOH (5-20 mL/gram of nitrile derivative) was added NH₂OH.HCl (1.5-2.5 eq) and Et₃N (1.5-2.5 eq). The resulting mixture was stirred at RT for 12 to 72 hours. The precipitate was filtered off and washed with an adequate solvent, such as EtOH, iPrOH, water or MTBE, or a mixture of them, and then dried under reduced pressure to give the expected amidoxime derivative.

Intermediate A1: 2-(methoxymethyl)-2'-methylbiphenyl-4-carboxylic acid

Step 1) methyl 4-bromo-3-(bromomethyl)benzoate

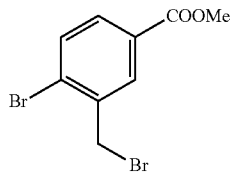 [SMILES: COC(=O)c1ccc(Br)c(CBr)c1]

NBS (46.6 g, 262 mmol) and AIBN (0.72 g, 4.4 mmol) were added in one portion into a solution of methyl 4-bromo-3-methylbenzoate (50.0 g, 218 mmol) in CHCl₃ (1 L) under N₂. The mixture was stirred at 70° C. for 2 days. The reaction mixture was cooled to RT and water (500 mL) was added. The organic layer was washed with a saturated solution of NaHCO₃ (50 mL), water (350 mL) and brine (500 mL). The organic layer was dried (MgSO₄) and concentrated under reduced pressure. The residue was washed with pentane (2×500 mL) affording the title compound as a yellow solid. HPLC (Method A), Rt 4.9 min (Purity: 98.2%). ¹H NMR (DMSO-d₆, 300 MHz) δ 8.24 (d, J=1.9 Hz, 1H), 7.85 (m, 2H), 4.87 (s, 2H), 3.91 (s, 3H).

Step 2) methyl 4-bromo-3-(methoxymethyl)benzoate

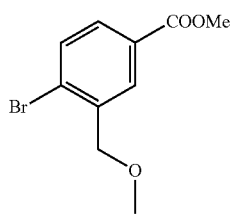

A solution of methyl 4-bromo-3-(bromomethyl)benzoate (37.5 g, 122 mmol) in MeOH (1.1 L) was refluxed for 4 days. After concentration, the mixture was partitioned between EtOAc (500 mL) and water (200 mL). The organic layer was washed with a 5% aqueous solution of NaHCO₃ (200 mL) and brine (200 mL), dried (MgSO₄) and concentrated affording the title compound as a beige solid (29.8 g, 94%). HPLC (Method A), Rt 4.4 min (purity: 93.0%). UPLC/MS, M−(ESI): 227.2. ¹H NMR (DMSO-d₆, 300 MHz) δ 8.06 (m, 1H), 7.83 (m, 2H), 4.54 (m, 2H), 3.90 (s, 3H), 3.45 (s, 3H).

Step 3) methyl 2-(methoxymethyl)-2'-methylbiphenyl-4-carboxylate

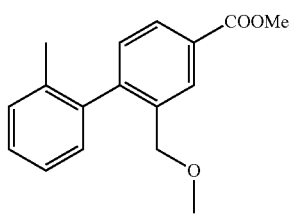 [SMILES: COCc1cc(C(=O)OC)ccc1-c1ccccc1C]

A mixture of methyl 4-bromo-3-(methoxymethyl)benzoate (40.0 g, 154 mmol), o-tolylboronic acid (23.1 g, 170 mmol), K₂CO₃ (106.7 g; 772 mmol) and tetrakis(triphenylphosphine)palladium (0) (1.8 g; 1.54 mmol) was prepared in toluene (200 mL) and water (200 mL) and degassed with N₂. The reaction mixture was heated at reflux for 1 hour, and then filtered through a pad of Celite and extracted with EtOAc (1 L). The organic layer was washed with a saturated aqueous solution of NaHCO₃ (250 mL), water (250 mL) and brine (250 mL), dried (MgSO₄) and concentrated affording the title compound as a yellow oil used without further purification (41.9 g, quantitative). HPLC (Method A), Rt 5.3 min (purity: 89.4%).

Step 4) 2-(methoxymethyl)-2'-methylbiphenyl-4-carboxylic acid

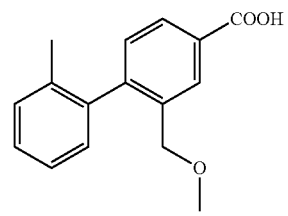 [SMILES: COCc1cc(C(=O)O)ccc1-c1ccccc1C]

A solution of methyl 2-(methoxymethyl)-2'-methylbiphenyl-4-carboxylate (40.0 g, 148 mmol) in EtOH (1.2 L) at RT was treated with a 5N aqueous solution of NaOH (90 mL, 450 mmol). The reaction mixture was stirred at 60° C. for 1 hour, and then concentrated under reduced pressure. The yellow solid was taken up with water (800 mL) and washed twice with EtOAc. The aqueous layer was acidified with a concentrated aqueous solution of HCl until pH=2 and was extracted with EtOAc (2×400 mL). The combined organic layers were washed with brine, dried (MgSO₄) and concentrated affording the title compound as a yellow solid (35.1 g, 92%). HPLC (Method A), Rt 4.5 min (Purity: 96.4%). UPLC/MS, M−(ESI): 255.2. ¹H NMR (DMSO-d₆, 300 MHz) δ 12.99 (br s, 1H), 8.09 (s, 1H), 7.91 (m, 1H), 7.33-7.22 (m, 4H), 7.09 (m, 1H), 4.11 (m, 2H), 3.18 (s, 3H), 1.99 (s, 3H).

Intermediate A2: 3-(methoxymethyl)-4-(2-methylpiperidin-1-yl)benzoic acid

Step 1) 5-bromo-2-(2-methylpiperidin-1-yl)benzaldehyde

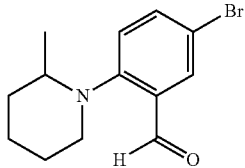 [SMILES: CC1CCCCN1c1ccc(Br)cc1C=O]

2-Methylpiperidine (15.4 mL, 130.0 mmol) and anhydrous sodium carbonate (13.8 g, 130.0 mmol) were added into a solution of 5-bromo-2-fluorobenzaldehyde (13.2 g, 65.0 mmol) in DMSO (160 mL) and water (40 mL). The resulting mixture was heated at 120° C. for 16 hours. The reaction mixture was diluted with water (1 L) and extracted with Et$_2$O (2×750 mL). The organic layers were washed with brine (500 mL, pH 5-6 adjusted with a 5N aqueous solution of HCl), combined and dried (MgSO$_4$). The solvents were removed under reduced pressure to give the title compound as a brown yellow oil (16.3 g, 89%) used without further purification in the next step. HPLC (Method A), Rt 2.20 min (purity: 93.7%). UPLC/MS, M+(ESI): 282.1, 284.1. $^1$H NMR (CDCl$_3$, 300 MHz) δ 10.40 (s, 1H), 7.93 (d, J=2.5 Hz, 1H), 7.62 (dd, J=8.6, 2.5 Hz, 1H), 7.12 (d, J=8.6 Hz, 1H), 3.17 (m, 1H), 3.06 (m, 1H), 2.81 (ddd, J=11.7, 7.6, 3.9 Hz, 1H), 1.89 (m, 1H), 1.83-1.65 (m, 3H), 1.58-1.42 (m, 2H), 0.91 (d, J=6.3 Hz, 3H).

Step 2) [5-bromo-2-(2-methylpiperidin-1-yl)phenyl]methanol

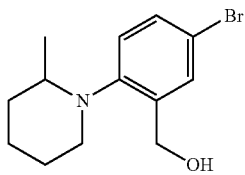 [SMILES: CC1CCCCN1c1ccc(Br)cc1CO]

Sodium borohydride (2.2 g, 57.8 mmol) was added portion-wise into a solution of 5-bromo-2-(2-methylpiperidin-1-yl)benzaldehyde (16.3 g, 57.8 mmol) in MeOH (300 mL) cooled at 5° C. After 30 min, the reaction mixture was diluted with a saturated aqueous solution of NH$_4$Cl (300 mL) and extracted with EtOAc (600 mL+300 mL). The organic layers were washed with a saturated aqueous solution of NH$_4$Cl (150 mL) and brine (300 mL). The organic layers were combined, dried (MgSO$_4$) and the solvents were removed under reduced pressure to give the title compound as a yellow oil (15.9 g, 97%) used without further purification in the next step. HPLC (Method A), Rt 2.1 min (Purity: 94.9%). UPLC/MS, M+(ESI): 284.1, 286.0. $^1$H NMR (CDCl$_3$, 300 MHz) δ 7.38 (dd, J=8.5, 2.4 Hz, 1H), 7.26 (d, J=2.4 Hz, 1H), 7.13 (d, J=8.5 Hz, 1H), 6.40 (brs, 1H), 4.86 (d, J=13.9 Hz, 1H), 4.67 (d, J=13.9 Hz, 1H), 3.06-2.88 (m, 2H), 2.61 (td, J=11.4, 3.2 Hz, 1H), 1.88-1.58 (m, 4H), 1.53-1.32 (m, 2H), 0.90 (d, J=6.2 Hz, 3H).

Step 3) 1-[4-bromo-2-(methoxymethyl)phenyl]-2-methylpiperidine

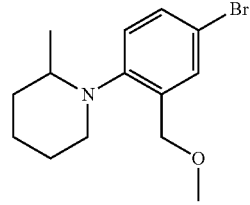 [SMILES: COCc1cc(Br)ccc1N1CCCCC1C]

Methanesulfonyl chloride (4.0 mL, 51.6 mmol) was added into a solution of [5-bromo-2-(2-methylpiperidin-1-yl)phenyl]methanol (13.43 g, 47.3 mmol) and DIEA (17.7 mL, 104 mmol) in anhydrous DCM (130 mL) cooled at 0° C. After 1 hour, the reaction mixture was diluted with MeOH (150 mL) and heated at 50° C. for 3 hours. The solvents were removed under reduced pressure to give a brown oil. The residue was taken up with Et$_2$O (450 mL), and then washed with water (150 mL, pH 8 adjusted with a 5N aqueous solution of NaOH), saturated aqueous solution of NH$_4$Cl (2×150 mL) and brine (150 mL). The aqueous layers were extracted with Et$_2$O (150 mL). The combined organic layers were dried (MgSO$_4$) and the solvent was removed under reduced pressure to give the title compound as a brown yellow oil (12.97 g, 92%) used without further purification in the next step. HPLC (Method A), Rt 2.9 min (Purity: 97.1%). UPLC/MS, M+(ESI): 298.1, 300.1. $^1$H NMR (CDCl$_3$, 300 MHz) δ 7.59 (d, J=2.5 Hz, 1H), 7.36 (dd, J=8.5, 2.5 Hz, 1H), 7.03 (d, J=8.5 Hz, 1H), 4.60 (d, J=12.8 Hz, 1H), 4.52 (d, J=12.8 Hz, 1H), 3.44 (s, 3H), 2.96-2.81 (m, 2H), 2.51 (m, 1H), 1.77 (m, 2H), 1.64 (m, 2H), 1.50-1.30 (m, 2H), 0.79 (d, J=6.1 Hz, 3H).

Step 4) 3-(methoxymethyl)-4-(2-methylpiperidin-1-yl)benzoic acid

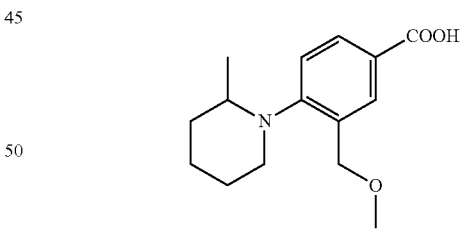

A 1.5M solution of tert-butyllithium in pentane (64 mL, 95 mmol) was added into anhydrous Et$_2$O (130 mL) cooled at −78° C. A solution of 1-[4-bromo-2-(methoxymethyl)phenyl]-2-methylpiperidine (13.0 g, 43.5 mmol) in anhydrous Et$_2$O (20 mL) was added slowly. After 40 minutes, the reaction mixture was poured on an excess of freshly crushed dry ice and stirred for 30 min. The mixture was diluted with Et$_2$O/EtOAc (1:1, 800 mL) and washed with water (200 mL, pH=4-5 adjusted with a 5N aqueous solution of HCl). The aqueous layer was extracted with EtOAc (400 mL). The organic layers were combined, dried (MgSO$_4$) and the solvents were removed under reduced pressure to give a yellow oil, which was triturated in iPr$_2$O (~20 mL) and pentane (~20 mL). The precipitate was filtered off, washed with pentane and dried under reduced pressure to give the title compound as a beige powder. HPLC (Method A), Rt: 1.6 min (purity: 93.5%). UPLC/MS, M+(ESI): 264.2, M−(ESI): 262.2. $^1$H NMR (CDCl$_3$, 300 MHz) δ 8.22 (d, J=2.1 Hz, 1H), 8.00 (dd, J=8.3, 2.1 Hz, 1H), 7.17 (d, J=8.3 Hz, 1H), 4.60 (d, J=12.3 Hz, 1H), 4.55 (d, J=12.3 Hz, 1H), 3.46 (s, 3H), 3.17 (m, 1H), 3.02 (m, 1H), 2.63 (m, 1H), 1.88-1.65 (m, 4H), 1.55-1.40 (m, 2H), 0.88 (d, J=6.2 Hz, 3H).

Intermediate A3: 2'-ethyl-2-(methoxymethyl)-1,1'-biphenyl-4-carboxylic acid

Step 1) methyl 2'-ethyl-2-(methoxymethyl)-1,1'-biphenyl-4-carboxylate

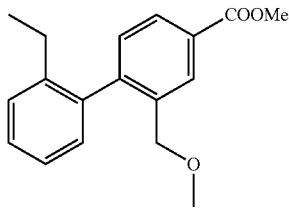 [SMILES: CCc1ccccc1-c1ccc(C(=O)OC)cc1COC]

To a solution of methyl 4-bromo-3-(methoxymethyl)benzoate (12.0 g, 46.3 mmol, Intermediate A1 step 2) in toluene (150 mL) and water (35 mL) was added 2-ethyl benzene boronic acid (9.0 g, 60.1 mmol) followed by potassium carbonate (19.0 g, 139 mmol) and Pd(PPh$_3$)$_4$ (2.7 g, 2.3 mmol). The resulting mixture was degassed with N$_2$ for 10 min and heated at 100° C. for 12 hours. The reaction mixture was diluted with EtOAc. The organic layer was washed with a saturated aqueous solution of NaHCO$_3$, water (2×) and brine, and then dried (Na$_2$SO$_4$). The solvents were removed under reduced pressure. The residue was purified by chromatography (silica, pet ether/EtOAc) to afford the title compound as a pale yellow oil (12.0 g, 83%). $^1$H NMR (CDCl$_3$, 400 MHz) δ 8.25 (1H, s), 8.00 (1H, d), 7.35 (2H, m), 7.25 (2H, m), 7.08 (1H, d), 4.17 (2H, m), 3.94 (3H, s), 3.29 (3H, s), 2.43-2.28 (2H, m), 1.03 (3H, t).

Step 2) 2'-ethyl-2-(methoxymethyl)-1,1'-biphenyl-4-carboxylic acid

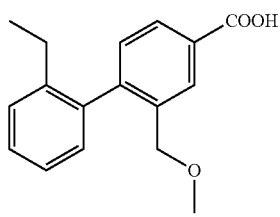 [SMILES: CCc1ccccc1-c1ccc(C(=O)O)cc1COC]

Lithium hydroxide monohydrate (5.31 g, 127 mmol) was added portion-wise into a solution of methyl 2'-ethyl-2-(methoxymethyl)-1,1'-biphenyl-4-carboxylate (12.0 g, 42.2 mmol) in THF (150 mL) and water (30 mL). The resulting mixture was stirred at RT for 12 hours. The reaction mixture was concentrated under reduced pressure. The resulting aqueous layer was acidified with a concentrated aqueous solution of HCl and extracted with EtOAc. The organic layers were washed with water and brine, combined and dried (Na$_2$SO$_4$). The solvents were removed under reduced pressure to afford the title compound as a white solid (9.0 g, 80%). HPLC (Method A), Rt 4.2 min (purity: 96.7%). UPLC/MS, M−(ESI): 269.2. $^1$H NMR (DMSO-d$_6$, 400 MHz) δ 12.9 (1H, bs), 8.08 (1H, s), 7.89 (1H, d), 7.35 (2H, m), 7.23 (2H, m), 7.04 (1H, d), 4.09 (2H, m), 3.17 (3H, s), 2.34 (1H, m), 2.22 (1H, m), 0.94 (3H, t).

Intermediate A4: 2'-methyl-2-(trifluoromethyl)biphenyl-4-carboxylic acid

Step 1) methyl 4-bromo-3-(trifluoromethyl)benzoate

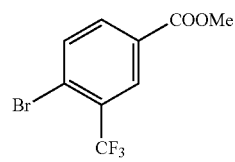 [SMILES: COC(=O)c1ccc(Br)c(C(F)(F)F)c1]

Thionyl chloride (16.2 mL, 223 mmol) was added dropwise over 15 min into a suspension of 4-bromo-3-(trifluoromethyl)benzoic acid (Acceledev 000625, 15.0 g, 55.8 mmol) in MeOH (300 mL). The resulting mixture was stirred at RT for 12 hours. The reaction mixture was concentrated under reduced pressure. The residue was taken up with EtOAc (500 mL) and washed with a saturated aqueous solution of NaHCO$_3$ (200 mL), water (200 mL) and brine (200 mL). The organic layer was dried (MgSO$_4$) and the solvent was removed under reduced pressure affording the title compound as an orange solid (14.8 g, 94%). HPLC (Method A), Rt 4.7 min (Purity: 99.0%). $^1$H NMR (DMSO-d$_6$, 300 MHz) δ 8.26 (m, 1H), 8.14 (m, 2H), 3.93 (s, 3H).

Step 2) methyl 2'-methyl-2-(trifluoromethyl)biphenyl-4-carboxylate

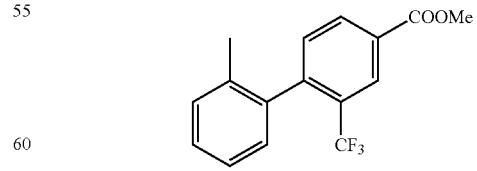

A degassed mixture of methyl 4-bromo-3-(trifluoromethyl)benzoate (6.00 g, 21.2 mmol), o-tolylboronic acid (3.17 g, 23.3 mmol), potassium carbonate (14.65 g, 106 mmol), Pd(PPh$_3$)$_4$ (2.45 g, 2.12 mmol) was prepared in toluene (30 mL) and water (30 mL), and then heated at reflux for 3 hours.

The reaction mixture was filtered through a pad of Celite and diluted with EtOAc (200 mL). The organic layer was washed with a saturated aqueous solution of NaHCO₃ (50 mL), water (50 mL) and brine (50 mL), and then dried (MgSO₄). The solvents were removed under reduced pressure affording the title compound as a brown oil (6.4 g, quantitative) used without further purification in the next step. HPLC (Method A), Rt 5.3 min (Purity: 60.0%).

Step 3) 2'-methyl-2-(trifluoromethyl)biphenyl-4-carboxylic acid

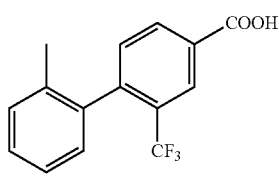 [SMILES: Cc1ccccc1-c1ccc(C(=O)O)cc1C(F)(F)F]

A 5N aqueous solution of NaOH (10.2 mL, 51.0 mmol) was added into a solution of methyl 2'-methyl-2-(trifluoromethyl)biphenyl-4-carboxylate (5.00 g, 17.0 mmol) in EtOH (150 mL). The resulting mixture was stirred at 60° C. for 1.5 hours. The reaction mixture was concentrated under reduced pressure to give a brown solid. The residue was taken up with water (300 mL) and washed twice with EtOAc. The aqueous layer was acidified with a concentrated aqueous solution of HCl until pH=2, and then concentrated until precipitation (half of the volume). The precipitate was filtered off affording the title compound as a beige solid (3.33 g, 70%). ¹H NMR (DMSO-d₆, 300 MHz) δ 13.55 (br s, 1H), 8.31 (s, 1H), 8.25 (d, J=7.9 Hz, 1H), 7.50 (d, J=7.9 Hz, 1H), 7.37-7.12 (m, 4H), 1.99 (s, 3H). HPLC (Method A), Rt 4.6 min (Purity: 98.7%). UPLC/MS, M−(ESI): 279.2.

Intermediate A5: 4-(2-methylpiperidin-1-yl)-3-(trifluoromethyl)benzoic acid

Step 1) 4-(2-methylpiperidin-1-yl)-3-(trifluoromethyl)benzonitrile

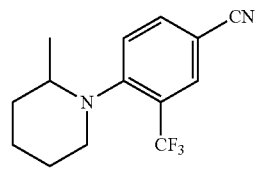 [SMILES: CC1CCCCN1c1ccc(C#N)cc1C(F)(F)F]

A mixture of 4-fluoro-3-(trifluoromethyl)benzonitrile (50.0 g, 0.26 mol, Combi-Blocks AN-1049) and 2-methylpiperidine (156 mL, 1.32 mol) in DMSO (500 mL) was heated at 100° C. under nitrogen for 12 hours. The reaction mixture was diluted with Et₂O and washed with water, a saturated aqueous solution of NaHCO₃ and a saturated aqueous solution of NH₄Cl. The organic layer was dried (MgSO₄) and the solvent was removed under reduced pressure to give the title compound as a beige powder. UPLC/MS, M−(ESI): 269.2. ¹H NMR (DMSO-d₆, 300 MHz) δ 8.19 (d, J=2.0 Hz, 1H), 8.12 (dd, J=8.4, 2.0 Hz, 1H), 7.75 (d, J=8.2 Hz, 1H), 3.13 (m, 1H), 2.88 (m, 1H), 2.56 (m, 1H), 1.77-1.25 (m, 6H), 0.72 (d, J=6.0 Hz, 3H).

Step 2) 4-(2-methylpiperidin-1-yl)-3-(trifluoromethyl)benzoic acid

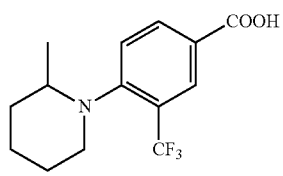 [SMILES: CC1CCCCN1c1ccc(C(=O)O)cc1C(F)(F)F]

A 5N aqueous solution of sodium hydroxide (336 mL, 1.68 mol) was added into a solution of 4-(2-methylpiperidin-1-yl)-3-(trifluoromethyl)benzonitrile (28.0 g, 104.4 mmol) in MeOH (280 mL) and the resulting mixture was heated at reflux for 7 hours. The reaction mixture was cooled to 0° C. and acidified to pH 2 with a 5N aqueous solution of HCl. The precipitate was filtered, washed with water and dried under vacuum to give the title compound as a white powder (27.5 g, 91%). HPLC (Method A), Rt 5.4 min (purity: 99.8%). UPLC/MS, M+(ESI): 288.2, M−(ESI): 286.2. ¹H NMR (DMSO-d₆, 300 MHz) δ 13.30 (bs, 1H), 8.17 (m, 2H), 7.68 (d, J=8.2 Hz, 1H), 3.08 (m, 1H), 3.08 (m, 1H), 2.88 (m, 1H), 2.57 (m, 1H), 1.77-1.25 (m, 6H), 0.72 (d, J=6.0 Hz, 3H).

Intermediate A6: 2-(methoxymethyl)-2'-methylbiphenyl-4-carbonyl chloride

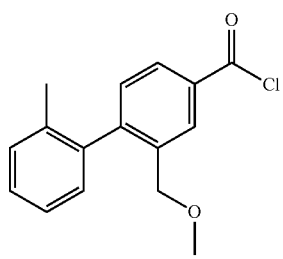 [SMILES: COCc1cc(C(=O)Cl)ccc1-c1ccccc1C]

Oxalyl chloride (2.0 mL, 23.6 mmol) and anhydrous DMF (0.060 mL, 0.78 mmol) were added into a solution of 2-(methoxymethyl)-2'-methylbiphenyl-4-carboxylic acid (2.0 g, 7.8 mmol) in anhydrous DCM (40 mL). After 15 hours at RT, the reaction mixture was concentrated under reduced pressure to give the title compound as a yellow oil (2.1 g, quantitative), which was used without further purification.

Intermediate A7:
4-(2-ethylpiperidin-1-yl)-3-(methoxymethyl)benzoic acid, hydrochloride salt

Step 1) 5-bromo-2-(2-ethylpiperidin-1-yl)benzaldehyde

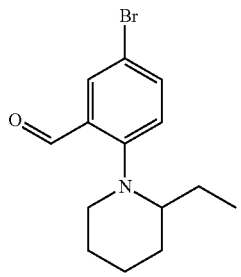 [SMILES: CCC1CCCCN1c1ccc(Br)cc1C=O]

To a solution of 5-bromo-2-fluorobenzaldehyde (20 g, 99 mmol) in DMSO (230 mL) and water (70 mL) were added 2-ethylpiperidine (14.4 mL, 108 mmol) and sodium carbonate (20.9 g, 197 mmol). The resulting mixture was heated at 110° C. for 30 hours. The reaction mixture was cooled at RT, diluted with water (1000 mL) and extracted with MTBE (2×500 mL). The organic layers were combined, dried ($Na_2SO_4$) and concentrated under reduced pressure. After purification by flash chromatography (silica, pet ether), the title compound was obtained as a yellow oil. $^1$H NMR (DMSO-$d_6$, 400 MHz) δ 10.15 (1H, s), 7.72 (2H, d), 7.24 (1H, m), 3.11 (2H, m), 2.85 (1H, m), 1.84 (1H, m), 1.34-1.67 (7H, m), 0.64 (3H, t).

Step 2) [5-bromo-2-(2-ethylpiperidin-1-yl)phenyl]methanol

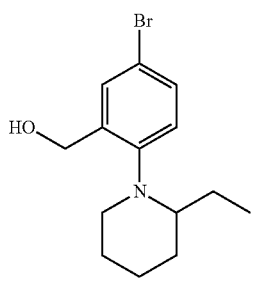 [SMILES: CCC1CCCCN1c1ccc(Br)cc1CO]

To a solution of 5-bromo-2-(2-ethylpiperidin-1-yl)benzaldehyde (10 g, 48.4 mmol) in methanol (100 mL) under nitrogen was added sodium borohydride (1.28 g, 48.4 mmol) at 0° C. in portions. The reaction mixture was stirred at RT for 1 hour, then evaporated to remove methanol. The resulting crude was taken up with water (100 mL) and extracted with EtOAc. The organic layer was washed with water, then dried ($Na_2SO_4$) and concentrated under reduced pressure to afford the title compound as a yellow oil (8.8 g, 88%). $^1$H NMR (DMSO-$d_6$, 400 MHz) δ 7.55 (1H, s), 7.34-7.54 (1H, m), 7.08 (1H, d), 5.19 (1H, t), 4.62 (1H, d), 4.46 (1H, d), 2.77-2.84 (2H, m), 2.45 (1H, m), 1.74 (2H, t), 1.55 (2H, t), 1.33 (2H, m), 1.17 (2H, m), 0.62 (3H, t).

Step 3) 1-[4-bromo-2-(methoxymethyl)phenyl]-2-ethylpiperidine

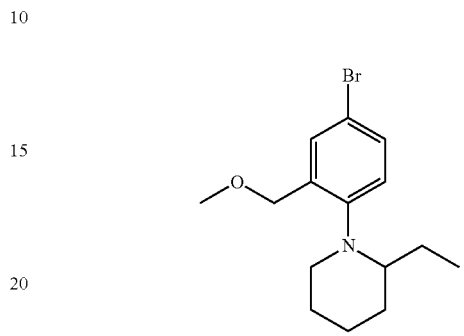

To a solution of sodium hydride (2.3 g, 93 mmol) in anhydrous DMF (130 mL) was added a solution of [5-bromo-2-(2-ethylpiperidin-1-yl)phenyl]methanol (15 g, 48.3 mmol) in DMF (20 mL) drop wise at 0° C. After 30 minutes, methyl iodide was added drop wise at 0° C. The reaction mixture was quenched with a saturated aqueous solution of $NH_4Cl$ (30 mL), then diluted with water (100 mL) and extracted with EtOAc. The organic layer was dried ($Na_2SO_4$) and concentrated under reduced pressure to afford the title compound as a yellow oil (15.2 g, 97%). $^1$H NMR (CDCl$_3$, 400 MHz) δ 7.59 (1H, s), 7.35 (1H, d), 7.02 (1H, d), 4.49-4.59 (2H, m), 3.43 (3H, s), 2.88 (1H, d), 2.75 (1H, bs), 2.51 (1H, bs), 1.79-1.86 (2H, m), 1.62 (3H, d), 1.40 (2H, m), 0.88 (2H, m), 0.70 (3H, t).

Step 4) 4-(2-ethylpiperidin-1-yl)-3-(methoxymethyl)benzoic acid, hydrochloride salt

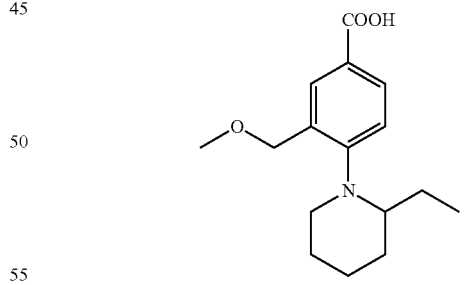

To a solution of 1-[4-bromo-2-(methoxymethyl)phenyl]-2-ethylpiperidine (1.42 g, 4.55 mmol) in anhydrous THF was added n-butyl lithium (2.4 mL, 6.82 mmol) in drops at −78° C. After 1 hour at −78° C., the reaction mixture was poured onto crushed dry-ice (100 g). Once the excess carbon dioxide was escaped, the reaction mixture was acidified with 2N HCl. The precipitate was filtered off and dried to afford the title compound as a solid (1.0 g, 70%). HPLC (Method A), Rt: 2.5 min (purity: 97.7%). LC/MS, M+(ESI): 278.0. $^1$H NMR (CD$_3$OD, 400 MHz) δ 8.20 (1H, d), 8.07 (1H, s), 7.92 (1H, d), 5.05 (2H, m), 3.89 (1H, bs), 3.69 (4H, m), 2.39 (1H, d), 2.02-2.14 (2H, m), 1.72-1.95 (3H, m), 1.46 (2H, m), 0.88 (3H, t).

Intermediate A8: 2'-Chloro-2-(methoxymethyl)biphenyl-4-carboxylic acid

Step 1) methyl 2'-chloro-2-(methoxymethyl)biphenyl-4-carboxylate

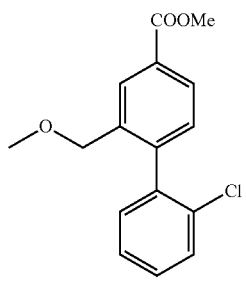 [SMILES: COCc1cc(C(=O)OC)ccc1-c1ccccc1Cl]

To a solution of methyl 4-bromo-3-(methoxymethyl)benzoate (15 g, 57.9 mmol) in toluene (120 mL) and water (30 mL) under nitrogen was added 2-chlorophenylboronic acid (19.9 g, 127.4 mmol), followed by potassium carbonate (16 g, 115.8 mmol) and Pd(PPh$_3$)$_4$ (3.34 g, 2.8 mmol). After 3 hours at 100° C., the reaction mixture was diluted with EtOAc (200 mL) and washed with a saturated aqueous solution of NaHCO$_3$ (100 mL), water (2×100 mL) and brine. The organic layer was dried (Na$_2$SO$_4$) and concentrated under reduced pressure. The residue was purified by chromatography (silica gel, pet ether/EtOAc) to afford of the title compound as a pale yellow oil. LC/MS, M+(ESI): 291.0. $^1$H NMR (CDCl$_3$, 400 MHz) δ 8.21 (1H, s), 8.01 (1H, d), 7.48 (1H, m), 7.34 (2H, m), 7.26 (2H, m), 4.33 (1H, dd), 4.20 (1H, dd), 3.94 (3H, s), 3.27 (3H, s).

Step 2) 2'-Chloro-2-(methoxymethyl)biphenyl-4-carboxylic acid

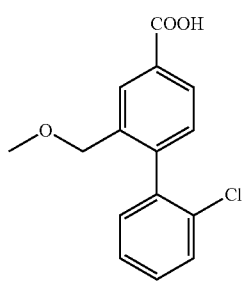 [SMILES: COCc1cc(C(=O)O)ccc1-c1ccccc1Cl]

To a solution of methyl 2'-chloro-2-(methoxymethyl)biphenyl-4-carboxylate (11 g, 37.8 mmol) in a mixture of THF (50 ml), MeOH (50 ml) and water (25 ml) was added lithium hydroxide monohydrate (4.76 g, 113.5 mmol) in portions. After 12 hours at RT, the reaction mixture was concentrated and the aqueous residual layer was acidified with a concentrated aqueous solution of HCl, and then extracted with EtOAc (2×100 mL). The organic layers were washed with water and brine, combined, dried (Na$_2$SO$_4$) and concentrated under reduced pressure to afford of the title compound as a white solid (7.5 g, 72%). LC/MS, M−(ESI): 275.0. $^1$H NMR (DMSO-d$_6$, 400 MHz) δ 13.0 (1H, brs), 8.08 (1H, s), 7.92 (1H, d), 7.58 (1H, d), 7.44 (2H, m), 7.29 (2H, m), 4.21 (1H, dd), 4.13 (1H, dd), 3.16 (3H, s).

Intermediate A9: 3-(methoxymethyl)-4-(2-methylpyrrolidin-1-yl)benzoic acid

Step 1) 5-bromo-2-(2-methylpyrrolidin-1-yl)benzaldehyde

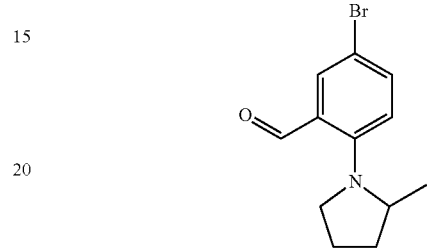

To a solution of 5-bromo-2-fluorobenzaldehyde (15 g, 73.8 mmol) in DMSO (150 mL) and water (40 mL) were added 2-methylpyrrolidine (9.8 mL, 96 mmol) and sodium carbonate (15.7 g, 148 mmol). The resulting mixture was heated at 110° C. for 8 hours. The reaction mixture was cooled at RT, diluted with water (1000 mL) and extracted with MTBE (2×100 mL). The organic layers were combined, dried (Na$_2$SO$_4$) and concentrated under reduced pressure. After purification by flash chromatography (silica, pet ether/EtOAc), the title compound was obtained as a yellow oil (17 g, 85%). $^1$H NMR (DMSO-d$_6$, 400 MHz) δ 9.94 (1H, s), 7.75 (1H, s), 7.51 (1H, d), 6.93 (1H, d), 3.92 (1H, m), 3.68 (1H, m), 2.97 (1H, t), 2.49-2.18 (1H, m), 1.88 (1H, m), 1.57-1.68 (2H, m), 1.10 (3H, d).

Step 2) [5-bromo-2-(2-methylpyrrolidin-1-yl)phenyl]methanol

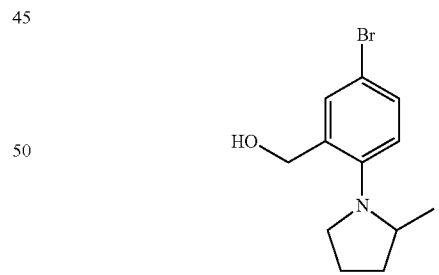

To a solution of 5-bromo-2-(2-methylpyrrolidin-1-yl)benzaldehyde (17 g, 63.4 mmol) in methanol (150 mL) under nitrogen was added sodium borohydride (2.41 g, 63.4 mmol) at 0° C. in portions. The reaction mixture was stirred at RT for 1 hour, then evaporated to remove methanol. The resulting crude was taken up with water (250 mL) and extracted with EtOAc (150 mL). The organic layer was washed with water, then dried (Na$_2$SO$_4$) and concentrated under reduced pressure to afford the title compound as a yellow oil (16 g, 93%). $^1$H NMR (DMSO-d$_6$, 400 MHz) δ 7.53 (1H, d), 7.27 (1H, d), 6.87 (1H, d), 5.22 (1H, t), 4.42 (2H, m), 3.56 (1H, m), 3.36

(1H, m), 2.70 (1H, m), 2.49 (1H, m) 2.09 (1H, m), 1.83 (1H, m), 1.73 (1H, m), 1.47 (1H, m), 0.90 (3H, d).

Step 3) 1-[4-bromo-2-(methoxymethyl)phenyl]-2-methylpyrrolidine

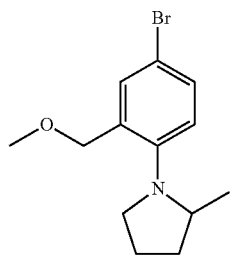

To a solution of sodium hydride (2.84 g, 119 mmol) in anhydrous DMF (80 mL) was added a solution of [5-Bromo-2-(2-methylpyrrolidin-1-yl)phenyl]methanol (16 g, 59.2 mmol) in DMF (50 mL) drop wise at 0° C. After 30 minutes, methyl iodide (7.3 mL, 119 mmol) was added drop wise at 0° C. The reaction mixture was quenched with a saturated aqueous solution of $NH_4Cl$ (20 mL), then diluted with water (200 mL) and extracted with EtOAc (150 ml). The organic layer was dried ($Na_2SO_4$) and concentrated under reduced pressure to afford the title compound as a yellow oil (16.5 g, 98%). $^1$H NMR ($CDCl_3$, 400 MHz) δ 7.55 (1H, s), 7.29 (1H, m), 6.86 (1H, d), 4.45 (2H, s), 3.55 (1H, m), 3.41 (1H, m), 2.82 (1H, m), 2.12-2.51 (1H, m), 1.91 (1H, m) 1.81 (1H, m), 1.58 (1H, m), 0.99 (3H, d).

Step 4) 3-(methoxymethyl)-4-(2-methylpyrrolidin-1-yl)benzoic acid

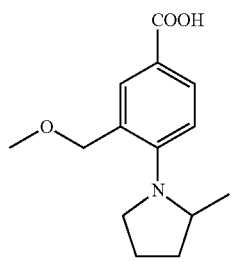

To a solution of 1-[4-Bromo-2-(methoxymethyl)phenyl]-2-methylpyrrolidine (16.5 g, 58 mmol) in anhydrous THF (160 mL) was added n-butyl lithium in drops at −78° C. After 3 hours at −78° C., the reaction mixture was poured onto crushed dry-ice (100 g). Once the excess carbon dioxide was escaped, the reaction mixture was evaporated, and then acidified with 1.5 N HCl. The precipitate was filtered off and washed with pet ether to afford title compound as a solid. LC/MS, M+(ESI): 249.9. $^1$H NMR (DMSO-$d_6$, 400 MHz) δ 12.4 (1H, brs), 7.84 (1H, s), 7.70 (1H, d), 6.85 (1H, d), 4.32-4.42 (2H, m), 3.59-3.87 (1H, m), 3.56 (1H, m), 3.29 (3H, s), 3.13 (1H, m), 2.14 (1H, m), 1.89 (1H, m), 1.74 (1H, m), 1.55 (1H, m), 0.99 (3H, d).

Intermediate A10: 2'-fluoro-2-(methoxymethyl)biphenyl-4-carboxylic acid

Step 3) methyl 2'-fluoro-2-(methoxymethyl)biphenyl-4-carboxylate

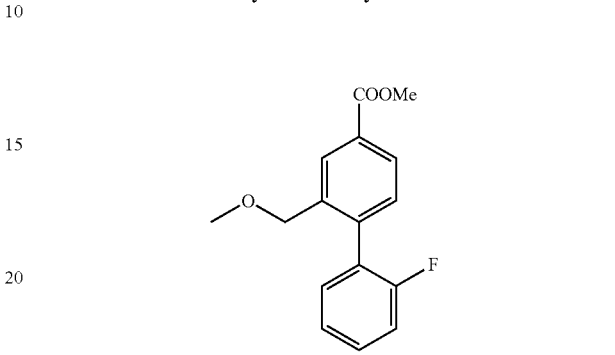

To a solution of methyl 4-bromo-3-(methoxymethyl)benzoate (10 g, 38.6 mmol) in toluene (80 mL) and water (20 mL) under nitrogen was added 2-fluorophenylboronic acid (7.0 g, 50.2 mmol), followed by potassium carbonate (16 g, 115.8 mmol) and Pd(PPh$_3$)$_4$ (2.23 g, 1.9 mmol). After 3 hours at 100° C., the reaction mixture was diluted with EtOAc (200 mL) and washed with a saturated aqueous solution of NaHCO$_3$ (100 mL), water (2×100 mL) and brine. The organic layer was dried (Na$_2$SO$_4$) and concentrated under reduced pressure. The residue was purified by chromatography (silica, pet ether/EtOAc) to afford of the title compound as a pale yellow oil. $^1$H NMR (CDCl$_3$, 400 MHz) δ 8.26 (1H, s), 8.04 (1H, d), 7.42 (1H, m), 7.35 (1H, d), 7.14-7.27 (3H, m), 4.34 (2H, s), 3.95 (3H, s), 3.30 (3H, s).

Step 4) 2'-fluoro-2-(methoxymethyl)biphenyl-4-carboxylic acid

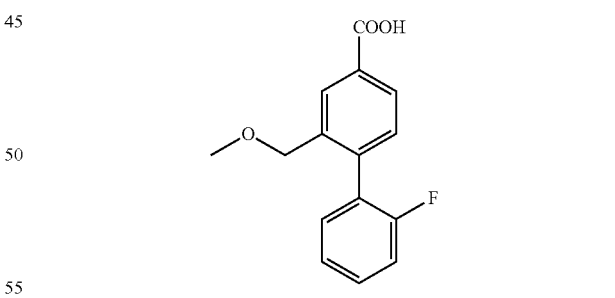

To a solution of methyl 2'-fluoro-2-(methoxymethyl)biphenyl-4-carboxylate (12 g, 43.7 mmol) in a mixture of THF (50 ml), MeOH (50 ml) and water (25 ml) was added lithium hydroxide monohydrate (5.50 g, 131.2 mmol) in portions. After 12 hours at RT, the reaction mixture was concentrated and the aqueous residual layer was acidified with a concentrated aqueous solution of HCl, and then extracted with EtOAc. The organic layers were washed with water and brine, combined, dried (Na$_2$SO$_4$) and concentrated under reduced pressure to afford of the title compound as a white solid (10.5 g, 92%). LC/MS, M−(ESI): 259.0. $^1$H NMR (DMSO-$d_6$, 400

MHz) δ 13.07 (1H, brs), 8.10 (1H, s), 7.92 (1H, d), 7.48 (1H, m), 7.27-7.37 (4H, m), 4.26 (2H, s), 3.18 (3H, s).

Intermediate A11: 2'-fluoro-2-(trifluoromethyl)biphenyl-4-carboxylic acid

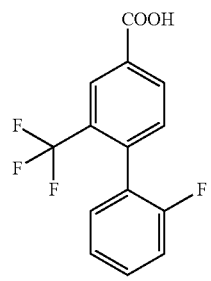 [SMILES: O=C(O)c1ccc(-c2ccccc2F)c(C(F)(F)F)c1]

A mixture of 4-bromo-3-(trifluoromethyl)benzoic acid (APAC Pharmaceutical 680578, 15.0 g, 55.7 mmol), 2-fluorophenylboronic acid (9.4 g, 66.9 mmol), cesium fluoride (25.4 g, 167 mmol), 2-dicyclohexylphosphino-2',6'-dimethoxybiphenyl (5.7 g, 13.9 mmol) and palladium(II) acetate (1.25 g, 5.6 mmol) was prepared in dioxane (150 mL) and water (150 mL) under $N_2$ atmosphere. The reaction mixture was purged with vacuum for 5 minutes, and then the reaction mixture was degassed with $N_2$ at RT for 10 min. The reaction mixture was heated at 110° C. for 3 hours. The reaction mixture was cooled to RT and was filtered through a pad of Celite. The filtrate was concentrated under vacuum to afford a yellow solid. After purification by flash chromatography (silica, DCM containing 1% of AcOH), the title compound was obtained as a pale yellow powder. HPLC (Method A), Rt: 4.3 min (purity: 99.9%). UPLC/MS, M−(ESI): 283.0. $^1$H NMR (DMSO-$d_6$, 300 MHz) δ 13.60 (s, 1H), 8.31 (d, J=1.4 Hz, 1H), 8.25 (dd, J=8.0, 1.4 Hz, 1H), 7.60 (d, J=8.0 Hz, 1H), 7.52 (m, 1H), 7.38-7.26 (m, 3H).

Intermediate A12: 2-ethoxy-2'-methyl-1,1'-biphenyl-4-carboxylic acid

Step 1) methyl 2-hydroxy-2'-methyl-1,1'-biphenyl-4-carboxylate

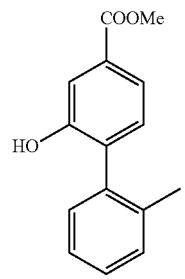 [SMILES: COC(=O)c1ccc(-c2ccccc2C)c(O)c1]

A mixture of methyl 4-bromo-3-hydroxybenzoate (Combi-Blocks CA-4189, 25 g, 108 mmol), o-tolylboronic acid (22 g, 162 mmol), anhydrous potassium carbonate (44 g, 324 mmol) and Pd(PPh3)4 (6.25 g, 5.4 mmol) was prepared in a mixture of toluene (500 mL) and water (100 mL), and then degassed with $N_2$. The reaction mixture was heated at 110° C. for 12 hours. The reaction mixture was cooled at RT, filtered through a Celite pad and washed with a 10% aqueous solution of $NaHCO_3$, water and brine. The organic layer was dried ($Na_2SO_4$) and concentrated under vacuum. The residue was purified by chromatography (silica, pet ether/EtOAc) to afford of the title compound as a pale yellow solid (20 g, 77%). $^1$H NMR (DMSO-$d_6$, 400 MHz) δ 9.85 (1H, s), 7.52 (1H, s), 7.45 (1H, d), 7.20-7.25, (3H, m), 7.15 (1H, d), 7.10 (1H, d), 3.84 (3H, s), 2.09 (3H, s).

Step 2) methyl 2-ethoxy-2'-methyl-1,1'-biphenyl-4-carboxylate

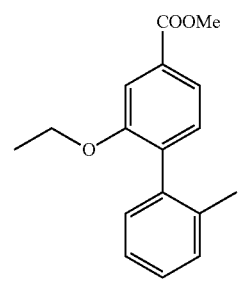 [SMILES: CCOc1cc(C(=O)OC)ccc1-c1ccccc1C]

To a stirred solution of methyl 2-hydroxy-2'-methyl-1,1'-biphenyl-4-carboxylate (10 g, 41.2 mmol) in anhydrous ACN (100 mL) was added anhydrous potassium carbonate (17.1 g, 123.6 mmol) followed by ethyl bromide (15.4 mL, 206 mmol). The reaction mixture was heated at 50° C. for 48 hours, and then cooled to RT and filtered. The filtrate was concentrated under vacuum to afford of the title compound as brown liquid (11 g, 98%). $^1$H NMR (DMSO-$d_6$, 400 MHz) δ 7.70 (1H, d), 7.62 (1H, s), 7.16-7.29 (5H, m), 4.09 (2H, q), 3.95 (3H, s), 2.15 (3H, s), 1.30 (3H, t).

Step 3) 2-ethoxy-2'-methyl-1,1'-biphenyl-4-carboxylic acid

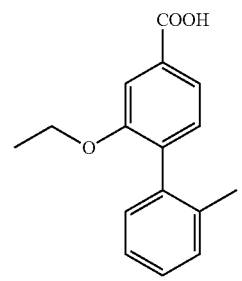 [SMILES: CCOc1cc(C(=O)O)ccc1-c1ccccc1C]

To a stirred solution of methyl 2-ethoxy-2'-methyl-1,1'-biphenyl-4-carboxylate (11 g, 40.6 mmol) in a mixture of THF (100 mL) and water (10 mL) was added lithium hydroxide (6.82 g, 162.7 mmol) in portions. After 24 hours at RT, the reaction mixture was evaporated and the residue was taken up with water. The aqueous layer was acidified with a concentrated aqueous solution of HCl and extracted with EtOAc. The organic layer was washed with brine, dried ($Na_2SO_4$) and concentrated under vacuum to afford of the title compound as pale yellow solid (9.7 g, 93%). LC/MS, M−(ESI): 255.0. $^1$H NMR (DMSO-d₆, 400 MHz) δ 13.02 (1H, bs), 7.57 (2H, m), 7.18-7.25 (4H, m), 7.09 (1H, d), 4.05 (2H, q), 2.05 (3H, s), 1.18 (3H, t).

Intermediate A13: 2-methyl-2'-(trifluoromethyl)biphenyl-4-carboxylic acid

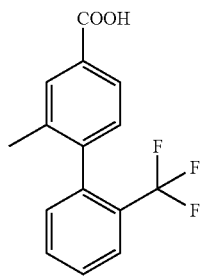 [SMILES: Cc1cc(C(=O)O)ccc1-c1ccccc1C(F)(F)F]

A mixture of methyl 4-bromo-3-methylbenzoate (20.0 g, 87.3 mmol), 2-(trifluoromethyl)benzeneboronic acid (24.9 g, 131.0 mmol), potassium carbonate (24.1 g, 174.6 mmol) and bis(tricyclohexylphosphine)palladium (II) dichloride (64.5 mg, 0.09 mmol) was prepared in dioxane (200 mL) and water (50 mL) under N₂ atmosphere. The mixture was heated at 100° C. for 3 hours. A 5N aqueous solution of NaOH (100 mL) was added and the reaction mixture was stirred at 100° C. for one additional hour. The reaction mixture was cooled at RT and the aqueous layer was removed. The organic layer was filtered through a Celite pad, concentrated until 75 ml under reduced pressure, diluted with water (125 ml) and washed with MTBE (2×200 mL). The aqueous layer was acidified with a 5N aqueous solution of HCl (25 ml, pH~1) and extracted with MTBE (2×100 ml). The organic layers were combined, dried (Na₂SO₄) and filtered through a Celite pad. The solution was concentrated until 100 mL, then heptane was added (200 mL). The mixture was concentrated until 100 mL. The precipitate was filtered off and rinsed twice with heptane, then dried under reduced pressure to give the title compound as a white powder (22.5 g, 92%). HPLC (Method A), Rt: 4.4 min (purity: 100%). UPLC/MS, M−(ESI): 279.0. ¹H NMR (DMSO-d₆, 300 MHz) δ 13.00 (s, 1H), 7.87 (m, 2H), 7.80 (dd, J=7.9, 1.6 Hz, 1H), 7.75 (m, 1H), 7.64 (m, 1H), 7.34 (d, J=7.6 Hz, 1H), 7.23 (d, J=7.9 Hz, 1H), 2.02 (s, 3H).

Intermediate A14: 2-ethoxy-2'-(trifluoromethyl)biphenyl-4-carboxylic acid

Step 1) methyl 2-hydroxy-2'-(trifluoromethyl)biphenyl-4-carboxylate

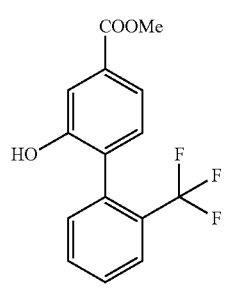

A mixture of methyl 4-bromo-3-hydroxybenzoate (Combi-Blocks CA-4189, 4.00 g, 17.3 mmol), 2-(trifluoromethyl)phenylboronic acid (3.95 g, 20.8 mmol), cesium fluoride (7.90 g, 52 mmol), palladium(II) acetate (78 mg, 0.35 mmol) and 2-dicyclohexylphosphino-2',6'-dimethoxybiphenyl (426 mg, 1.05 mmol) was prepared in dioxane (40 mL) and water (20 mL) under N₂ atmosphere. The reaction mixture was heated at 90° C. After 90 minutes, additional amounts of 2-(trifluoromethyl)phenylboronic acid (1.90 g, 10 mmol), palladium(II) acetate (78 mg, 0.35 mmol) and 2-dicyclohexylphosphino-2',6'-dimethoxybiphenyl (426 mg, 1.05 mmol) were added. After 45 additional minutes, additional amounts of 2-(trifluoromethyl)phenylboronic acid (2.7 g, 14.2 mmol), palladium(II) acetate (78 mg, 0.35 mmol) and 2-dicyclohexylphosphino-2',6'-dimethoxybiphenyl (426 mg, 1.05 mmol) were added. After 15 hours, the reaction mixture was cooled at RT, diluted with MTBE (200 mL), and then washed with water (30 mL) and brine (50 mL). The aqueous layers were extracted with MTBE (100 mL). The organic layers were combined, dried (MgSO₄) and concentrated under reduced pressure. After purification by flash chromatography (silica, EtOAc/heptane), the title compound was obtained as a yellow oil (5.03 g containing 12% w/w of DCM). HPLC (Method A), Rt: 3.6 min (purity: 98.8%). UPLC/MS, M+(ESI): 297.0, M−(ESI): 295.0.

Step 2) methyl 2-ethoxy-2'-(trifluoromethyl)biphenyl-4-carboxylate

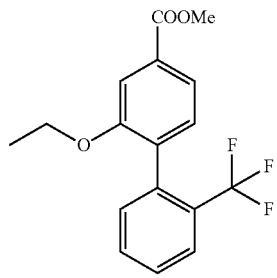 [SMILES: CCOc1cc(C(=O)OC)ccc1-c1ccccc1C(F)(F)F]

A mixture of methyl 2-hydroxy-2'-(trifluoromethyl)biphenyl-4-carboxylate (5.03 g), anhydrous potassium carbonate (7.05 g, 51 mmol) and bromoethane (6.35 mL, 85 mmol) was prepared in anhydrous ACN (75 mL) and heated at 50° C. for 15 hours. The reaction mixture was cooled at RT, filtered and concentrated under reduced pressure. After purification by flash chromatography (silica, EtOAc/heptane), the title was obtained as a colorless oil (4.45 g, 79% over 2 steps). HPLC (Method A), Rt: 5.3 min (purity: 99.0%). UPLC/MS, M+(ESI): 325.0.

Step 3) 2-ethoxy-2'-(trifluoromethyl)biphenyl-4-carboxylic acid

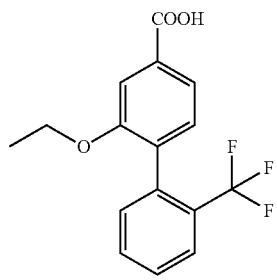 [SMILES: CCOc1cc(C(=O)O)ccc1-c1ccccc1C(F)(F)F]

A 5N aqueous solution of NaOH (4.1 mL, 20.5 mmol) was added into a solution of methyl 2-ethoxy-2'-(trifluoromethyl)biphenyl-4-carboxylate (4.45 g, 13.7 mmol) in EtOH (45 mL). The reaction mixture was heated at 60° C. for 30 minutes, and then concentrated under reduced pressure. The residue was taken up with water (50 mL) and a 5N aqueous solution of HCl (7 ml), and then extracted with MTBE (2×100 mL). The organic layers were washed with brine (50 mL), dried (MgSO$_4$) and concentrated under reduced pressure to give a colorless oil. After precipitation from pentane, the title compound was obtained as a white powder. HPLC (Method A), Rt: 4.3 min (purity: 99.7%). UPLC/MS, M−(ESI): 309.0. $^1$H NMR (DMSO-d$_6$, 300 MHz) δ 13.08 (s, 1H), 7.81 (d, J=7.7 Hz, 1H), 7.70 (m, 1H), 7.64-7.54 (m, 3H), 7.33 (d, J=7.5 Hz, 1H), 7.24 (d, J=7.7 Hz, 1H), 4.04 (m, 2H), 1.12 (t, J=7.0 Hz, 3H).

Intermediate A15: 3'-fluoro-2-(methoxymethyl)-2'-methylbiphenyl-4-carboxylic acid Step 1) methyl 3'-fluoro-2-(methoxymethyl)-2'-methylbiphenyl-4-carboxylate

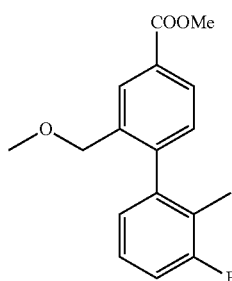

A mixture of methyl 4-bromo-3-(methoxymethyl)benzoate (5.00 g, 19.3 mmol), 3-fluoro-2-methylphenylboronic acid (Combi-Blocks BB-3475, 4.46 g, 29.0 mmol), bis(triphenylphosphine)palladium(II) chloride (271 mg, 0.39 mmol) and cesium fluoride (8.79 g, 57.9 mmol) was prepared in dioxane (50 mL) and water (20 mL) under N$_2$ atmosphere. The reaction mixture was heated at 100° C. for 1 hour. The reaction mixture was cooled at RT, diluted with MTBE (250 mL) and the layers were separated. The organic layer was washed with water (100 mL) and brine (100 mL). The aqueous layers were extracted with MTBE (150 mL). The organic layers were combined, dried (MgSO$_4$) and concentrated under reduced pressure. After purification by flash chromatography (silica, EtOAc/n-hexane), the title compound was obtained as a colorless oil (4.85 g, 87%). HPLC (Method A), Rt: 5.0 min (purity: 99.5%). UPLC/MS, M+(ESI): 289.0.

Step 2) 3'-fluoro-2-(methoxymethyl)-2'-methylbiphenyl-4-carboxylic acid

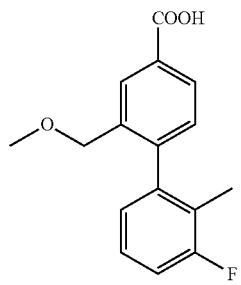 [SMILES: COCc1cc(C(=O)O)ccc1-c1cccc(F)c1C]

A 5N aqueous solution of NaOH (5.0 mL, 25 mmol) was added into a solution of methyl 3'-fluoro-2-(methoxymethyl)-2'-methylbiphenyl-4-carboxylate (4.85 g, 16.8 mmol) in EtOH (50 mL). The reaction mixture was heated at 60° C. for 1 hour, and then was concentrated under reduced pressure. The residue was taken up with MTBE (100 mL), water (50 mL) and a 5N aqueous solution of HCl (6 mL). The layers were separated and the organic layer was washed with water (50 mL) and brine (50 mL). The aqueous layers were extracted with MTBE (50 mL). The organic layers were combined, dried (MgSO$_4$) and concentrated under reduced pressure. After purification by crystallization from a mixture of MTBE and pentane, the title compound was obtained as a white powder (3.85 g, 83%). HPLC (Method A), Rt: 4.2 min (purity: 99.8%). UPLC/MS, M−(ESI): 273.0. $^1$H NMR (DMSO-d$_6$, 300 MHz) δ 13.06 (s, 1H), 8.09 (d, J=1.7 Hz, 1H), 7.92 (dd, J=7.9, 1.7 Hz, 1H), 7.35-7.17 (m, 3H), 6.97 (d, J=7.6 Hz, 1H), 4.13 (s, 2H), 3.18 (s, 3H), 1.90 (d, J=2.3 Hz, 3H).

Intermediate A16: 2,2'-dimethyl-1,1'-biphenyl-4-carboxylic acid

Step 1) methyl 2,2'-dimethyl-1,1'-biphenyl-4-carboxylate

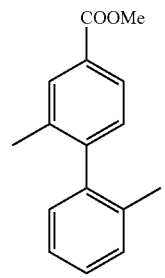

To a solution of methyl 4-bromo-3-methylbenzoate (ABCR, 15 g, 65 mmol) in toluene (200 mL) and water (200 mL), was added o-tolylboronic acid (10.68 g, 78 mmol) followed by potassium carbonate (45.25 g, 32.7 mmol) and Pd(PPh$_3$)$_4$ (3.78 g, 3.3 mmol). The mixture was degassed with N$_2$ and refluxed at 120° C. for 6 hours. After the completion of reaction, the reaction mixture was cooled to RT. The organic phase was separated and evaporated under reduced pressure. The crude compound was passed through a silica column (60-120) using hexane as eluent to get the title compound as a white solid (15 g, 95%). $^1$H NMR (DMSO-$d_6$, 400 MHz) δ 7.91 (s, 1H), 7.83-7.81 (m, 1H), 7.33-7.30 (m, 2H), 7.28-7.26 (m, 1H), 7.25-7.22 (m, 1H), 7.07-7.05 (d, 1H), 3.86-3.81 (s, 3H), 2.09-2 (s, 3H), 1.97-1.92 (s, 3H).

Step 2) 2,2'-dimethyl-1,1'-biphenyl-4-carboxylic acid

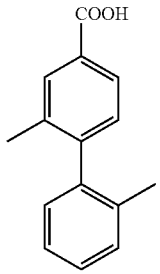

To a solution of methyl 2,2'-dimethyl-1,1'-biphenyl-4-carboxylate (15 g, 62.2 mmol) in THF (100 mL) was added 10% sodium hydroxide (100 mL) and the mixture was heated to 100° C. overnight. THF was removed under reduced pressure and the aqueous residue was washed with EtOAc. The aqueous layer was then acidified with 3N HCl to pH 2-3 and extracted with DCM. The organic phase was washed with water and dried over sodium sulfate and concentrated under reduced pressure to obtain get the title compound as a white solid (13.5 g, 95%). $^1$H NMR (DMSO-$d_6$, 400 MHz) δ 12.89 (brs, 1H), 7.89 (s, 1H), 7.82-7.80 (d, 1H), 7.32-7.23 (m, 3H), 7.19-7.11 (d, 1H), 7.07-7.05 (d, 1H), 2.04 (s, 3H), 1.98 (s, 3H). LC/MS, M+(ESI): 227.0.

Intermediate B1: tert-butyl N-{5-[amino(hydroxyimino)methyl]pyridin-2-yl}-beta-alaninate Step 1) tert-butyl N-(5-cyanopyridin-2-yl)-beta-alaninate

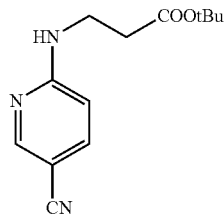

A solution of 6-chloronicotinonitrile (1.0 g, 7.2 mmol), beta-alanine tert-butyl ester hydrochloride (2.0 g, 11.0 mmol) and DIEA (4.9 mL, 28.9 mmol) in anhydrous dioxane (20 mL) was heated at reflux. After 24 hours, an additional amount of beta-alanine tert-butyl ester hydrochloride (0.5 g, 2.75 mmol) was added. After 24 additional hours at reflux, the reaction mixture was concentrated under reduced pressure. The residue was taken up with EtOAc (50 mL) and washed with water (2×20 mL) and brine (20 mL). The organic layer was dried (MgSO$_4$) and the solvent was removed under reduced pressure. After precipitation from MTBE/pentane, the title compound was obtained as an off-white powder (1.28 g, 72%). HPLC (Method A), Rt: 2.7 min (purity: 99.9%). UPLC/MS, M+(ESI): 248.1, M−(ESI): 246.2. $^1$H NMR (DMSO-$d_6$, 300 MHz) δ 8.40 (d, J=2.0 Hz, 1H), 7.67 (m, 2H), 6.56 (d, J=8.9 Hz, 1H), 3.50 (td, J=6.8, 6.0 Hz, 2H), 2.48 (t, J=6.8 Hz, 2H), 1.38 (s, 9H).

Step 2) tert-butyl N-{5-[amino(hydroxyimino)methyl]pyridin-2-yl}-beta-alaninate

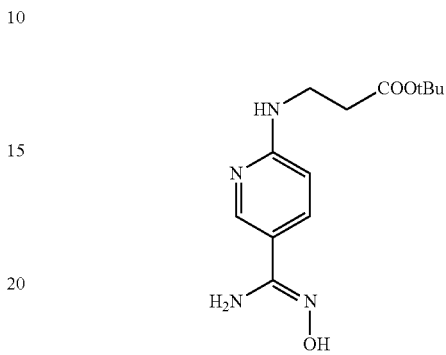

The title compound was prepared following procedure described in Method A starting from tert-butyl N-(5-cyanopyridin-2-yl)-beta-alaninate. The title compound was obtained as a white powder (1.25 g, 90%). HPLC (Method A), Rt: 1.6 min (purity: 98.4%). UPLC/MS, M+(ESI): 281.2. $^1$H NMR (DMSO-$d_6$, 300 MHz) δ 9.35 (s, 1H), 8.25 (d, J=2.3 Hz, 1H), 7.61 (dd, J=8.8, 2.3 Hz, 1H), 6.78 (t, J=5.7 Hz, 1H), 6.44 (d, J=8.8 Hz, 1H), 5.66 (s, 2H), 3.45 (td, J=6.8, 5.7 Hz, 2H), 2.46 (t, J=6.8 Hz, 2H), 1.39 (s, 9H).

Intermediate B2: tert-butyl N-{5-[amino(hydroxyimino)methyl]pyridin-2-yl}glycinate Step 1) tert-butyl N-(5-cyanopyridin-2-yl)glycinate

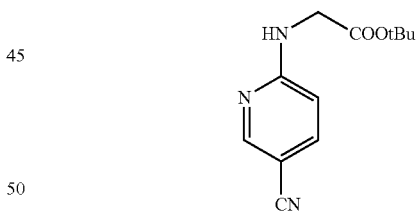

A solution of 6-chloronicotinonitrile (1.00 g, 7.2 mmol), glycine tert-butyl ester (1.04 g, 7.9 mmol) and DIEA (4.9 mL, 29 mmol) in anhydrous dioxane (20 mL) was heated at reflux. After 24 hours, an additional amount of glycine tert-butyl ester (0.5 g, 3.8 mmol) was added. After 24 additional hours at reflux, the reaction mixture was concentrated under reduced pressure. The residue was taken up with EtOAc (50 mL) and washed with water (20 mL). The organic layer was dried (MgSO$_4$) and the solvent was removed under reduced pressure. After precipitation from EtOAc/Et$_2$O/heptane, the title compound was obtained as an off-white powder (1.55 g, 92%). HPLC (Method A), Rt: 3.1 min (purity: 95.1%). UPLC/MS, M+(ESI): 178.0 ([M-tBu+2H]+), M−(ESI): 232.1. $^1$H NMR (DMSO-$d_6$, 300 MHz) δ 8.39 (d, J=2.1 Hz, 1H), 7.91 (m, 1H), 7.72 (dd, J=8.8, 2.1 Hz, 1H), 6.66 (d, J=8.8 Hz, 1H), 3.98 (d, J=6.1 Hz, 2H), 1.39 (s, 9H).

Step 2) tert-butyl N-{5-[amino(hydroxyimino)methyl]pyridin-2-yl}glycinate

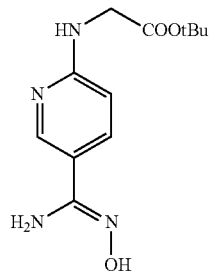

The title compound was prepared following procedure described in Method A starting from tert-butyl N-(5-cyanopyridin-2-yl)glycinate. The title compound was obtained as an off-white powder (1.35 g, 79%). HPLC (Method A), Rt: 1.6 min (purity: 100%). UPLC/MS, M+(ESI): 267.1. $^1$H NMR (DMSO-d$_6$, 300 MHz) δ 9.38 (s, 1H), 8.23 (d, J=2.2 Hz, 1H), 7.64 (dd, J=8.7, 2.2 Hz, 1H), 7.08 (t, J=6.1 Hz, 1H), 6.52 (d, J=8.7 Hz, 1H), 5.69 (s, 2H), 3.91 (d, J=6.1 Hz, 2H), 1.39 (s, 9H).

Intermediate B3: tert-butyl N-{4-[amino(hydroxyimino)methyl]pyridin-2-yl}-beta-alaninate Step 1) tert-butyl N-(4-cyanopyridin-2-yl)-beta-alaninate

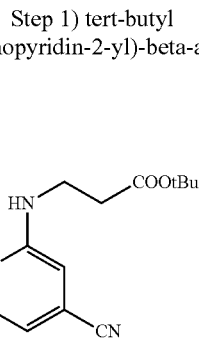

A solution of 2-chloro-4-cyanopyridine (2.00 g, 14.4 mmol), beta-alanine tert-butyl ester hydrochloride (3.14 g, 17.3 mmol) and DIEA (9.88 mL, 57.7 mmol) in anhydrous DMSO (30 mL) was heated at 150° C. for 3 days. The reaction mixture was diluted with Et$_2$O (100 mL) and washed with water (3×60 mL) and brine (60 mL). The organic layer was dried (MgSO$_4$) and the solvents were removed under reduced pressure. Purification by flash chromatography (silica, EtOAc/cHex) gave the title compound as a brown oil. HPLC (Method A), Rt: 2.8 min (purity: 92.2%). UPLC/MS, M+(ESI): 248.1, M−(ESI): 246.2. $^1$H NMR (DMSO-d$_6$, 300 MHz) δ 8.16 (dd, J=5.2, 0.7 Hz, 1H), 7.16 (t, J=5.7 Hz, 1H), 6.83 (m, 1H), 6.79 (dd, J=5.2, 1.4 Hz, 1H), 3.46 (td, J=6.8, 5.7 Hz, 2H), 2.46 (t, J=6.8 Hz, 2H), 1.38 (s, 9H).

Step 2) tert-butyl N-{4-[amino(hydroxyimino)methyl]pyridin-2-yl}-beta-alaninate

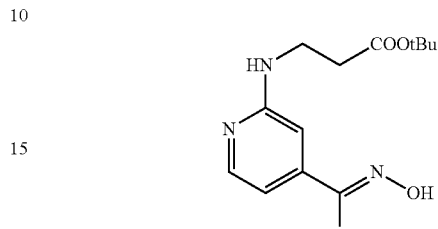

The title compound was prepared following procedure described in Method A starting from tert-butyl N-(4-cyanopyridin-2-yl)-beta-alaninate. The title compound was obtained as a yellow powder. HPLC (Method A), Rt: 2.2 min (purity: 94.3%). UPLC/MS, M+(ESI): 281.1, M−(ESI): 279.1. $^1$H NMR (DMSO-d$_6$, 300 MHz) δ 9.79 (s, 1H), 7.94 (d, J=5.3 Hz, 1H), 6.74 (dd, J=5.3, 1.4 Hz, 1H), 6.71 (brs, 1H), 6.57 (t, J=5.7 Hz, 1H), 5.77 (s, 2H), 3.44 (td, J=7.0, 5.7 Hz, 2H), 2.46 (t, J=7.0 Hz, 2H), 1.39 (s, 9H).

Intermediate B4: tert-butyl 4-({5-[amino(hydroxyimino)methyl]pyridin-2-yl}amino)butanoate Step 1) tert-butyl 4-[(5-cyanopyridin-2-yl)amino]butanoate

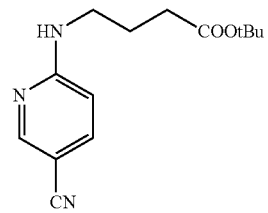

A solution of 6-chloronicotinonitrile (1.0 g, 7.2 mmol), 4-aminobutyric acid tert-butyl ester hydrochloride (2.12 g, 10.8 mmol, Sennchem 09600) and DIEA (4.9 mL, 28.9 mmol) in anhydrous dioxane (20 mL) was heated at 80° C. After 48 hours, an additional amount of 4-aminobutyric acid tert-butyl ester hydrochloride (0.55 g, 2.80 mmol) was added. After 24 additional hours at 80° C., the reaction mixture was diluted with Et$_2$O (100 mL) and washed with water (2×50 mL) and brine (50 mL). The organic layer was dried (MgSO$_4$) and the solvents were removed under reduced pressure. After purification by flash chromatography (silica, EtOAc/cHex), the title compound was obtained as a beige powder. HPLC (Method A), Rt: 3.3 min (purity: 91%). UPLC/MS, M+(ESI): 262.1, M−(ESI): 260.2. $^1$H NMR (DMSO-d$_6$, 300 MHz) δ

8.37 (d, J=2.2 Hz, 1H), 7.63 (m, 2H), 6.52 (d, J=8.9 Hz, 1H), 3.29 (m, 2H), 2.26 (t, J=7.4 Hz, 2H), 1.73 (tt, J=7.4, 7.0 Hz, 2H), 1.38 (s, 9H).

Step 2) tert-butyl 4-({5-[amino(hydroxyimino)methyl]pyridin-2-yl}amino)butanoate

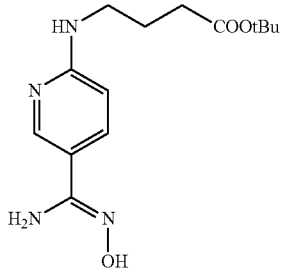

The title compound was prepared following procedure described in Method A starting from tert-butyl 4-[(5-cyanopyridin-2-yl)amino]butanoate. The title compound was obtained as a white powder (0.83 g, 75%). HPLC (Method A), Rt: 2.4 min (purity: 97.3%). UPLC/MS, M+(ESI): 295.2. $^1$H NMR (DMSO-$d_6$, 300 MHz) δ 9.34 (s, 1H), 8.24 (d, J=2.3 Hz, 1H), 7.60 (dd, J=8.7, 2.3 Hz, 1H), 6.75 (t, J=5.6 Hz, 1H), 6.41 (d, J=8.7 Hz, 1H), 5.65 (s, 2H), 3.24 (td, J=6.9, 5.6 Hz, 2H), 2.26 (t, J=7.5 Hz, 2H), 1.72 (tt, J=7.5, 6.9 Hz, 2H), 1.39 (s, 9H).

Intermediate B5: tert-butyl N-{4-[amino(hydroxyimino)methyl]pyridin-2-yl}glycinate Step 1) tert-butyl N-(4-cyanopyridin-2-yl)glycinate

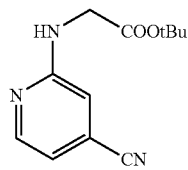

A solution of 2-chloro-4-cyanopyridine (1.00 g, 7.2 mmol), glycine tert-butyl ester (1.5 mL, 10.8 mmol) and DIEA (4.9 mL, 28.9 mmol) in anhydrous DMA (15 mL) was heated at 150° C. for 48 hours. The reaction mixture was diluted with Et$_2$O (100 mL) and washed with water (2×50 mL) and brine (50 mL). The organic layer was dried (MgSO$_4$) and the solvents were removed under reduced pressure. After purification by flash chromatography (silica, DCM), the title compound was obtained as a yellow oil. HPLC (Method A), Rt: 3.1 min (purity: 94%). UPLC/MS, M+(ESI): 178.0 ([M−tBu+2H]+), M−(ESI): 232.1. $^1$H NMR (DMSO-$d_6$, 300 MHz) δ 8.15 (d, J=5.2 Hz, 1H), 7.44 (t, J=6.2 Hz, 1H), 6.93 (brs, 1H), 6.85 (dd, J=5.2, 1.3 Hz, 1H), 3.94 (d, J=6.2 Hz, 2H), 1.38 (s, 9H).

Step 2) tert-butyl N-{4-[amino(hydroxyimino)methyl]pyridin-2-yl}glycinate

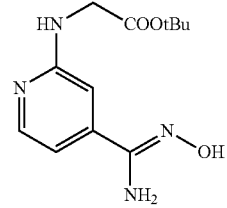

The title compound was prepared following procedure described in Method A starting from tert-butyl N-(4-cyanopyridin-2-yl)glycinate. The title compound was obtained as a yellow powder. HPLC (Method A), Rt: 2.0 min (purity: 99.3%). UPLC/MS, M+(ESI): 267.1, M−(ESI): 265.2. $^1$H NMR (DMSO-$d_6$, 300 MHz) δ 9.81 (s, 1H), 7.92 (d, J=5.3 Hz, 1H), 6.89 (t, J=6.3 Hz, 1H), 6.80 (brs, 1H), 6.78 (d, J=5.3 Hz, 1H), 5.79 (s, 2H), 3.89 (d, J=6.3 Hz, 2H), 1.39 (s, 9H).

Intermediate B6: 6-amino-5-chloro-N'-hydroxypyridine-3-carboximidamide

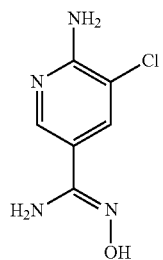

The title compound was prepared following procedure described in Method A starting from 2-amino-3-chloro-5-cyanopyridine (Synchem SC-21933). The title compound was obtained as a beige powder (1.48 g, 85%). HPLC (Method A), Rt: <1.0 min. UPLC/MS, M+(ESI): 187.1. $^1$H NMR (DMSO-$d_6$, 300 MHz) δ 9.49 (s, 1H), 8.22 (d, J=2.0 Hz, 1H), 7.78 (d, J=2.0 Hz, 1H), 6.50 (s, 2H), 5.78 (s, 2H).

Intermediate B7: 2-amino-N'-hydroxypyridine-4-carboximidamide

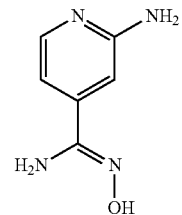

The title compound was prepared following procedure described in Method A starting from 2-amino-4-cyanopyridine (ABCR L19841). The title compound was obtained as a white powder. HPLC (Method A), Rt: <1.0 min. UPLC/MS, M+(ESI): 153.1. $^1$H NMR (DMSO-$d_6$, 300 MHz) δ 9.79 (s, 1H), 7.87 (d, J=5.3 Hz, 1H), 6.72 (dd, J=5.3, 1.3 Hz, 1H), 6.69 (brs, 1H), 5.93 (s, 2H), 5.74 (s, 2H).

Intermediate B8: 5-amino-N'-hydroxypyrazine-2-carboximidamide

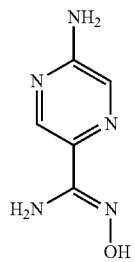

The title compound was prepared following procedure described in Method A starting from 2-amino-5-cyanopyrazine (Synchem SC-21935). The title compound was obtained as a green powder (0.92 g, 72%). HPLC (Method A), Rt: <1.0 min. UPLC/MS, M+(ESI): 154.1. $^1$H NMR (DMSO-$d_6$, 300 MHz) δ 9.53 (s, 1H), 8.35 (d, J=1.3 Hz, 1H), 7.81 (d, J=1.3 Hz, 1H), 6.63 (s, 2H), 5.62 (s, 2H).

Intermediate B9: 2-amino-N'-hydroxypyrimidine-5-carboximidamide

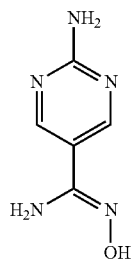

The title compound was prepared following procedure described in Method A starting from 2-aminopyrimidine-5-carbonitrile (Synchem SC-17302). The reaction mixture was diluted with iPrOH, and then the precipitate was filtered off to give the title compound as a beige powder (1.19 g, 93%). HPLC (Method A), Rt: <1.0 min. UPLC/MS, M+(ESI): 154.1. $^1$H NMR (DMSO-$d_6$, 300 MHz) δ 9.47 (s, 1H), 8.45 (s, 2H), 6.84 (s, 2H), 5.79 (s, 2H).

Intermediate B10: 6-amino-N'-hydroxy-5-methylpyridine-3-carboximidamide

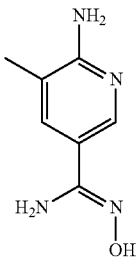

The title compound was prepared following procedure described in Method A starting from 6-amino-5-methylnicotinonitrile (Cgenetech 20053). The title compound was obtained as a beige powder. HPLC (Method A), Rt: <1.0 min. UPLC/MS, M+(ESI): 167.2. $^1$H NMR (DMSO-$d_6$, 300 MHz) δ 9.30 (s, 1H), 8.08 (d, J=1.9 Hz, 1H), 7.48 (d, J=1.9 Hz, 1H), 5.90 (s, 2H), 5.63 (s, 2H), 2.04 (s, 3H).

Intermediate B11: N',6-dihydroxypyridine-3-carboximidamide

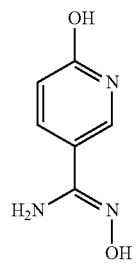

The title compound was prepared following procedure described in Method A starting from 6-hydroxynicotinonitrile (Combi-Blocks CA-4240). The title compound was obtained as a white powder (1.15 g, 99%). HPLC (Method A), Rt: <1.0 min. UPLC/MS, M+(ESI): 154.1, M+(ESI): 152.1. $^1$H NMR (DMSO-$d_6$, 300 MHz) δ 11.63 (s, 1H), 9.51 (s, 1H), 7.72 (dd, J=9.6, 2.7 Hz, 1H), 7.65 (d, J=2.7 Hz, 1H), 6.31 (d, J=9.6 Hz, 1H), 5.73 (s, 2H).

Intermediate B12: methyl 5-[amino(hydroxyimino)methyl]pyridine-2-carboxylate

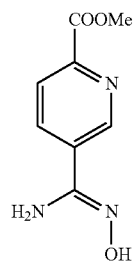

The title compound was prepared following procedure described in Method A starting from methyl 5-cyanopyridine-2-carboxylate (Chemical & Pharmaceutical Bulletin, 1980, 1408-1414). The title compound was obtained as a beige powder. HPLC (Method A), Rt: <1.0 min. UPLC/MS, M+(ESI): 196.1, M−(ESI): 194.0. $^1$H NMR (DMSO-$d_6$, 300 MHz) δ 10.12 (s, 1H), 8.99 (dd, J=2.1, 0.6 Hz, 1H), 8.20 (dd, J=8.2, 2.1 Hz, 1H), 8.06 (dd, J=8.2, 0.6 Hz, 1H), 6.12 (s, 2H), 3.89 (s, 3H).

Intermediate B13: N'-hydroxy-6-[(2-hydroxyethyl)amino]pyridine-3-carboximidamide

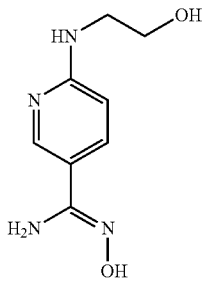

The title compound was prepared following procedure described in Method E starting from 6-[(2-hydroxyethyl)amino]nicotinonitrile (UkrOrgSynthesis BBR-022920). The title compound was obtained as a white powder (505 mg, 70%). UPLC/MS, M+(ESI): 197.1, M−(ESI): 195.1. $^1$H NMR (DMSO-$d_6$, 300 MHz) δ 9.34 (s, 1H), 8.24 (d, J=2.4 Hz, 1H), 7.60 (dd, J=8.8, 2.4 Hz, 1H), 6.71 (t, J=5.6 Hz, 1H), 6.46 (d, J=8.8 Hz, 1H), 5.67 (s, 2H), 4.74 (s, 1H), 3.51 (m, 2H), 3.33 (m, 2H).

Intermediate B14: N'-hydroxy-6-(methylamino)pyridine-3-carboximidamide

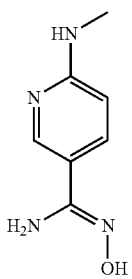

The title compound was prepared following procedure described in Method E starting from 6-(methylamino)nicotinonitrile (ABCR AB235839). The title compound was obtained as a white powder. UPLC/MS, M+(ESI): 167.1. $^1$H NMR (DMSO-$d_6$, 300 MHz): δ 9.36 (s, 1H), 8.27 (d, J=2.3 Hz, 1H), 7.62 (dd, J=8.7, 2.4 Hz, 1H), 6.68 (m, 1H), 6.41 (d, J=8.8 Hz, 1H), 5.70 (s, 2H), 2.77 (d, J=4.8 Hz, 3H).

Intermediate B15: 5-Chloro-W-hydroxy-6-[(2-methoxyethyl)amino]pyridine-3-carboximidamide Step 1) 5-chloro-6-[(2-methoxyethyl)amino]nicotinonitrile

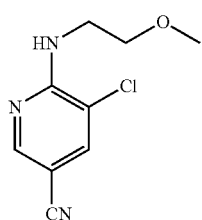

A mixture of 2-methoxyethyl amine (4.11 mL, 43.9 mmol), TEA (6.11 mL, 43.9 mmol) and 5,6-dichloronicotinonitrile (Bionet GC-0755, 7.6 g, 43.9 mmol) was prepared in dioxane and stirred at RT for 24 hours. The reaction mixture was filtered to remove inorganic solids and filtrate was concentrated under reduced pressure. The residue taken up with EtOAc (100 mL) and washed with water (3×100 mL). The organic layer was dried (Na$_2$SO$_4$) and concentrated under reduced pressure. After purification by flash chromatography (silica, pet ether/EtOAc), the title compound was obtained as a white powder (6.9 g, 75%). LC/MS, M+(ESI): 212.1. $^1$H NMR (DMSO-$d_6$, 400 MHz) δ 8.42 (1H, d), 8.07 (1H, d), 7.48 (1H, t), 3.58 (2H, m), 3.47 (2H, m), 3.23 (3H, s).

Step 2) 5-Chloro-N'-hydroxy-6-[(2-methoxyethyl)amino]pyridine-3-carboximidamide

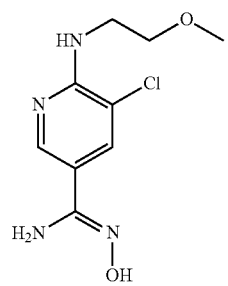

Hydroxylamine (5.39 g, 164 mmol) was added into a solution of 5-chloro-6-[(2-methoxyethyl)amino]nicotinonitrile (6.9 g, 32.7 mmol) in THF (70 mL) under nitrogen. The reaction mixture was stirred at RT for 36 hours, and then was concentrated under reduced pressure to afford the title compound as a pale yellow solid (8.2 g, quantitative). LC/MS, M+(ESI): 245.1. $^1$H NMR (DMSO-$d_6$, 400 MHz) δ 9.49 (1H, s), 8.27 (1H, s), 7.78 (1H, s), 6.57 (1H, t), 5.77 (2H, s), 3.53 (2H, m), 3.46 (2H, m), 3.25 (3H, s).

Intermediate B16: tert-butyl 3-({5-[amino(hydroxyimino)methyl]-3-chloropyridin-2-yl}amino)propanoate Step 1) tert-butyl 3-[(3-chloro-5-cyanopyridin-2-yl)amino]propanoate

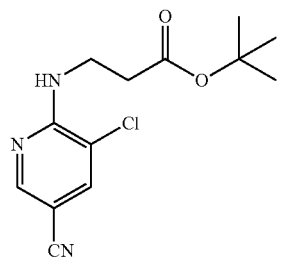 [SMILES: CC(C)(C)OC(=O)CCNc1ncc(C#N)cc1Cl]

A mixture of beta-alanine tert-butyl ester (5.88 g, 40.4 mmol), TEA (5.6 mL, 40.4 mmol) and 5,6-dichloronicotinonitrile (Bionet GC-0755, 7.0 g, 40.4 mmol) was prepared and stirred at RT for 24 hours. The reaction mixture was filtered to remove inorganic solids and filtrate was concentrated under reduced pressure. The residue taken up with EtOAc (100 mL) and washed with water (2×100 mL). The organic layer was dried (Na$_2$SO$_4$) and concentrated under reduced pressure.

After purification by flash chromatography (silica, pet ether/EtOAc), the title compound was obtained as a white powder (8.3 g, 72%). $^1$H NMR (DMSO-$d_6$, 400 MHz) δ 8.44 (1H, d), 8.08 (1H, d), 7.52 (1H, t), 3.62 (2H, m), 2.50 (2H, m), 1.35 (9H, s).

Step 2) tert-butyl 3-({4-[amino(hydroxyimino)methyl]-3-chloropyridin-2-yl}amino)propanoate

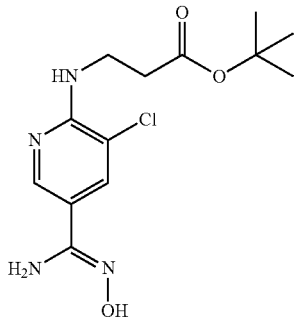 [SMILES: CC(C)(C)OC(=O)CCNc1ncc(/C(N)=N/O)cc1Cl]

Hydroxylamine (4.8 g, 147 mmol) was added into a solution of tert-butyl 3-[(3-chloro-5-cyanopyridin-2-yl)amino]propanoate (8.3 g, 29.4 mmol) in THF (90 mL) under nitrogen. The reaction mixture was stirred at RT for 24 hours, and then was concentrated under reduced pressure to afford the title compound as a pale yellow solid (9.0 g, quantitative). LC/MS, M+(ESI): 315.0. $^1$H NMR (DMSO-$d_6$, 400 MHz) δ 9.49 (1H, s), 8.28 (1H, s), 7.78 (1H, s), 6.66 (1H, t), 5.78 (2H, s), 3.58 (2H, m), 2.50 (2H, t), 1.37 (9H, s).

Intermediate B17: tert-butyl ({5-[amino(hydroxyimino)methyl]-3-chloropyridin-2-yl}amino)acetate Step 1) tert-butyl [(3-chloro-5-cyanopyridin-2-yl)amino]acetate

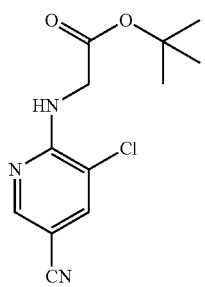 [SMILES: CC(C)(C)OC(=O)CNc1ncc(C#N)cc1Cl]

A mixture of glycine tert-butyl ester (5.3 g, 40.4 mmol), TEA (5.6 mL, 40.4 mmol) and 5,6-dichloronicotinonitrile (Bionet GC-0755, 7.0 g, 40.4 mmol) was prepared and stirred at RT for 24 hours. The reaction mixture was filtered to remove inorganic solids and filtrate was concentrated under reduced pressure. The residue taken up with EtOAc (100 mL) and washed with water (2×100 mL). The organic layer was dried (Na$_2$SO$_4$) and concentrated under reduced pressure. After purification by flash chromatography (silica, pet ether/EtOAc), the title compound was obtained as a white powder. $^1$H NMR (DMSO-$d_6$, 400 MHz) δ 8.41 (1H, d), 8.15 (1H, d), 7.84 (1H, t), 4.00 (2H, m), 1.38 (9H, s).

Step 2) tert-butyl ({5-[amino(hydroxyimino)methyl]-3-chloropyridin-2-yl}amino)acetate

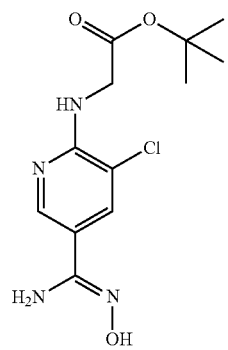

Hydroxylamine (1.5 mL, 39.5 mmol) was added into a solution of tert-butyl [(3-chloro-5-cyanopyridin-2-yl)amino]acetate (2.1 g, 7.9 mmol) in THF (30 mL) under nitrogen. The reaction mixture was stirred at RT for 48 hours, and then was concentrated under reduced pressure to afford the title compound as a white solid (2.4 g, quantitative). LC/MS, M+(ESI): 301.0. $^1$H NMR (DMSO-$d_6$, 400 MHz) δ 9.52 (1H, s), 8.24 (1H, d), 7.81 (1H, d), 7.04 (1H, t), 5.80 (2H, s), 3.95 (2H, m), 1.37 (9H, s).

Intermediate B18: N'-hydroxy-6-[(3-hydroxypropyl)amino]pyridine-3-carboximidamide

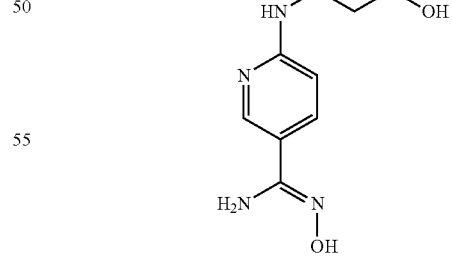

The title compound was prepared following procedure described in Method E starting from 6-[(3-hydroxypropyl)amino]nicotinonitrile (UkrOrgSynthesis BBR-037216). The title compound was obtained as a white powder. UPLC/MS, M+(ESI): 211.1, M−(ESI): 209.2. $^1$H NMR (DMSO-$d_6$, 300 MHz) δ 9.33 (s, 1H), 8.24 (d, J=2.2 Hz, 1H), 7.60 (dd, J=8.8, 2.2 Hz, 1H), 6.69 (t, J=5.6 Hz, 1H), 6.41 (d, J=8.8 Hz, 1H), 5.66 (s, 2H), 4.50 (brs, 1H), 3.47 (m, 2H), 3.29 (m, 2H), 1.66 (m, 2H).

Intermediate B19: N'-hydroxy-6-[(2-hydroxypropyl) amino]pyridine-3-carboximidamide

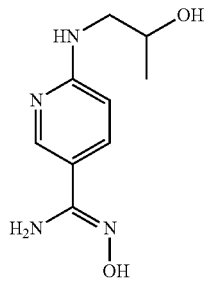

The title compound was prepared following procedure described in Method E starting from 6-[(2-hydroxypropyl) amino]nicotinonitrile (UkrOrgSynthesis BBV-24876482). The title compound was obtained as a white powder. UPLC/MS, M+(ESI): 211.1, M−(ESI): 209.0. $^1$H NMR (DMSO-$d_6$, 300 MHz) δ 9.34 (s, 1H), 8.23 (d, J=2.1 Hz, 1H), 7.60 (dd, J=8.8, 2.1 Hz, 1H), 6.69 (t, J=5.5 Hz, 1H), 6.49 (d, J=8.8 Hz, 1H), 5.66 (s, 2H), 4.78 (s, 1H), 3.77 (m, 1H), 3.20 (m, 2H), 1.07 (d, J=6.2 Hz, 3H).

Intermediate B20: 6-[(2,3-dihydroxypropyl)amino]-N'-hydroxypyridine-3-carboximidamide Step 1) 6-[(2,3-dihydroxypropyl)amino]nicotinonitrile

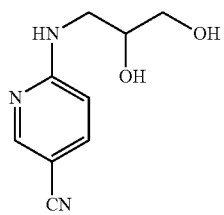 [SMILES: N#Cc1ccc(NCC(O)CO)nc1]

A mixture of 3-amino-1,2-propanediol (4.93 g, 54.1 mmol) and 6-chloronicotinonitrile (1.50 g, 10.8 mmol) was prepared in anhydrous dioxane (20 mL), and then stirred at RT for hours and 80° C. for additional hours. The reaction mixture was diluted with EtOAc (100 mL) and washed with a half saturated solution of brine (2×50 mL) and brine (50 mL). The aqueous layers were extracted with EtOAc (2×50 mL). The organic layers were combined, dried (Na$_2$SO$_4$) and concentrated under reduced pressure. After purification by trituration in hot MTBE (10 mL) and filtration, the title compound was obtained as a white powder (970 mg, 46%). UPLC/MS, M+(ESI): 193.9, M−(ESI): 192.1.

Step 2) 6-[(2,3-dihydroxypropyl)amino]-N'-hydroxypyridine-3-carboximidamide

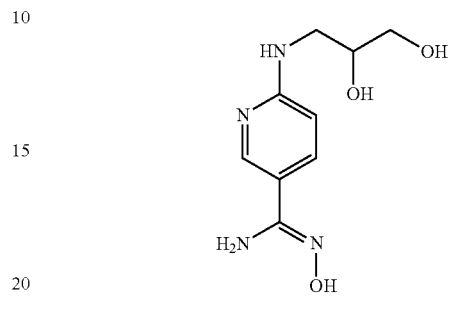

The title compound was prepared following procedure described in Method E starting from 6-[(2,3-dihydroxypropyl)amino]nicotinonitrile. After completion, the reaction mixture was filtered through a NH$_2$ SPE column (20 g, elution with EtOH). The filtrate was concentrated under reduced pressure to give the title compound as a beige foam (750 mg, 70%). UPLC/MS, M+(ESI): 227.1, M−(ESI): 225.1.

Intermediate B21: tert-butyl 3-({5-[amino(hydroxyimino)methyl]-3-methylpyridin-2-yl}amino)propanoate Step 1) tert-butyl 3-[(5-cyano-3-methylpyridin-2-yl)amino]propanoate

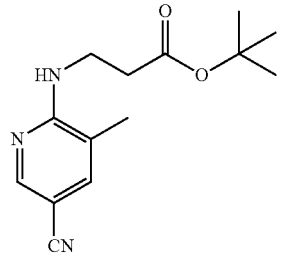 [SMILES: Cc1cc(C#N)cnc1NCCC(=O)OC(C)(C)C]

A mixture of 6-fluoro-5-methylnicotinonitrile (Molekula 11370, 10 g, 73.4 mmol), beta-alanine tert-butyl ester hydrochloride (16 g, 88.1 mmol) and TEA (25.6 mL, 183.6 mmol) was prepared in DMSO (100 mL) under nitrogen, and then heated at 150° C. for 4 hours. The reaction mixture was cooled to 100° C. and water (100 mL) was added drop wise. The resulting mixture was stirred at RT for 2 hours, and then the precipitate was filtered off, washed with water and dried under reduced pressure to afford the title compound as a white solid (18 g, 94%). ¹H NMR (DMSO-d₆, 400 MHz) δ 8.31 (1H, s), 7.56 (1H, s), 6.97 (1H, m), 3.59 (2H, m), 2.50 (2H, m), 2.02 (3H, s), 1.36 (9H, s).

Step 2) tert-butyl 3-({5-[amino(hydroxyimino)methyl]-3-methylpyridin-2-yl}amino)propanoate

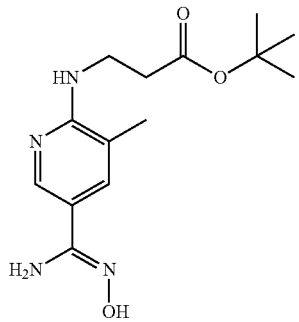 [SMILES: Cc1cc(/C(N)=N/O)cnc1NCCC(=O)OC(C)(C)C]

The title compound was prepared following procedure described in Method A starting from tert-butyl 3-[(5-cyano-3-methylpyridin-2-yl)amino]propanoate. The title compound was obtained as a white powder (11.2 g, quantitative). LC/MS, M+(ESI): 295.3. ¹H NMR (DMSO-d₆, 400 MHz) δ 9.31 (1H, s), 8.15 (1H, s), 7.47 (1H, s), 6.12 (1H, m), 5.63 (2H, s), 3.54 (2H, m), 2.48 (2H, m), 2.01 (3H, s), 1.37 (9H, s).

Intermediate B22: tert-butyl 4-({5-[amino(hydroxyimino)methyl]-3-chloropyridin-2-yl}amino)butanoate Step 1) tert-butyl 4-[(3-chloro-5-cyanopyridin-2-yl)amino]butanoate

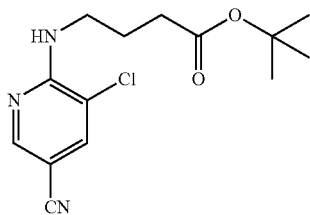 [SMILES: CC(C)(C)OC(=O)CCCNc1ncc(C#N)cc1Cl]

A mixture of tert-butyl 4-aminobutanoate hydrochloride (Bachem F-3755, 8.54 g, 28.9 mmol), sodium bicarbonate (6.0 g, 72.2 mmol) and 5,6-dichloronicotinonitrile (Bionet GC-0755, 5.0 g, 28.9 mmol) was prepared in dioxane under nitrogen, and then heated at 50° C. for 16 hours. The reaction mixture was filtered to remove inorganic solids and filtrate was concentrated under reduced pressure. After purification by flash chromatography (silica, pet ether/EtOAc), the title compound was obtained as a white powder. ¹H NMR (DMSO-d₆, 400 MHz) δ 8.40 (1H, d), 8.05 (1H, d), 7.58 (1H, t), 3.42 (2H, m), 2.21 (2H, t), 1.76 (2H, m), 1.37 (9H, s).

Step 2) tert-butyl 4-({5-[amino(hydroxyimino)methyl]-3-chloropyridin-2-yl}amino)butanoate

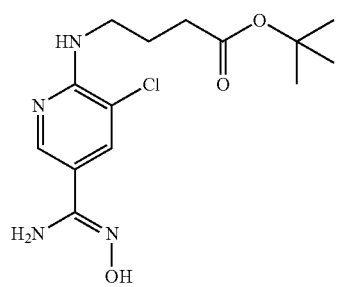 [SMILES: CC(C)(C)OC(=O)CCCNc1ncc(/C(N)=N/O)cc1Cl]

The title compound was prepared following procedure described in Method A starting from tert-butyl 4-[(3-chloro-5-cyanopyridin-2-yl)amino]butanoate. The title compound was obtained as a white powder (4.8 g, quantitative). LC/MS, M+(ESI): 329.0. ¹H NMR (DMSO-d₆, 400 MHz) δ 9.47 (1H, s), 8.26 (1H, d), 7.76 (1H, d), 6.73 (1H, t), 5.76 (2H, s), 3.31-3.39 (2H, m), 2.21 (2H, t), 1.76 (2H, t), 1.37 (9H, s).

Intermediate B23: tert-butyl 4-({5-[amino(hydroxyimino)methyl]-3-methylpyridin-2-yl}amino)butanoate Step 1) tert-butyl 4-[(5-cyano-3-methylpyridin-2-yl)amino]butanoate

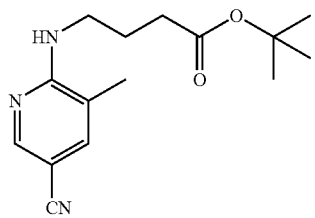 [SMILES: Cc1cc(C#N)cnc1NCCCC(=O)OC(C)(C)C]

A mixture of 6-fluoro-5-methylnicotinonitrile (10.0 g, 73.4 mmol), tert-butyl 4-aminobutanoate (Bachem F-3755, 17.4 g, 88.1 mmol) and TEA (25.6 mL, 183.6 mmol) was prepared in DMSO (100 mL) under nitrogen, and the heated at 150° C. for 4 hours. The reaction mixture was cooled to 100° C., and then water was added (100 mL) drop wise. The resulting mixture was stirred at RT for 2 hours, and then the precipitate was filtered off, washed with water and dried under reduced pressure to afford the title compound as a white solid. ¹H NMR (DMSO-d$_6$, 400 MHz) δ 8.27 (1H, s), 7.53 (1H, s), 6.95 (1H, m), 3.40 (2H, t), 2.23 (2H, t), 2.03 (3H, s), 1.75 (2H, m), 1.37 (9H, s).

Step 2) tert-butyl 4-({5-[amino(hydroxyimino) methyl]-3-methylpyridin-2-yl}amino)butanoate

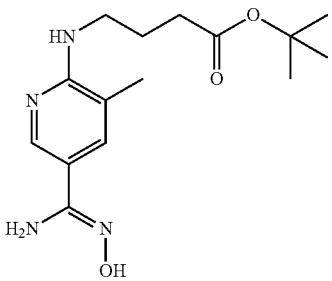 [SMILES: Cc1cc(/C(N)=N/O)cnc1NCCCC(=O)OC(C)(C)C]

The title compound was prepared following procedure described in Method A starting from tert-butyl 4-[(5-cyano-3-methylpyridin-2-yl)amino]butanoate. The title compound was obtained as a white powder (10.7 g, 91%). LC/MS, M+(ESI): 309.2. $^1$H NMR (DMSO-d$_6$, 400 MHz) δ 9.30 (1H, s), 8.14 (1H, s), 7.46 (1H, s), 6.11 (1H, bs), 5.62 (2H, bs), 3.35 (2H, m), 2.23 (2H, m), 2.03 (3H, s), 1.76 (2H, m), 1.38 (9H, s).

Intermediate B24: 6-chloro-5-fluoro-N'-hydroxypyridine-3-carboximidamide

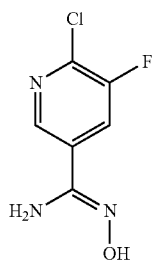

The title compound was prepared following procedure described in Method A starting from 6-chloro-5-fluoronicotinonitrile (Combiblocks PY-7266). The title compound was obtained as a pale yellow powder. HPLC (Method A), Rt: <1.0 min. UPLC/MS, M+(ESI): 189.8. $^1$H NMR (DMSO-d$_6$, 300 MHz) δ 9.74 (s, 1H), 8.51 (d, J=3.1 Hz, 1H), 7.90 (dd, J=8.4, 3.1 Hz, 1H), 6.03 (s, 2H).

Intermediate B25: 5-chloro-N'-hydroxy-6-[(2-hydroxyethyl)amino]pyridine-3-carboximidamide Step 1) 5-chloro-6-[(2-hydroxyethyl)amino]nicotinonitrile

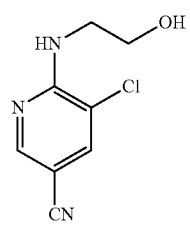 [SMILES: N#Cc1cnc(NCCO)c(Cl)c1]

A mixture of 5,6-dichloro-nicotinonitrile (Bionet GC-0755, 500 mg, 2.89 mmol) and ethanolamine (0.87 mL, 14.45 mmol) was prepared in anhydrous dioxane (5 mL) and heated at 80° C. for 24 hours. The reaction mixture was diluted with MTBE (50 mL) and washed with water (2×25 mL) and brine (25 ml). The aqueous layers were extracted with MTBE (50 mL). The organic layers were combined, dried (Na$_2$SO$_4$) and concentrated under reduced pressure to give the title compound as a white powder (510 mg, 89%). HPLC (Method A), Rt: 1.9 min (purity: 99.9%). UPLC/MS, M−(ESI): 196.0.

Step 2) 5-chloro-N'-hydroxy-6-[(2-hydroxyethyl) amino]pyridine-3-carboximidamide

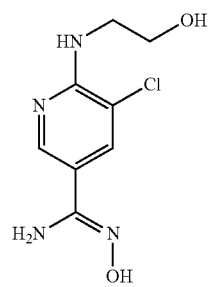 [SMILES: N/C(=N\O)c1cnc(NCCO)c(Cl)c1]

The title compound was prepared following procedure described in Method A starting from 5-chloro-6-[(2-hydroxyethyl)amino]nicotinonitrile. After purification by precipitation from a mixture of MTBE and EtOH, the title compound was obtained as a white powder (400 mg, 70%). UPLC/MS, M+(ESI): 230.9, M−(ESI): 228.8. $^1$H NMR (DMSO-d$_6$, 300 MHz) δ 9.49 (s, 1H), 8.27 (d, J=2.0 Hz, 1H), 7.79 (d, J=2.0 Hz, 1H), 6.53 (t, J=5.4 Hz, 1H), 5.79 (s, 2H), 4.74 (t, J=5.3 Hz, 1H), 3.57-3.41 (m, 4H).

Example 1 tert-butyl N-(5-{5-[2-(methoxymethyl)-2'-methylbiphenyl-4-yl]-1,2,4-oxadiazol-3-yl}pyridin-2-yl)-beta-alaninate

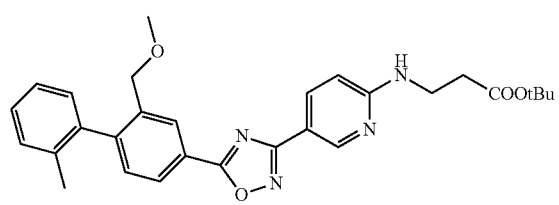

A solution of Intermediate A1 (100 mg, 0.39 mmol) was prepared in anhydrous DMF (2 mL) and cooled at 0° C. DIEA (0.13 mL, 0.78 mmol) and HATU (149 mg, 0.39 mmol) were added and the resulting mixture was stirred at 0° C. for 15 minutes. A solution of Intermediate B1 (100 mg, 0.36 mmol) in anhydrous DMF (1 mL) was added. The resulting mixture was stirred at 0° C. for 40 minutes, then heated at 80° C. for 15 additional hours. The reaction mixture was diluted with Et$_2$O (20 mL) and washed with water (2×10 mL) and brine (10 mL). The aqueous layers were extracted with Et$_2$O (10 mL). The organic layers were combined, dried (MgSO$_4$) and the solvents were removed under reduced pressure. After purification by flash chromatography (silica, heptane/EtOAc) and filtration through a NH$_2$ SPE column, the title compound was obtained as a colorless gummy oil. HPLC (Method A), Rt: 4.6 min (purity: 98.8%). UPLC/MS, M+(ESI): 501.3, M−(ESI): 499.3.

Example 2

N-(5-{5-[2-(methoxymethyl)-2'-methylbiphenyl-4-yl]-1,2,4-oxadiazol-3-yl}pyridin-2-yl)-beta-alanine, hydrochloride salt

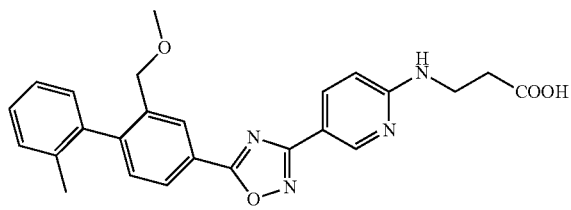 [SMILES: COCc1cc(-c2nc(-c3ccc(NCCC(=O)O)nc3)no2)ccc1-c1ccccc1C]

A solution of tert-butyl N-(5-{5-[2-(methoxymethyl)-2'-methylbiphenyl-4-yl]-1,2,4-oxadiazol-3-yl}pyridin-2-yl)-beta-alaninate (58 mg, 0.12 mmol) was prepared in a 4M solution of HCl in dioxane (1 mL) and stirred at RT for 15 hours. The reaction mixture was diluted with Et$_2$O (10 mL). The precipitate was filtered off, washed with Et$_2$O and pentane, and then dried under reduced pressure to give the title compound as a white powder (53 mg, 95%). HPLC (Method A), Rt: 3.8 min (purity: 97.5%). UPLC/MS, M+(ESI): 445.2, M−(ESI): 443.3. $^1$H NMR (DMSO-d$_6$, 300 MHz) δ 8.60 (s, 1H), 8.30 (d, J=1.7 Hz, 1H), 8.24 (d, J=9.1 Hz, 1H), 8.15 (dd, J=7.9, 1.7 Hz, 1H), 7.42 (d, J=7.9 Hz, 1H), 7.36 (m, 2H), 7.30 (m, 1H), 7.14 (d, J=7.1 Hz, 1H), 7.04 (d, J=9.1 Hz, 1H), 4.22 (d, J=12.7 Hz, 1H), 4.16 (d, J=12.7 Hz, 1H), 3.62 (m, 2H), 3.24 (s, 3H), 2.64 (t, J=6.5 Hz, 2H), 2.02 (s, 3H).

Example 3

N-(5-{5-[2-(methoxymethyl)-2'-methylbiphenyl-4-yl]-1,2,4-oxadiazol-3-yl}pyridin-2-yl)glycine, hydrochloride salt Step 1) tert-butyl N-(5-{5-[2-(methoxymethyl)-2'-methylbiphenyl-4-yl]-1,2,4-oxadiazol-3-yl}pyridin-2-yl)glycinate

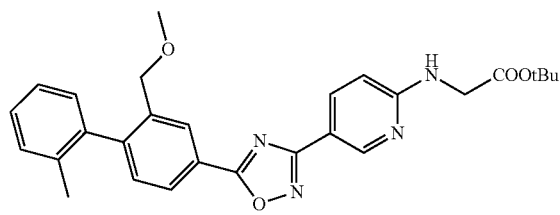

A solution of Intermediate A1 (133 mg, 0.50 mmol), Intermediate B2 (154 mg, 0.60 mmol) and EDC (115 mg, 0.60 mmol) was prepared in a mixture of anhydrous THF (2 mL) and anhydrous ACN (2 mL) and stirred at RT for 2 hours. DIEA (0.2 mL, 1.20 mmol) was added and the resulting mixture was heated at 150° C. for 30 minutes under microwave irradiation. The reaction mixture was concentrated under reduced pressure. The residue was taken up with DCM and filtered through a NH$_2$ SPE column. After evaporation, the residue was purified by flash chromatography (silica, EtOAc/heptane) to give the title compound as a colorless oil. HPLC (Method A), Rt: 4.7 min (purity: 97.2%). UPLC/MS, M+(ESI): 487.2, M−(ESI): 485.3.

Step 2) N-(5-{5-[2-(methoxymethyl)-2'-methylbiphenyl-4-yl]-1,2,4-oxadiazol-3-yl}pyridin-2-yl)glycine, hydrochloride salt

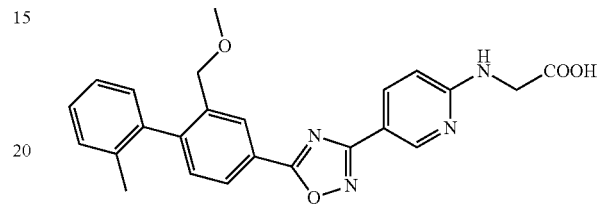

A solution of tert-butyl N-(5-{5-[2-(methoxymethyl)-2'-methylbiphenyl-4-yl]-1,2,4-oxadiazol-3-yl}pyridin-2-yl) glycinate (45 mg, 0.09 mmol) was prepared in a 4M solution of HCl in dioxane (1 mL) and stirred at RT for 15 hours. The reaction mixture was diluted with Et$_2$O (10 mL). The precipitate was filtered off, washed with Et$_2$O and pentane, and then dried under reduced pressure to give the title compound as a white powder (43 mg, 93%). HPLC (Method A), Rt: 3.8 min (purity: 98.1%). UPLC/MS, M+(ESI): 431.2, M−(ESI): 429.3. $^1$H NMR (DMSO-d$_6$, 300 MHz) δ 8.66 (s, 1H), 8.30 (s, 1H), 8.17 (m, 2H), 7.42 (d, J=7.9 Hz, 1H), 7.37-7.23 (m, 3H), 7.14 (d, J=7.4 Hz, 1H), 6.99 (d, J=8.6 Hz, 1H), 4.19 (m, 4H), 3.24 (s, 3H), 2.03 (s, 3H).

Example 4

5-{5-[2-(methoxymethyl)-2'-methylbiphenyl-4-yl]-1,2,4-oxadiazol-3-yl}pyridin-2-amine, hydrochloride salt

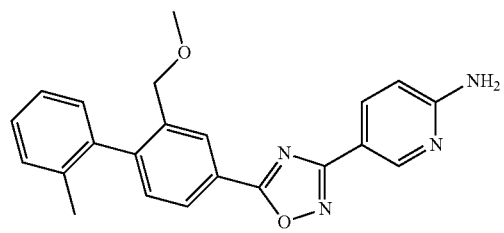 [SMILES: COCc1cc(-c2nc(-c3ccc(N)nc3)no2)ccc1-c1ccccc1C]

The title compound was prepared following procedure described in Method B starting from Intermediate A1 and 6-amino-N'-hydroxypyridine-3-carboximidamide (J. Med. Chem., 2007, 3442-3456). The parent compound was purified by precipitation from a toluene/heptane mixture (1:1), followed by a filtration through a NH$_2$ SPE column (10 g, DCM as eluent). The hydrochloride salt was obtained by crystallization from EtOH after addition of a 1M solution of HCl in Et$_2$O. The title compound was obtained as an off-white powder. HPLC (Method A), Rt: 3.8 min (purity: 99.8%). UPLC/MS, M+(ESI): 373.3. $^1$H NMR (DMSO-d$_6$, 300 MHz) δ 8.67 (d, J=2.0 Hz, 1H), 8.40 (dd, J=9.3, 2.0 Hz, 1H), 8.30 (d, J=1.8 Hz, 1H), 8.14 (dd, J=7.9, 1.8 Hz, 1H), 7.42 (d, J=7.9 Hz, 1H), 7.35 (m, 2H), 7.29 (m, 1H), 7.17 (d, J=9.3 Hz, 1H), 7.13 (d, J=7.1 Hz, 1H), 4.21 (d, J=12.8 Hz, 1H), 4.15 (d, J=12.8 Hz, 1H), 3.24 (s, 3H), 2.02 (s, 3H).

Example 5

N-(5-{5-[2-(methoxymethyl)-2'-methylbiphenyl-4-yl]-1,2,4-oxadiazol-3-yl}pyridin-2-yl)acetamide, hydrochloride salt

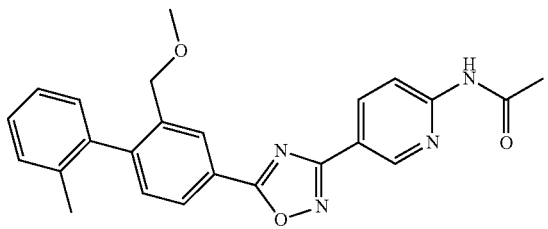 [SMILES: COCc1cc(-c2nc(-c3ccc(NC(C)=O)nc3)no2)ccc1-c1ccccc1C]

Acetic anhydride (0.08 mL, 0.81 mmol) was added into a solution of 5-{5-[2-(methoxymethyl)-2'-methylbiphenyl-4-yl]-1,2,4-oxadiazol-3-yl}pyridin-2-amine (60 mg, 0.16 mmol) in anhydrous pyridine (0.6 mL). The resulting mixture was stirred at RT for 6 days. The reaction mixture was diluted with water (5 mL) and stirred at RT for 2 hours, and then extracted with Et₂O (2×10 mL). The organic layers were combined, dried (MgSO₄) and the solvents were removed under reduced pressure. The residue was taken up with toluene and evaporated to remove pyridine traces. The crude compound was taken up with Et₂O (3 mL) and a 1M solution of HCl in Et₂O (0.5 mL) was added. The precipitate was filtered off, washed with Et₂O and pentane, and then dried under reduced pressure to give the title compound as an off-white powder. HPLC (Method A), Rt: 4.8 min (purity: 98.2%). UPLC/MS, M+(ESI): 415.2, M−(ESI): 413.2. ¹H NMR (DMSO-d₆, 300 MHz) δ 10.94 (s, 1H), 9.01 (d, J=2.3 Hz, 1H), 8.45 (dd, J=8.8, 2.3 Hz, 1H), 8.31 (d, J=1.8 Hz, 1H), 8.29 (d, J=8.8 Hz, 1H), 8.16 (dd, J=7.9, 1.8 Hz, 1H), 7.42 (d, J=7.9 Hz, 1H), 7.35 (m, 2H), 7.29 (m, 1H), 7.14 (d, J=7.1 Hz, 1H), 4.22 (d, J=12.7 Hz, 1H), 4.16 (d, J=12.7 Hz, 1H), 3.24 (s, 3H), 2.15 (s, 3H), 2.02 (s, 3H).

Example 6

4-{5-[2-(methoxymethyl)-2'-methylbiphenyl-4-yl]-1,2,4-oxadiazol-3-yl}-N,N-dimethylpyridin-2-amine, hydrochloride salt

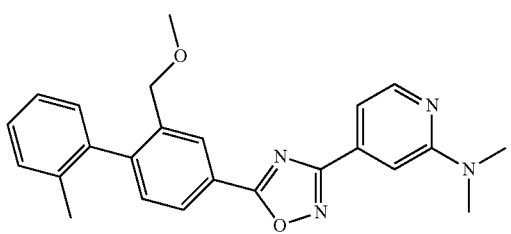 [SMILES: COCc1cc(-c2nc(-c3ccnc(N(C)C)c3)no2)ccc1-c1ccccc1C]

A mixture of Intermediate A6 (480 mg, 1.75 mmol) and 2-(dimethylamino)-N'-hydroxypyridine-4-carboximidamide (315 mg, 1.75 mmol, WO2002079200) was prepared in anhydrous toluene (4.5 mL) and anhydrous pyridine (1.5 mL). The resulting mixture was stirred at RT for 1 hour, and then refluxed for 15 additional hours. The reaction mixture was diluted with EtOAc (50 mL) and washed with a saturated aqueous solution of NH₄Cl (3×50 mL). The organic layer was dried (MgSO₄) and the solvents were removed under reduced pressure. Purification by flash chromatography (silica, EtOAc/cHex), followed by a filtration through a NH₂ SPE column (1 g, DCM as eluent), gave the parent compound as a yellow oil. This oil was taken up in DCM/Et₂O and a 1M solution of HCl in Et₂O was added. The precipitate was filtered off, washed with Et₂O and pentane, and then dried under reduced pressure to give the title compound as a pale yellow powder. HPLC (Method A), Rt: 4.5 min (purity: 97.9%). UPLC/MS, M+(ESI): 401.2. ¹H NMR (DMSO-d₆, 300 MHz) δ 8.33 (s, 1H), 8.21 (m, 2H), 7.60 (s, 1H), 7.44 (d, J=7.9 Hz, 1H), 7.39-7.24 (m, 4H), 7.14 (d, J=7.0 Hz, 1H), 4.22 (d, J=12.7 Hz, 1H), 4.16 (d, J=12.7 Hz, 1H), 3.31 (s, 6H), 3.24 (s, 3H), 2.03 (s, 3H).

Example 7

N-(4-{5-[2-(methoxymethyl)-2'-methylbiphenyl-4-yl]-1,2,4-oxadiazol-3-yl}pyridin-2-yl)-beta-alanine, hydrochloride salt Step 1) tert-butyl N-(4-{5-[2-(methoxymethyl)-2'-methylbiphenyl-4-yl]-1,2,4-oxadiazol-3-yl}pyridin-2-yl)-beta-alaninate

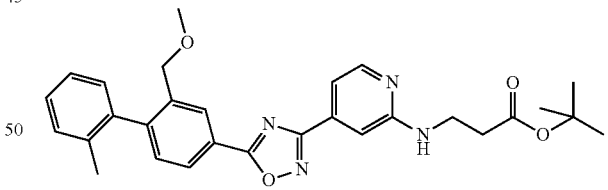

The title compound was prepared following procedure described in Method B starting from Intermediate A1 and Intermediate B3. After purification by flash chromatography (silica, DCM/MeOH), followed by a second chromatography (silica, EtOAc/cHex), the title compound was obtained as a colorless oil. HPLC (Method A), Rt: 4.5 min (purity: 98.1%). UPLC/MS, M+(ESI): 501.3, M−(ESI): 499.4. ¹H NMR (DMSO-d₆, 300 MHz) δ 8.31 (d, J=1.8 Hz, 1H), 8.19 (d, J=5.3 Hz, 1H), 8.14 (dd, J=7.9, 1.8 Hz, 1H), 7.42 (d, J=7.9 Hz, 1H), 7.36 (m, 2H), 7.29 (m, 1H), 7.24 (s, 1H), 7.14 (d, J=7.2

Hz, 1H), 7.09 (m, 2H), 4.22 (d, J=12.9 Hz, 1H), 4.16 (d, J=12.9 Hz, 1H), 3.53 (m, 2H), 3.25 (s, 3H), 2.50 (m, 2H), 2.03 (s, 3H), 1.40 (s, 9H).

Step 2) N-(4-{5-[2-(methoxymethyl)-2'-methylbiphenyl-4-yl]-1,2,4-oxadiazol-3-yl}pyridin-2-yl)-beta-alanine, hydrochloride salt

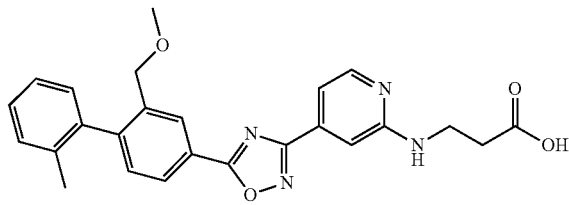 [SMILES: COCc1cc(-c2nc(-c3ccnc(NCCC(=O)O)c3)no2)ccc1-c1ccccc1C]

A solution of tert-butyl N-(4-{5-[2-(methoxymethyl)-2'-methylbiphenyl-4-yl]-1,2,4-oxadiazol-3-yl}pyridin-2-yl)-beta-alaninate (90 mg, 0.18 mmol) was prepared in a 4M solution of HCl in dioxane (1 mL) and stirred at RT for 6 hours. The reaction mixture was concentrated under reduced pressure. The residue was purified by flash chromatography (silica, DCM/MeOH) to give an oil. The oil was taken up in a 4M solution of HCl in dioxane and the resulting mixture was evaporated under reduced pressure. The residue was taken up with Et$_2$O to give a precipitate. The precipitate was filtered off and dried under reduced pressure to give the title compound as a white powder. HPLC (Method A), Rt: 4.4 min (purity: 98.1%). UPLC/MS, M+(ESI): 445.2, M−(ESI): 443.3. $^1$H NMR (DMSO-d$_6$, 300 MHz) δ 8.32 (s, 1H), 8.14 (m, 2H), 7.65 (s, 1H), 7.44 (d, J=8.0 Hz, 1H), 7.36 (m, 2H), 7.30 (m, 2H), 7.14 (d, J=7.3 Hz, 1H), 4.23 (d, J=12.8 Hz, 1H), 4.15 (d, J=12.8 Hz, 1H), 3.61 (m, 2H), 3.26 (s, 3H), 2.64 (t, J=6.3 Hz, 2H), 2.03 (s, 3H).

Example 8

4-[(5-{5-[2-(methoxymethyl)-2'-methylbiphenyl-4-yl]-1,2,4-oxadiazol-3-yl}pyridin-2-yl)amino]butanoic acid, hydrochloride salt Step 1) tert-butyl 4-[(5-{5-[2-(methoxymethyl)-2'-methylbiphenyl-4-yl]-1,2,4-oxadiazol-3-yl}pyridin-2-yl)amino]butanoate

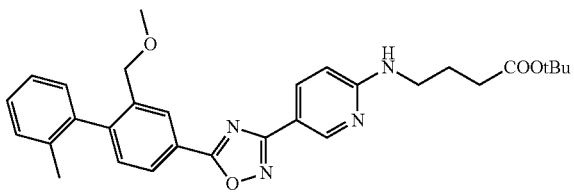

The title compound was prepared following procedure described in Method B starting from Intermediate A1 and Intermediate B4. After purification by flash chromatography (silica, EtOAc/cHex), the title compound was obtained as a colorless oil. HPLC (Method A), Rt: 4.6 min (purity: 98.4%). UPLC/MS, M+(ESI): 515.3. $^1$H NMR (DMSO-d$_6$, 300 MHz) δ 8.70 (d, J=2.4 Hz, 1H), 8.28 (d, J=1.8 Hz, 1H), 8.13 (dd, J=7.9, 1.8 Hz, 1H), 7.98 (dd, J=8.9, 2.4 Hz, 1H), 7.41 (d, J=7.9 Hz, 1H), 7.36-7.26 (m, 4H), 7.14 (d, J=7.3 Hz, 1H), 6.63 (d, J=8.9 Hz, 1H), 4.22 (d, J=12.6 Hz, 1H), 4.16 (d, J=12.6 Hz, 1H), 3.32 (m, 2H), 3.24 (s, 3H), 2.30 (t, J=7.5 Hz, 2H), 2.03 (s, 3H), 1.77 (m, 2H), 1.40 (s, 9H).

Step 2) 4-[(5-{5-[2-(methoxymethyl)-2'-methylbiphenyl-4-yl]-1,2,4-oxadiazol-3-yl}pyridin-2-yl)amino]butanoic acid, hydrochloride salt

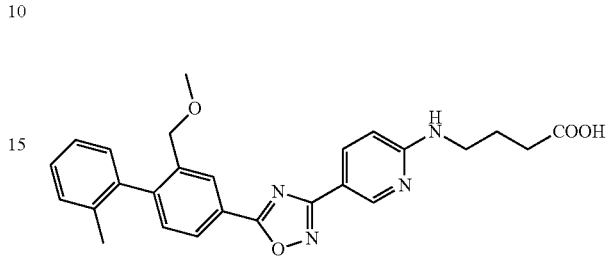

A solution of tert-butyl 4-[(5-{5-[2-(methoxymethyl)-2'-methylbiphenyl-4-yl]-1,2,4-oxadiazol-3-yl}pyridin-2-yl)amino]butanoate (90 mg, 0.17 mmol) was prepared in a 4M solution of HCl in dioxane (1 mL) and stirred at RT for 8 hours. The reaction mixture was diluted with Et$_2$O. The precipitate was filtered off and dried under reduced pressure to give the title compound as a white powder (60 mg, 75%). HPLC (Method A), Rt: 4.4 min (purity: 99.7%). UPLC/MS, M+(ESI): 459.2, M−(ESI): 457.3. $^1$H NMR (DMSO-d$_6$, 300 MHz) δ 8.57 (s, 1H), 8.30 (d, J=1.8 Hz, 1H), 8.26 (d, J=9.1 Hz, 1H), 8.15 (dd, J=7.9, 1.8 Hz, 1H), 7.42 (d, J=7.9 Hz, 1H), 7.35 (m, 2H), 7.29 (m, 1H), 7.14 (d, J=7.0 Hz, 1H), 7.05 (d, J=9.1 Hz, 1H), 4.22 (d, J=12.7 Hz, 1H), 4.16 (d, J=12.7 Hz, 1H), 3.44 (t, J=6.5 Hz, 2H), 3.24 (s, 3H), 2.38 (t, J=7.4 Hz, 2H), 2.03 (s, 3H), 1.85 (m, 2H).

Example 9

5-{5-[3-(methoxymethyl)-4-(2-methylpiperidin-1-yl)phenyl]-1,2,4-oxadiazol-3-yl}pyridin-2-amine

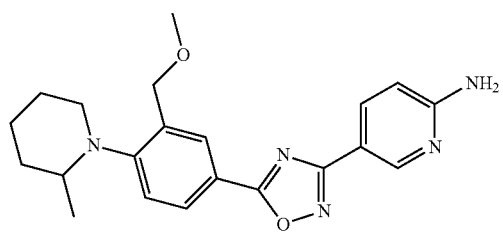 [SMILES: COCc1cc(-c2nc(-c3ccc(N)nc3)no2)ccc1N1CCCCC1C]

The title compound was prepared following procedure described in Method B starting from Intermediate A2 and 6-amino-N'-hydroxypyridine-3-carboximidamide (J. Med. Chem., 2007, 3442-3456). After purification by filtration through a SPE NH$_2$ column (2 g, DCM as eluent), followed by precipitation from iPr$_2$O, the title compound was obtained as a white powder. HPLC (Method A), Rt: 2.2 min (purity: 98.9%). UPLC/MS, M+(ESI): 380.3. $^1$H NMR (CDCl$_3$, 300 MHz) δ 8.89 (dd, J=2.2, 0.7 Hz, 1H), 8.31 (d, J=2.1 Hz, 1H), 8.18 (dd, J=8.6, 2.2 Hz, 1H), 8.08 (dd, J=8.4, 2.1 Hz, 1H), 7.25 (d, J=8.4 Hz, 1H), 6.60 (dd, J=8.6, 0.7 Hz, 1H), 4.80 (s, 2H), 4.66 (d, J=12.4 Hz, 1H), 4.58 (d, J=12.4 Hz, 1H), 3.49 (s, 3H), 3.16 (m, 1H), 3.03 (m, 1H), 2.64 (m, 1H), 1.89-1.66 (m, 4H), 1.56-1.43 (m, 2H), 0.89 (d, J=6.2 Hz, 3H).

Example 10 tert-butyl N-(4-{5-[2-(methoxymethyl)-2'-methylbiphenyl-4-yl]-1,2,4-oxadiazol-3-yl}pyridin-2-yl)glycinate

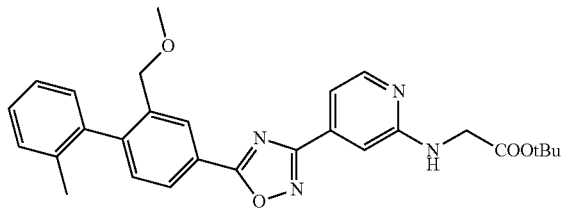

A mixture of Intermediate A6 (155 mg, 0.56 mmol) and Intermediate B5 (150 mg, 0.56 mmol) was prepared in anhydrous toluene (2.25 mL) and anhydrous pyridine (0.75 mL). The resulting mixture was stirred at RT for 3 hours, and then refluxed for 24 additional hours. The reaction mixture was diluted with EtOAc (50 mL) and washed with a saturated aqueous solution of NH$_4$Cl (3×50 mL). The organic layer was dried (MgSO$_4$) and the solvents were removed under reduced pressure. After purification by flash chromatography (silica, DCM/MeOH), the title compound was obtained as a brown oil. HPLC (Method A), Rt: 5.2 min (purity: 87.2%). UPLC/MS, M+(ESI): 487.2. $^1$H NMR (DMSO-d$_6$, 300 MHz) δ 8.32 (d, J=1.8 Hz, 1H), 8.16 (m, 2H), 7.43 (d, J=7.9 Hz, 1H), 7.39-7.26 (m, 5H), 7.14 (m, 2H), 4.22 (d, J=12.8 Hz, 1H), 4.16 (d, J=12.8 Hz, 1H), 3.99 (d, J=6.2 Hz, 2H), 3.24 (s, 3H), 2.03 (s, 3H), 1.41 (s, 9H).

Example 11

N-(4-{5-[2-(methoxymethyl)-2'-methylbiphenyl-4-yl]-1,2,4-oxadiazol-3-yl}pyridin-2-yl)glycine, hydrochloride salt

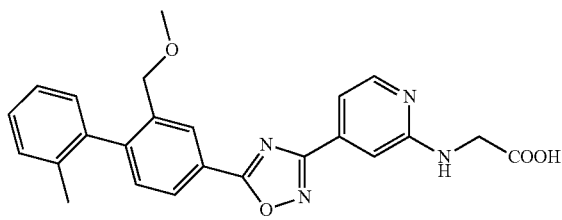 [SMILES: COCc1cc(-c2nc(-c3ccnc(NCC(=O)O)c3)no2)ccc1-c1ccccc1C]

A solution of tert-butyl N-(4-{5-[2-(methoxymethyl)-2'-methylbiphenyl-4-yl]-1,2,4-oxadiazol-3-yl}pyridin-2-yl)glycinate (145 mg, 0.30 mmol) was prepared in a 4M solution of HCl in dioxane (2 mL) and stirred at RT for 72 hours. The reaction mixture was concentrated under reduced pressure. The residue was purified by flash chromatography (silica, DCM/MeOH) to give a pale yellow oil. The oil was taken up in dioxane and a 1M solution of HCl in Et$_2$O was added. The precipitate was filtered off to give the title compound as a pale green powder. HPLC (Method A), Rt: 4.3 min (purity: 93.6%). UPLC/MS, M+(ESI): 431.3, M−(ESI): 429.3. $^1$H NMR (DMSO-d$_6$, 300 MHz) δ 8.33 (s, 1H), 8.16 (m, 2H), 7.75 (s, 1H), 7.44 (d, J=7.9 Hz, 1H), 7.40-7.25 (m, 4H), 7.14 (d, J=7.3 Hz, 1H), 4.28-4.12 (m, 4H), 3.25 (s, 3H), 2.03 (s, 3H).

Example 12

5-{5-[2'-ethyl-2-(methoxymethyl)biphenyl-4-yl]-1,2,4-oxadiazol-3-yl}pyridin-2-amine, hydrochloride salt

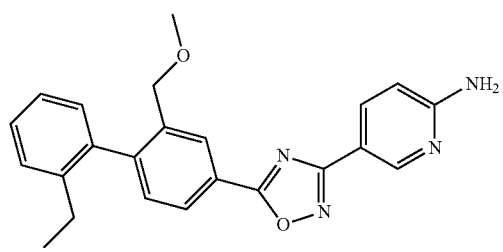 [SMILES: CCc1ccccc1-c1ccc(-c2nc(-c3ccc(N)nc3)no2)cc1COC]

The title compound was prepared following procedure described in Method B starting from Intermediate A3 and 6-amino-N'-hydroxypyridine-3-carboximidamide (J. Med. Chem., 2007, 3442-3456). The parent compound was purified by flash chromatography (silica, DCM/MeOH). The hydrochloride salt was obtained by precipitation from Et$_2$O (5 mL) after addition of a 1M solution of HCl in Et$_2$O (2 mL). The title compound was obtained as a white powder. HPLC (Method A), Rt: 4.1 min (purity: 100%). UPLC/MS, M+(ESI): 387.3. $^1$H NMR (DMSO-d$_6$, 300 MHz) δ 8.68 (d, J=2.0 Hz, 1H), 8.40 (dd, J=9.2, 2.0 Hz, 1H), 8.30 (d, J=1.6 Hz, 1H), 8.14 (dd, J=7.9, 1.6 Hz, 1H), 7.44 (d, J=7.9 Hz, 1H), 7.40 (m, 2H), 7.29 (m, 1H), 7.13 (d, J=9.2 Hz, 1H), 7.11 (d, J=7.2 Hz, 1H), 4.22 (d, J=12.8 Hz, 1H), 4.13 (d, J=12.8 Hz, 1H), 3.25 (s, 3H), 2.46-2.21 (m, 2H), 0.98 (t, J=7.5 Hz, 3H).

Example 13

2,3-dichloro-5-{5-[2-(methoxymethyl)-2'-methylbiphenyl-4-yl]-1,2,4-oxadiazol-3-yl}pyridine

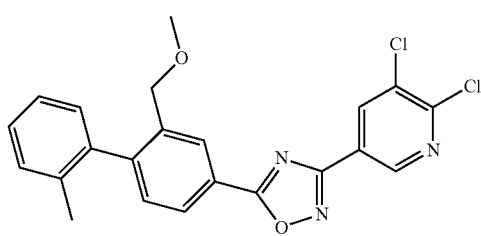 [SMILES: COCc1cc(-c2nc(-c3cnc(Cl)c(Cl)c3)no2)ccc1-c1ccccc1C]

The title compound was prepared following procedure described in Method B starting from Intermediate A1 and 5,6-dichloro-N'-hydroxypyridine-3-carboximidamide (WO2000015637). The title compound was obtained as a white powder. HPLC (Method A), Rt: 6.7 min (purity: 95.0%). UPLC/MS, M+(ESI): 426.1. $^1$H NMR (DMSO-d$_6$, 300 MHz) δ 9.08 (d, J=2.1 Hz, 1H), 8.72 (d, J=2.1 Hz, 1H), 8.34 (d, J=1.8 Hz, 1H), 8.19 (dd, J=7.9, 1.8 Hz, 1H), 7.44 (d, J=7.9 Hz, 1H), 7.36 (m, 2H), 7.30 (m, 1H), 7.15 (d, J=7.1 Hz, 1H), 4.23 (d, J=12.7 Hz, 1H), 4.16 (d, J=12.7 Hz, 1H), 3.25 (s, 3H), 2.03 (s, 3H).

Example 14

3-chloro-5-{5-[2-(methoxymethyl)-2'-methylbiphenyl-4-yl]-1,2,4-oxadiazol-3-yl}pyridin-2-amine

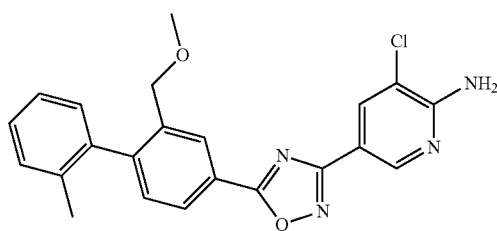

The title compound was prepared following procedure described in Method B starting from Intermediate A1 and Intermediate B6. After purification by precipitation from toluene, the title compound was obtained as a white powder. HPLC (Method A), Rt: 5.3 min (purity: 99.6%). UPLC/MS, M+(ESI): 407.2. $^1$H NMR (DMSO-d$_6$, 300 MHz) δ 8.64 (d, J=1.9 Hz, 1H), 8.29 (s, 1H), 8.14 (m, 2H), 7.41 (d, J=7.9 Hz, 1H), 7.35 (m, 2H), 7.29 (m, 1H), 7.14 (d, J=7.2 Hz, 1H), 7.10 (s, 2H), 4.21 (d, J=12.6 Hz, 1H), 4.15 (d, J=12.6 Hz, 1H), 3.24 (s, 3H), 2.03 (s, 3H).

Example 15

4-{5-[2-(methoxymethyl)-2'-methylbiphenyl-4-yl]-1,2,4-oxadiazol-3-yl}pyridin-2-amine, hydrochloride salt

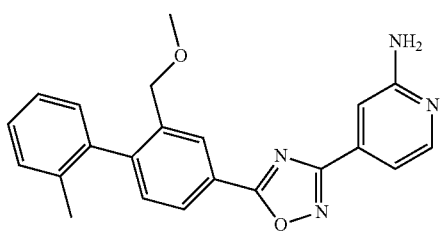 [SMILES: COCc1cc(-c2nc(-c3ccnc(N)c3)no2)ccc1-c1ccccc1C]

The title compound was prepared following procedure described in Method B starting from Intermediate A1 and Intermediate B7. The parent compound was purified by flash chromatography (silica, EtOAc/cHex). The hydrochloride salt was obtained by precipitation from Et$_2$O/DCM after addition of a 1M solution of HCl in Et$_2$O. The title compound was obtained as a white powder. HPLC (Method A), Rt: 3.9 min (purity: 98%). UPLC/MS, M+(ESI): 373.3. $^1$H NMR (DMSO-d$_6$, 300 MHz) δ 8.32 (s, 1H), 8.16 (m, 2H), 7.74 (s, 1H), 7.45 (d, J=8.0 Hz, 1H), 7.40-7.26 (m, 4H), 7.14 (d, J=7.2 Hz, 1H), 4.23 (d, J=12.9 Hz, 1H), 4.16 (d, J=12.9 Hz, 1H), 3.26 (s, 3H), 2.03 (s, 3H).

Example 16

5-{5-[2-(methoxymethyl)-2'-methylbiphenyl-4-yl]-1,2,4-oxadiazol-3-yl}pyrazin-2-amine

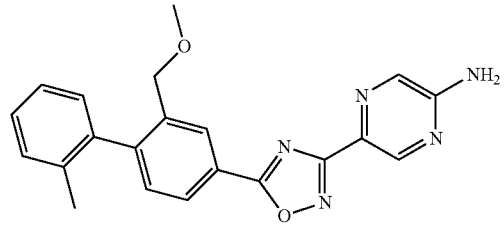

The title compound was prepared following procedure described in Method B starting from Intermediate A1 and Intermediate B8. After purification by precipitation from Et$_2$O/toluene, the title compound was obtained as a brown powder. HPLC (Method A), Rt: 4.3 min (purity: 99.5%). UPLC/MS, M+(ESI): 374.3, M−(ESI): 372.3. $^1$H NMR (DMSO-d$_6$, 300 MHz) δ 8.66 (d, J=1.4 Hz, 1H), 8.30 (d, J=1.9 Hz, 1H), 8.14 (dd, J=7.9, 1.9 Hz, 1H), 8.05 (d, J=1.4 Hz, 1H), 7.41 (d, J=7.9 Hz, 1H), 7.35 (m, 2H), 7.29 (m, 1H), 7.23 (s, 2H), 7.14 (d, J=7.0 Hz, 1H), 4.22 (d, J=12.7 Hz, 1H), 4.15 (d, J=12.7 Hz, 1H), 3.24 (s, 3H), 2.03 (s, 3H).

Example 17

5-{5-[2-(methoxymethyl)-2'-methylbiphenyl-4-yl]-1,2,4-oxadiazol-3-yl}pyrimidin-2-amine

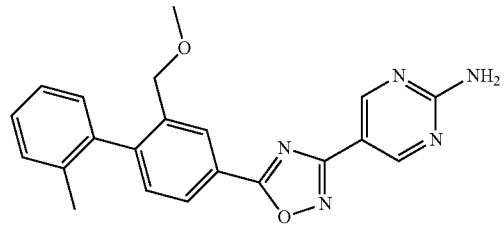 [SMILES: COCc1cc(-c2nc(-c3cnc(N)nc3)no2)ccc1-c1ccccc1C]

The title compound was prepared following procedure described in Method B starting from Intermediate A1 and Intermediate B9. After purification by precipitation from DCM/MeOH, the title compound was obtained as a white powder. HPLC (Method A), Rt: 4.5 min (purity: 98.1%). UPLC/MS, M+(ESI): 374.3. $^1$H NMR (DMSO-d$_6$, 300 MHz) δ 8.88 (s, 2H), 8.29 (d, J=1.7 Hz, 1H), 8.14 (dd, J=7.9, 1.7 Hz, 1H), 7.42-7.26 (m, 6H), 7.14 (d, J=7.1 Hz, 1H), 4.21 (d, J=12.7 Hz, 1H), 4.15 (d, J=12.7 Hz, 1H), 3.24 (s, 3H), 2.03 (s, 3H).

Example 18

5-{5-[2-(methoxymethyl)-2'-methylbiphenyl-4-yl]-1,2,4-oxadiazol-3-yl}-3-methylpyridin-2-amine, hydrochloride salt

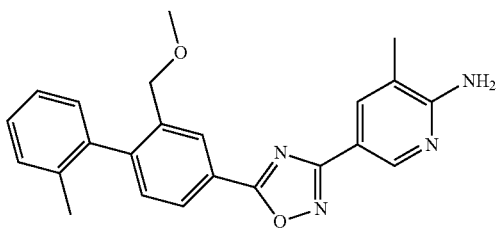 [SMILES: COCc1cc(-c2nc(-c3cnc(N)c(C)c3)no2)ccc1-c1ccccc1C]

The title compound was prepared following procedure described in Method B starting from Intermediate A1 and Intermediate B10. The parent compound was purified by flash chromatography (silica, EtOAc/cHex). The hydrochloride salt was obtained by precipitation from Et₂O/DCM after addition of a 1M solution of HCl in Et₂O. The title compound was obtained as a white powder. HPLC (Method A), Rt: 4.0 min (purity: 99.5%). UPLC/MS, M+(ESI): 387.3. ¹H NMR (DMSO-d₆, 300 MHz) δ 8.59 (d, J=1.7 Hz, 1H), 8.30 (m, 2H), 8.15 (dd, J=7.9, 1.8 Hz, 1H), 7.43 (d, J=7.9 Hz, 1H), 7.36 (m, 2H), 7.29 (m, 1H), 7.14 (d, J=7.1 Hz, 1H), 4.22 (d, J=12.8 Hz, 1H), 4.16 (d, J=12.8 Hz, 1H), 3.25 (s, 3H), 2.29 (s, 3H), 2.03 (s, 3H).

Example 19

5-{5-[2'-methyl-2-(trifluoromethyl)biphenyl-4-yl]-1,2,4-oxadiazol-3-yl}pyridin-2-amine

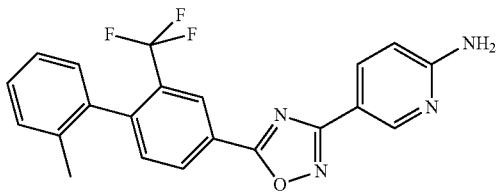 [SMILES: Cc1ccccc1-c1ccc(-c2nc(-c3ccc(N)nc3)no2)cc1C(F)(F)F]

The title compound was prepared following procedure described in Method B starting from Intermediate A4 and 6-amino-N'-hydroxypyridine-3-carboximidamide (J. Med. Chem., 2007, 3442-3456). After purification by flash chromatography (silica, EtOAc/cHex), the title compound was obtained as a white powder. HPLC (Method A), Rt: 4.1 min (purity: 99.7%). UPLC/MS, M+(ESI): 397.2, M−(ESI): 395.3. ¹H NMR (DMSO-d₆, 300 MHz) δ 8.67 (dd, J=2.4, 0.7 Hz, 1H), 8.50 (d, J=1.5 Hz, 1H), 8.46 (dd, J=7.9, 1.5 Hz, 1H), 8.01 (dd, J=8.7, 2.4 Hz, 1H), 7.64 (d, J=7.9 Hz, 1H), 7.37 (m, 2H), 7.28 (m, 1H), 7.17 (d, J=7.4 Hz, 1H), 6.73 (s, 2H), 6.60 (dd, J=8.7, 0.7 Hz, 1H), 2.02 (s, 3H).

Example 20

5-{5-[4-(2-methylpiperidin-1-yl)-3-(trifluoromethyl)phenyl]-1,2,4-oxadiazol-3-yl}pyridin-2-amine

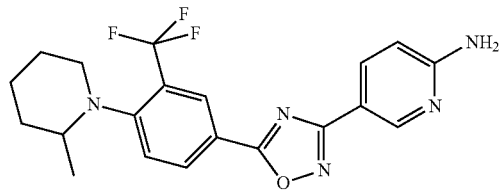 [SMILES: CC1CCCCN1c1ccc(-c2nc(-c3ccc(N)nc3)no2)cc1C(F)(F)F]

The title compound was prepared following procedure described in Method B starting from Intermediate A5 and 6-amino-N'-hydroxypyridine-3-carboximidamide (J. Med. Chem., 2007, 3442-3456). After purification by flash chromatography (silica, EtOAc/cHex), the title compound was obtained as a white powder. HPLC (Method A), Rt: 4.5 min (purity: 99.9%). UPLC/MS, M+(ESI): 404.3, M−(ESI): 402.4. ¹H NMR (CDCl₃, 300 MHz) δ 8.64 (dd, J=2.4, 0.6 Hz, 1H), 8.41 (dd, J=8.5, 2.0 Hz, 1H), 8.34 (d, J=2.0 Hz, 1H), 7.98 (dd, J=8.7, 2.4 Hz, 1H), 7.84 (d, J=8.5 Hz, 1H), 6.70 (s, 2H), 6.58 (dd, J=8.7, 0.6 Hz, 1H), 3.16 (m, 1H), 2.95 (m, 1H), 2.61 (m, 1H), 1.79 (m, 2H), 1.70-1.22 (m, 4H), 0.77 (d, J=6.1 Hz, 3H).

Example 21

5-{5-[2-(methoxymethyl)-2'-methylbiphenyl-4-yl]-1,2,4-oxadiazol-3-yl}pyridin-2-ol

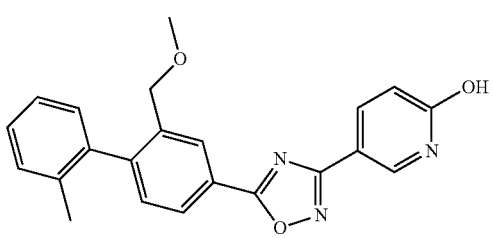 [SMILES: COCc1cc(-c2nc(-c3ccc(O)nc3)no2)ccc1-c1ccccc1C]

The title compound was prepared following procedure described in Method B starting from Intermediate A1 and Intermediate B11. After purification by precipitation from MeOH, the title compound was obtained as a pale pink powder. HPLC (Method A), Rt: 4.8 min (purity: 99.9%). UPLC/MS, M+(ESI): 374.2, M−(ESI): 372.3. ¹H NMR (DMSO-d₆, 300 MHz) δ 12.18 (s, 1H), 8.28 (d, J=1.9 Hz, 1H), 8.15 (d, J=2.6 Hz, 1H), 8.13 (dd, J=7.9, 1.9 Hz, 1H), 7.99 (dd, J=9.6, 2.6 Hz, 1H), 7.40 (d, J=7.9 Hz, 1H), 7.35 (m, 2H), 7.29 (m, 1H), 7.14 (d, J=7.1 Hz, 1H), 6.53 (d, J=9.6 Hz, 1H), 4.21 (d, J=12.7 Hz, 1H), 4.15 (d, J=12.7 Hz, 1H), 3.24 (s, 3H), 2.03 (s, 3H).

Example 22

5-{5-[3-(methoxymethyl)-4-(2-methylpiperidin-1-yl)phenyl]-1,2,4-oxadiazol-3-yl}pyridin-2-ol

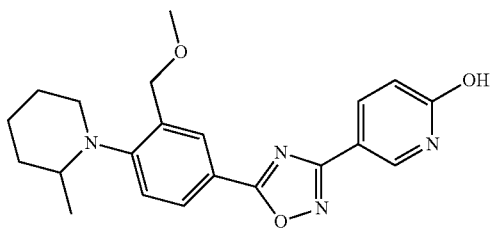 [SMILES: COCc1cc(-c2nc(-c3ccc(O)nc3)no2)ccc1N1CCCCC1C]

The title compound was prepared following procedure described in Method B starting from Intermediate A2 and Intermediate B11. After purification by precipitation from MeOH, the title compound was obtained as an orange powder. HPLC (Method A), Rt: 2.4 min (purity: 98.3%). UPLC/MS, M+(ESI): 381.4, M−(ESI): 379.4. $^1$H NMR (300 MHz, DMSO): δ 12.15 (s, 1H), 8.14 (d, J=2.2 Hz, 1H), 8.11 (d, J=2.6 Hz, 1H), 8.03 (dd, J=8.4, 2.2 Hz, 1H), 7.97 (dd, J=9.6, 2.6 Hz, 1H), 7.36 (d, J=8.4 Hz, 1H), 6.52 (d, J=9.6 Hz, 1H), 4.60-4.47 (m, 2H), 3.40 (s, 3H), 3.21 (m, 1H), 3.03 (m, 1H), 2.61 (m, 1H), 1.90-1.59 (m, 4H), 1.51-1.32 (m, 2H), 0.85 (d, J=6.1 Hz, 3H).

Example 23

2-methoxy-5-{5-[2-(methoxymethyl)-2'-methylbiphenyl-4-yl]-1,2,4-oxadiazol-3-yl}pyridine

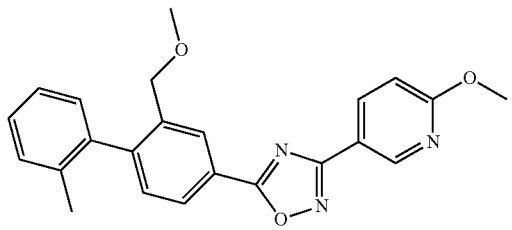 [SMILES: COCc1cc(-c2nc(-c3ccc(OC)nc3)no2)ccc1-c1ccccc1C]

The title compound was prepared following procedure described in Method B starting from Intermediate A1 and N'-hydroxy-6-methoxypyridine-3-carboximidamide (UkrOrgSynthesis BBV-066226). After purification by precipitation from MeOH, the title compound was obtained as a white powder. HPLC (Method A), Rt: 5.8 min (purity: 99.8%). UPLC/MS, M+(ESI): 388.3. $^1$H NMR (DMSO-$d_6$, 300 MHz) δ 8.91 (d, J=2.2 Hz, 1H), 8.34 (dd, J=8.7, 2.2 Hz, 1H), 8.31 (d, J=1.4 Hz, 1H), 8.16 (dd, J=7.9, 1.4 Hz, 1H), 7.42 (d, J=7.9 Hz, 1H), 7.36-7.26 (m, 3H), 7.14 (d, J=7.1 Hz, 1H), 7.06 (d, J=8.7 Hz, 1H), 4.22 (d, J=12.8 Hz, 1H), 4.16 (d, J=12.8 Hz, 1H), 3.96 (s, 3H), 3.24 (s, 3H), 2.03 (s, 3H).

Example 24 methyl 5-{5-[2-(methoxymethyl)-2'-methylbiphenyl-4-yl]-1,2,4-oxadiazol-3-yl}pyridine-2-carboxylate

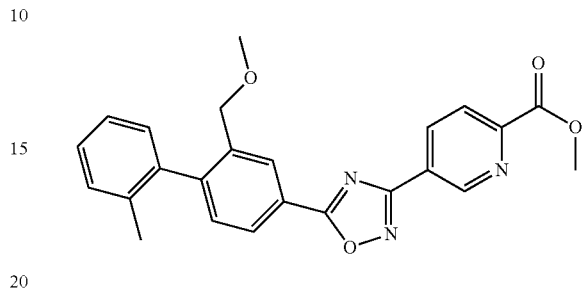

To a solution of Intermediate A1 (1.00 g, 3.9 mmol) in anhydrous toluene (15 mL) was added oxalyl chloride (0.50 mL, 5.9 mmol) and DMF (0.006 mL). The reaction mixture was stirred at RT for 1 hour, and then poured into a solution of Intermediate B12 (0.76 mg, 3.9 mmol) in toluene (15 mL) and pyridine (5 mL). The resulting mixture was stirred at RT for 1 hour, and then heated at reflux for 15 hours. The reaction mixture was concentrated under reduced pressure. The residue was taken up with EtOAc and washed with a 1M aqueous solution of HCl (3×). The organic layer was dried (MgSO$_4$) and the solvent was removed under reduced pressure. After purification by flash chromatography (silica, EtOAc/cHex), the title compound was obtained as a sticky foam. HPLC (Method A), Rt: 5.0 min (purity: 93.3%). UPLC/MS, M+(ESI): 416.3. $^1$H NMR (CDCl$_3$, 300 MHz) δ 9.54 (d, J=2.0 Hz, 1H), 8.65 (dd, J=8.2, 2.0 Hz, 1H), 8.45 (d, J=1.7 Hz, 1H), 8.31 (d, J=8.2 Hz, 1H), 8.20 (dd, J=7.9, 1.7 Hz, 1H), 7.36 (d, J=7.9 Hz, 1H), 7.33-7.24 (m, 3H), 7.13 (d, J=7.1 Hz, 1H), 4.24 (m, 2H), 4.07 (s, 3H), 3.34 (s, 3H), 2.08 (s, 3H).

Example 25

5-{5-[2-(methoxymethyl)-2'-methylbiphenyl-4-yl]-1,2,4-oxadiazol-3-yl}pyridine-2-carboxylic acid, hydrochloride salt

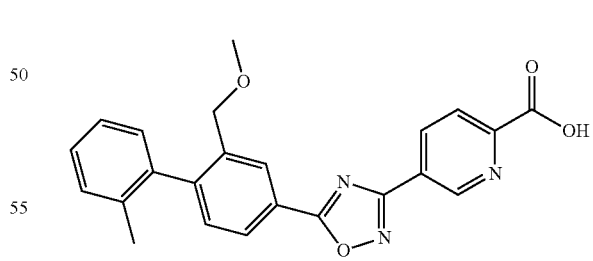

A 5N aqueous solution of NaOH (0.77 mL, 3.9 mmol) was added into a solution of methyl 5-{5-[2-(methoxymethyl)-2'-methylbiphenyl-4-yl]-1,2,4-oxadiazol-3-yl}pyridine-2-carboxylate (400 mg, 0.96 mmol) in MeOH (6 mL). The resulting mixture was stirred at RT for 1.5 hours. The reaction mixture was diluted with DCM and washed with a 1N aqueous solution of HCl (3×). The organic layer was dried (MgSO$_4$) and the solvents were removed under reduced pressure. The residue was taken up with Et$_2$O and an excess of a 1N solution of HCl in Et₂O was added. The precipitate was filtered off and dried under reduced pressure to give the title compound as a white powder (370 mg, 88%). HPLC (Method A), Rt: 5.0 min (purity: 94.7%). UPLC/MS, M+(ESI): 402.4. $^1$H NMR (DMSO-d$_6$, 300 MHz) δ 9.38 (d, J=2.1 Hz, 1H), 8.66 (dd, J=8.2, 2.1 Hz, 1H), 8.34 (d, J=1.8 Hz, 1H), 8.27 (d, J=8.2 Hz, 1H), 8.19 (dd, J=7.9, 1.8 Hz, 1H), 7.44 (d, J=7.9 Hz, 1H), 7.36 (m, 2H), 7.29 (m, 1H), 7.15 (d, J=7.0 Hz, 1H), 4.23 (d, J=12.7 Hz, 1H), 4.16 (d, J=12.7 Hz, 1H), 3.25 (s, 3H), 2.04 (s, 3H).

Example 26

5-{5-[2-(methoxymethyl)-2'-methylbiphenyl-4-yl]-1,2,4-oxadiazol-3-yl}pyridine-2-carboxamide

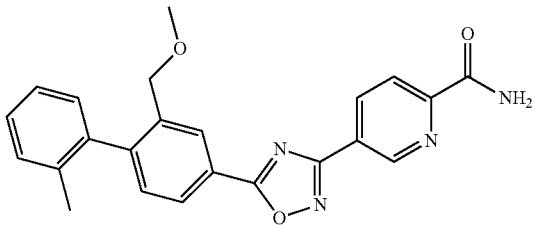 [SMILES: COCc1cc(-c2nc(-c3ccc(C(N)=O)nc3)no2)ccc1-c1ccccc1C]

To a solution of 5-{5-[2-(methoxymethyl)-2'-methylbiphenyl-4-yl]-1,2,4-oxadiazol-3-yl}pyridine-2-carboxylic acid hydrochloride (100 mg, 0.23 mmol) in anhydrous DCM (5 mL) was added oxalyl chloride (0.058 mL, 0.69 mmol) and DMF (1 drop). The resulting mixture was stirred at RT for 1 hour. The reaction mixture was concentrated under reduced pressure. The residue was taken up with anhydrous THF (2 mL) and a 0.5N solution of ammonia in dioxane (4.5 mL, 2.25 mmol) was added. The mixture was stirred at RT for 1 hour, and then concentrated under reduced pressure. The residue was taken up with Et₂O. The precipitate was filtered off, washed with Et₂O and dried under reduced pressure to give the title compound as a beige powder (88 mg, 96%). HPLC (Method A), Rt: 4.7 min (purity: 95.4%). UPLC/MS, M+(ESI): 401.2. $^1$H NMR (CD₃OD, 300 MHz) δ 9.41 (dd, J=2.1, 0.9 Hz, 1H), 8.71 (dd, J=8.2, 2.1 Hz, 1H), 8.44 (d, J=1.8 Hz, 1H), 8.31 (dd, J=8.2, 0.9 Hz, 1H), 8.24 (dd, J=7.9, 1.8 Hz, 1H), 7.41 (d, J=7.9 Hz, 1H), 7.34 (m, 2H), 7.28 (m, 1H), 7.13 (d, J=7.1 Hz, 1H), 4.24 (s, 2H), 3.32 (s, 3H), 2.09 (s, 3H).

Example 27

5-{5-[4-(2-ethylpiperidin-1-yl)-3-(methoxymethyl)phenyl]-1,2,4-oxadiazol-3-yl}pyridin-2-amine

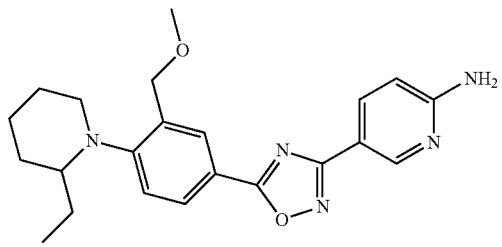 [SMILES: CCC1CCCCN1c1ccc(-c2nc(-c3ccc(N)nc3)no2)cc1COC]

The title compound was prepared following procedure described in Method B starting from Intermediate A7 and 6-amino-N'-hydroxypyridine-3-carboximidamide (J. Med. Chem., 2007, 3442-3456). After purification by flash chromatography (silica, EtOAc/cHex), the title compound was obtained as a white powder. HPLC (Method A), Rt: 2.6 min (purity: 100%). UPLC/MS, M+(ESI): 394.4. Elemental analysis: [C₂₂H₂₇N₅O₂.0.125EtOAc] calculated: C, 66.81%; H, 6.98%; N, 17.31%. found: C, 66.75%; H, 6.94%; N, 17.04%.

Example 28

2-[(5-{5-[2-(methoxymethyl)-2'-methylbiphenyl-4-yl]-1,2,4-oxadiazol-3-yl}pyridin-2-yl)amino]ethanol

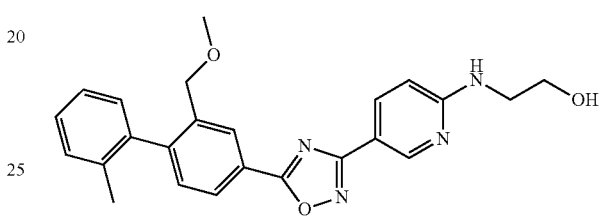

The title compound was prepared following procedure described in Method B starting from Intermediate A1 and Intermediate B13. After purification by crystallization from hot EtOH, the title compound was obtained as a white powder. HPLC (Method A), Rt: 3.7 min (purity: 98.6%). UPLC/MS, M+(ESI): 417.1, M−(ESI): 415.2. Elemental analysis: [C24H24N4O3-0.1C2H6O-0.1H2O] calculated: C, 68.73%; H, 5.91%; N, 13.25%. found: C, 68.68%; H, 5.93%; N, 13.24%. $^1$H NMR (DMSO-d$_6$, 300 MHz) δ 8.70 (d, J=2.3 Hz, 1H), 8.26 (d, J=1.8 Hz, 1H), 8.13 (dd, J=7.9, 1.8 Hz, 1H), 7.97 (dd, J=8.8, 2.3 Hz, 1H), 7.40 (d, J=7.9 Hz, 1H), 7.36-7.26 (m, 4H), 7.14 (d, J=7.1 Hz, 1H), 6.67 (d, J=8.8 Hz, 1H), 4.76 (t, J=5.4 Hz, 1H), 4.21 (d, J=12.7 Hz, 1H), 4.15 (d, J=12.7 Hz, 1H), 3.55 (m, 2H), 3.41 (m, 2H), 3.24 (s, 3H), 2.03 (s, 3H).

Example 29

5-{5-[2-(methoxymethyl)-2'-methylbiphenyl-4-yl]-1,2,4-oxadiazol-3-yl}-N-methylpyridin-2-amine

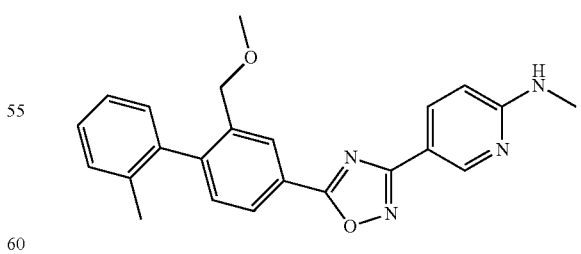

The title compound was prepared following procedure described in Method B starting from Intermediate A1 and Intermediate B14. After purification by flash chromatography (silica, EtOAc/heptane), the title compound was obtained as a white powder. HPLC (Method A), Rt: 3.9 min (purity: 99.9%). UPLC/MS, M+(ESI): 387.1. Elemental analysis:

[C₂₃H₂₂N₄O₂·0.2H₂O] calculated: C, 70.82%; H, 5.79%; N, 14.36%. found: C, 70.84%; H, 5.70%; N, 14.34%.

Example 30

5-{5-[2-(methoxymethyl)-2'-methylbiphenyl-4-yl]-1,2,4-oxadiazol-3-yl}-N,N-dimethylpyridin-2-amine

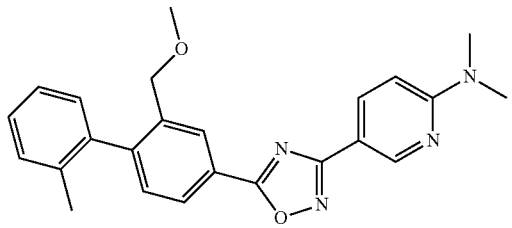 [SMILES: COCc1cc(-c2nc(-c3ccc(N(C)C)nc3)no2)ccc1-c1ccccc1C]

The title compound was prepared following procedure described in Method B starting from Intermediate A1 and 6-(dimethylamino)-N'-hydroxypyridine-3-carboximidamide (UkrOrgSynthesis, BBV-073023). After purification by flash chromatography (silica, EtOAc/cHex) followed by a crystallization from a hot mixture of MTBE and heptane, the title compound was obtained as a white powder. HPLC (Method A), Rt: 4.0 min (purity: 100%). UPLC/MS, M+(ESI): 401.1. Elemental analysis: [C₂₄H₂₄N₄O₂·0.1H₂O] calculated: C, 71.66%; H, 6.06%; N, 13.93%. found: C, 71.66%; H, 6.06%; N, 13.91%.

Example 31

5-{5-[2-(methoxymethyl)-2'-methylbiphenyl-4-yl]-1,2,4-oxadiazol-3-yl}-2-pyrrolidin-1-ylpyridine

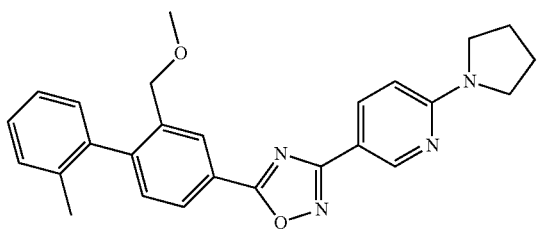 [SMILES: COCc1cc(-c2nc(-c3ccc(N4CCCC4)nc3)no2)ccc1-c1ccccc1C]

The title compound was prepared following procedure described in Method B starting from Intermediate A1 and N'-hydroxy-6-pyrrolidin-1-ylpyridine-3-carboximidamide (UkrOrgSynthesis, BBV-073346). After purification by flash chromatography (silica, EtOAc/cHex) followed by a crystallization from a mixture of MTBE and heptane, the title compound was obtained as an off-white powder. HPLC (Method A), Rt: 4.1 min (purity: 99%). UPLC/MS, M+(ESI): 417.1, M−(ESI): 415.2. Elemental analysis: [C₂₆H₂₆N₄O₂·0.2H₂O]

calculated: C, 72.60%; H, 6.19%; N, 13.03%. found: C, 72.68%; H, 6.45%; N, 13.05%.

Example 32

5-{5-[2'-chloro-2-(methoxymethyl)biphenyl-4-yl]-1,2,4-oxadiazol-3-yl}pyridin-2-amine

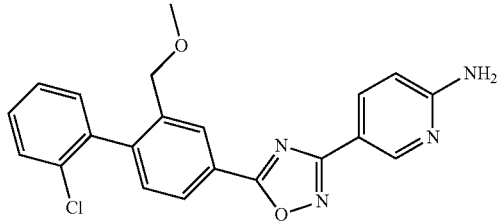

The title compound was prepared following procedure described in Method B starting from Intermediate A8 and 6-amino-N'-hydroxypyridine-3-carboximidamide (J. Med. Chem., 2007, 3442-3456). After purification by crystallization from EtOH, the title compound was obtained as an off-white powder. HPLC (Method A), Rt: 3.8 min (purity: 100%). UPLC/MS, M+(ESI): 393.0. Elemental analysis: [C₂₁H₁₇N₄O₂Cl] calculated: C, 64.21%; H, 4.36%; N, 14.26%; Cl, 9.02%. found: C, 64.11%; H, 4.40%; N, 14.23%; Cl 8.82%.

Example 33

5-{5-[3-(methoxymethyl)-4-(2-methylpyrrolidin-1-yl)phenyl]-1,2,4-oxadiazol-3-yl}pyridin-2-amine

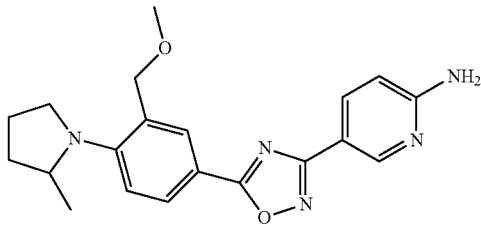 [SMILES: COCc1cc(-c2nc(-c3ccc(N)nc3)no2)ccc1N1CCCC1C]

The title compound was prepared following procedure described in Method B starting from Intermediate A9 and 6-amino-N'-hydroxypyridine-3-carboximidamide (J. Med. Chem., 2007, 3442-3456). After purification by flash chromatography (silica, EtOAc) followed by a crystallization from MeOH, the title compound was obtained as a pale beige powder. HPLC (Method A), Rt: 2.8 min (purity: 97.6%). UPLC/MS, M+(ESI): 366.1. Elemental analysis: [C₂₀

H$_{23}$N$_5$O$_2$] calculated: C, 65.74%; H, 6.34%; N, 19.16%. found: C, 65.41%; H, 6.29%; N, 19.08%.

Example 34

3-chloro-N-(2-methoxyethyl)-5-{5-[2-(methoxymethyl)-2'-methylbiphenyl-4-yl]-1,2,4-oxadiazol-3-yl}pyridin-2-amine

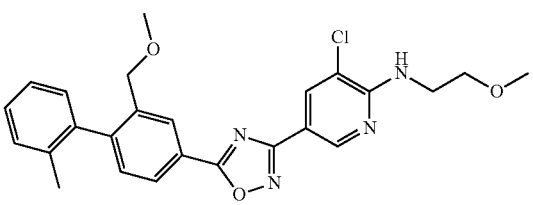 [SMILES: COCCNc1ncc(-c2noc(-c3ccc(-c4ccccc4C)c(COC)c3)n2)cc1Cl]

The title compound was prepared following procedure described in Method B starting from Intermediate A1 and Intermediate B15. After purification by crystallization from MTBE, the title compound was obtained as a pale beige powder (397 mg, 71%). HPLC (Method A), Rt: 5.8 min (purity: 99.9%). UPLC/MS, M+(ESI): 465.0. Elemental analysis: [C$_{25}$H$_{25}$N$_4$O$_3$Cl-0.4 H$_2$0] calculated: C, 63.60%; H, 5.51%; N, 11.87%; Cl 7.51%. found: C, 63.68%; H, 5.39%; N, 11.65%; Cl 7.42%. $^1$H NMR (DMSO-d$_6$, 300 MHz) δ 8.70 (d, J=1.9 Hz, 1H), 8.29 (d, J=1.5 Hz, 1H), 8.14 (m, 2H), 7.41 (d, J=8.0 Hz, 1H), 7.36-7.26 (m, 3H), 7.15 (m, 2H), 4.21 (d, J=12.7 Hz, 1H), 4.15 (d, J=12.7 Hz, 1H), 3.64 (m, 2H), 3.53 (t, J=5.7 Hz, 2H), 3.28 (s, 3H), 3.24 (s, 3H), 2.03 (s, 3H).

Example 35 tert-butyl N-(3-chloro-5-{5-[2-(methoxymethyl)-2'-methylbiphenyl-4-yl]-1,2,4-oxadiazol-3-yl}pyridin-2-yl)-beta-alaninate

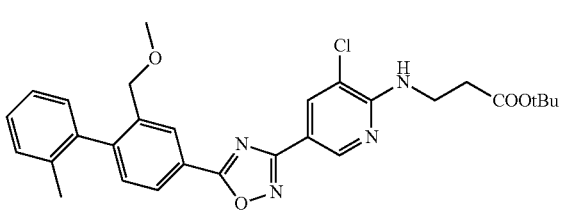

The title compound was prepared following procedure described in Method B starting from Intermediate A1 and Intermediate B16. After purification by flash chromatography (silica, EtOAc/cHex), the title compound was obtained as a colorless oil (454 mg, 71%). HPLC (Method A), Rt: 6.6 min (purity: 100%). UPLC/MS, M+(ESI): 535.1, M−(ESI): 533.3. $^1$H NMR (DMSO-d$_6$, 300 MHz) δ 8.72 (d, J=2.0 Hz, 1H), 8.29 (d, J=1.7 Hz, 1H), 8.14 (m, 2H), 7.41 (d, J=8.0 Hz, 1H), 7.36-7.26 (m, 3H), 7.21 (t, J=5.7 Hz, 1H), 7.14 (d, J=7.1 Hz, 1H), 4.21 (d, J=12.7 Hz, 1H), 4.15 (d, J=12.7 Hz, 1H), 3.68 (m, 2H), 3.24 (s, 3H), 2.57 (t, J=7.1 Hz, 2H), 2.03 (s, 3H), 1.39 (s, 9H).

Example 36 tert-butyl N-(3-chloro-5-{5-[2-(methoxymethyl)-2'-methylbiphenyl-4-yl]-1,2,4-oxadiazol-3-yl}pyridin-2-yl)glycinate

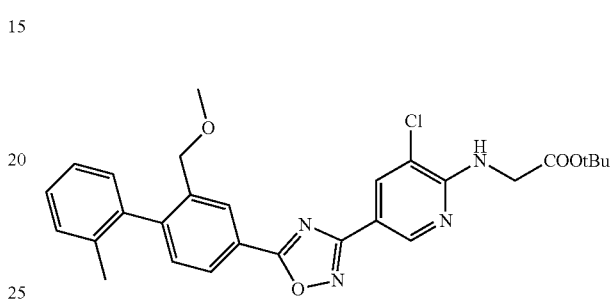

The title compound was prepared following procedure described in Method B starting from Intermediate A1 and Intermediate B17. After purification by flash chromatography (silica, EtOAc/cHex), the title compound was obtained as a colorless oil (504 mg, 81%). HPLC (Method A), Rt: 6.5 min (purity: 99.3%). UPLC/MS, M+(ESI): 521.0, M−(ESI): 519.2.

Example 37

N-(3-chloro-5-{5-[2-(methoxymethyl)-2'-methylbiphenyl-4-yl]-1,2,4-oxadiazol-3-yl}pyridin-2-yl)-beta-alanine, hydrochloride salt

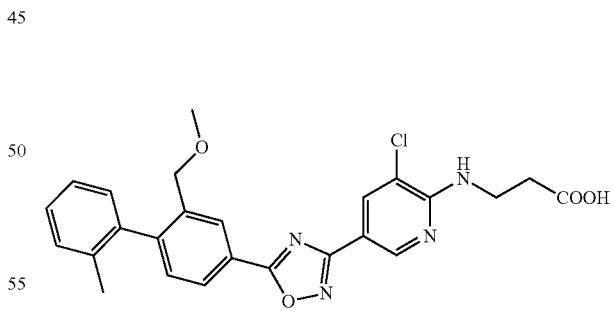

The title compound was prepared following procedure described in Method D starting from Example 35. After purification by crystallization from a mixture of ACN and water, the title compound was obtained as a white powder (885 mg, 81%). HPLC (Method A), Rt: 5.1 min (purity: 99.6%). UPLC/MS, M+(ESI): 479.2, M−(ESI): 477.2. Elemental analysis: [C$_{25}$H$_{23}$N$_4$O$_4$Cl-HCl] calculated: C, 58.26%; H, 4.69%; N, 10.87%; Cl, 13.76%. found: C, 58.02%; H, 4.81%; N, 10.94%; Cl, 13.57%. $^1$H NMR (DMSO-$d_6$, 300 MHz) δ 8.72 (d, J=2.0 Hz, 1H), 8.29 (d, J=1.4 Hz, 1H), 8.14 (m, 2H), 7.41 (d, J=7.9 Hz, 1H), 7.37-7.23 (m, 4H), 7.14 (d, J=7.0 Hz, 1H), 4.21 (d, J=12.7 Hz, 1H), 4.15 (d, J=12.7 Hz, 1H), 3.67 (m, 2H), 3.24 (s, 3H), 2.60 (t, J=7.1 Hz, 2H), 2.03 (s, 3H).

Example 38

N-(3-chloro-5-{5-[2-(methoxymethyl)-2'-methylbiphenyl-4-yl]-1,2,4-oxadiazol-3-yl}pyridin-2-yl)glycine, hydrochloride salt

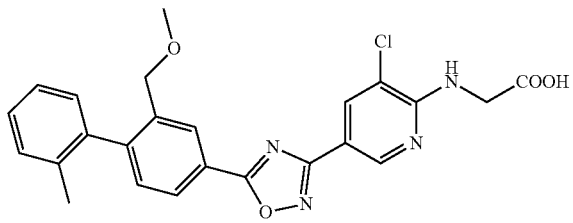 [SMILES: COCc1cc(-c2nc(-c3cnc(NCC(=O)O)c(Cl)c3)no2)ccc1-c1ccccc1C]

The title compound was prepared following procedure described in Method D starting from Example 36. After purification by crystallization from EtOAc, the title compound was obtained as a white powder. HPLC (Method A), Rt: 5.2 min (purity: 100%). UPLC/MS, M+(ESI): 465.2, M−(ESI): 463.2. Elemental analysis: [$C_{24}H_{21}N_4O_4Cl$—HCl] calculated: C, 57.50%; H, 4.42%; N, 11.17%; Cl, 14.14%. found: C, 57.32%; H, 4.35%; N, 11.09%; Cl, 13.74%. $^1$H NMR (DMSO-$d_6$, 300 MHz) δ 8.68 (d, J=2.0 Hz, 1H), 8.29 (d, J=1.8 Hz, 1H), 8.19 (d, J=2.0 Hz, 1H), 8.14 (dd, J=7.9, 1.8 Hz, 1H), 7.52 (brs, 1H), 7.41 (d, J=7.9 Hz, 1H), 7.37-7.25 (m, 3H), 7.14 (d, J=7.0 Hz, 1H), 4.21 (d, J=12.7 Hz, 1H), 4.15 (d, J=12.7 Hz, 1H), 4.10 (brs, 2H), 3.24 (s, 3H), 2.03 (s, 3H).

Example 39

3-chloro-5-{5-[4-(2-methylpiperidin-1-yl)-3-(trifluoromethyl)phenyl]-1,2,4-oxadiazol-3-yl}pyridin-2-amine

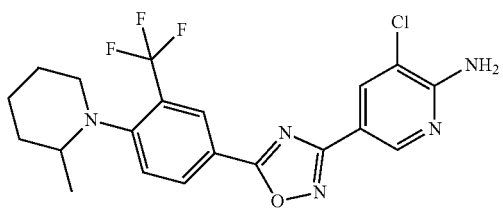 [SMILES: CC1CCCCN1c1ccc(-c2nc(-c3cnc(N)c(Cl)c3)no2)cc1C(F)(F)F]

The title compound was prepared following procedure described in Method B starting from Intermediate A5 and Intermediate B6. After purification by crystallization from EtOH, the title compound was obtained as a pale beige powder. HPLC (Method A), Rt: 5.8 min (purity: 100%). UPLC/MS, M+(ESI): 421.0. Elemental analysis: [$C_{20}H_{19}N_5OClF_3$-0.5H$_2$O] calculated: C, 53.76%; H, 4.51%; N, 15.67%; Cl, 7.93%. found: C, 53.64%; H, 4.25%; N, 15.63%; Cl, 7.93%.

Example 40

2-chloro-5-{5-[2-(methoxymethyl)-2'-methylbiphenyl-4-yl]-1,2,4-oxadiazol-3-yl}pyridine

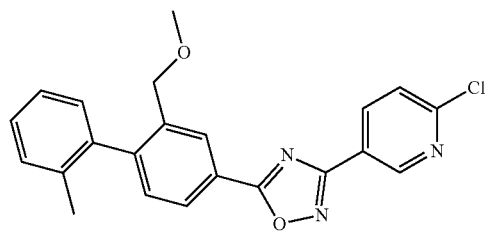 [SMILES: COCc1cc(-c2nc(-c3ccc(Cl)nc3)no2)ccc1-c1ccccc1C]

The title compound was prepared following procedure described in Method B starting from Intermediate A1 and 6-chloro-N'-hydroxypyridine-3-carboximidamide (J. Med. Chem., 2005, 5215-5223). After purification by flash chromatography (silica, EtOAc/cHex), the title compound was obtained as a colorless oil (661 mg, 70%). HPLC (Method A), Rt: 5.8 min (purity: 99%). UPLC/MS, M+(ESI): 392.2.

Example 41

3-[(5-{5-[2-(methoxymethyl)-2'-methylbiphenyl-4-yl]-1,2,4-oxadiazol-3-yl}pyridin-2-yl)amino]propan-1-ol

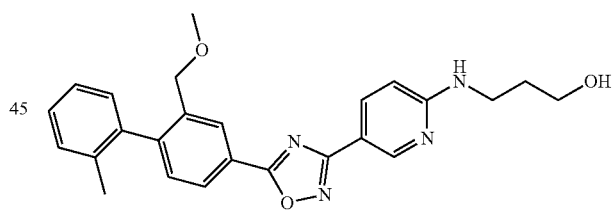

The title compound was prepared following procedure described in Method B starting from Intermediate A1 and Intermediate B18. After purification by filtration through a NH$_2$ SPE column (2 g) using DCM as eluent, followed by a crystallization from MeOH, the title compound was obtained as a white powder. HPLC (Method A), Rt: 3.8 min (purity: 100%). UPLC/MS, M+(ESI): 431.1, M−(ESI): 429.3. Elemental analysis: [$C_{25}H_{26}N_4O_3$-0.15H$_2$O] calculated: C, 69.31%; H, 6.12%; N, 12.93%. found: C, 69.28%; H, 5.96%; N, 12.94%. $^1$H NMR (DMSO-$d_6$, 300 MHz) δ 8.70 (d, J=2.3 Hz, 1H), 8.28 (d, J=1.9 Hz, 1H), 8.13 (dd, J=7.9, 1.9 Hz, 1H), 7.98 (dd, J=8.7, 2.3 Hz, 1H), 7.40 (d, J=7.9 Hz, 1H), 7.36-7.25 (m, 4H), 7.14 (d, J=7.0 Hz, 1H), 6.63 (d, J=8.7 Hz, 1H), 4.52 (t, J=5.2 Hz, 1H), 4.21 (d, J=12.7 Hz, 1H), 4.15 (d, J=12.7 Hz, 1H), 3.50 (m, 2H), 3.37 (m, 2H), 3.24 (s, 3H), 2.03 (s, 3H), 1.71 (m, 2H).

Example 42

3-chloro-5-{5-[3-(methoxymethyl)-4-(2-methylpiperidin-1-yl)phenyl]-1,2,4-oxadiazol-3-yl}pyridin-2-amine

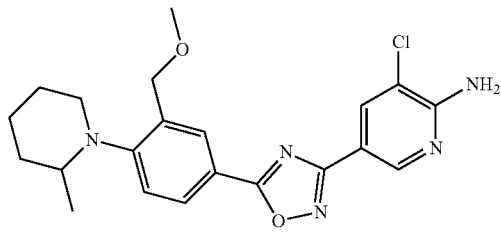 [SMILES: COCc1cc(-c2nc(-c3cnc(N)c(Cl)c3)no2)ccc1N1CCCCC1C]

The title compound was prepared following procedure described in Method B starting from Intermediate A2 and Intermediate B6. After purification by flash chromatography (silica, EtOAc/cHex), the title compound was obtained as a white powder. HPLC (Method A), Rt: 3.0 min (purity: 98.6%). UPLC/MS, M+(ESI): 414.0. Elemental analysis: [$C_{21}H_{24}N_5O_2Cl$] calculated: C, 60.94%; H, 5.84%; N, 16.92%; Cl, 8.57%. found: C, 61.05%; H, 5.97%; N, 16.51%; Cl, 8.35%.

Example 43

3-chloro-5-{5-[2'-ethyl-2-(methoxymethyl)biphenyl-4-yl]-1,2,4-oxadiazol-3-yl}pyridin-2-amine

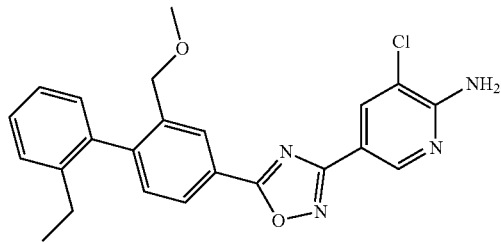 [SMILES: CCc1ccccc1-c1ccc(-c2nc(-c3cnc(N)c(Cl)c3)no2)cc1COC]

The title compound was prepared following procedure described in Method B starting from Intermediate A3 and Intermediate B6. After purification by flash chromatography (silica, EtOAc/cHex) followed by a crystallization from MeOH, the title compound was obtained as a white powder (454 mg, 90%). HPLC (Method A), Rt: 5.2 min (purity: 100%). UPLC/MS, M+(ESI): 421.0. Elemental analysis: [$C_{23}H_{21}N_4O_2Cl \cdot 0.2H_2O$] calculated: C, 65.08%; H, 5.08%; N, 13.20%; Cl, 8.35%. found: C, 64.97%; H, 4.92%; N, 13.20%; Cl, 8.43%.

Example 44

1-[(5-{5-[2-(methoxymethyl)-2'-methylbiphenyl-4-yl]-1,2,4-oxadiazol-3-yl}pyridin-2-yl)amino]propan-2-ol

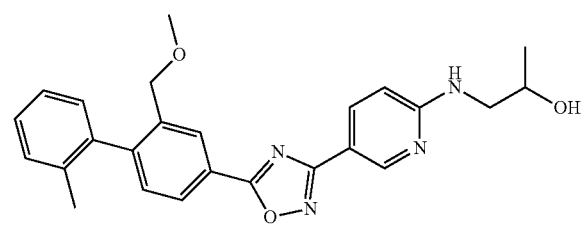 [SMILES: COCc1cc(-c2nc(-c3ccc(NCC(C)O)nc3)no2)ccc1-c1ccccc1C]

The title compound was prepared following procedure described in Method B starting from Intermediate A1 and Intermediate B19. After purification by filtration through a NH$_2$ SPE column (2 g) using DCM as eluent, followed by a crystallization from ACN, the title compound was obtained as a white powder. HPLC (Method A), Rt: 3.8 min (purity: 100%). UPLC/MS, M+(ESI): 431.2, M-(ESI): 429.3. Elemental analysis: [$C_{25}H_{26}N_4O_3$] calculated: C, 69.75%; H, 6.09%; N, 13.01%. found: C, 69.68%; H, 6.06%; N, 13.10%. $^1$H NMR (DMSO-$d_6$, 300 MHz) δ 8.69 (d, J=2.3 Hz, 1H), 8.28 (d, J=1.8 Hz, 1H), 8.13 (dd, J=7.9, 1.8 Hz, 1H), 7.97 (dd, J=8.8, 2.3 Hz, 1H), 7.40 (d, J=7.9 Hz, 1H), 7.36-7.25 (m, 4H), 7.14 (d, J=7.0 Hz, 1H), 6.70 (d, J=8.8 Hz, 1H), 4.78 (d, J=4.7 Hz, 1H), 4.21 (d, J=12.7 Hz, 1H), 4.15 (d, J=12.7 Hz, 1H), 3.82 (m, 1H), 3.29 (m, 2H), 3.24 (s, 3H), 2.03 (s, 3H), 1.10 (d, J=6.2 Hz, 3H).

Example 45

3-[(5-{5-[2-(methoxymethyl)-2'-methylbiphenyl-4-yl]-1,2,4-oxadiazol-3-yl}pyridin-2-yl)amino]propane-1,2-diol, hydrochloride salt

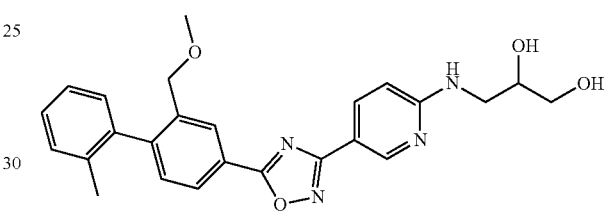

The title compound was prepared following procedure described in Method B starting from Intermediate A1 and Intermediate B20. The crude compound was purified by flash chromatography (silica, DCM/MeOH) to give a gummy solid. The solid was taken up with ACN and an excess of a 1N solution of HCl in Et$_2$O was added. The solution was concentrated until precipitation. The precipitate was filtered off, washed with ACN, Et$_2$O and pentane, and then dried under reduced pressure. The title compound was obtained as a white powder. HPLC (Method A), Rt: 3.6 min (purity: 100%). UPLC/MS, M$^+$(ESI): 447.2, M$^-$(ESI): 445.2. $^1$H NMR (DMSO-$d_6$+3 drops CD$_3$OD, 300 MHz) δ 8.56 (brs, 1H), 8.32 (m, 2H), 8.16 (d, J=7.9 Hz, 1H), 7.42 (d, J=7.9 Hz, 1H), 7.36-7.22 (m, 4H), 7.14 (d, J=7.3 Hz, 1H), 4.21 (d, J=12.9 Hz, 1H), 4.15 (d, J=12.9 Hz, 1H), 3.75 (m, 1H), 3.59 (dd, J=13.9, 3.5 Hz, 1H), 3.50-3.36 (m, 3H), 3.24 (s, 3H), 2.03 (s, 3H).

Example 46

3-chloro-5-{5-[2'-fluoro-2-(methoxymethyl)biphenyl-4-yl]-1,2,4-oxadiazol-3-yl}pyridin-2-amine

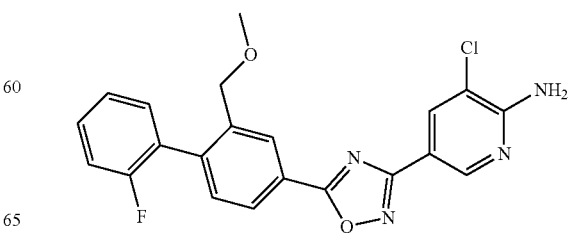

The title compound was prepared following procedure described in Method B starting from Intermediate A10 and Intermediate B6. After purification by filtration through a NH$_2$ SPE column (2 g) using DCM as eluent, followed by a crystallization from EtOH, the title compound was obtained as a white powder. HPLC (Method A), Rt: 4.6 min (purity: 99.2%). UPLC/MS, M$^+$(ESI): 411.1.

Example 47

3-chloro-5-{5-[2'-chloro-2-(methoxymethyl)biphenyl-4-yl]-1,2,4-oxadiazol-3-yl}pyridin-2-amine

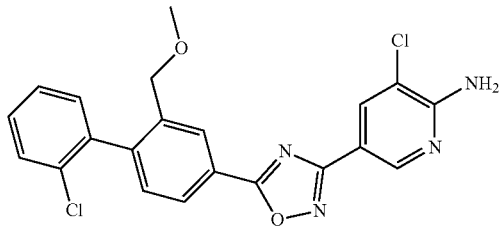 [SMILES: COCc1cc(-c2nc(-c3cnc(N)c(Cl)c3)no2)ccc1-c1ccccc1Cl]

The title compound was prepared following procedure described in Method B starting from Intermediate A8 and Intermediate B6. After purification by crystallization from EtOH, the title compound was obtained as a pale beige powder. HPLC (Method A), Rt: 4.8 min (purity: 100%). UPLC/MS, M$^+$(ESI): 426.9. Melting point: 182-184° C. Elemental analysis: [C$_{21}$H$_{16}$N$_4$O$_2$Cl$_2$] calculated: C, 59.03%; H, 3.77%; N, 13.11%; Cl, 16.59%. found: C, 58.74%; H, 3.73%; N, 13.05%; Cl, 16.33%.

Example 48

N-(3-chloro-5-{5-[2'-fluoro-2-(methoxymethyl)biphenyl-4-yl]-1,2,4-oxadiazol-3-yl}pyridin-2-yl)-beta-alanine, hydrochloride salt Step 1) tert-butyl N-(3-chloro-5-{5-[2'-fluoro-2-(methoxymethyl)biphenyl-4-yl]-1,2,4-oxadiazol-3-yl}pyridin-2-yl)-beta-alaninate

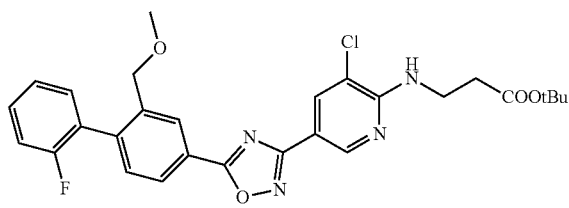

The title compound was prepared following procedure described in Method B starting from Intermediate A10 and Intermediate B16. After purification by flash chromatography (silica, EtOAc/cHex), the title compound was obtained as a pale yellow oil (477 mg, 74%). HPLC (Method A), Rt: 6.3 min (purity: 99.6%). UPLC/MS, M+(ESI): 539.0.

Step 2) N-(3-chloro-5-{5-[2'-fluoro-2-(methoxymethyl)biphenyl-4-yl]-1,2,4-oxadiazol-3-yl}pyridin-2-yl)-beta-alanine, hydrochloride salt

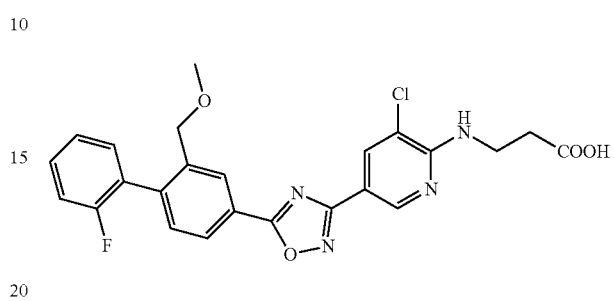

The title compound was prepared following procedure described in Method D starting from tert-butyl N-(3-chloro-5-{5-[2'-fluoro-2-(methoxymethyl)biphenyl-4-yl]-1,2,4-oxadiazol-3-yl}pyridin-2-yl)-beta-alaninate. After purification by crystallization from ACN, the title compound was obtained as a white powder. HPLC (Method A), Rt: 4.9 min (purity: 97.2%). UPLC/MS, M$^+$(ESI): 483.0, M$^-$(ESI): 481.1. Elemental analysis: [C$_{24}$H$_{20}$N$_4$O$_4$ClF—HCl] calculated: C, 55.50%; H, 4.08%; N, 10.79%; Cl, 13.65%. found: C, 55.10%; H, 4.12%; N, 10.90%; Cl, 13.35%. $^1$H NMR (DMSO-d$_6$, 300 MHz) δ 8.72 (d, J=2.0 Hz, 1H), 8.31 (d, J=1.8 Hz, 1H), 8.17 (dd, J=8.0, 1.8 Hz, 1H), 8.15 (d, J=2.0 Hz, 1H), 7.57-7.49 (m, 2H), 7.46-7.32 (m, 3H), 7.25 (m, 1H), 4.35 (s, 2H), 3.68 (m, 2H), 3.26 (s, 3H), 2.60 (t, J=7.2 Hz, 2H).

Example 49

2-[(5-{5-[2'-chloro-2-(methoxymethyl)biphenyl-4-yl]-1,2,4-oxadiazol-3-yl}pyridin-2-yl)amino]ethanol

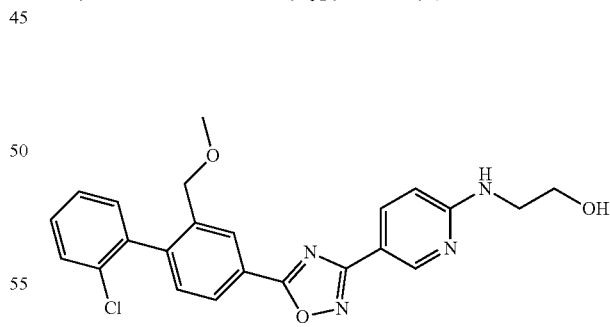

The title compound was prepared following procedure described in Method B starting from Intermediate A8 and Intermediate B13. After purification by crystallization from EtOH, the title compound was obtained as a white powder. HPLC (Method A), Rt: 5.1 min (purity: 98%). UPLC/MS, M$^+$(ESI): 437.0, M$^-$(ESI): 435.1. Elemental analysis: [C$_{23}$H$_{21}$N$_4$O$_3$Cl·0.3H$_2$O] calculated: C, 62.46%; H, 4.92%; N, 12.67%; Cl, 8.02%. found: C, 62.42%; H, 4.74%; N, 12.65%; Cl, 8.01%.

Example 50

N-(3-chloro-5-{5-[2'-chloro-2-(methoxymethyl)biphenyl-4-yl]-1,2,4-oxadiazol-3-yl}pyridin-2-yl)-beta-alanine, hydrochloride salt Step 1) tert-butyl N-(3-chloro-5-{5-[2'-chloro-2-(methoxymethyl)biphenyl-4-yl]-1,2,4-oxadiazol-3-yl}pyridin-2-yl)-beta-alaninate

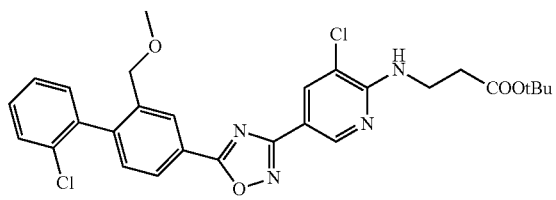

The title compound was prepared following procedure described in Method B starting from Intermediate A8 and Intermediate B16. After purification by flash chromatography (silica, EtOAc/cHex), the title compound was obtained as a yellow oil (478 mg, 72%). HPLC (Method A), Rt: 6.5 min (purity: 100%). UPLC/MS, M+(ESI): 555.0, M−(ESI): 553.1.

Step 2) N-(3-chloro-5-{5-[2'-chloro-2-(methoxymethyl)biphenyl-4-yl]-1,2,4-oxadiazol-3-yl}pyridin-2-yl)-beta-alanine, hydrochloride salt

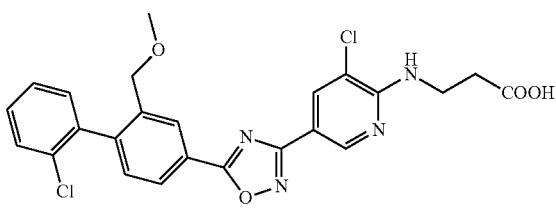 [SMILES: COCc1cc(-c2nc(-c3cnc(NCCC(=O)O)c(Cl)c3)no2)ccc1-c1ccccc1Cl]

The title compound was prepared following procedure described in Method D starting from tert-butyl N-(3-chloro-5-{5-[2'-chloro-2-(methoxymethyl)biphenyl-4-yl]-1,2,4-oxadiazol-3-yl}pyridin-2-yl)-beta-alaninate. After purification by crystallization from ACN, the title compound was obtained as a white powder. HPLC (Method A), Rt: 5.1 min (purity: 98.0%). UPLC/MS, M+(ESI): 498.9, M−(ESI): 497.0. Elemental analysis: [$C_{24}H_{20}N_4O_4Cl_2$—HCl] calculated: C, 53.80%; H, 3.95%; N, 10.46%; Cl, 19.85%. found: C, 53.59%; H, 3.93%; N, 10.53%; Cl, 19.44%. $^1$H NMR (DMSO-$d_6$, 300 MHz) δ 8.73 (d, J=2.0 Hz, 1H), 8.30 (d, J=1.8 Hz, 1H), 8.17 (dd, J=8.1, 1.8 Hz, 1H), 8.15 (d, J=2.0 Hz, 1H), 7.63 (m, 1H), 7.54-7.44 (m, 3H), 7.39 (m, 1H), 7.25 (m, 1H), 4.30 (d, J=12.8 Hz, 1H), 4.22 (d, J=12.8 Hz, 1H), 3.68 (m, 2H), 3.24 (s, 3H), 2.60 (t, J=7.2 Hz, 2H).

Example 51

4-[(5-{5-[2-(methoxymethyl)-2'-methylbiphenyl-4-yl]-1,2,4-oxadiazol-3-yl}pyridin-2-yl)amino]butan-1-ol, hydrochloride salt

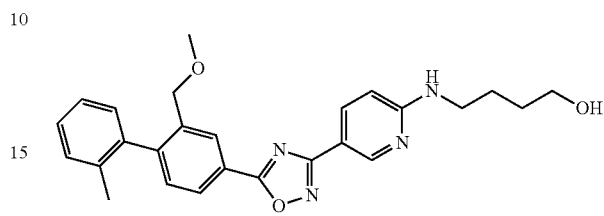

A solution of Example 40 (150.00 mg, 0.38 mmol) and 4-amino-1-butanol (0.18 ml, 1.91 mmol) was prepared in DMSO (1.00 ml) and heated at 180° C. for 1 hour under microwave irradiation conditions. The reaction mixture was diluted with a mixture of MTBE (40 ml), EtOAc (20 ml) and MeOH (5 ml), and then washed with water (30 ml) and brine (20 ml). The aqueous layers were extracted with a mixture of MTBE (40 ml) and EtOAc (20 ml). The organic layers were combined, dried ($Na_2SO_4$) and the solvents were removed under reduced pressure. The residue was purified by flash chromatography (silica, EtOAc/cHex) to give a colorless oil. This oil was taken up with an excess of 1N solution of HCl in $Et_2O$. After evaporation, the title compound was obtained as a white foam. HPLC (Method A), Rt: 3.8 min (purity: 98.0%). UPLC/MS, M+(ESI): 445.2, M−(ESI): 443.3. $^1$H NMR (DMSO-$d_6$, 300 MHz) δ 8.55 (brs, 1H), 8.28 (m, 2H), 8.16 (dd, J=7.9, 1.8 Hz, 1H), 7.42 (d, J=7.9 Hz, 1H), 7.36-7.26 (m, 3H), 7.13 (m, 2H), 4.22 (d, J=12.7 Hz, 1H), 4.16 (d, J=12.7 Hz, 1H), 3.45 (m, 4H), 3.24 (s, 3H), 2.03 (s, 3H), 1.66 (m, 2H), 1.53 (m, 2H).

Example 52

5-{5-[2'-fluoro-2-(methoxymethyl)biphenyl-4-yl]-1,2,4-oxadiazol-3-yl}pyridin-2-amine

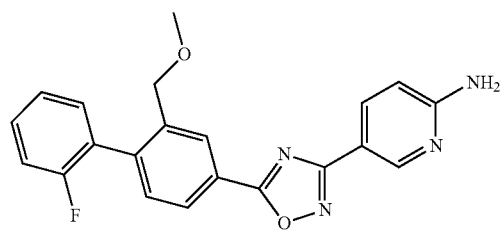

The title compound was prepared following procedure described in Method B starting from Intermediate A10 and 6-amino-N'-hydroxypyridine-3-carboximidamide (J. Med. Chem., 2007, 3442-3456). After purification by crystallization from MTBE, the title compound was obtained as a white powder. HPLC (Method A), Rt: 3.6 min (purity: 97.4%). UPLC/MS, M⁺(ESI): 377.0.

Example 53

N-(5-{5-[2'-fluoro-2-(methoxymethyl)biphenyl-4-yl]-1,2,4-oxadiazol-3-yl}-3-methylpyridin-2-yl)-beta-alanine, hydrochloride salt Step 1) tert-butyl N-(5-{5-[2'-fluoro-2-(methoxymethyl)biphenyl-4-yl]-1,2,4-oxadiazol-3-yl}-3-methylpyridin-2-yl)-beta-alaninate

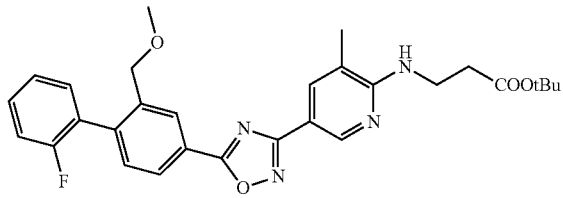

The title compound was prepared following procedure described in Method B starting from Intermediate A10 and Intermediate B21. After purification by flash chromatography (silica, EtOAc/cHex), the title compound was obtained as a white powder. HPLC (Method A), Rt: 4.5 min (purity: 99.2%). UPLC/MS, M⁺(ESI): 519.0.

Step 2) N-(5-{5-[2'-fluoro-2-(methoxymethyl)biphenyl-4-yl]-1,2,4-oxadiazol-3-yl}-3-methylpyridin-2-yl)-beta-alanine, hydrochloride salt

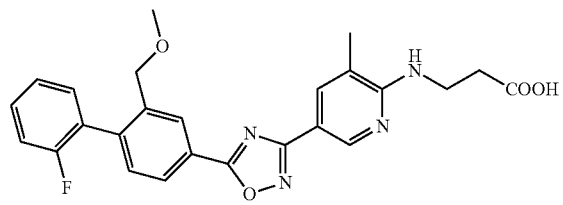 [SMILES: COCc1cc(-c2nc(-c3cnc(NCCC(=O)O)c(C)c3)no2)ccc1-c1ccccc1F]

The title compound was prepared following procedure described in Method D starting from tert-butyl N-(5-{5-[2'-fluoro-2-(methoxymethyl)biphenyl-4-yl]-1,2,4-oxadiazol-3-yl}-3-methylpyridin-2-yl)-beta-alaninate. After purification by crystallization from ACN, the title compound was obtained as a white powder (230 mg, 81%). HPLC (Method A), Rt: 3.7 min (purity: 99.3%). UPLC/MS, M⁺(ESI): 463.0, M⁻(ESI): 461.1. Elemental analysis: [$C_{25}H_{23}N_4O_4F$—HCl-0.2$H_2O$] calculated: C, 59.75%; H, 4.89%; N, 11.15%; Cl, 7.05%. found: C, 59.76%; H, 5.11%; N, 11.20%; Cl, 7.17%. ¹H NMR (DMSO-$d_6$, 300 MHz) δ 8.48 (d, J=1.8 Hz, 1H), 8.33 (d, J=1.5 Hz, 1H), 8.19 (m, 2H), 7.58-7.50 (m, 2H), 7.46-7.32 (m, 3H), 4.36 (s, 2H), 3.73 (t, J=6.9 Hz, 2H), 3.26 (s, 3H), 2.70 (t, J=6.9 Hz, 2H), 2.26 (s, 3H).

Example 54

4-[(3-chloro-5-{5-[2'-fluoro-2-(methoxymethyl)biphenyl-4-yl]-1,2,4-oxadiazol-3-yl}pyridin-2-yl)amino]butanoic acid, hydrochloride salt Step 1) tert-butyl 4-[(3-chloro-5-{5-[2'-fluoro-2-(methoxymethyl)biphenyl-4-yl]-1,2,4-oxadiazol-3-yl}pyridin-2-yl)amino]butanoate

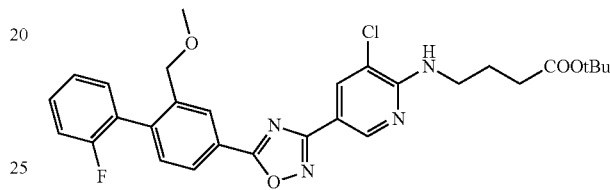

The title compound was prepared following procedure described in Method B starting from Intermediate A10 and Intermediate B22. After purification by flash chromatography (silica, EtOAc/cHex), the title compound was obtained as a colorless oil (449 mg, 81%). HPLC (Method A), Rt: 6.3 min (purity: 98.7%). UPLC/MS, M⁺(ESI): 553.0, M⁻(ESI): 551.1.

Step 2) 4-[(3-chloro-5-{5-[2'-fluoro-2-(methoxymethyl)biphenyl-4-yl]-1,2,4-oxadiazol-3-yl}pyridin-2-yl)amino]butanoic acid, hydrochloride salt

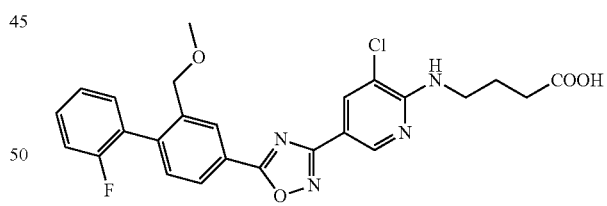

The title compound was prepared following procedure described in Method D starting from tert-butyl 4-[(3-chloro-5-{5-[2'-fluoro-2-(methoxymethyl)biphenyl-4-yl]-1,2,4-oxadiazol-3-yl}pyridin-2-yl)amino]butanoate. After purification by crystallization from ACN, the title compound was obtained as a white powder. HPLC (Method A), Rt: 4.8 min (purity: 99.3%). UPLC/MS, M⁺(ESI): 497.0, M⁻(ESI): 495.0. Elemental analysis: [$C_{25}H_{22}N_4O_4ClF$—HCl] calculated: C, 56.30%; H, 4.35%; N, 10.50%; Cl, 13.29%. found: C, 56.23%; H, 4.34%; N, 10.47%; Cl, 13.25%. ¹H NMR (DMSO-$d_6$, 300 MHz) δ 8.69 (d, J=2.0 Hz, 1H), 8.31 (d, J=1.8 Hz, 1H), 8.17 (dd, J=7.9, 1.8 Hz, 1H), 8.13 (d, J=2.0 Hz, 1H), 7.57-7.49 (m, 2H), 7.45-7.31 (m, 4H), 4.35 (s, 2H), 3.49 (m, 2H), 3.25 (s, 3H), 2.29 (t, J=7.3 Hz, 2H), 1.83 (m, 2H).

Example 55

4-[(5-{5-[2'-fluoro-2-(methoxymethyl)biphenyl-4-yl]-1,2,4-oxadiazol-3-yl}-3-methylpyridin-2-yl)amino]butanoic acid, hydrochloride salt Step 1) tert-butyl 4-[(5-{5-[2'-fluoro-2-(methoxymethyl)biphenyl-4-yl]-1,2,4-oxadiazol-3-yl}-3-methylpyridin-2-yl)amino]butanoate

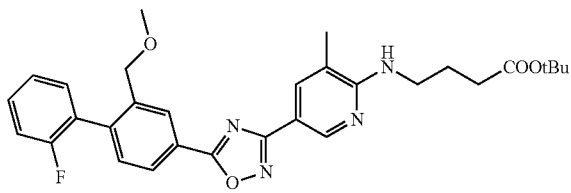

The title compound was prepared following procedure described in Method B starting from Intermediate A10 and Intermediate B23. After purification by flash chromatography (silica, EtOAc/cHex), the title compound was obtained as a colorless oil. HPLC (Method A), Rt: 4.6 min (purity: 99.4%). UPLC/MS, M⁺(ESI): 533.0.

Step 2) 4-[(5-{5-[2'-fluoro-2-(methoxymethyl)biphenyl-4-yl]-1,2,4-oxadiazol-3-yl}-3-methylpyridin-2-yl)amino]butanoic acid, hydrochloride salt

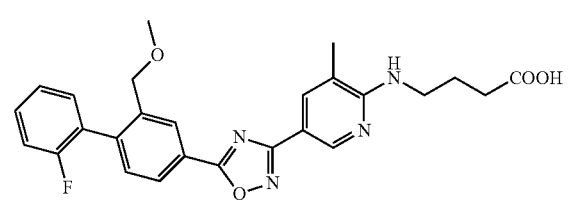

The title compound was prepared following procedure described in Method D starting from tert-butyl 4-[(5-{5-[2'-fluoro-2-(methoxymethyl)biphenyl-4-yl]-1,2,4-oxadiazol-3-yl}-3-methylpyridin-2-yl)amino]butanoate. After purification by crystallization from ACN, the title compound was obtained as a white powder (297 mg, 77%). HPLC (Method A), Rt: 3.8 min (purity: 98.8%). UPLC/MS, M⁺(ESI): 477.0, M⁻(ESI): 475.1. Elemental analysis: [$C_{26}H_{25}N_4O_4F$—HCl] calculated: C, 60.88%; H, 5.11%; N, 10.92%; Cl, 6.91%. found: C, 60.95%; H, 5.22%; N, 10.91%; Cl, 6.97%. ¹H NMR (DMSO-d₆, 300 MHz) δ 8.44 (s, 1H), 8.33 (s, 1H), 8.19 (m, 2H), 7.54 (m, 2H), 7.46-7.32 (m, 3H), 4.35 (s, 2H), 3.60 (m, 2H), 3.26 (s, 3H), 2.40 (t, J=7.3 Hz, 2H), 2.29 (s, 3H), 1.89 (m, 2H).

Example 56

4-[(3-chloro-5-{5-[2-(methoxymethyl)-2'-methylbiphenyl-4-yl]-1,2,4-oxadiazol-3-yl}pyridin-2-yl)amino]butanoic acid, hydrochloride salt Step 1) tert-butyl 4-[(3-chloro-5-{5-[2-(methoxymethyl)-2'-methylbiphenyl-4-yl]-1,2,4-oxadiazol-3-yl}pyridin-2-yl)amino]butanoate

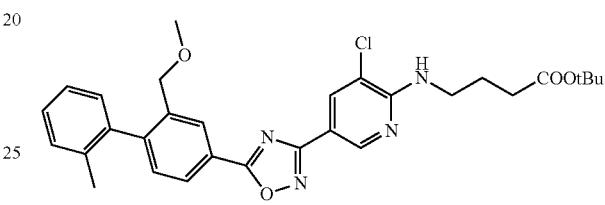

The title compound was prepared following procedure described in Method B starting from Intermediate A1 and Intermediate B22. After purification by flash chromatography (silica, EtOAc/cHex), the title compound was obtained as a colorless oil (434 mg, 79%). HPLC (Method A), Rt: 6.6 min (purity: 99.6%). UPLC/MS, M⁺(ESI): 549.0.

Step 2) 4-[(3-chloro-5-{5-[2-(methoxymethyl)-2'-methylbiphenyl-4-yl]-1,2,4-oxadiazol-3-yl}pyridin-2-yl)amino]butanoic acid, hydrochloride salt

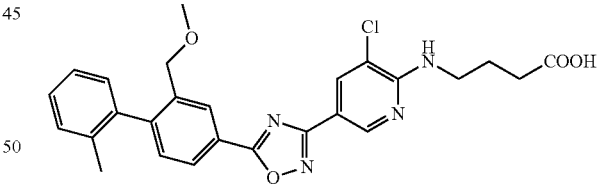

The title compound was prepared following procedure described in Method D starting from tert-butyl 4-[(3-chloro-5-{5-[2-(methoxymethyl)-2'-methylbiphenyl-4-yl]-1,2,4-oxadiazol-3-yl}pyridin-2-yl)amino]butanoate. After purification by crystallization from ACN, the title compound was obtained as a white powder (274 mg, 70%). HPLC (Method A), Rt: 5.1 min (purity: 100%). UPLC/MS, M⁺(ESI): 493.0, M⁻(ESI): 491.1. Elemental analysis: [$C_{26}H_{25}N_4O_4Cl$—HCl-0.4H₂O] calculated: C, 58.19%; H, 5.03%; N, 10.44%; Cl, 13.21%. found: C, 58.56%; H, 4.96%; N, 10.04%; Cl, 13.29%. ¹H NMR (DMSO-d₆, 300 MHz) δ 8.69 (d, J=2.0 Hz, 1H), 8.29 (d, J=1.5 Hz, 1H), 8.14 (m, 2H), 7.41 (d, J=8.0 Hz, 1H), 7.37-7.25 (m, 4H), 7.14 (d, J=7.1 Hz, 1H), 4.21 (d, J=12.7 Hz, 1H), 4.15 (d, J=12.7 Hz, 1H), 3.48 (m, 2H), 3.24 (s, 3H), 2.29 (t, J=7.4 Hz, 2H), 2.03 (s, 3H), 1.83 (m, 2H).

Example 57

4-[(5-{5-[2-(methoxymethyl)-2'-methylbiphenyl-4-yl]-1,2,4-oxadiazol-3-yl}-3-methylpyridin-2-yl)amino]butanoic acid, hydrochloride salt Step 1) tert-butyl 4-[(5-{5-[2-(methoxymethyl)-2'-methylbiphenyl-4-yl]-1,2,4-oxadiazol-3-yl}-3-methylpyridin-2-yl)amino]butanoate

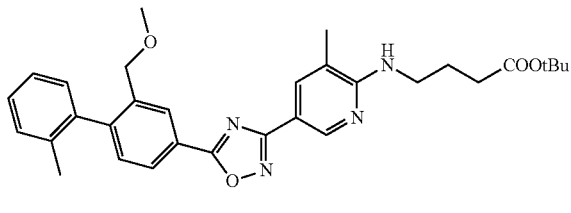

The title compound was prepared following procedure described in Method B starting from Intermediate A1 and Intermediate B23. After purification by flash chromatography (silica, EtOAc/cHex), the title compound was obtained as a colorless oil (471 mg, 74%). HPLC (Method A), Rt: 4.8 min (purity: 99.7%). UPLC/MS, M⁺(ESI): 529.1.

Step 2) 4-[(5-{5-[2-(methoxymethyl)-2'-methylbiphenyl-4-yl]-1,2,4-oxadiazol-3-yl}-3-methylpyridin-2-yl)amino]butanoic acid, hydrochloride salt

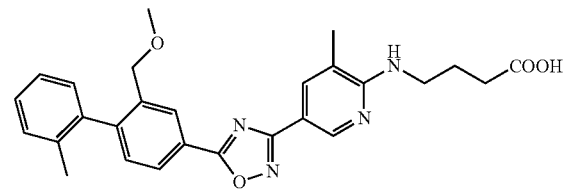 [SMILES: COCc1cc(-c2nc(-c3cnc(NCCCC(=O)O)c(C)c3)no2)ccc1-c1ccccc1C]

The title compound was prepared following procedure described in Method D starting from tert-butyl 4-[(5-{5-[2-(methoxymethyl)-2'-methylbiphenyl-4-yl]-1,2,4-oxadiazol-3-yl}-3-methylpyridin-2-yl)amino]butanoate. After purification by crystallization from a mixture of ACN and water, the title compound was obtained as a white powder. HPLC (Method A), Rt: 4.0 min (purity: 100%). UPLC/MS, M⁺(ESI): 473.1, M⁻(ESI): 471.2. Elemental analysis: [$C_{27}H_{28}N_4O_4$—HCl-0.3$H_2O$] calculated: C, 63.04%; H, 5.80%; N, 10.89%; Cl, 6.89%. found: C, 63.26%; H, 5.73%; N, 10.51%; Cl, 6.66%. ¹H NMR (DMSO-$d_6$, 300 MHz) δ 8.45 (s, 1H), 8.31 (s, 1H), 8.17 (m, 2H), 7.43 (d, J=7.9 Hz, 1H), 7.37-7.26 (m, 3H), 7.14 (d, J=7.2 Hz, 1H), 4.22 (d, J=12.8 Hz, 1H), 4.16 (d, J=12.8 Hz, 1H), 3.57 (m, 2H), 3.24 (s, 3H), 2.39 (t, J=7.3 Hz, 2H), 2.28 (s, 3H), 2.03 (s, 3H), 1.88 (m, 2H).

Example 58

N-(5-{5-[2-(methoxymethyl)-2'-methylbiphenyl-4-yl]-1,2,4-oxadiazol-3-yl}-3-methylpyridin-2-yl)-beta-alanine, hydrochloride salt Step 1) tert-butyl N-(5-{5-[2-(methoxymethyl)-2'-methylbiphenyl-4-yl]-1,2,4-oxadiazol-3-yl}-3-methylpyridin-2-yl)-beta-alaninate

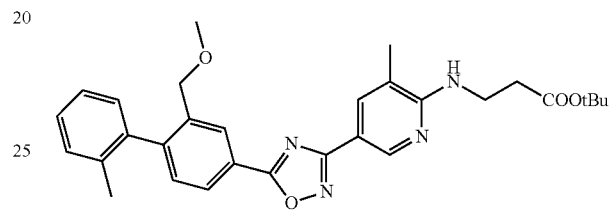

The title compound was prepared following procedure described in Method B starting from Intermediate A1 and Intermediate B21. After purification by flash chromatography (silica, EtOAc/cHex), the title compound was obtained as a colorless oil. HPLC (Method A), Rt: 4.8 min (purity: 99.5%). UPLC/MS, M⁺(ESI): 515.0.

Step 2) N-(5-{5-[2-(methoxymethyl)-2'-methylbiphenyl-4-yl]-1,2,4-oxadiazol-3-yl}-3-methylpyridin-2-yl)-beta-alanine, hydrochloride salt

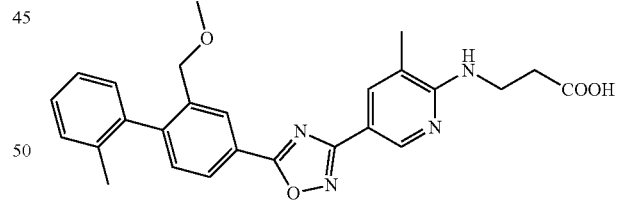

The title compound was prepared following procedure described in Method D starting from tert-butyl N-(5-{5-[2-(methoxymethyl)-2'-methylbiphenyl-4-yl]-1,2,4-oxadiazol-3-yl}-3-methylpyridin-2-yl)-beta-alaninate. After purification by crystallization from ACN, the title compound was obtained as a white powder (341 mg, 89%). HPLC (Method A), Rt: 3.9 min (purity: 98.5%). UPLC/MS, M⁺(ESI): 459.2, M⁻(ESI): 457.2. Elemental analysis: [$C_{26}H_{26}N_4O_4$—HCl-0.5$H_2O$] calculated: C, 61.96%; H, 5.60%; N, 11.12%; Cl, 7.03%. found: C, 61.95%; H, 5.47%; N, 11.22%; Cl, 7.12%. ¹H NMR (DMSO-$d_6$, 300 MHz) δ 8.47 (d, J=1.7 Hz, 1H), 8.30 (d, J=1.4 Hz, 1H), 8.16 (m, 2H), 7.42 (d, J=8.0 Hz, 1H), 7.37-7.25 (m, 3H), 7.14 (d, J=7.0 Hz, 1H), 4.22 (d, J=12.7 Hz, 1H), 4.16 (d, J=12.7 Hz, 1H), 3.74 (t, J=7.0 Hz, 2H), 3.24 (s, 3H), 2.70 (t, J=7.0 Hz, 2H), 2.27 (s, 3H), 2.03 (s, 3H).

Example 59

N-(3-methyl-5-{5-[2'-methyl-2-(trifluoromethyl)biphenyl-4-yl]-1,2,4-oxadiazol-3-yl}pyridin-2-yl)-beta-alanine, hydrochloride salt Step 1) tert-butyl N-(3-methyl-5-{5-[2'-methyl-2-(trifluoromethyl)biphenyl-4-yl]-1,2,4-oxadiazol-3-yl}pyridin-2-yl)-beta-alaninate

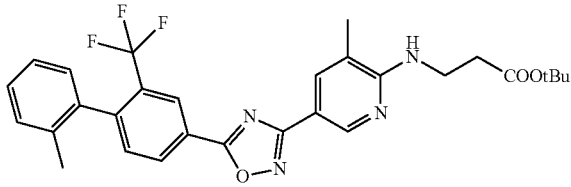

The title compound was prepared following procedure described in Method B starting from Intermediate A4 and Intermediate B21. After purification by flash chromatography (silica, EtOAc/cHex), the title compound was obtained as a pale yellow oil (436 mg, 67%). HPLC (Method A), Rt: 5.0 min (purity: 99.3%). UPLC/MS, M⁺(ESI): 539.3, M⁻(ESI): 537.2.

Step 2) N-(3-methyl-5-{5-[2'-methyl-2-(trifluoromethyl)biphenyl-4-yl]-1,2,4-oxadiazol-3-yl}pyridin-2-yl)-beta-alanine, hydrochloride salt

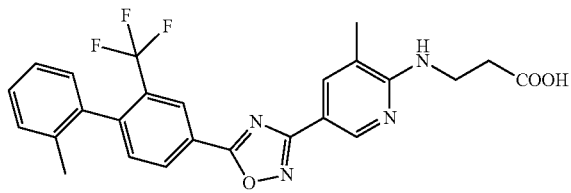 [SMILES: Cc1ccccc1-c1ccc(-c2nc(-c3cnc(NCCC(=O)O)c(C)c3)no2)cc1C(F)(F)F]

The title compound was prepared following procedure described in Method D starting from tert-butyl N-(3-methyl-5-{5-[2'-methyl-2-(trifluoromethyl)biphenyl-4-yl]-1,2,4-oxadiazol-3-yl}pyridin-2-yl)-beta-alaninate. After purification by crystallization from ACN, the title compound was obtained as a white powder. HPLC (Method A), Rt: 4.2 min (purity: 99.7%). UPLC/MS, M⁺(ESI): 483.0, M⁻(ESI): 481.1. Elemental analysis: [C$_{25}$H$_{21}$N$_4$O$_3$F$_3$—HCl] calculated: C, 57.87%; H, 4.27%; N, 10.80%; Cl, 6.83%. found: C, 57.54%; H, 4.33%; N, 10.41%; Cl, 6.70%. ¹H NMR (DMSO-d$_6$, 300 MHz) δ 8.50 (m, 3H), 8.16 (s, 1H), 7.66 (d, J=7.9 Hz, 1H), 7.38 (m, 2H), 7.28 (m, 1H), 7.17 (d, J=7.5 Hz, 1H), 3.73 (t, J=6.9 Hz, 2H), 2.69 (t, J=6.9 Hz, 2H), 2.26 (s, 3H), 2.02 (s, 3H).

Example 60

2-chloro-3-fluoro-5-{5-[2-(methoxymethyl)-2'-methylbiphenyl-4-yl]-1,2,4-oxadiazol-3-yl}pyridine

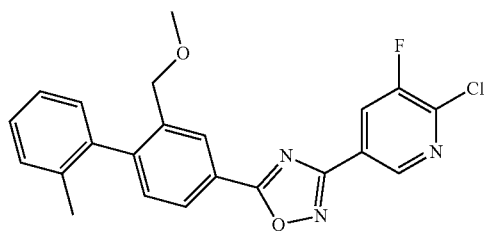 [SMILES: COCc1cc(-c2nc(-c3cnc(Cl)c(F)c3)no2)ccc1-c1ccccc1C]

The title compound was prepared following procedure described in Method B starting from Intermediate A1 and Intermediate B24. After purification by flash chromatography (silica, EtOAc/heptane), the title compound was obtained as a colorless oil. HPLC (Method A), Rt: 5.5 min (purity: 97.1%). UPLC/MS, M⁺(ESI): 410.0.

Example 61

N-(3-chloro-5-{5-[2'-methyl-2-(trifluoromethyl)biphenyl-4-yl]-1,2,4-oxadiazol-3-yl}pyridin-2-yl)-beta-alanine, hydrochloride salt Step 1) tert-butyl N-(3-chloro-5-{5-[2'-methyl-2-(trifluoromethyl)biphenyl-4-yl]-1,2,4-oxadiazol-3-yl}pyridin-2-yl)-beta-alaninate

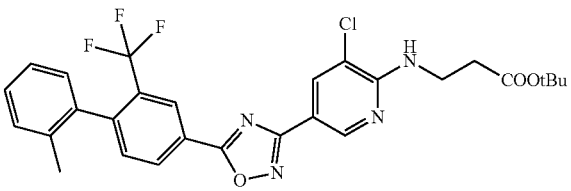

The title compound was prepared following procedure described in Method B starting from Intermediate A4 and Intermediate B16. After purification by flash chromatography (silica, EtOAc/cHex), the title compound was obtained as a Step 2) N-(3-chloro-5-{5-[2'-methyl-2-(trifluoromethyl)biphenyl-4-yl]-1,2,4-oxadiazol-3-yl}pyridin-2-yl)-beta-alanine, hydrochloride salt

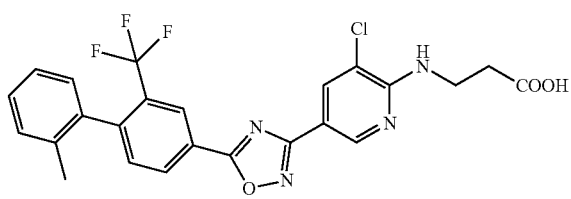

The title compound was prepared following procedure described in Method D starting from tert-butyl N-(3-chloro-5-{5-[2'-methyl-2-(trifluoromethyl)biphenyl-4-yl]-1,2,4-oxadiazol-3-yl}pyridin-2-yl)-beta-alaninate. After purification by crystallization from ACN, the title compound was obtained as a white powder. HPLC (Method A), Rt: 5.5 min (purity: 99.2%). UPLC/MS, M$^+$(ESI): 502.9, M$^-$(ESI): 501.1. Elemental analysis: [$C_{24}H_{18}N_4O_3ClF_3$—HCl-0.6H$_2$O] calculated: C, 52.40%; H, 3.70%; N, 10.18%; Cl, 12.89%. found: C, 52.48%; H, 3.68%; N, 9.68%; Cl, 12.59%. $^1$H NMR (DMSO-d$_6$, 300 MHz) δ 8.74 (d, J=2.0 Hz, 1H), 8.51 (d, J=1.5 Hz, 1H), 8.47 (dd, J=7.9, 1.5 Hz, 1H), 8.17 (d, J=2.0 Hz, 1H), 7.65 (d, J=7.9 Hz, 1H), 7.41-7.33 (m, 2H), 7.31-7.25 (m, 2H), 7.17 (d, J=7.5 Hz, 1H), 3.68 (m, 2H), 2.60 (t, J=7.2 Hz, 2H), 2.01 (s, 3H).

Example 62

2-[(3-chloro-5-{5-[2'-fluoro-2-(methoxymethyl)biphenyl-4-yl]-1,2,4-oxadiazol-3-yl}pyridin-2-yl)amino]ethanol

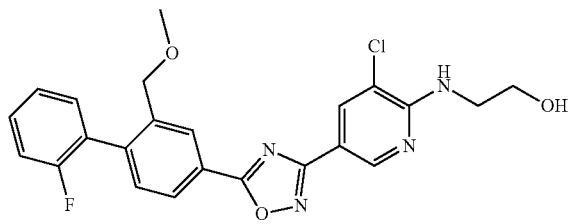 [SMILES: COCc1cc(-c2nc(-c3cnc(NCCO)c(Cl)c3)no2)ccc1-c1ccccc1F]

The title compound was prepared following procedure described in Method B starting from Intermediate A10 and Intermediate B25. After purification by crystallization from ACN, the title compound was obtained as an off-white powder. HPLC (Method A), Rt: 4.6 min (purity: 99.8%). UPLC/MS, M$^+$(ESI): 454.9, M$^-$(ESI): 453.0. Elemental analysis: [$C_{23}H_{20}N_4O_3ClF$-0.2H$_2$O] calculated: C, 60.25%; H, 4.48%; N, 12.22%; Cl, 7.73%. found: C, 60.19%; H, 4.43%; N, 11.92%; Cl, 7.76%.

Example 63

N-(3-chloro-5-{5-[2'-fluoro-2-(trifluoromethyl)biphenyl-4-yl]-1,2,4-oxadiazol-3-yl}pyridin-2-yl)-beta-alanine Step 1) tert-butyl N-(3-chloro-5-{5-[2'-fluoro-2-(trifluoromethyl)biphenyl-4-yl]-1,2,4-oxadiazol-3-yl}pyridin-2-yl)-beta-alaninate

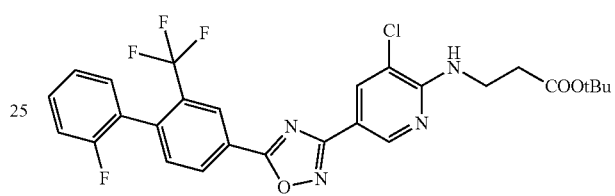

The title compound was prepared following procedure described in Method B starting from Intermediate A11 and Intermediate B16. After purification by flash chromatography (silica, EtOAc/cHex), the title compound was obtained as a colorless oil. HPLC (Method A), Rt: 6.6 min (purity: 99.8%). UPLC/MS, M$^+$(ESI): 563.0, M$^-$(ESI): 561.1.

Step 2) N-(3-chloro-5-{5-[2'-fluoro-2-(trifluoromethyl)biphenyl-4-yl]-1,2,4-oxadiazol-3-yl}pyridin-2-yl)-beta-alanine

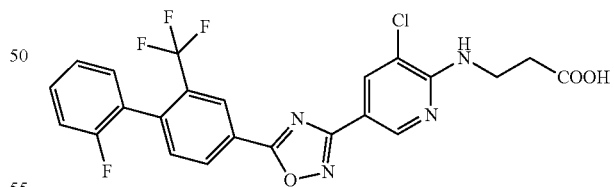

The title compound was prepared following procedure described in Method D starting from tert-butyl N-(3-chloro-5-{5-[2'-fluoro-2-(trifluoromethyl)biphenyl-4-yl]-1,2,4-oxadiazol-3-yl}pyridin-2-yl)-beta-alaninate. After purification by crystallization from ACN, the title compound was obtained as a white powder (327 mg, 75%). HPLC (Method A), Rt: 5.2 min (purity: 99.6%). UPLC/MS, M$^+$(ESI): 506.9, M$^-$(ESI): 505.0. $^1$H NMR (DMSO-d$_6$, 300 MHz) δ 8.73 (d, J=2.0 Hz, 1H), 8.50 (m, 2H), 8.15 (d, J=2.0 Hz, 1H), 7.77 (d, J=7.9 Hz, 1H), 7.60-7.52 (m, 1H), 7.44-7.31 (m, 3H), 7.23 (m, 1H), 3.67 (m, 2H), 2.60 (t, J=7.2 Hz, 2H).

Example 64

N-(5-{5-[2'-fluoro-2-(trifluoromethyl)biphenyl-4-yl]-1,2,4-oxadiazol-3-yl}-3-methylpyridin-2-yl)-beta-alanine, hydrochloride salt Step 1) tert-butyl N-(5-{5-[2'-fluoro-2-(trifluoromethyl)biphenyl-4-yl]-1,2,4-oxadiazol-3-yl}-3-methylpyridin-2-yl)-beta-alaninate

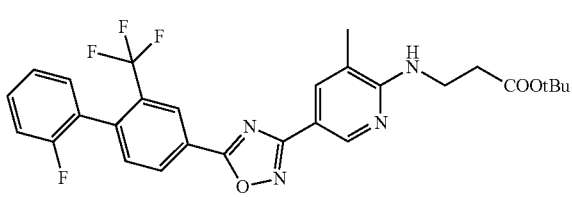

The title compound was prepared following procedure described in Method B starting from Intermediate A11 and Intermediate B21. After purification by flash chromatography (silica, EtOAc/cHex), the title compound was obtained as a colorless oil. HPLC (Method A), Rt: 4.8 min (purity: 94.5%). UPLC/MS, M$^+$(ESI): 543.1, M$^-$(ESI): 541.1.

Step 2) N-(5-{5-[2'-fluoro-2-(trifluoromethyl)biphenyl-4-yl]-1,2,4-oxadiazol-3-yl}-3-methylpyridin-2-yl)-beta-alanine, hydrochloride salt

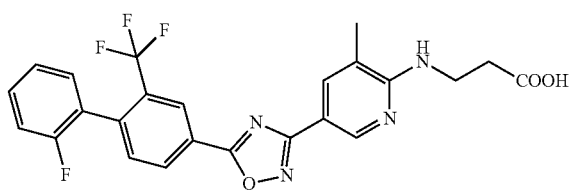 [SMILES: Cc1cc(-c2noc(-c3ccc(-c4ccccc4F)c(C(F)(F)F)c3)n2)cnc1NCCC(=O)O]

The title compound was prepared following procedure described in Method D starting from tert-butyl N-(5-{5-[2'-fluoro-2-(trifluoromethyl)biphenyl-4-yl]-1,2,4-oxadiazol-3-yl}-3-methylpyridin-2-yl)-beta-alaninate. After purification by crystallization from ACN, the title compound was obtained as a white powder (282 mg, 74%). HPLC (Method A), Rt: 4.0 min (purity: 99.5%). UPLC/MS, M$^+$(ESI): 486.9, M$^-$(ESI): 485.0. Elemental analysis: [$C_{24}H_{18}N_4O_3F_4$—HCl] calculated: C, 55.13%; H, 3.66%; N, 10.71%; Cl, 6.78%. found: C, 54.70%; H, 3.70%; N, 10.75%; Cl, 6.75%. $^1$H NMR (DMSO-d$_6$, 300 MHz) δ 8.54-8.47 (m, 3H), 8.20 (s, 1H), 7.78 (d, J=8.5 Hz, 1H), 7.61-7.52 (m, 1H), 7.44-7.31 (m, 3H), 3.75 (t, J=6.9 Hz, 2H), 2.71 (t, J=6.9 Hz, 2H), 2.27 (s, 3H).

Example 65

N-{3-chloro-5-[5-(2-ethoxy-2'-methylbiphenyl-4-yl)-1,2,4-oxadiazol-3-yl]pyridin-2-yl}-beta-alanine, hydrochloride salt Step 1) tert-butyl N-{3-chloro-5-[5-(2-ethoxy-2'-methylbiphenyl-4-yl)-1,2,4-oxadiazol-3-yl]pyridin-2-yl}-beta-alaninate

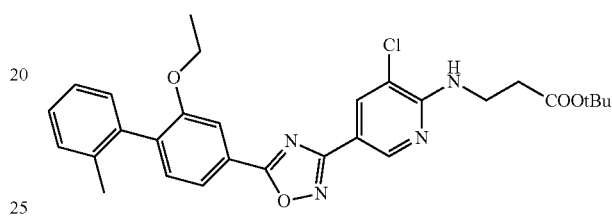

The title compound was prepared following procedure described in Method B starting from Intermediate A12 and Intermediate B16. After purification by flash chromatography (silica, EtOAc/cHex), the title compound was obtained as a colorless oil (500 mg, 78%). HPLC (Method A), Rt: 6.8 min (purity: 99.7%). UPLC/MS, M$^+$(ESI): 535.0, M$^-$(ESI): 533.2.

Step 2) N-{3-chloro-5-[5-(2-ethoxy-2'-methylbiphenyl-4-yl)-1,2,4-oxadiazol-3-yl]pyridin-2-yl}-beta-alanine, hydrochloride salt

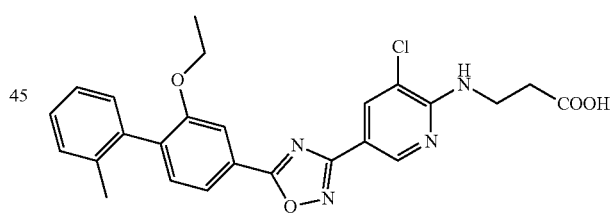

The title compound was prepared following procedure described in Method D starting from tert-butyl N-{3-chloro-5-[5-(2-ethoxy-2'-methylbiphenyl-4-yl)-1,2,4-oxadiazol-3-yl]pyridin-2-yl}-beta-alaninate. After purification by crystallization from ACN, the title compound was obtained as a white powder (370 mg, 77%). HPLC (Method A), Rt: 5.4 min (purity: 99.4%). UPLC/MS, M$^+$(ESI): 479.0, M$^-$(ESI): 477.1. Elemental analysis: [$C_{25}H_{23}N_4O_4Cl$—HCl-0.2H$_2$0] calculated: C, 57.86%; H, 4.74%; N, 10.80%; Cl, 13.66%. found: C, 57.75%; H, 4.79%; N, 10.95%; Cl, 13.45%. $^1$H NMR (DMSO-d$_6$, 300 MHz) δ 11.36 (brs, 2H), 8.70 (d, J=2.0 Hz, 1H), 8.13 (d, J=2.0 Hz, 1H), 7.80 (dd, J=7.8, 1.5 Hz, 1H), 7.74 (d, J=1.5 Hz, 1H), 7.37 (d, J=7.8 Hz, 1H), 7.30-7.21 (m, 4H), 7.15 (d, J=6.8 Hz, 1H), 4.16 (q, J=6.9 Hz, 2H), 3.67 (t, J=7.1 Hz, 2H), 2.60 (t, J=7.1 Hz, 2H), 2.11 (s, 3H), 1.23 (t, J=6.9 Hz, 3H).

Example 66

2-(methyl((4-(5-(4-(2-methylpiperidin-1-yl)-3-(trifluoromethyl)phenyl)-1,2,4-oxadiazol-3-yl)pyridin-2-yl)methyl)amino)acetic acid

Step 1) N'-hydroxy-2-(hydroxymethyl)isonicotinimidamide

A solution of 2-(hydroxymethyl)isonicotinonitrile (ChemPacific, 0.496 g; 3.7 mmol) and 50% aqueous hydroxylamine (1.2 mL) in ethanol (4.8 mL) was heated at 75° C. for 18 hours. The solvent was evaporated in vacuo. The residue was partitioned between DCM and water. The organic phase was poured through a hydrophobic frit and evaporated in vacuo to afford the title compound. $^1$H NMR (400 MHz, DMSO-d$_6$) δ 10.02 (1 H, s), 8.50 (1 H, d, J=5.2 Hz), 7.80 (1 H, s), 7.52 (1 H, dd, J=5.2, 1.7 Hz), 5.99 (2 H, br s), 5.45 (1 H, t, J=5.8 Hz), 4.60 (2 H, d, J=5.8 Hz).

Step 2) (4-(5-(4-(2-methylpiperidin-1-yl)-3-(trifluoromethyl)phenyl)-1,2,4-oxadiazol-3-yl)pyridin-2-yl)methanol To a solution of N'-hydroxy-2-(hydroxymethyl)isonicotinimidamide (0.100 g; 0.30 mmol) and Intermediate A5 (0.121 mg; 0.42 mmol) in MeCN (3 mL) was added EDC (0.060 g; 0.38 mmol). The reaction mixture was stirred at ambient temperature for 18 h. The reaction mixture was diluted with pyridine (2 mL) and heated at 150° C. in the microwave for 30 minutes. This process was repeated twice and combined for work-up. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (100% iso-hexane to 100% EtOAc) to afford the title product. $^1$H NMR (CDCl$_3$, 400 MHz) δ 8.76 (1 H, d, J=5.1 Hz), 8.51 (1 H, d, J=2.1 Hz), 8.34 (1 H, dd, J=8.4, 2.1 Hz), 8.03 (1 H, s), 7.96 (1 H, d, J=5.2 Hz), 7.55 (1 H, d, J=8.4 Hz), 4.90 (2 H, d, J=5.2 Hz), 3.62 (1 H, t, J=5.2 Hz), 3.14-3.03 (2 H, m), 2.59 (1 H, td, J=11.0, 3.1 Hz), 1.84-1.41 (6 H, m), 0.86 (3 H, d, J=6.2 Hz). LC/MS: 419 (M+H)$^+$. HPLC (Method B) Rt 4.56 min (Purity: 99.4%)

Step 3) 3-(2-(chloromethyl)pyridin-4-yl)-5-(4-(2-methylpiperidin-1-yl)-3-(trifluoromethyl)phenyl)-1,2,4-oxadiazole To a solution of (4-(5-(4-(2-methylpiperidin-1-yl)-3-(trifluoromethyl)phenyl)-1,2,4-oxadiazol-3-yl)pyridin-2-yl)methanol (0.125 g; 0.30 mmol) and DIEA (0.10 mL; 0.60 mmol) in DCM (2.5 mL) was added methanesulfonyl chloride (0.026 mL; 0.33 mmol). The reaction mixture was stirred at ambient temperature for 1 hour. Water was added to the reaction mixture and the mixture poured through a hydrophobic frit. The solvent was evaporated in vacuo. The residue was purified by flash chromatography on silica, eluting with iso-hexane/EtOAc (100% iso-hexane to 100% EtOAc) to afford the title product (0.129 g, 98%). $^1$H NMR (CDCl$_3$, 400 MHz) δ 8.77 (1 H, dd, J=5.1, 0.9 Hz), 8.51 (1 H, d, J=2.1 Hz), 8.34 (1H, dd, J=8.4, 2.1 Hz), 8.23 (1 H, s), 7.99 (1 H, dd, J=5.1, 1.6 Hz), 7.56 (1 H, d, J=8.4 Hz), 4.78 (2 H, s), 3.12-3.03 (2 H, m), 2.59 (1 H, td, J=11.0, 3.1 Hz), 1.86-1.62 (4 H, m), 1.53-1.38 (2 H, m), 0.86 (3 H, d, J=6.2 Hz).

Step 4) tert-butyl 2-(methyl((4-(5-(4-(2-methylpiperidin-1-yl)-3-(trifluoromethyl)phenyl)-1,2,4-oxadiazol-3-yl)pyridin-2-yl)methyl)amino)acetate A solution of 3-(2-(chloromethyl)pyridin-4-yl)-5-(4-(2-methylpiperidin-1-yl)-3-(trifluoromethyl)phenyl)-1,2,4-oxadiazole (0.065 g; 0.15 mmol), sarcosine t-butyl ester hydrochloride (0.031 g; 0.17 mmol) and K$_2$CO$_3$ (0.046 g; 0.34 mmol) in dioxan (2 mL) was heated at 70° C. for 96 hours. DCM and water were added to the reaction mixture. The mixture was poured through a hydrophobic frit. The solvent was evaporated in vacuo. The residue was purified by flash chromatography on silica, eluting with DCM/MeOH (100% DCM to 10% MeOH/DCM) to afford the title product. $^1$H NMR (CDCl$_3$, 400 MHz) δ 8.75 (1H, dd, J=5.1, 0.9 Hz), 8.51 (1 H, d, J=2.1 Hz), 8.34 (1 H, dd, J=8.4, 2.1 Hz), 8.21 (1 H, s), 7.91 (1 H, dd, J=5.1, 1.7 Hz), 7.55 (1 H, d, J=8.4 Hz), 3.98 (2 H, s), 3.34 (2 H, s), 3.12-3.01 (2 H, m), 2.59 (1 H, td, J=11.0, 3.0 Hz), 2.48 (3 H, s), 1.87-1.40 (6 H, m), 1.51 (9 H, s), 0.86 (3 H, d, J=6.2 Hz).

Step 5) 2-(methyl((4-(5-(4-(2-methylpiperidin-1-yl)-3-(trifluoromethyl)phenyl)-1,2,4-oxadiazol-3-yl)pyridin-2-yl)methyl)amino)acetic acid

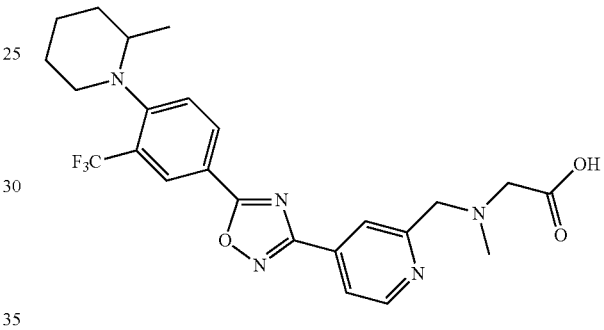

To tert-butyl 2-(methyl((4-(5-(4-(2-methylpiperidin-1-yl)-3-(trifluoromethyl)phenyl)-1,2,4-oxadiazol-3-yl)pyridin-2-yl)methyl)amino)acetate (0.056 g; 0.10 mmol) was added HCl solution in dioxan (4 M; 3 mL) and the reaction mixture stirred at 70° C. for 4 hours. The solvent was evaporated in vacuo and the residue purified by preparative HPLC, affording the title product as a brown oil. $^1$H NMR (CDCl$_3$, 400 MHz) δ 8.79 (1 H, d, J=5.1 Hz), 8.49 (1 H, d, J=2.1 Hz), 8.33 (1 H, dd, J=8.4, 2.1 Hz), 8.04-8.00 (2 H, m), 7.55 (1 H, d, J=8.4 Hz), 4.11 (2 H, s), 3.50 (2 H, s), 3.15-3.01 (2 H, m), 2.62 (3 H, s), 2.62-2.54 (1 H, m), 1.90-1.44 (6 H, m), 0.86 (3 H, d, J=6.2 Hz). LC/MS: 490 (M+H)$^+$. HPLC (Method B) Rt 3.46 min (Purity: 98.9%).

Example 67

3-(methyl((4-(5-(4-(2-methylpiperidin-1-yl)-3-(trifluoromethyl)phenyl)-1,2,4-oxadiazol-3-yl)pyridin-2-yl)methyl)amino)propanoic acid

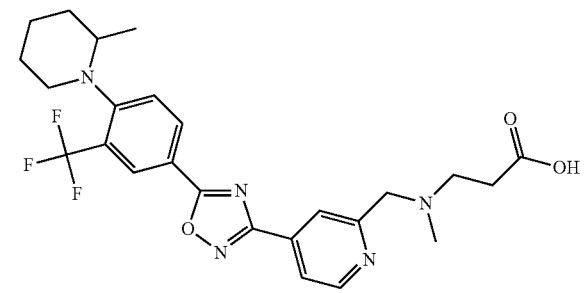 [SMILES: CC1CCCCN1c1ccc(-c2nc(-c3ccnc(CN(C)CCC(=O)O)c3)no2)cc1C(F)(F)F]

The title product was prepared as in Example 66 with tert-butyl 3-(methylamino)propanoate replacing sarcosine t-butyl ester hydrochloride in Step 4, and was isolated as a brown oil. $^1$H NMR (CDCl$_3$, 400 MHz) δ 8.81 (1 H, d, J=5.1 Hz), 8.50 (1 H, d, J=2.1 Hz), 8.35 (1 H, dd, J=8.4, 2.1 Hz), 8.04 (1 H, s), 8.00 (1 H, dd, J=5.1, 1.5 Hz), 7.56 (1 H, d, J=8.4 Hz), 3.99 (2 H, s), 3.15-3.03 (2 H, m), 2.96 (2 H, t, J=6.2 Hz), 2.63-2.53 (3 H, m), 2.49 (3 H, s), 1.86-1.44 (6 H, m), 0.86 (3 H, d, J=6.2 Hz). LC/MS: 490 (M+H)$^+$. HPLC (Method B) Rt 2.93 min (Purity: 98.3%).

Example 68

2-(((4-(5-(2-(methoxymethyl)-2'-methylbiphenyl-4-yl)-1,2,4-oxadiazol-3-yl)pyridin-2-yl)methyl)(methyl)amino)acetic acid Step 1) (4-(5-(2-(methoxymethyl)-2'-methylbiphenyl-4-yl)-1,2,4-oxadiazol-3-yl)pyridin-2-yl)methanol To a solution of N'-hydroxy-2-(hydroxymethyl)isonicotinimidamide (Example 66, Step 1; 0.100 g; 0.30 mmol) and Intermediate A1 (0.108 g; 0.42 mmol) in MeCN (3 mL) was added EDC (0.060 g; 0.38 mmol). The reaction mixture was stirred at ambient temperature for 18 h. The reaction mixture was diluted with pyridine (2 mL) and heated at 150° C. in the microwave for 30 minutes. This process was repeated 4 times and combined for work-up. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (100% iso-hexane to 100% EtOAc) to afford the title compound. $^1$H NMR (CDCl$_3$, 400 MHz) δ 8.76 (1 H, d, J=5.2 Hz), 8.44 (1 H, s), 8.18 (1 H, dd, J=7.9, 1.9 Hz), 8.06 (1 H, s), 7.99 (1 H, d, J=5.2 Hz), 7.39-7.22 (4 H, m), 7.13 (1 H, d, J=7.5 Hz), 4.90 (2 H, s), 4.28-4.18 (2 H, m), 3.65 (1 H, br s), 3.34 (3 H, s), 2.08 (3 H, s). LC/MS: 388 (M+H)$^+$. HPLC (Method B) Rt 3.91 min (Purity: 98.1%).

Step 2) 3-(2-(chloromethyl)pyridin-4-yl)-5-(2-(methoxymethyl)-2'-methylbiphenyl-4-yl)-1,2,4-oxadiazole To a solution of (4-(5-(2-(methoxymethyl)-2'-methylbiphenyl-4-yl)-1,2,4-oxadiazol-3-yl)pyridin-2-yl)methanol (0.282 g; 0.73 mmol) and DIEA (0.25 mL; 1.46 mmol) in DCM (6 mL) was added methanesulfonyl chloride (0.062 mL; 0.80 mmol). The mixture was stirred at ambient temperature for 1 hour and water added. The mixture was passed through a hydrophobic frit and the solvent was evaporated in vacuo. The residue was purified by flash chromatography on silica, eluting with iso-hexane/EtOAc (100% iso-hexane to 100% EtOAc) to afford the title compound. $^1$H NMR (CDCl$_3$, 400 MHz) δ 8.78 (1 H, d, J=5.1 Hz), 8.44 (1 H, d, J=1.8 Hz), 8.26 (1 H, s), 8.18 (1 H, dd, J=7.9, 1.9 Hz), 8.02 (1 H, dd, J=5.1, 1.5 Hz), 7.37-7.22 (4 H, m), 7.13 (1 H, d, J=7.5 Hz), 4.79 (2 H, s), 4.28-4.18 (2 H, m), 3.34 (3 H, s), 2.08 (3 H, s).

Step 3) 2-(((4-(5-(2-(methoxymethyl)-2'-methylbiphenyl-4-yl)-1,2,4-oxadiazol-3-yl)pyridin-2-yl)methyl)(methyl)amino)acetic acid

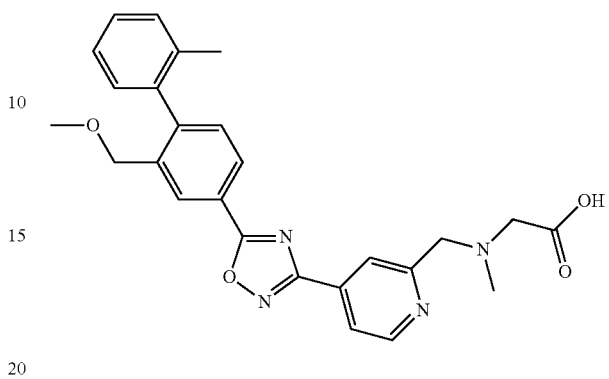

A solution of 3-(2-(chloromethyl)pyridin-4-yl)-5-(2-(methoxymethyl)-2'-methylbiphenyl-4-yl)-1,2,4-oxadiazole (0.097 g; 0.24 mmol), sarcosine t-butyl ester hydrochloride (0.037 g; 0.27 mmol) and K$_2$CO$_3$ (0.043 g; 0.27 mmol) in dioxan (3 mL) was heated at 70° C. for 7 days. DCM and water were added to the reaction mixture. The mixture was poured through a hydrophobic frit. The solvent was evaporated in vacuo. The material was purified by SCX chromatography and the material treated with HCl solution in dioxan (5 M; 3 mL) and the reaction mixture stirred at 70° C. for 18 hours. The solvent was evaporated in vacuo and the residue purified by preparative HPLC, affording the title product as a white solid. $^1$H NMR (CDCl$_3$, 400 MHz) δ 8.78 (1 H, d, J=5.1 Hz), 8.42 (1 H, s), 8.16 (1 H, dd, J=8.2, 2.0 Hz), 8.08 (1 H, s), 8.04 (1 H, dd, J=5.2, 1.5 Hz), 7.38-7.21 (4 H, m), 7.12 (1 H, d, J=7.4 Hz), 5.39 (1 H, br s), 4.23 (2 H, dd, J=17.0, 12.7 Hz), 4.17 (2 H, s), 3.54 (2 H, s), 3.34 (3 H, s), 2.66 (3 H, s), 2.08 (3 H, s). LC/MS: 388 (M+H)$^+$. HPLC (Method B) Rt 2.97 min (Purity: 99.2

Example 69

2-((4-(5-(2-(methoxymethyl)-2'-methylbiphenyl-4-yl)-1,2,4-oxadiazol-3-yl)pyridin-2-yl)methylamino) acetic acid

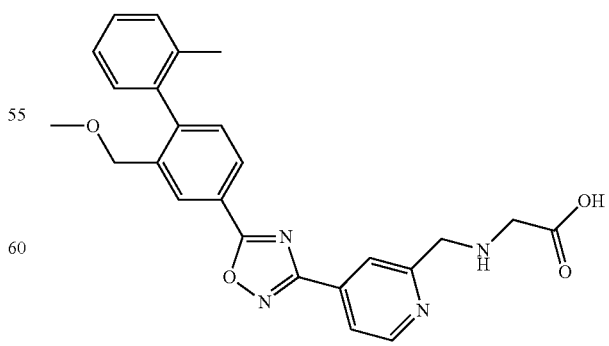

The title compound was prepared as in Example 68 with glycine t-butyl ester replacing sarcosine t-butyl ester hydrochloride in Step 3. It was isolated as an off-white solid. $^1$H NMR (CDCl$_3$, 400 MHz) δ 8.70 (1 H, d, J=5.2 Hz), 8.34 (1 H, s), 8.11 (1 H, s), 8.07 (1 H, dd, J=8.0, 1.9 Hz), 7.92 (1 H, d, J=5.2 Hz), 7.34-7.20 (4 H, m), 7.08 (1 H, d, J=7.5 Hz), 5.37 (2 H, br s), 4.55 (2 H, s), 4.17 (2 H, dd, J=15.6, 12.7 Hz), 3.76 (2 H, s), 3.29 (3 H, s), 2.04 (3 H, s). LC/MS: 445 (M+H)$^+$. HPLC (Method B) Rt 2.85 min (Purity: 99.6%).

Example 70

N-(3-chloro-5-{5-[2-methyl-2'-(trifluoromethyl)biphenyl-4-yl]-1,2,4-oxadiazol-3-yl}pyridin-2-yl)-beta-alanine, hydrochloride salt Step 1) tert-butyl N-(3-chloro-5-{5-[2-methyl-2'-(trifluoromethyl)biphenyl-4-yl]-1,2,4-oxadiazol-3-yl}pyridin-2-yl)-beta-alaninate

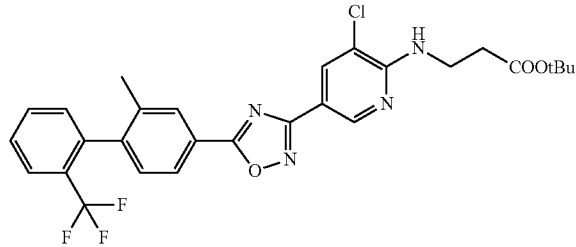

The title compound was prepared following procedure described in Method B starting from Intermediate A13 and Intermediate B16. After purification by flash chromatography (silica, EtOAc/cHex), the title compound was obtained as a colorless oil (507 mg, 76%). HPLC (Method A), Rt: 6.7 min (purity: 100%). UPLC/MS, M+(ESI): 559.2, M−(ESI): 557.3.

Step 2) N-(3-chloro-5-{5-[2-methyl-2'-(trifluoromethyl)biphenyl-4-yl]-1,2,4-oxadiazol-3-yl}pyridin-2-yl)-beta-alanine, hydrochloride salt

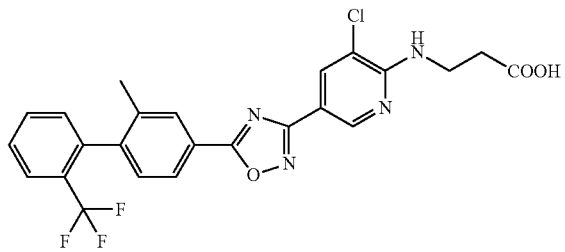 [SMILES: Cc1cc(-c2nc(-c3cnc(NCCC(=O)O)c(Cl)c3)no2)ccc1-c1ccccc1C(F)(F)F]

The title compound was prepared following procedure described in Method D starting from tert-butyl N-(3-chloro-5-{5-[2-methyl-2'-(trifluoromethyl)biphenyl-4-yl]-1,2,4-oxadiazol-3-yl}pyridin-2-yl)-beta-alaninate. After purification by crystallization from ACN, the title compound was obtained as a white powder. HPLC (Method A), Rt: 5.3 min (purity: 100%). UPLC/MS, M+(ESI): 503.0, M−(ESI): 501.1. $^1$H NMR (DMSO-d$_6$, 300 MHz) δ 10.71 (brs, 2H), 8.70 (d, J=2.0 Hz, 1H), 8.14 (m, 2H), 8.03 (dd, J=7.9, 1.7 Hz, 1H), 7.90 (d, J=7.6 Hz, 1H), 7.78 (m, 1H), 7.68 (m, 1H), 7.40 (m, 2H), 7.28 (brs, 1H), 3.67 (t, J=7.1 Hz, 2H), 2.60 (t, J=7.1 Hz, 2H), 2.10 (s, 3H).

Example 71

N-(3-chloro-5-{5-[2-ethoxy-2'-(trifluoromethyl)biphenyl-4-yl]-1,2,4-oxadiazol-3-yl}pyridin-2-yl)-beta-alanine, hydrochloride salt Step 1) tert-butyl N-(3-chloro-5-{5-[2-ethoxy-2'-(trifluoromethyl)biphenyl-4-yl]-1,2,4-oxadiazol-3-yl}pyridin-2-yl)-beta-alaninate

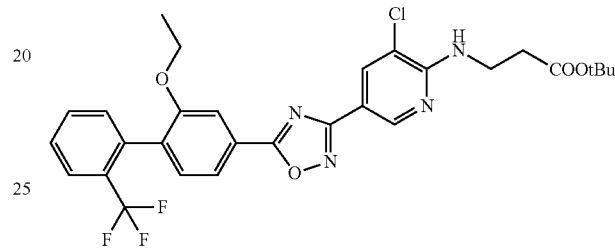

The title compound was prepared following procedure described in Method B starting from Intermediate A14 and Intermediate B16. After purification by flash chromatography (silica, EtOAc/cHex), the title compound was obtained as a colorless oil (544 mg, 77%). HPLC (Method A), Rt: 6.7 min (purity: 100%). UPLC/MS, M+(ESI): 589.1, M−(ESI): 587.2.

Step 2) N-(3-chloro-5-{5-[2-ethoxy-2'-(trifluoromethyl)biphenyl-4-yl]-1,2,4-oxadiazol-3-yl}pyridin-2-yl)-beta-alanine, hydrochloride salt

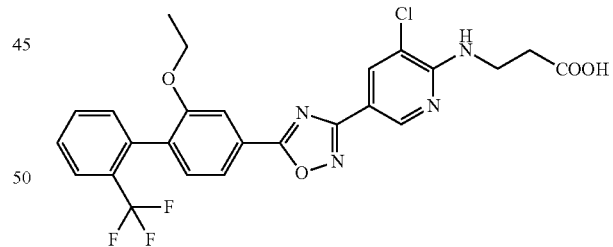

The title compound was prepared following procedure described in Method D starting from tert-butyl N-(3-chloro-5-{5-[2-ethoxy-2'-(trifluoromethyl)biphenyl-4-yl]-1,2,4-oxadiazol-3-yl}pyridin-2-yl)-beta-alaninate. After purification by crystallization from ACN, the title compound was obtained as a white powder. HPLC (Method A), Rt: 5.4 min (purity: 100%). UPLC/MS, M+(ESI): 533.0, M−(ESI): 531.1. Elemental analysis: [C$_{25}$H$_{20}$N$_4$O$_4$ClF$_3$—HCl-0.7H$_2$O] calculated: C, 51.60%; H, 3.88%; N, 9.63%; Cl, 12.18%. found: C, 51.66%; H, 3.96%; N, 9.67%; Cl, 11.89%. $^1$H NMR (DMSO-d$_6$, 300 MHz) δ 8.71 (d, J=2.0 Hz, 1H), 8.14 (d, J=2.0 Hz, 1H), 7.83 (d, J=8.3 Hz, 1H), 7.80 (dd, J=7.9, 1.6 Hz, 1H), 7.73 (m, 2H), 7.63 (m, 1H), 7.39 (m, 2H), 7.30 (brs, 1H), 4.14 (m, 2H), 3.67 (t, J=7.1 Hz, 2H), 2.60 (t, J=7.1 Hz, 2H), 1.15 (t, J=7.0 Hz, 3H).

Example 72

N-(3-chloro-5-{5-[3'-fluoro-2-(methoxymethyl)-2'-methylbiphenyl-4-yl]-1,2,4-oxadiazol-3-yl}pyridin-2-yl)-beta-alanine, hydrochloride salt Step 1) tert-butyl N-(3-chloro-5-{5-[3'-fluoro-2-(methoxymethyl)-2'-methylbiphenyl-4-yl]-1,2,4-oxadiazol-3-yl}pyridin-2-yl)-beta-alaninate

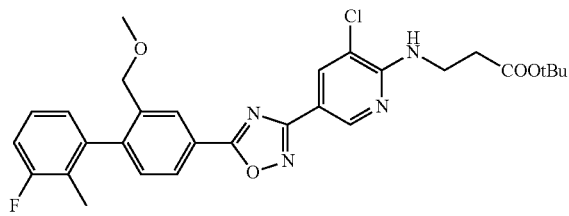

The title compound was prepared following procedure described in Method B starting from Intermediate A15 and Intermediate B16. After purification by flash chromatography (silica, EtOAc/cHex), the title compound was obtained as a colorless oil (549 mg, 83%). HPLC (Method A), Rt: 6.6 min (purity: 100%). UPLC/MS, M+(ESI): 553.0, M−(ESI): 551.2.

Step 2) N-(3-chloro-5-{5-[3'-fluoro-2-(methoxymethyl)-2'-methylbiphenyl-4-yl]-1,2,4-oxadiazol-3-yl}pyridin-2-yl)-beta-alanine, hydrochloride salt

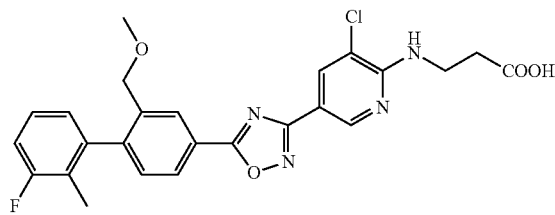 [SMILES: COCc1cc(-c2nc(-c3cnc(NCCC(=O)O)c(Cl)c3)no2)ccc1-c1cccc(F)c1C]

The title compound was prepared following procedure described in Method D starting from tert-butyl N-(3-chloro-5-{5-[3'-fluoro-2-(methoxymethyl)-2'-methylbiphenyl-4-yl]-1,2,4-oxadiazol-3-yl}pyridin-2-yl)-beta-alaninate. After purification by crystallization from ACN, the title compound was obtained as a white powder (391 mg, 77%). HPLC (Method A), Rt: 5.2 min (purity: 100%). UPLC/MS, M+(ESI): 497.0, M−(ESI): 495.1. Elemental analysis: $[C_{25}H_{22}N_4O_4ClF \cdot HCl]$ calculated: C, 56.30%; H, 4.35%; N, 10.50%; Cl, 13.29%. found: C, 56.15%; H, 4.32%; N, 10.65%; Cl, 13.12%. $^1$H NMR (DMSO-$d_6$, 300 MHz) δ 11.03 (brs, 2H), 8.71 (d, J=1.9 Hz, 1H), 8.29 (d, J=1.5 Hz, 1H), 8.15 (m, 2H), 7.43 (d, J=7.9 Hz, 1H), 7.37-7.21 (m, 3H), 7.02 (d, J=7.2 Hz, 1H), 4.22 (d, J=12.8 Hz, 1H), 4.17 (d, J=12.8 Hz, 1H), 3.67 (t, J=7.0 Hz, 2H), 3.24 (s, 3H), 2.60 (t, J=7.0 Hz, 2H), 1.94 (d, J=2.1 Hz, 3H).

Example 73

N-{3-chloro-5-[5-(2,2'-dimethylbiphenyl-4-yl)-1,2,4-oxadiazol-3-yl]pyridin-2-yl}-beta-alanine, hydrochloride salt Step 1) tert-butyl N-{3-chloro-5-[5-(2,2'-dimethylbiphenyl-4-yl)-1,2,4-oxadiazol-3-yl]pyridin-2-yl}-beta-alaninate

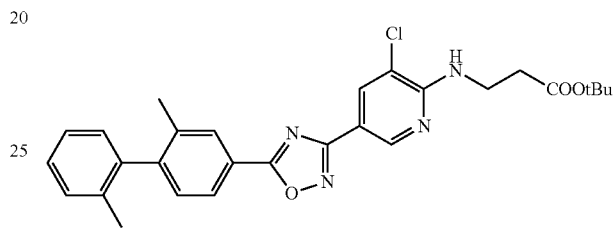

The title compound was prepared following procedure described in Method B starting from Intermediate A16 and Intermediate B16. After purification by flash chromatography (silica, EtOAc/cHex), the title compound was obtained as a colorless oil (475 mg, 78%). HPLC (Method A), Rt: 6.8 min (purity: 100%). UPLC/MS, M+(ESI): 505.1, M−(ESI): 503.2.

Step 2) N-{3-chloro-5-[5-(2,2'-dimethylbiphenyl-4-yl)-1,2,4-oxadiazol-3-yl]pyridin-2-yl}-beta-alanine, hydrochloride salt

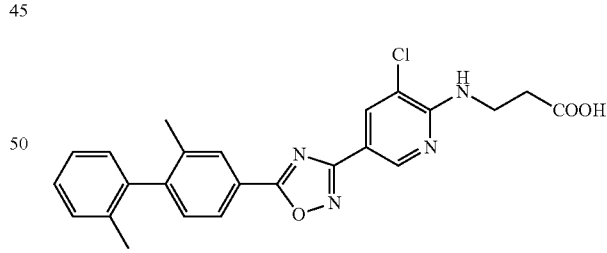

The title compound was prepared following procedure described in Method D starting from tert-butyl N-{3-chloro-5-[5-(2,2'-dimethylbiphenyl-4-yl)-1,2,4-oxadiazol-3-yl]pyridin-2-yl}-beta-alaninate. After purification by crystallization from ACN, the title compound was obtained as a white powder. HPLC (Method A), Rt: 5.4 min (purity: 100%). UPLC/MS, M+(ESI): 449.1, M−(ESI): 447.2. $^1$H NMR (DMSO-$d_6$, 300 MHz) δ 8.70 (d, J=2.0 Hz, 1H), 8.13 (m, 2H), 8.03 (dd, J=8.0, 1.7 Hz, 1H), 7.37-7.25 (m, 5H), 7.12 (d, J=7.4 Hz, 1H), 3.67 (t, J=7.2 Hz, 2H), 2.60 (t, J=7.2 Hz, 2H), 2.12 (s, 3H), 2.02 (s, 3H).

Example 74

2-(methyl((5-(5-(2'-methyl-2-(trifluoromethyl)biphenyl-4-yl)-1,2,4-oxadiazol-3-yl)pyridin-2-yl)methyl)amino)acetic acid

Step 1) N'-hydroxy-6-(hydroxymethyl)nicotinimidamide

A solution of 6-(hydroxymethyl)nicotinonitrile (ChemPacific, 0.698 g; 5.2 mmol) and 50% aqueous hydroxylamine (1.6 mL) in ethanol (10 mL) was heated at 80° C. for 3 hours. The solvent was evaporated in vacuo. The residue was partitioned between DCM and water. The organic phase was passed through a hydrophobic frit and evaporated in vacuo. The resultant solid was washed with MeCN and dried to afford the title product (0.850 g, 98%). $^1$H NMR (DMSO-$d_6$, 400 MHz) δ 9.79 (1 H, s), 8.79 (1 H, d, J=2.2 Hz), 8.05 (1 H, dd, J=8.2, 2.3 Hz), 7.49 (1 H, d, J=8.2 Hz), 5.98 (2 H, s), 5.56-5.40 (1 H, m), 4.60 (2 H, d, J=4.8 Hz).

Step 2) (5-(5-(2'-methyl-2-(trifluoromethyl)biphenyl-4-yl)-1,2,4-oxadiazol-3-yl)pyridin-2-yl)methanol To a solution of N'-hydroxy-6-(hydroxymethyl)nicotinimidamide, (0.075 g; 0.45 mmol) and Intermediate A4 (0.107 mg; 0.375 mmol) in MeCN (2.5 mL) was added EDC (0.101 g; 0.53 mmol). The reaction mixture was stirred at ambient temperature for 18 h. The reaction mixture was diluted with pyridine (2.5 mL) and heated at 150° C. in the microwave for 30 minutes. The reaction was repeated twice and combined for the work up. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (100% iso-hexane to 100% EtOAc) to afford the title compound. $^1$H NMR (CDCl$_3$, 400 MHz) δ 9.37 (1 H, d, J=2.0 Hz), 8.64 (1 H, s), 8.47 (1 H, dd, J=8.1, 2.1 Hz), 8.41 (1 H, dd, J=8.0, 1.8 Hz), 7.48 (2 H, t, J=8.7 Hz), 7.40-7.20 (3 H, m), 7.16 (1 H, d, J=7.6 Hz), 4.98 (2 H, s), 3.74 (1 H, s), 2.07 (3 H, s). LC/MS: 388 (M+H)$^+$. HPLC (Method C) Rt 3.44 min (Purity: 94.7%).

Step 3) 2-(methyl((5-(5-(2'-methyl-2-(trifluoromethyl)biphenyl-4-yl)-1,2,4-oxadiazol-3-yl)pyridin-2-yl)methyl)amino)acetic acid

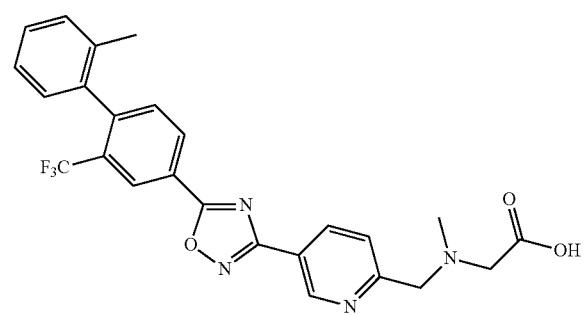 [SMILES: Cc1ccccc1-c1ccc(-c2nc(-c3ccc(CN(C)CC(=O)O)nc3)no2)cc1C(F)(F)F]

The title compound was prepared following the procedure described for Example 68, Steps 2 and 3, but starting from (5-(5-(2'-methyl-2-(trifluoromethyl)biphenyl-4-yl)-1,2,4-oxadiazol-3-yl)pyridin-2-yl)methanol, obtained in Step 2. It was isolated as a white solid. $^1$H NMR (DMSO-$d_6$, 400 MHz) δ 9.25-9.23 (1 H, m), 8.60-8.47 (3 H, m), 7.78 (1 H, d, J=8.1 Hz), 7.70 (1 H, d, J=7.9 Hz), 7.44-7.37 (2 H, m), 7.34-7.29 (1 H, m), 7.21 (1 H, d, J=7.5 Hz), 3.96 (2 H, s), 3.37 (2 H, s), 2.41-2.32 (3 H, m), 2.06 (3 H, s). LC/MS: 483 (M+H)$^+$. HPLC (Method B) Rt 3.09 min (Purity: 97.8%).

Example 75

2-(((4-(5-(2-(trifluoromethyl)-2'-methylbiphenyl-4-yl)-1,2,4-oxadiazol-3-yl)pyridin-2-yl)methyl)(methyl)amino)acetic acid

Step 1) (4-(5-(2'-methyl-2-(trifluoromethyl)biphenyl-4-yl)-1,2,4-oxadiazol-3-yl)pyridin-2-yl)methanol The title compound was prepared as in Example 68, Step 1, with Intermediate A4 replacing Intermediate A1. It was isolated as colorless oil. $^1$H NMR (CDCl$_3$, 400 MHz) δ 8.78 (1 H, dd, J=5.1, 0.9 Hz), 8.64 (1 H, d, J=1.7 Hz), 8.41 (1 H, dd, J=8.0, 1.7 Hz), 8.06 (1 H, dd, J=1.5, 0.9 Hz), 8.02-7.96 (1 H, m), 7.50 (1 H, d, J=8.0 Hz), 7.39-7.23 (3 H, m), 7.15 (1 H, d, J=7.6 Hz), 4.91 (2 H, d, J=5.1 Hz), 3.58 (1 H, t, J=5.1 Hz), 2.07 (3 H, s). LC/MS: 412 (M+H)$^+$. HPLC (Method B) Rt 4.06 min (Purity: 98.4%).

Step 2) 2-(((4-(5-(2-(trifluoromethyl)-2'-methylbiphenyl-4-yl)-1,2,4-oxadiazol-3-yl)pyridin-2-yl)methyl)(methyl)amino)acetic acid

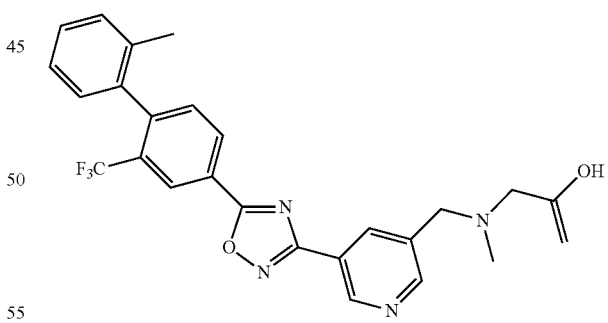

The title compound was prepared as Example 68, Steps 2 and 3 with (4-(5-(2'-methyl-2-(trifluoromethyl)biphenyl-4-yl)-1,2,4-oxadiazol-3-yl)pyridin-2-yl)methanol replacing (4-(5-(2-(methoxymethyl)-2'-methylbiphenyl-4-yl)-1,2,4-oxadiazol-3-yl)pyridin-2-yl)methanol. It was isolated as an off-white solid. $^1$H NMR (CDCl$_3$, 400 MHz) δ 8.86 (1 H, d, J=5.0 Hz), 8.57 (1H, s), 8.38 (2 H, t, J=7.6 Hz), 8.13 (1 H, d, J=4.8 Hz), 7.47 (1 H, d, J=8.0 Hz), 7.37-7.17 (3 H, m), 7.12 (1 H, d, J=7.6 Hz), 4.91 (2 H, br s), 4.46 (2 H, br s), 3.20 (3 H, br s), 2.05 (3 H, s). LC/MS: 483 (M+H)+. HPLC (Method B) Rt 3.11 min (Purity: 98.4%).

Example 76

5-{5-[2'-chloro-2-(methoxymethyl)biphenyl-4-yl]-1,2,4-oxadiazol-3-yl}-3-methylpyridin-2-amine

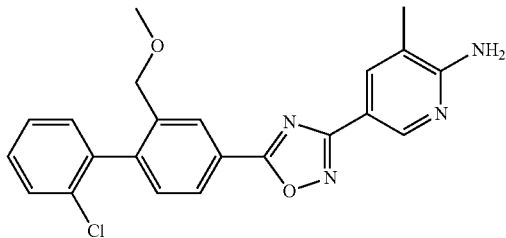 [SMILES: COCc1cc(-c2nc(-c3cnc(N)c(C)c3)no2)ccc1-c1ccccc1Cl]

The title compound was prepared following procedure described in Method C starting from Intermediate A8 and Intermediate B10. After purification by flash chromatography (silica, MTBE), followed by a crystallization from MTBE, the title compound was obtained as an off-white powder. HPLC (Method A), Rt: 3.9 min (purity: 99.8%). UPLC/MS, M+(ESI): 407.2. Melting point: 143-145° C. $^1$H NMR (DMSO-$d_6$, 300 MHz) δ 8.55 (d, J=2.2 Hz, 1H), 8.29 (d, J=1.7 Hz, 1H), 8.17 (dd, J=8.0, 1.7 Hz, 1H), 7.87 (brs, 1H), 7.62 (m, 1H), 7.53-7.44 (m, 3H), 7.39 (m, 1H), 6.50 (s, 2H), 4.29 (d, J=12.8 Hz, 1H), 4.22 (d, J=12.8 Hz, 1H), 3.24 (s, 3H), 2.14 (s, 3H).

Example 77

5-{5-[2-ethoxy-2'-(trifluoromethyl)biphenyl-4-yl]-1,2,4-oxadiazol-3-yl}-3-methylpyridin-2-amine

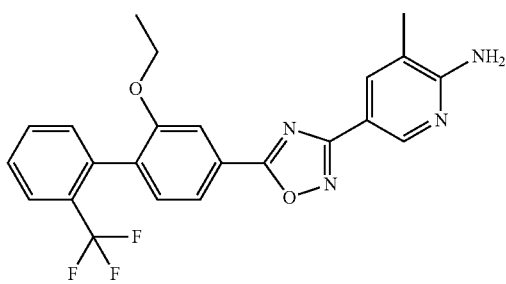 [SMILES: CCOc1cc(-c2nc(-c3cnc(N)c(C)c3)no2)ccc1-c1ccccc1C(F)(F)F]

The title compound was prepared following procedure described in Method B starting from Intermediate A14 and Intermediate B10. After purification by flash chromatography (silica, MTBE), followed by a crystallization from a mixture of MTBE and pentane, the title compound was obtained as a white powder. HPLC (Method A), Rt: 4.2 min (purity: 100%). UPLC/MS, M+(ESI): 441.1. Melting point: 163-165° C. Elemental analysis: [$C_{23}H_{19}N_4O_2F_3$-0.3$H_2O$] calculated: C, 61.96%; H, 4.43%; N, 12.57%. found: C, 62.02%; H, 4.21%; N, 12.49%.

Example 78

2-(((5-(5-(2-(methoxymethyl)-2'-methylbiphenyl-4-yl)-1,2,4-oxadiazol-3-yl)pyridin-2-yl)methyl)(methyl)amino)acetic acid Step 1: tert-butyl 2-(((5-cyanopyridin-2-yl)methyl)(methyl)amino)acetate A mixture of 6-bromomethylnicotinonitrile (Advanced Chemical Intermediates, 1.39 g; 7.06 mmol), sarcosine tert-butyl ester hydrochloride (1.54 g; 8.47 mmol) and $K_2CO_3$ (2.34 g; 17.0 mmol) in MeCN (25 mL) heated at 60° C. for 18 hours. The solvent was evaporated in vacuo. The residue was dissolved in a mixture of DCM and water and then poured through a hydrophobic frit. The filtrate was evaporated to afford the title product (2.17 g, quantitative). $^1$H NMR (CDCl$_3$, 400 MHz) δ 8.82 (1 H, d, J=2 Hz), 7.95-7.92 (1 H, dd, J=8.4, 2 Hz), 7.73 (1 H, d, J=8 Hz), 3.91 (2 H, s), 3.28 (2 H, s), 2.41 (3 H, s), 1.48 (9 H, s).

Step 2: tert-butyl 2-(((5-(N'-hydroxycarbamimidoyl)pyridin-2-yl)methyl)(methyl)amino)acetate A solution of tert-butyl 2-(((5-cyanopyridin-2-yl)methyl)(methyl)amino)acetate (2.17 g; 8.31 mmol) and 50% aqueous hydroxylamine (2.50 mL; 40.8 mmol) in ethanol (40 mL) was heated at 60° C. for 2 hours. The solvent was evaporated in vacuo. The residue was partitioned between DCM and water. The organic phase was poured through a hydrophobic frit and evaporated in vacuo. The residue was triturated with ether to afford the title product as an off-white solid (1.87 g, 77%). $^1$H NMR (DMSO-$d_6$, 400 MHz) δ 9.81 (1 H, s), 8.79 (1 H, d, J=2 Hz), 8.03 (1 H, dd, J=8.2, 2.2 Hz), 7.48 (1 H, d, J=8.2 Hz), 5.97 (2 H, br s), 3.80 (2 H, s), 2.32 (3 H, s), 1.46 (9 H, s).

Step 3: tert-butyl N-[(5-{5-[2-(methoxymethyl)-2'-methylbiphenyl-4-yl]-1,2,4-oxadiazol-3-yl}pyridin-2-yl)methyl]-N-methylglycinate To a solution of tert-butyl 2-(((5-(N'-hydroxycarbamimidoyl)pyridin-2-yl)methyl)(methyl)amino)acetate (0.750 g; 2.55 mmol) and Intermediate A1 (0.654 mg; 2.55 mmol) in MeCN (9 mL) was added EDC (0.538 g; 2.81 mmol). The reaction mixture was stirred at ambient temperature for 18 h. The reaction mixture was diluted with pyridine (9 mL) and heated at 150° C. in the microwave for 30 minutes. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (1:1), affording the title product. $^1$H NMR (CDCl$_3$, 400 MHz) δ 9.35-9.34 (1 H, m), 8.46-8.43 (2 H, m), 8.19-8.17 (1 H, m), 7.71-7.68 (1 H, m), 7.36-7.28 (4 H, m), 7.14-7.12 (1 H, m), 4.27-4.20 (2 H, m), 3.95 (2 H, s), 3.33 (3 H, s), 3.21 (2 H, s), 2.46 (3 H, s), 2.05 (3 H, s), 1.50 (9 H, s).

Step 4: 2-(((5-(5-(2-(methoxymethyl)-2'-methylbiphenyl-4-yl)-1,2,4-oxadiazol-3-yl)pyridin-2-yl)methyl)(methyl)amino)acetic acid

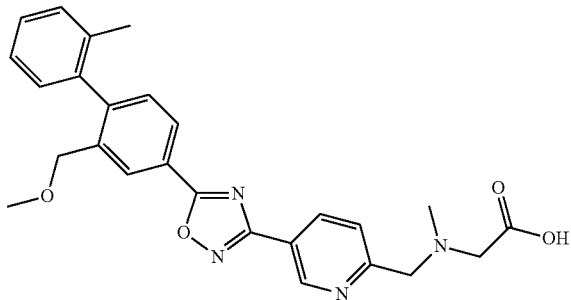 [SMILES: COCc1cc(-c2nc(-c3ccc(CN(C)CC(=O)O)nc3)no2)ccc1-c1ccccc1C]

To tert-butyl N-[(5-{5-[2-(methoxymethyl)-2'-methylbiphenyl-4-yl]-1,2,4-oxadiazol-3-yl}pyridin-2-yl)methyl]-N-methylglycinate (0.550 g; 1.07 mmol) was added HCl solution in dioxan (4 M; 15 mL) and the reaction mixture stirred at ambient temperature for 2 hours and at 80° C. for 1 hour. The reaction mixture was allowed to cool and the suspension was filtered. The solid was washed with ether and dried under vacuum. The residue was triturated with DCM to afford the title compound as an off-white solid (0.420 g, 74%). $^1$H NMR (DMSO-d$_6$/D$_2$O, 400 MHz) δ 9.31 (1 H, s), 8.58-8.55 (1 H, dd, J=8, 2 Hz), 8.30 (1 H, J=2 Hz), 8.19-8.16 (1 H, m), 7.77 (1 H, d, J=7.6 Hz), 7.42-7.26 (4 H, m), 7.11-7.10 (1 H, m), 4.65 (2 H, s), 4.26-4.12 (4 H, m), 3.21 (3 H, s), 2.92 (3 H, s), 2.00 (3 H, s). LC/MS: 459 (M+H)$^+$. HPLC (Method D) Rt 8.60 min (Purity: 98.5%).

Example 79

5-{5-[2'-fluoro-2-(methoxymethyl)biphenyl-4-yl]-1,2,4-oxadiazol-3-yl}-3-methylpyridin-2-amine

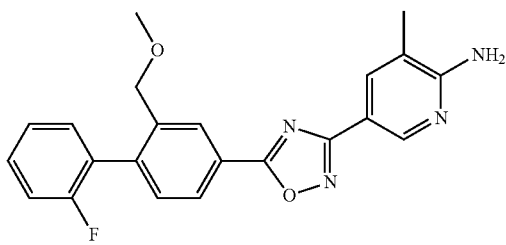 [SMILES: COCc1cc(-c2nc(-c3cnc(N)c(C)c3)no2)ccc1-c1ccccc1F]

The title compound was prepared following procedure described in Method C starting from Intermediate A10 and Intermediate B10. After purification by crystallization from EtOAc, the title compound was obtained as a pale yellow powder. HPLC (Method A), Rt: 3.7 min (purity: 99.9%). UPLC/MS, M+(ESI): 391.2. Melting point: 162-164° C. Elemental analysis: [C$_{22}$H$_{19}$N$_4$O$_2$F·0.6H$_2$O] calculated: C, 65.86%; H, 5.07%; N, 13.96%. found: C, 65.80%; H, 4.85%; N, 13.80%.

Example 80

2-(methyl((4-(5-(2-methyl-2'-(trifluoromethyl)biphenyl-4-yl)-1,2,4-oxadiazol-3-yl)pyridin-2-yl)methyl)amino)acetic acid Step 1) (5-(5-(2-methyl-2'-(trifluoromethyl)biphenyl-4-yl)-1,2,4-oxadiazol-3-yl)pyridin-2-yl)methanol To a solution of N'-hydroxy-2-(hydroxymethyl)isonicotinimidamide (prepared in Example 66, Step 1) (0.075 g; 0.45 mmol) and Intermediate A13 (0.107 mg; 0.38 mmol) in MeCN (2.5 mL) was added EDC (0.101 g; 0.53 mmol). The reaction mixture was stirred at ambient temperature for 18 h. The reaction mixture was diluted with pyridine (2.5 mL) and heated at 150° C. in the microwave for 30 minutes. This process was repeated twice and combined for work-up. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (100% iso-hexane to 100% EtOAc) to afford the title product. $^1$H NMR (CDCl$_3$, 400 MHz) δ 9.37 (1 H, d, J=2.0 Hz), 8.46 (1 H, dd, J=8.1, 2.0 Hz), 8.14 (1 H, d, J=1.7 Hz), 8.07 (1 H, dd, J=7.9, 1.8 Hz), 7.81 (1 H, d, J=7.9 Hz), 7.62 (1 H, t, J=7.5 Hz), 7.54 (1 H, t, J=7.7 Hz), 7.44 (1 H, dd, J=8.1, 0.9 Hz), 7.35 (1 H, d, J=7.9 Hz), 7.28-7.24 (2 H, m), 4.87 (2 H, d, J=5.2 Hz), 3.59 (1 H, t, J=5.2 Hz), 2.16 (3 H, s).

Step 2) 3-(2-(chloromethyl)pyridin-4-yl)-5-(2-methyl-2'-(trifluoromethyl)biphenyl-4-yl)-1,2,4-oxadiazole To a solution of (5-(5-(2-methyl-2'-(trifluoromethyl)biphenyl-4-yl)-1,2,4-oxadiazol-3-yl)pyridin-2-yl)methanol (0.103 g; 0.28 mmol) and DIEA (0.087 mL; 0.50 mmol) in DCM (2.5 mL) was added methanesulfonyl chloride (0.021 mL; 0.27 mmol). The mixture was stirred at ambient temperature for 1 hour and water added. The mixture was passed through a hydrophobic frit and the solvent was evaporated in vacuo. The residue was purified by flash chromatography on silica, eluting with iso-hexane/EtOAc (100% iso-hexane to 100% EtOAc) to afford the title product (0.085 g, 79%). $^1$H NMR (CDCl$_3$, 400 MHz) δ 8.78 (1 H, d, J=5.1 Hz), 8.25 (1 H, s), 8.15 (1 H, s), 8.08 (1 H, dd, J=8.0, 1.7 Hz), 8.01 (1 H, dd, J=5.0, 1.5 Hz), 7.81 (1 H, d, J=8.0 Hz), 7.63 (1 H, t, J=7.6 Hz), 7.54 (1 H, t, J=7.8 Hz), 7.36 (1 H, d, J=7.9 Hz), 7.29-7.23 (1 H, m), 4.79 (2 H, s), 2.16 (3 H, s).

Step 3) tert-butyl 2-(methyl((5-(5-(2-methyl-2'-(trifluoromethyl)biphenyl-4-yl)-1,2,4-oxadiazol-3-yl)pyridin-2-yl)methyl)amino)acetate A solution of the 3-(2-(chloromethyl)pyridin-4-yl)-5-(2-methyl-2'-(trifluoromethyl)biphenyl-4-yl)-1,2,4-oxadiazole (0.100 g; 0.23 mmol), sarcosine t-butyl ester hydrochloride (0.084 g; 0.46 mmol) and K$_2$CO$_3$ (0.127 g; 0.92 mmol) in dioxan (4 mL) was heated at 80° C. for 18 hours. DCM and water were added to the reaction mixture. The residue was purified by flash chromatography on silica, eluting with iso-hexane/EtOAc (100% iso-hexane to 100% EtOAc) to afford the title product (0.138 g, 100%). $^1$H NMR (CDCl$_3$, 400 MHz) δ 8.75 (1 H, d, J=5.1 Hz), 8.23 (1 H, s), 8.15 (1 H, s), 8.10-8.05 (1 H, m), 7.93 (1 H, dd, J=5.1, 1.6 Hz), 7.81 (1 H, d, J=7.9 Hz), 7.62 (1 H, t, J=7.5 Hz), 7.54 (1 H, t, J=7.7 Hz), 7.35 (1 H, d, J=7.9 Hz), 7.30-7.23 (1 H, m), 3.99 (2 H, s), 3.35 (2 H, s), 2.49 (3 H, s), 2.16 (3 H, s), 1.51 (9 H, s).

Step 4) 2-(methyl((4-(5-(2-methyl-2'-(trifluoromethyl)biphenyl-4-yl)-1,2,4-oxadiazol-3-yl)pyridin-2-yl)methyl)amino)acetic acid

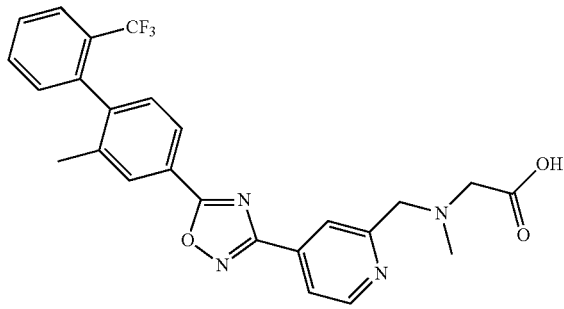 [SMILES: Cc1cc(-c2nc(-c3ccnc(CN(C)CC(=O)O)c3)no2)ccc1-c1ccccc1C(F)(F)F]

To tert-butyl 2-(methyl((5-(5-(2-methyl-2'-(trifluoromethyl)biphenyl-4-yl)-1,2,4-oxadiazol-3-yl)pyridin-2-yl)methyl)amino)acetate (0.138 g; 0.26 mmol) was added HCl solution in dioxan (4M, 8 mL). The reaction mixture was stirred at 80° C. for 2 hours. The solvent was evaporated in vacuo and the residue purified by preparative HPLC to afford the title compound as an off-white solid. $^1$H NMR (DMSO-$d_6$, 400 MHz) δ 8.80 (1 H, d, J=5.1 Hz), 8.21 (2 H, d, J=11.7 Hz), 8.13 (1 H, d, J=8.0 Hz), 8.00-7.92 (2 H, m), 7.82 (1 H, t, J=7.6 Hz), 7.72 (1 H, t, J=7.8 Hz), 7.45 (2 H, t, J=8.6 Hz), 3.99 (2 H, s), 3.48 (2 H, s), 2.41 (3 H, s), 2.15 (3 H, s). LC/MS: 483 (M+H)$^+$. HPLC (Method B) Rt 3.02 min (Purity: 99.2%).

Example 81

2-(methyl((5-(5-(2-methyl-2'-(trifluoromethyl)biphenyl-4-yl)-1,2,4-oxadiazol-3-yl)pyridin-2-yl)methyl)amino)acetic acid

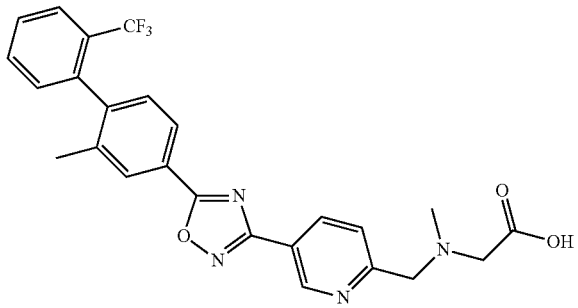 [SMILES: Cc1cc(-c2nc(-c3ccc(CN(C)CC(=O)O)nc3)no2)ccc1-c1ccccc1C(F)(F)F]

The title compound was prepared as in Example 80 with Intermediate A13 replacing Intermediate A1 in step 3. $^1$H NMR (DMSO-$d_6$, 400 MHz) 9.22 (1 H, d, J=2.2 Hz), 8.49 (1 H, dd, J=8.1, 2.2 Hz), 8.22 (1 H, s), 8.12 (1 H, dd, J=7.9, 1.8 Hz), 7.95 (1 H, d, J=7.9 Hz), 7.86-7.69 (3 H, m), 7.45 (2 H, t, J=7.8 Hz), 3.95 (2 H, s), 3.34 (2 H, s), 2.39 (3 H, s), 2.15 (3 H, s). LC/MS: 483 (M+H)$^+$. HPLC (Method B) Rt 3.02 min (Purity: 99.2%).

Example 82

3-chloro-5-(5-(2-(methoxymethyl)-2'-methylbiphenyl-4-yl)-1,2,4-oxadiazol-3-yl)-N-(3-methoxypropyl)pyridin-2-amine Step 1) 3-chloro-5-(5-(2-(methoxymethyl)-2'-methylbiphenyl-4-yl)-1,2,4-oxadiazol-3-yl)pyridin-2-ol To a solution of 5-chloro-N',6-dihydroxynicotinimidamide (Bionet, 1.46 g; 7.78 mmol) and Intermediate A1 (1.66 g; 6.48 mmol) in MeCN (50 mL) was added EDC (1.61 g; 8.42 mmol). The reaction mixture was stirred at ambient temperature for 18 h. The reaction mixture was diluted with pyridine (20 mL) and heated at 115° C. for 24 hours. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (100% iso-hexane to 100% EtOAc) to afford the title product as an off-white solid. $^1$H NMR (DMSO-$d_6$, 400 MHz) δ 12.84 (1 H, s), 8.32 (1 H, s), 8.26 (1 H, d, J=2.3 Hz), 8.21 (1 H, d, J=2.4 Hz), 8.17 (1 H, dd, J=7.9, 1.9 Hz), 7.45 (1 H, d, J=7.9 Hz), 7.41-7.37 (2 H, m), 7.34-7.29 (1 H, m), 7.17 (1 H, d, J=7.4 Hz), 4.22 (2 H, q, J=9.4 Hz), 3.27 (3 H, s), 2.06 (3 H, s). LC/MS: 408 (M+H)$^+$. HPLC (Method C) Rt 3.79 min (Purity: 99.4%).

Step 2) 3-chloro-5-(5-(2-(methoxymethyl)-2'-methylbiphenyl-4-yl)-1,2,4-oxadiazol-3-yl)-N-(3-methoxypropyl)pyridin-2-amine

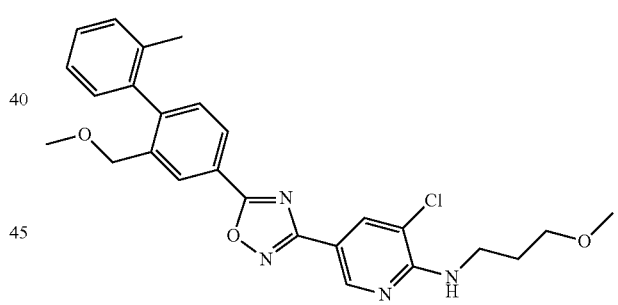

To a solution of 3-chloro-5-(5-(2-(methoxymethyl)-2'-methylbiphenyl-4-yl)-1,2,4-oxadiazol-3-yl)pyridin-2-ol (0.702 g; 1.72 mmol) and DIEA (0.24 mL; 1.38 mmol) in toluene (30 mL) was added phosphorus oxychloride (0.192 mL; 2.06 mmol). The reaction mixture was heated at 120° C. for 2 hours. The solvent was removed in vacuo and the residue tritutrated with MeCN to afford a solid. A portion of the solid (0.150 g) combined with 3-methoxypropylamine (0.039 mL; 0.39 mmol) and DIEA (0.104 mL; 0.60 mmol) in MeCN (2 mL). The reaction mixture was heated under reflux for 18 hours. The solvent was evaporated in vacuo and the residue was purified by flash chromatography on silica, eluting with iso-hexane/EtOAc (100% iso-hexane to 100% EtOAc) to afford the title compound as a colorless oil. $^1$H NMR (CDCl$_3$, 400 MHz) δ 8.84 (1 H, d, J=2.0 Hz), 8.40 (1 H, d, J=1.7 Hz), 8.20 (1 H, d, J=2.0 Hz), 8.15 (1 H, dd, J=7.9, 1.9 Hz), 7.36-7.23 (4 H, m), 7.13 (1 H, d, J=7.4 Hz), 6.03 (1 H, t, J=5.2 Hz), 4.22 (2 H, d, J=2.1 Hz), 3.67 (2 H, q, J=6.0 Hz), 3.58 (2 H, t, J=5.67 Hz), 3.40 (3 H, s), 3.32 (3 H, s), 2.08 (3 H, s), 2.01-1.92 (2 H, m). LC/MS: 479 (M+H)⁺. HPLC (Method E) Rt 5.76 min (Purity: 99.8%).

Example 83

3-(3-chloro-5-(5-(2-(methoxymethyl)-2'-methylbiphenyl-4-yl)-1,2,4-oxadiazol-3-yl)pyridin-2-ylamino)propan-1-ol

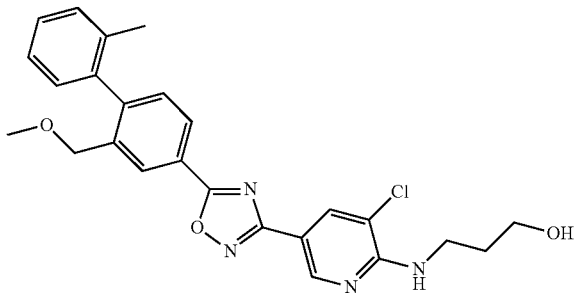 [SMILES: COCc1cc(-c2nc(-c3cnc(NCCCO)c(Cl)c3)no2)ccc1-c1ccccc1C]

The title compound was prepared as in Example 82 with 3-aminopropanol replacing 3-methoxypropylamine in step 2. ¹H NMR (CDCl₃, 400 MHz) δ 8.82 (1 H, d, J=2.0 Hz), 8.40 (1H, s), 8.22 (1 H, d, J=2.0 Hz), 8.14 (1 H, dd, J=7.9, 1.8 Hz), 7.35-7.22 (4 H, m), 7.13 (1 H, d, J=7.4 Hz), 5.80 (1 H, t, J=6.2 Hz), 4.22 (2 H, d, J=2.5 Hz), 3.75 (2 H, q, J=6.1 Hz), 3.69 (2 H, t, J=5.5 Hz), 3.33 (3 H, s), 2.08 (3 H, s), 1.90-1.81 (2 H, m). LC/MS: 465 (M+H)⁺. HPLC (Method C) Rt 4.31 min (Purity: 99.8%).

Example 84 cis-2-(3-chloro-5-(5-(2-(methoxymethyl)-2'-methylbiphenyl-4-yl)-1,2,4-oxadiazol-3-yl)pyridin-2-ylamino)cyclopentanecarboxylic acid Step 1) cis-methyl 2-(3-chloro-5-cyanopyridin-2-ylamino)cyclopentanecarboxylate A solution of cis-2-amino-1-cyclopentanecarboxylic acid (0.403 g; 3.12 mmol) and 2,2-dimethoxypropane (3 mL) in MeOH (5 mL) was treated with concentrated hydrochloric acid (2 mL). The reaction mixture was heated under reflux for 8 hours. The solvent was evaporated in vacuo. The residue was combined with 5,6-dichloronicotinonitrile (Bionet, 0.346 g; 2.00 mmol), DIEA (0.348 mL; 2.00 mmol) in MeCN (10 mL). The reaction mixture was heated under reflux for 24 hours. The reaction mixture was diluted with DCM and washed with water. The organic phase was passed through a hydrophobic frit and the solvent evaporated in vacuo. The residue was purified by flash chromatography on silica, eluting with iso-hexane/EtOAc (60 iso-hexane to 10 EtOAc) to afford the title product. ¹H NMR (CDCl₃, 400 MHz) δ 8.29 (1H, d, J=2 Hz), 7.61 (1H, d, J=2 Hz), 6.29 (1H, br d, J=7.6 Hz), 4.76-4.68 (1H, m), 3.63 (3H, s), 3.16-3.10 (1H, m), 2.16-1.78 (6H, m).

Step 2) cis-methyl 2-(3-chloro-5-(N'-hydroxycarbamimidoyl)pyridin-2-ylamino)cyclopentanecarboxylate A solution of cis-methyl 2-(3-chloro-5-cyanopyridin-2-ylamino)cyclopentanecarboxylate (0.154 g; 0.55 mmol), hydroxylamine hydrochloride (0.057 g; 0.82 mmol) and DIEA (0.143 mL; 0.82 mmol) in EtOH (2 mL) was stirred at ambient temperature for 42 hours. The solvent was evaporated in vacuo and the residue dissolved in DCM/water. The mixture was passed through a hydrophobic frit and the solvent evaporated in vacuo to afford the title product (0.172 g; quantitative). ¹H NMR (CDCl₃, 400 MHz) δ 8.25 (1H, d, J=2 Hz), 7.74 (1H, d, J=2 Hz), 5.74 (1H, d, J=8.4 Hz), 4.77-4.70 (3H, m), 3.61 (3H, s), 3.19-3.14 (1H, m), 2.14-1.70 (6H, m).

Step 3) methyl cis-2-(3-chloro-5-(5-(2-(methoxymethyl)-2'-methylbiphenyl-4-yl)-1,2,4-oxadiazol-3-yl)pyridin-2-ylamino)cyclopentanecarboxylate To a solution of cis-methyl 2-(3-chloro-5-(N'-hydroxycarbamimidoyl)pyridin-2-ylamino)cyclopentanecarboxylate (0.172 g; 0.55 mmol) and Intermediate A1 (0.155 g; 0.60 mmol) in MeCN (2 mL) was added EDC (0.117 g; 0.61 mmol). The reaction mixture was stirred at ambient temperature for 18 h. The reaction mixture was diluted with pyridine (2 mL) and heated at 150° C. in the microwave for 30 minutes. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (4:1) to afford the title product. ¹H NMR (CDCl₃, 400 MHz) δ 8.84 (1H, d, J=2 Hz), 8.40 (1H, s), 8.21 (1H, d, J=2), 8.15-8.10 (1H, m), 7.34-7.26 (4H, m), 7.13 (1H, d, J=7.5 Hz), 5.91 (1H, d, J=8.3 Hz), 4.83 (1H, m), 4.22-4.13 (2H, m), 3.63 (3H, s), 3.33 (3H, s), 3.23-3.17 (1H, m), 2.21-1.63 (9H, m).

Step 4) cis-2-(3-chloro-5-(5-(2-(methoxymethyl)-2'-methylbiphenyl-4-yl)-1,2,4-oxadiazol-3-yl)pyridin-2-ylamino)cyclopentanecarboxylic acid

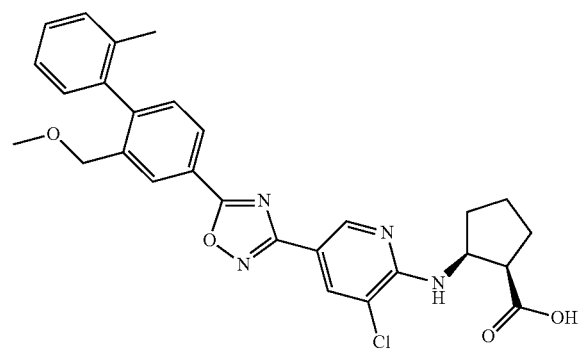 [SMILES: COCc1cc(-c2nc(-c3cnc(N[C@H]4CCC[C@H]4C(=O)O)c(Cl)c3)no2)ccc1-c1ccccc1C]

A solution of methyl cis-2-(3-chloro-5-(5-(2-(methoxymethyl)-2'-methylbiphenyl-4-yl)-1,2,4-oxadiazol-3-yl)pyridin-2-ylamino)cyclopentanecarboxylate (0.099 g; 0.19 mmol) in dioxan (2 mL) was added hydrochloric acid (1 mL). The mixture was heated at 60° C. for 24 hours. The solvent was evaporated and the residue purified by preparative HPLC to afford the title compound. ¹H NMR (DMSO-d₆, 400 MHz) δ 8.76 (1H, d, J=2.0 Hz), 8.33 (1H, s), 8.23-8.14 (2H, s), 7.45-7.26 (4H, m), 7.18 (1H, d, J=7.4 Hz), 6.86 (1H, s), 4.76-4.66 (1H, m), 4.28-4.16 (2H, m), 3.28 (3H, s), 3.11-3.02

(1H, m), 2.15-1.88 (6H, m), 1.88-1.78 (2H, m), 1.71-1.59 (1H, m). LC/MS: 519 (M+H)+. HPLC (Method F) Rt 9.03 min (Purity: 90.9%).

Example 85

3-(3-chloro-5-(5-(2-(methoxymethyl)-2'-methylbiphenyl-4-yl)-1,2,4-oxadiazol-3-yl)pyridin-2-ylamino)butanoic acid

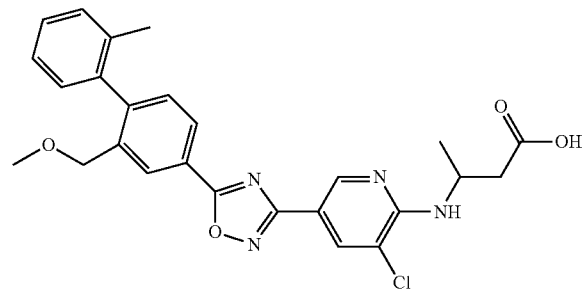 [SMILES: COCc1cc(-c2nc(-c3cnc(NC(C)CC(=O)O)c(Cl)c3)no2)ccc1-c1ccccc1C]

The title compound was prepared as in Example 84 with 3-aminobutanoic acid replacing cis-2-amino-1-cyclopentanecarboxylic acid in Step 1. $^1$H NMR (DMSO-d$_6$, 400 MHz) δ 8.72 (1 H, d, J=2.0 Hz), 8.29 (1 H, s), 8.19-8.15 (2 H, m), 7.42 (1 H, d, J=7.9 Hz), 7.37 (2 H, d, J=4.4 Hz), 7.34-7.28 (1 H, m), 7.14 (1 H, d, J=7.4 Hz), 4.66-4.60 (1 H, m), 4.19 (2 H, d, J=5.8 Hz), 3.24 (3 H, s), 2.71-2.48 (2 H, m), 2.04 (3 H, s), 1.26 (3 H, d, J=6.6 Hz). LC/MS: 493 (M+H)+. HPLC (Method C) Rt 3.00 min (Purity: 96.99%).

Example 86

3-(3-chloro-5-(5-(2-(methoxymethyl)-2'-methylbiphenyl-4-yl)-1,2,4-oxadiazol-3-yl)pyridin-2-ylamino)-2-methylpropanoic acid

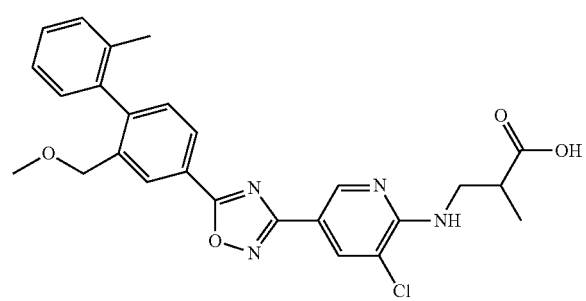 [SMILES: COCc1cc(-c2nc(-c3cnc(NCC(C)C(=O)O)c(Cl)c3)no2)ccc1-c1ccccc1C]

The title compound was prepared as in Example 84 with 3-amino-2-methylpropanoic acid replacing cis-2-amino-1-cyclopentanecarboxylic acid in Step 1. $^1$H NMR (DMSO-d$_6$, 400 MHz) δ 8.75 (1 H, d, J=1.99 Hz), 8.33 (1 H, s), 8.20-8.16 (2 H, m), 7.45 (1 H, d, J=7.93 Hz), 7.39 (2 H, d, J=4.38 Hz), 7.35-7.24 (2 H, m), 7.18 (1 H, d, J=7.43 Hz), 4.27-4.17 (2 H, m), 3.77-3.69 (1 H, m), 3.58-3.48 (1 H, m), 3.27 (3H, s), 2.89-2.83 (1 H, m), 2.07 (3 H, s), 1.14 (3 H, d, J=7.07 Hz). LC/MS: 493 (M+H)+. HPLC (Method G) Rt 8.99 min (Purity: 96.4%)

Example 87

1-(3-chloro-5-(5-(2-(methoxymethyl)-2'-methylbiphenyl-4-yl)-1,2,4-oxadiazol-3-yl)pyridin-2-yl)piperidine-4-carboxylic acid

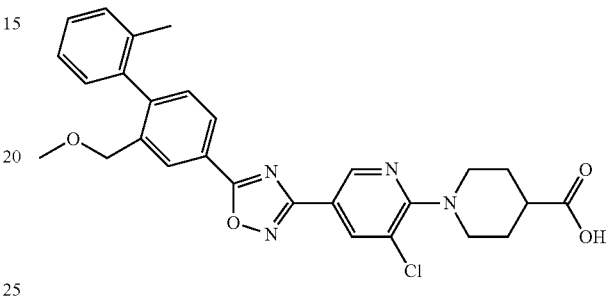

The title compound was prepared as in Example 84 with piperidine-4-carboxylic acid replacing cis-2-amino-1-cyclopentanecarboxylic acid in Step 1. $^1$H NMR (DMSO-d$_6$, 400 MHz) δ 8.84 (1 H, d, J=2.0 Hz), 8.30 (2 H, s), 8.18 (1 H, d, J=8.0 Hz), 7.42 (1 H, d, J=7.9 Hz), 7.37 (2 H, d, J=4.4 Hz), 7.34-7.27 (1 H, m), 7.14 (1 H, d, J=7.4 Hz), 4.19 (2 H, d, J=5.8 Hz), 3.95 (2 H, d, J=13.1 Hz), 3.24 (3 H, s), 3.03 (2 H, t, J=12.0 Hz), 2.62-2.48 (1 H, m), 2.04 (3 H, s), 1.97 (2 H, d, J=13.3 Hz), 1.77-1.64 (2 H, m). LC/MS: 519 (M+H)+. HPLC (Method C) Rt 3.00 min (Purity: 98.96%).

Examples 88 and 89

(2S,4R)-1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylic acid and (2R,4R)-1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylic acid

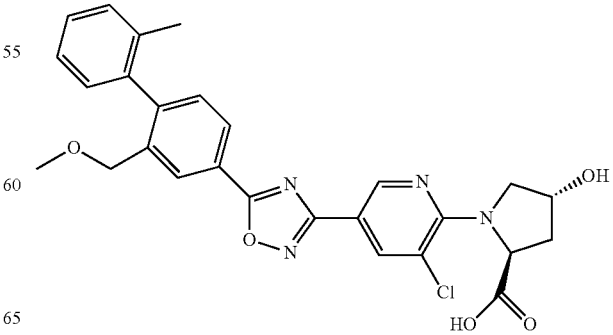

-continued

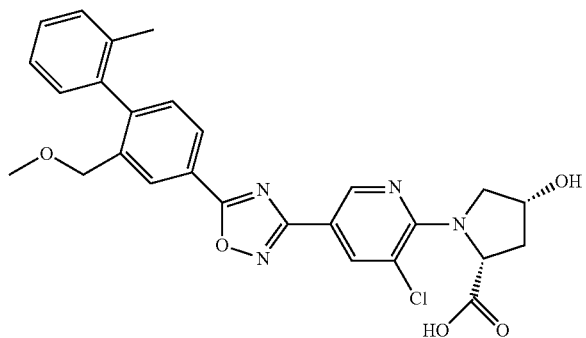

Step 1) methyl (2S,4R)-1-(3-chloro-5-cyanopyridin-2-yl)-4-hydroxypyrrolidine-2-carboxylate trans-4-Hydroxy-L-proline methyl ester hydrochloride salt (0.272 g; 1.50 mmol), 5,6-dichloronicotinonitrile (Bionet, 0.173 g; 1.00 mmol) and DIEA (0.523 mL; 3.00 mmol) were combined in a microwave vial with MeCN (4 mL). The vial was heated under microwave irradiation at 120° C. for 20 minutes. The reaction mixture was diluted with DCM and water and then passed through a hydrophobic frit. The solvent was evaporated to afford the title compound (0.275 g; 98%). $^1$H NMR (CDCl$_3$, 400 MHz) δ 8.25 (1H, d, J=1.6 Hz), 7.66 (1H, d, J=1.6 Hz), 4.95 (1H, t, J=8 Hz), 4.65 (1H, br s), 4.29-4.25 (1H, dd, J=11.6, 4.4 Hz), 4.02-3.99 (1H, m), 3.72 (3H, s), 2.40-2.35 (1H, m), 2.17-2.11 (1H, m), 1.49 (1H, br s).

Step 2) methyl (2S,4R)-4-(tert-butyldimethylsilyloxy)-1-(3-chloro-5-cyanopyridin-2-yl)pyrrolidine-2-carboxylate To a solution of methyl (2S,4R)-1-(3-chloro-5-cyanopyridin-2-yl)-4-hydroxypyrrolidine-2-carboxylate (0.270 g; 0.96 mmol) and imidazole (0.098 g; 1.44 mmol) in DMF (3 mL) was added tert-butyl dimethylsilylchloride (0.159 g; 1.05 mmol). The reaction mixture was stirred at ambient temperature for 18 hours. Further imidazole (0.049 g; 0.72 mmol) and tert-butyldimethylsilyl chloride (0.080 g; 0.53 mmol) was added and the reaction stirred at ambient temperature for 3 hours. The reaction mixture was diluted with EtOAc and washed sequentially with water and brine. The organic phase was poured through a hydrophobic frit and the solvent evaporated in vacuo. The residue was purified by flash chromatography on silica, eluting with iso-hexane/EtOAc (6:1) to afford the title product (0.311 g, 82%). $^1$H NMR (CDCl$_3$, 400 MHz) δ 8.16 (1H, d, J=2 Hz), 7.57 (1H, d, J=2 Hz), 4.79 (1H, t, J=8 Hz), 4.46-4.44 (1H, m), 4.17-4.13 (1H, dd, J=11.2, 4.8 Hz), 3.77-3.74 (1H, m), 3.63 (3H, s), 2.15 (1H, m), 1.96 (1H, m), 0.79 (9H, s), 0.14-0.02 (6H, m).

Step 3) methyl (2S,4R)-4-(tert-butyldimethylsilyloxy)-1-(3-chloro-5-(N'-hydroxycarbamimidoyl)pyridin-2-yl)pyrrolidine-2-carboxylate A solution of methyl (2S,4R)-4-(tert-butyldimethylsilyloxy)-1-(3-chloro-5-cyanopyridin-2-yl)pyrrolidine-2-carboxylate (0.306 g; 0.77 mmol), hydroxylamine hydrochloride (0.064 g; 0.92 mmol) and DIEA (0.176 mL; 1.01 mmol) in EtOH/DCM (4 mL/2 mL) was stirred at ambient temperature for 96 hours. The solvent was evaporated in vacuo and the residue dissolved in DCM/water. The mixture was passed through a hydrophobic frit and the solvent evaporated in vacuo to afford the title product (0.335 g, 100%). $^1$H NMR (CDCl$_3$, 400 MHz) δ 8.22 (1H, d, J=2 Hz), 7.76 (1H, d, J=1.6 Hz), 6.60 (1H, br s), 4.87-4.83 (1H, m), 4.73 (2H, br s), 4.54-4.53 (1H, m), 4.26-4.22 (1H, m), 3.75-3.67 (4H, m), 2.26-2.20 (1H, m), 2.09-2.02 (1H, m), 0.85 (9H, s), 0.05-0.08 (6H, m).

Step 4) methyl (2S,4R)-1-(3-chloro-5-(5-(2-(methoxymethyl)-2'-methylbiphenyl-4-yl)-1,2,4-oxadiazol-3-yl)pyridin-2-yl)-4-(tert-butyldimethylsilyloxy)-pyrrolidine-2-carboxylate To a solution of methyl (2S,4R)-4-(tert-butyldimethylsilyloxy)-1-(3-chloro-5-(N'-hydroxycarbamimidoyl)pyridin-2-yl)pyrrolidine-2-carboxylate (0.320 g; 0.75 mmol) and Intermediate A1 (0.210 g; 0.82 mmol) in MeCN (3 mL) was added EDC (0.157 g; 0.82 mmol). The reaction mixture was stirred at ambient temperature for 18 h. The reaction mixture was diluted with pyridine (2 mL) and heated at 150° C. in the microwave for 30 minutes. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (6:1) to afford the title product. $^1$H NMR (CDCl$_3$, 400 MHz) δ 8.69 (1H, d, J=2 Hz), 8.30 (1H, d, J=1.6 Hz), 8.15 (1H, d, J=1.6 Hz), 8.06-8.03 (1H, m), 7.24-7.16 (4H, m), 7.04 (1H, d, J=7.2 Hz), 4.82 (1H, m), 4.50 (1H, m), 4.22-4.18 (1H, m), 4.13-4.12 (2H, m), 3.76 (1H, m), 3.64 (3H, s), 3.23 (3H, s), 2.20 (1H, m), 1.99-1.98 (4H, m), 0.79 (9H, s), 0.00 (3H, s), −0.02 (3H, s).

Step 5) methyl (2S,4R)-1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylate To a solution of methyl (2S,4R)-1-(3-chloro-5-(5-(2-(methoxymethyl)-2'-methylbiphenyl-4-yl)-1,2,4-oxadiazol-3-yl)pyridin-2-yl)-4-(tert-butyldimethylsilyloxy)-pyrrolidine-2-carboxylate (0.118 g; 0.18 mmol) in THF (2 mL) was added a solution of tetrabutylammonium fluoride (1.0 M in THF; 0.36 mL; 0.36 mmol). The reaction mixture was stirred at ambient temperature for 18 hours. The mixture was diluted with DCM and water and poured through a hydrophobic frit. The solvent was evaporated in vacuo and the residue was purified by flash chromatography on silica, eluting with iso-hexane/EtOAc (100% iso-hexane to 50%/50% iso-hexane/EtOAc) to afford the title product (0.085 g; 88%). $^1$H NMR (CDCl$_3$, 400 MHz) δ 8.81 (1H, d, J=2 Hz), 8.40 (1H, d, J=1.2 Hz), 8.26 (1H, d, J=1.6 Hz), 8.15-8.13 (1H, m), 7.34-7.24 (4H, m), 7.14-7.12 (1H, m), 5.01 (1H, t, J=8 Hz), 4.66 (1H, s), 4.34-4.30 (1H, m), 4.22-4.21 (2H, m), 4.02-3.99 (1H, m), 3.74 (3H, s), 3.33 (3H, s), 2.38 (1H, m), 2.21-2.14 (1H, m), 2.08 (3H, s), 1.76 (1H, d, J=3.6 Hz).

Step 6) (2S,4R)-1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylic acid and (2R,4R)-1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylic acid

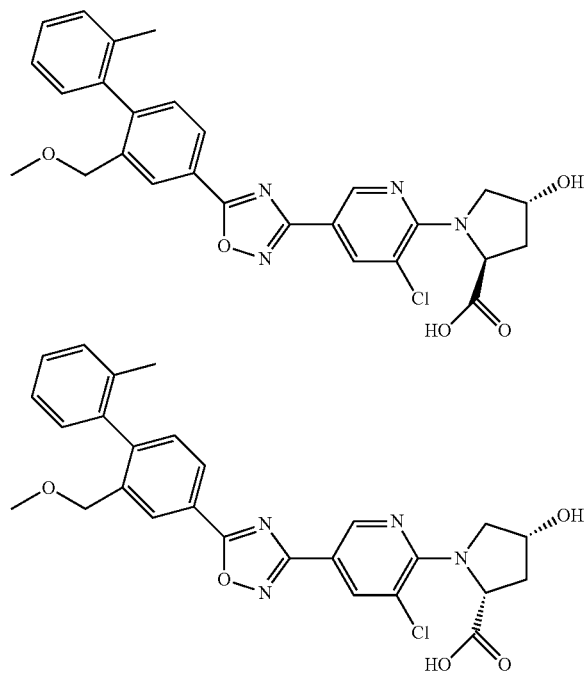

A solution of (2S,4R)-methyl 1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylate (0.080 g; 0.15 mmol) in dioxan (2 mL) was added hydrochloric acid (1 mL). The mixture was heated at 60° C. for 24 hours. The solvent was evaporated and the residue purified by preparative HPLC to afford two title diastereomers. (2S,4R)-1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylic acid. $^1$H NMR (DMSO-$d_6$, 400 MHz) δ 12.60 (1H, br s), 8.73 (1H, m), 8.33 (1H, s), 8.22-8.17 (2H, m), 7.46-7.30 (4H, m), 7.19-7.17 (1H, d, J=8 Hz), 5.17 (1H, br s), 4.89-4.85 (1H, m), 4.44 (1H, br s), 4.27-4.18 (2H, m), 4.14-4.11 (1H, m), 3.78-3.75 (1H, m), 3.30 (3H, s), 2.28-2.25 (1H, m), 2.07 (3H, s), 2.05-2.02 (1H, m). LC/MS: 521 (M+H)$^+$. HPLC (Method C) Rt 2.68 min (Purity: 98.7%), and (2R,4R)-1-(3-chloro-5-(5-(2-(methoxymethyl)-2'-methylbiphenyl-4-yl)-1,2,4-oxadiazol-3-yl)pyridin-2-yl)-4-hydroxypyrrolidine-2-carboxylic acid. $^1$H NMR (DMSO-$d_6$, 400 MHz) δ 8.73 (1H, d, J=1.2 Hz), 8.33 (1H, d, J=1.2 Hz), 8.19-8.17 (2H, m), 7.46 (1H, d, J=8 Hz), 7.40-7.31 (3H, m), 7.19 (1H, d, J=7.2 Hz), 4.95-4.91 (1H, m), 4.38-4.35 (1H, m), 4.26-4.18 (2H, m), 4.09-4.05 (1H, m), 3.86-3.81 (1H, m), 3.29 (3H, s), 2.47-2.45 (1H, m), 2.07 (3H, s), 1.99-1.94 (1H, m). LC/MS: 521 (M+H)$^+$. HPLC (Method F) Rt 8.50 min (Purity: 96.9%).

Example 97

In vitro Assays

Membranes Preparation: Membranes were prepared from CHO cells expressing S1P1 or S1P3 for use in ligand and 35S-GTPγS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by N2 decompression using a cell disruption bomb (Parr Instrument). Following centrifugation at 1000 RPM for 10 min at 4° C., the supernatant was diluted (2×) in buffer A and centrifuged again at 19000 RPM for 75 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid $N_2$ and stored at −80° C.

Receptor binding assay: [33P]sphingosine 1-phosphate (3000 Ci/mmol; American Radiolabeled Chemicals, Inc.) was added to test compounds in 20% DMSO by competition. Membranes and WGA SPA beads (GE Healthcare) were added to give a final volume of 100 μl in 96-well plates or 50 μl in 384-well plates with assay concentrations of 30 pM or 15 pM [33P]sphingosine 1-phosphate (respectively for S1P1 or S1P3), 50 mM HEPES, pH 7.5, 5 mM MgCl2, 100 mM NaCl, 0.4% fatty acid-free BSA, 1-5 μg/well of proteins in 96-well plates vs 0.6-1 μg/well of proteins in 384-well plates and 100 μg/well of WGA SPA beads in 96-well plates vs 75 μg/well of WGA SPA beads in 384-well plates. Binding was performed for 60 min at RT on a shaker and bound radioactivity was measured on a PerkinElmer 1450 MicroBeta counter. Triplicate samples were averaged and normalized as percentage of inhibition relative to total binding (only DMSO in well) and non specific binding (1000-fold excess of unlabeled S1P). Binding data were analyzed using the GraphPad Prism program or Genedata software.

Measurements of 35S-GTPγS Binding: Membranes (1 to 10 μg protein) prepared as described above, were incubated in 96-well Scintiplates (PerkinElmer) with test compounds diluted in DMSO, in 140 μl of 20 mM HEPES, pH 7.4, 10 mM MgCl2, 2 μg/well Saponin, 0.2% fatty acid free BSA (Assay buffer), 125 mM NaCl and 1.5 μM GDP. The assay was initiated with the addition of 60 μl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as % response relative to S1P activation in absence of compound (n=2).

Cellular Functional Assays: Internalization of Sphingosine-1-Phosphate Receptor 1 (S1P$_1$) in a Human Cell Line (U2OS) in a 384-Well Format Using a Cell Imaging Analysis.

The S1P$_1$ internalization assay was performed in 384 well plates (Corning® 384 black with clear bottom 3712) using S1P$_1$-U2OS cells from BioImage (C039A), a human epithelial cell line (Human Bone Osteosarcoma Epithelial Cells). These cells expressed the human S1P$_1$ Receptor fused to the green fluorescent protein (EGFP). A standard CMV promoter (cytomegalovirus promoter) controls the expression of S1P1-EGFP and continuous expression was maintained by addition of geneticin to the culture medium.

S1P$_1$ Receptor desensitization induced the internalization of the membrane-localized S1P$_1$-EGFP fusion protein to endosomes, which can be monitored by cell imaging analysis.

The cells are plated in low serum medium (Dulbecco's Modified Eagle Medium (DMEM) with Glutamax-1 and high glucose, 1% Penicillin/Streptomycin, 1% Fetal Calf Serum (FCS), 0.5 mg/ml Geneticin) overnight.

The next day, $S1P_1$-U2OS cells are incubated in 20 μl serum free medium (DMEM with Glutamax-1 and high glucose, 0.1% of fatty-acid free Bovin Serum Albumin (BSA), 10 mM, N'-2-Hydroxyethylpiperazine-N'-2 ethanesulphonic acid (HEPES) 1M) for 2 hours at 37° C./5% $CO_2$.

The cells are then treated with 4 μl compounds/agonists (6×/3% DMSO) for a total volume of 24 μl, and plates are incubated for 1 hour at 37° C./5% $CO_2$.

$S1P_1$-U2OS cells are fixed with 25 μl Paraformaldehyde 8% and stained with Hoechst 33345 dye (1:1000) for 20 minutes.

They were then washed 3 times with Phosphate Buffered Saline (PBS) and plates are sealed.

The internalization of the receptor $S1P_1$-EGFP is measured on Cellomics by calculating the "spot count per object" ("object" corresponds to nuclear and "spot" corresponds to $S1P_1$-EGFP receptor). Internalization data were observed thanks to vHCS View and analyzed using Genedata® software.

The compounds of formula (I) have utility as immunoregulatory agents as demonstrated by their activity as potent and selective agonists of the S1P1 receptor over the S1P3 receptor as measured in the assays described above. In particular, the compounds of formula (I) exhibit a selectivity for the S1P1 receptor over the S1P3 receptor as measured by the ratio of EC50 for the S1P1 receptor to the EC50 for the S1P3 receptor as evaluated in the 35S-GTPγS binding assay described above.

The "potency" or the "activity" of the compounds is determined by the EC50 values as evaluated in the above described 35S-GTPγS binding assay. The lowest EC50 values characterize the most potent or active compounds, according to the present invention.

The following results have been obtained:

| Ex | formula | S1P1/ GTPG EC50 (M) | S1P3/ GTPG EC50 (M) |
|---|---|---|---|
| 1 | | 1.340E−07 | — |
| 2 | | 2.110E−08 | 1.890E−06 |
| 3 | | 1.310E−07 | — |
| 4 | | 4.110E−09 | 2.690E−06 |

| | | | |
|---|---|---|---|
| 5 | 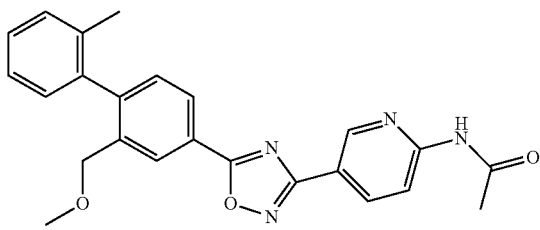 [SMILES: COCc1cc(-c2nc(-c3ccc(NC(C)=O)nc3)no2)ccc1-c1ccccc1C] | 1.460E−08 | — |
| 6 | 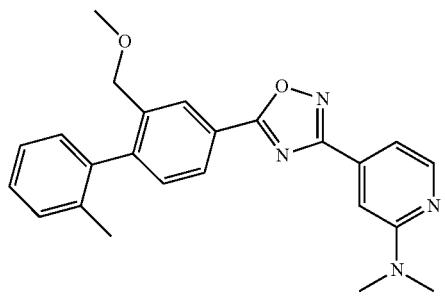 [SMILES: COCc1cc(-c2nc(-c3ccnc(N(C)C)c3)no2)ccc1-c1ccccc1C] | 1.450E−07 | — |
| 7 | 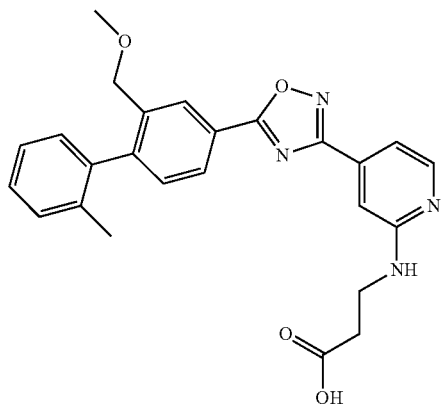 [SMILES: COCc1cc(-c2nc(-c3ccnc(NCCC(=O)O)c3)no2)ccc1-c1ccccc1C] | 5.120E−09 | 1.180E−07 |
| 8 | 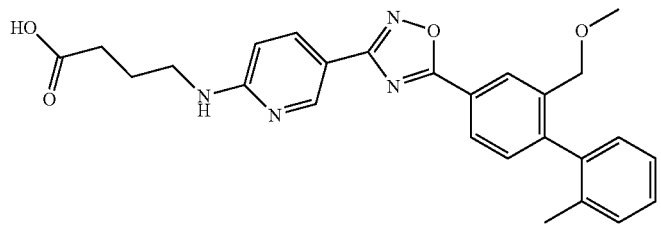 [SMILES: COCc1cc(-c2nc(-c3ccc(NCCCC(=O)O)nc3)no2)ccc1-c1ccccc1C] | 9.990E−09 | — |
| 9 | 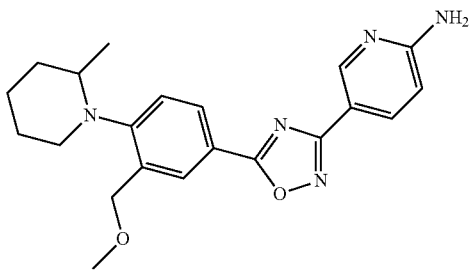 [SMILES: COCc1cc(-c2nc(-c3ccc(N)nc3)no2)ccc1N1CCCCC1C] | 1.770E−09 | 2.620E−06 |

| | | | |
|---|---|---|---|
| 10 | 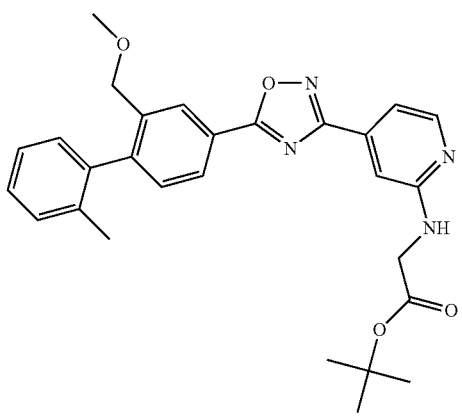 [SMILES: COCc1cc(-c2nc(-c3ccnc(NCC(=O)OC(C)(C)C)c3)no2)ccc1-c1ccccc1C] | 1.400E−07 | — |
| 11 | 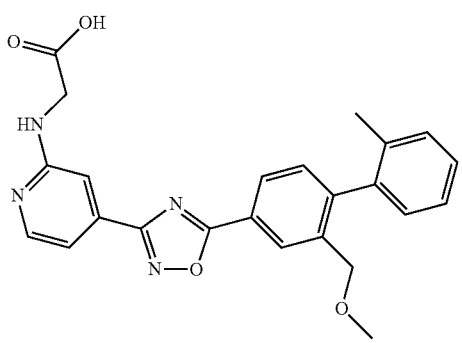 [SMILES: COCc1cc(-c2nc(-c3ccnc(NCC(=O)O)c3)no2)ccc1-c1ccccc1C] | 2.220E−08 | — |
| 12 | 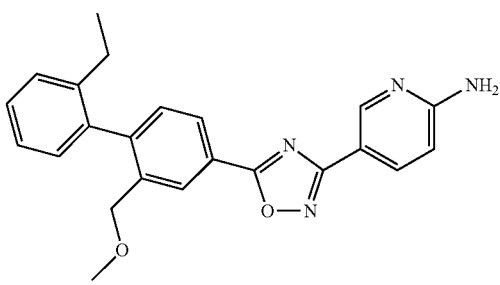 [SMILES: CCc1ccccc1-c1ccc(-c2nc(-c3ccc(N)nc3)no2)cc1COC] | 1.630E−09 | — |
| 13 | 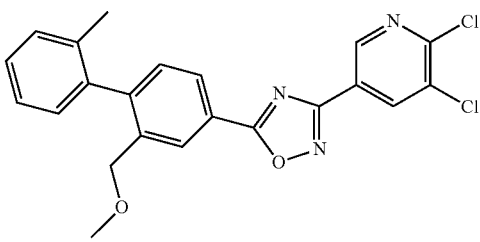 [SMILES: COCc1cc(-c2nc(-c3cnc(Cl)c(Cl)c3)no2)ccc1-c1ccccc1C] | — | — |
| 14 | 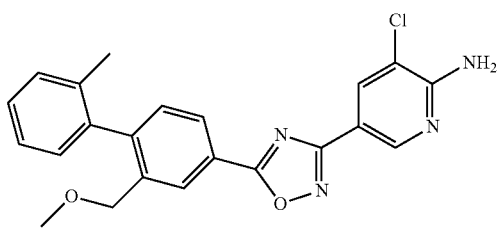 [SMILES: COCc1cc(-c2nc(-c3cnc(N)c(Cl)c3)no2)ccc1-c1ccccc1C] | 5.870E−09 | 1.460E−06 |

| | | | |
|---|---|---|---|
| 15 | 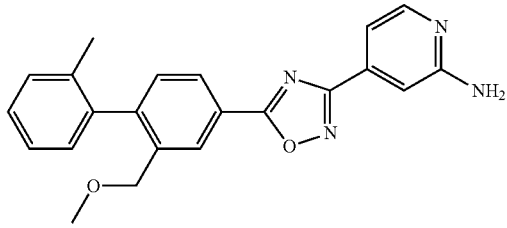 [SMILES: COCc1cc(-c2nc(-c3ccnc(N)c3)no2)ccc1-c1ccccc1C] | 3.520E−09 | 4.140E−07 |
| 16 | 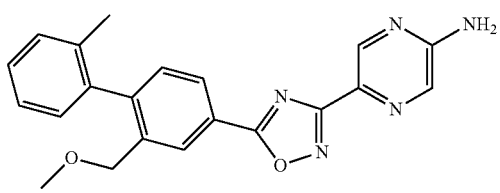 [SMILES: COCc1cc(-c2nc(-c3cnc(N)cn3)no2)ccc1-c1ccccc1C] | 7.280E−08 | — |
| 17 | 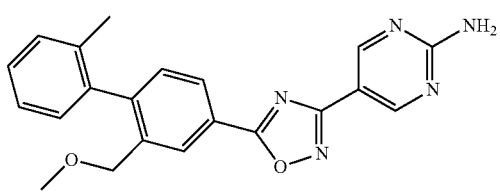 [SMILES: COCc1cc(-c2nc(-c3cnc(N)nc3)no2)ccc1-c1ccccc1C] | 1.520E−07 | — |
| 18 | 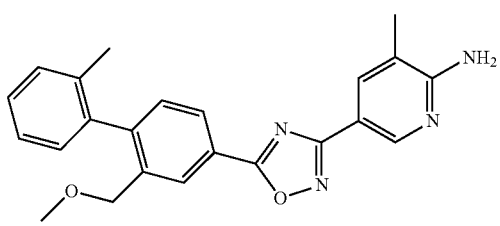 [SMILES: COCc1cc(-c2nc(-c3cnc(N)c(C)c3)no2)ccc1-c1ccccc1C] | 4.870E−09 | — |
| 19 | 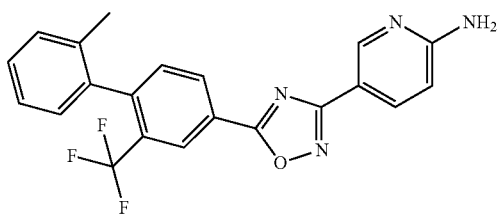 [SMILES: Cc1ccccc1-c1ccc(-c2nc(-c3ccc(N)nc3)no2)cc1C(F)(F)F] | 2.230E−08 | — |
| 20 | 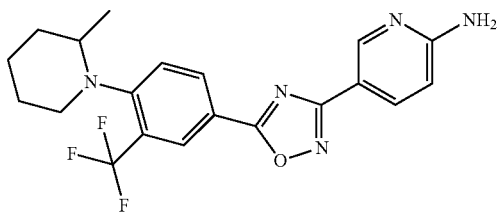 [SMILES: CC1CCCCN1c1ccc(-c2nc(-c3ccc(N)nc3)no2)cc1C(F)(F)F] | 1.470E−08 | — |
| 21 | 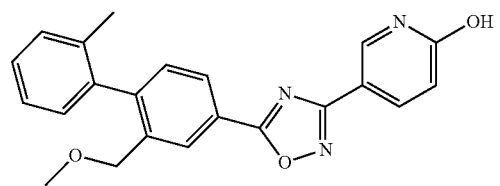 [SMILES: COCc1cc(-c2nc(-c3ccc(O)nc3)no2)ccc1-c1ccccc1C] | 3.970E−09 | 4.220E−07 |

| | | | |
|---|---|---|---|
| 22 | 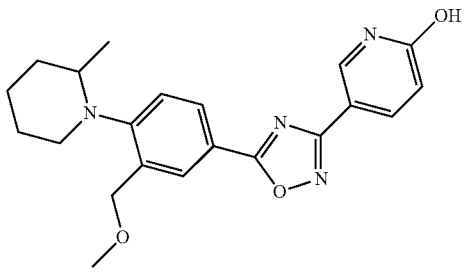 [SMILES: COCc1cc(-c2nc(-c3ccc(O)nc3)no2)ccc1N1CCCCC1C] | 5.290E−09 | 1.530E−07 |
| 23 | 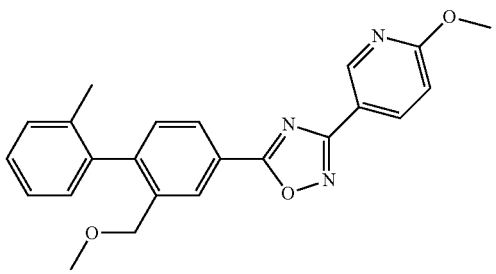 [SMILES: COCc1cc(-c2nc(-c3ccc(OC)nc3)no2)ccc1-c1ccccc1C] | 7.410E−08 | — |
| 24 | 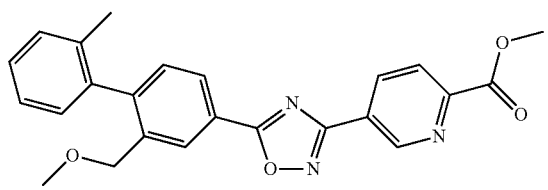 [SMILES: COCc1cc(-c2nc(-c3ccc(C(=O)OC)nc3)no2)ccc1-c1ccccc1C] | 2.770E−07 | — |
| 25 | 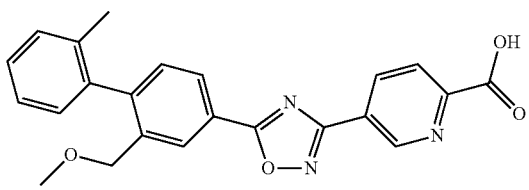 [SMILES: COCc1cc(-c2nc(-c3ccc(C(=O)O)nc3)no2)ccc1-c1ccccc1C] | 3.990E−08 | — |
| 26 | 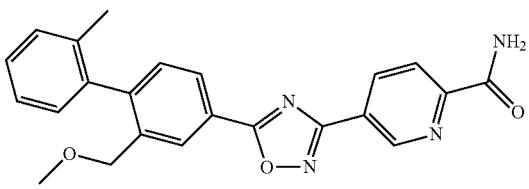 [SMILES: COCc1cc(-c2nc(-c3ccc(C(N)=O)nc3)no2)ccc1-c1ccccc1C] | 4.520E−08 | — |
| 27 | 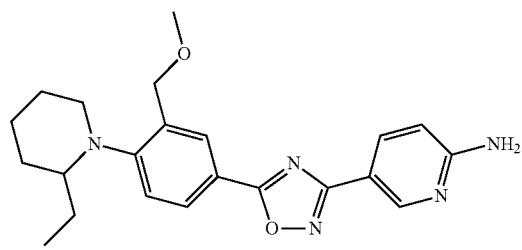 [SMILES: CCC1CCCCN1c1ccc(-c2nc(-c3ccc(N)nc3)no2)cc1COC] | 1.340E−08 | 1.660E−06 |
| 28 | 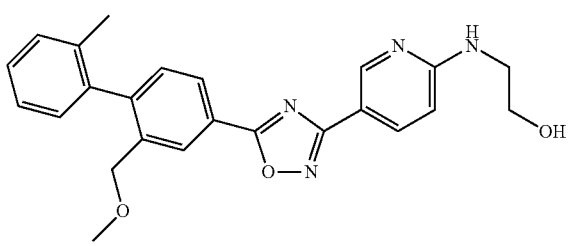 [SMILES: COCc1cc(-c2nc(-c3ccc(NCCO)nc3)no2)ccc1-c1ccccc1C] | 5.250E−09 | — |

| | | | |
|---|---|---|---|
| 29 | 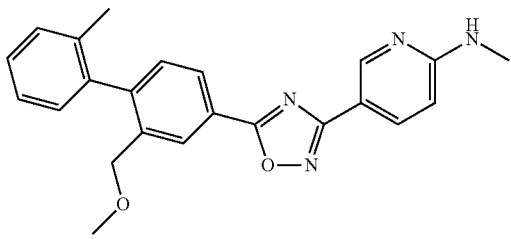 [SMILES: CNc1ccc(-c2noc(-c3ccc(-c4ccccc4C)c(COC)c3)n2)cn1] | 4.380E−08 | — |
| 30 | 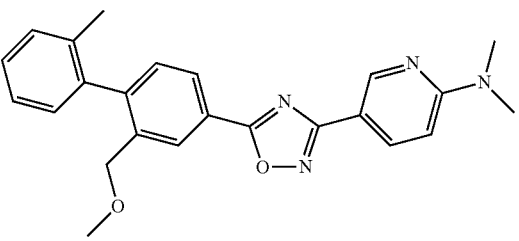 [SMILES: COCc1cc(-c2nc(-c3ccc(N(C)C)nc3)no2)ccc1-c1ccccc1C] | 6.880E−07 | — |
| 31 | 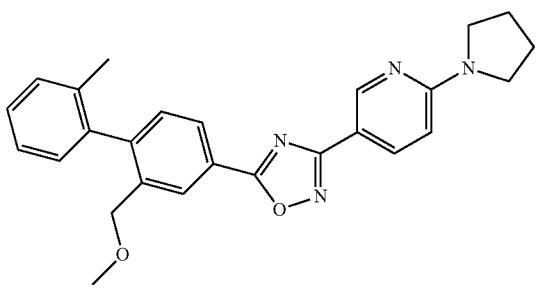 [SMILES: COCc1cc(-c2nc(-c3ccc(N4CCCC4)nc3)no2)ccc1-c1ccccc1C] | 8.730E−07 | — |
| 32 | 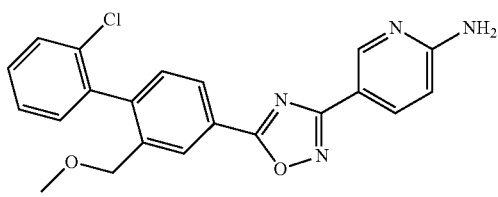 | 2.980E−09 | — |
| 33 | 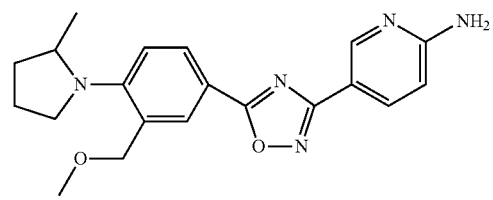 [SMILES: COCc1cc(-c2nc(-c3ccc(N)nc3)no2)ccc1N1CCCC1C] | 7.390E−09 | — |
| 34 | 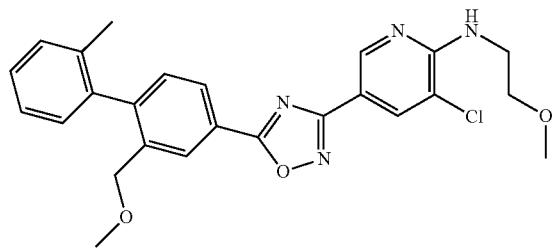 [SMILES: COCCNc1ncc(-c2noc(-c3ccc(-c4ccccc4C)c(COC)c3)n2)cc1Cl] | 1.180E−08 | — |

-continued
| | | | |
|---|---|---|---|
| 35 | 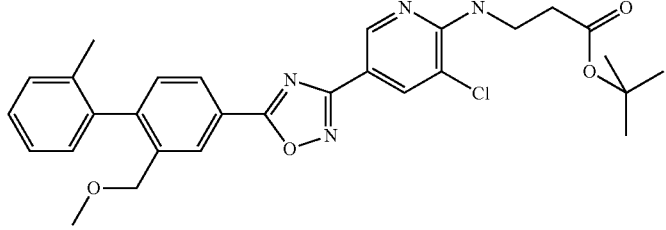 | 9.450E−09 | — |
| 36 | 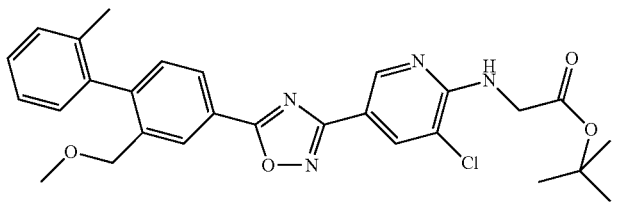 [SMILES: COCc1cc(-c2nc(-c3cnc(NCC(=O)OC(C)(C)C)c(Cl)c3)no2)ccc1-c1ccccc1C] | 1.210E−07 | — |
| 37 | 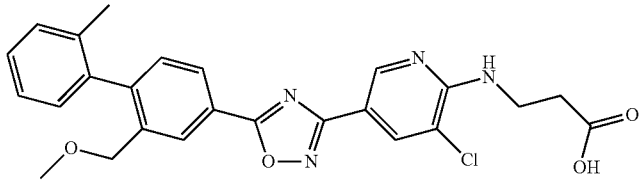 [SMILES: COCc1cc(-c2nc(-c3cnc(NCCC(=O)O)c(Cl)c3)no2)ccc1-c1ccccc1C] | 2.370E−09 | 2.110E−06 |
| 38 | 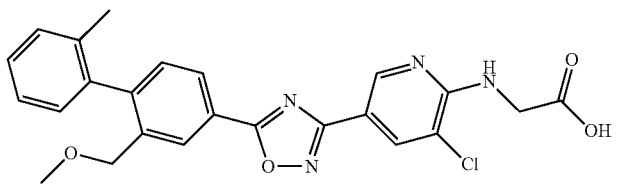 [SMILES: COCc1cc(-c2nc(-c3cnc(NCC(=O)O)c(Cl)c3)no2)ccc1-c1ccccc1C] | 2.910E−08 | — |
| 39 | 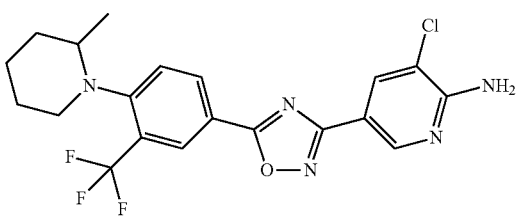 [SMILES: CC1CCCCN1c1ccc(-c2nc(-c3cnc(N)c(Cl)c3)no2)cc1C(F)(F)F] | 3.260E−08 | — |
| 40 | 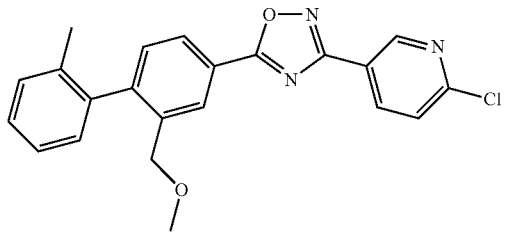 [SMILES: COCc1cc(-c2nc(-c3ccc(Cl)nc3)no2)ccc1-c1ccccc1C] | — | — |
| 41 | 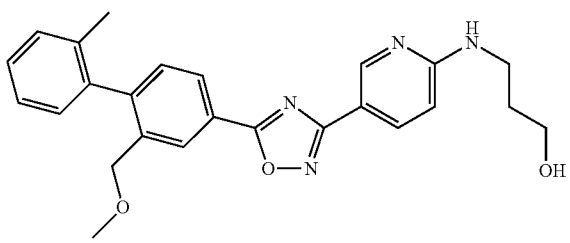 [SMILES: COCc1cc(-c2nc(-c3ccc(NCCCO)nc3)no2)ccc1-c1ccccc1C] | — | — |

-continued
| 42 | 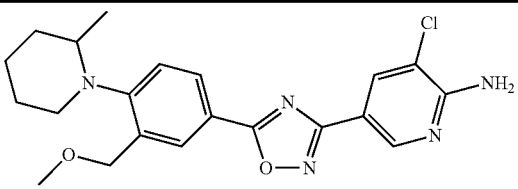 | — | — |
| 43 | 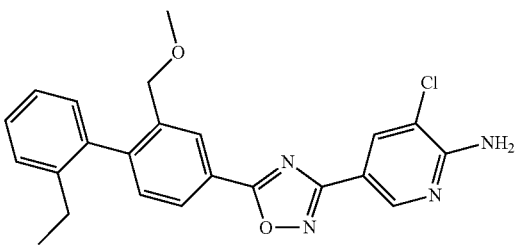 [SMILES: CCc1ccccc1-c1ccc(-c2nc(-c3cnc(N)c(Cl)c3)no2)cc1COC] | — | — |
| 44 | 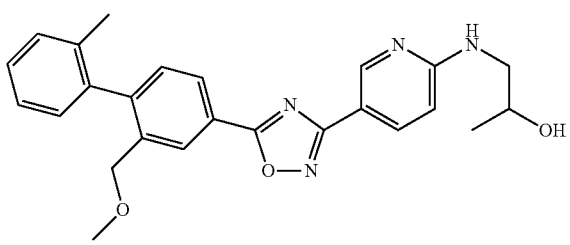 [SMILES: COCc1cc(-c2nc(-c3ccc(NCC(C)O)nc3)no2)ccc1-c1ccccc1C] | — | — |
| 45 | 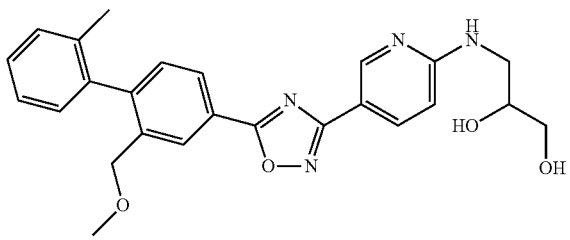 [SMILES: COCc1cc(-c2nc(-c3ccc(NCC(O)CO)nc3)no2)ccc1-c1ccccc1C] | — | — |
| 46 | 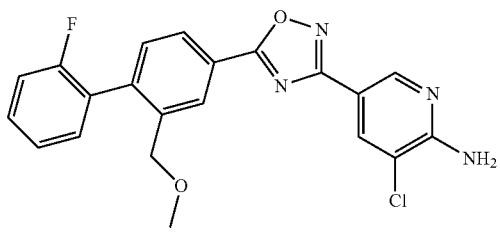 [SMILES: COCc1cc(-c2nc(-c3cnc(N)c(Cl)c3)no2)ccc1-c1ccccc1F] | — | — |
| 47 | 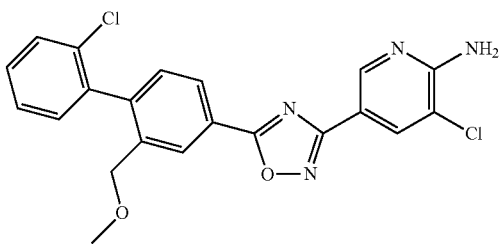 [SMILES: COCc1cc(-c2nc(-c3cnc(N)c(Cl)c3)no2)ccc1-c1ccccc1Cl] | — | — |
| 48 | 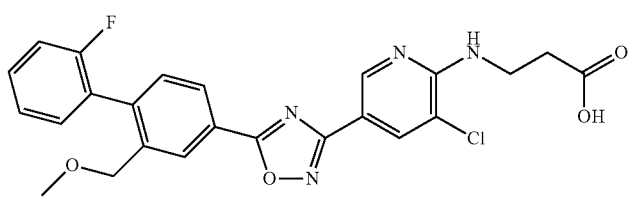 [SMILES: COCc1cc(-c2nc(-c3cnc(NCCC(=O)O)c(Cl)c3)no2)ccc1-c1ccccc1F] | — | — |

| | | | |
|---|---|---|---|
| 49 | 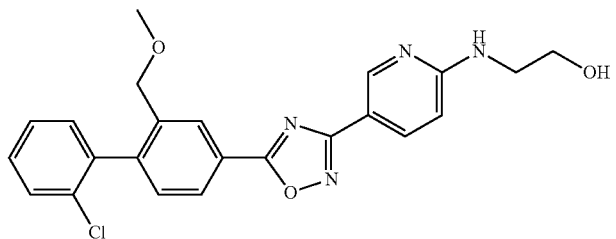 [SMILES: COCc1cc(-c2nc(-c3ccc(NCCO)nc3)no2)ccc1-c1ccccc1Cl] | — | — |
| 50 | 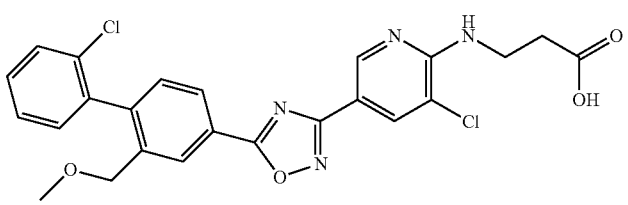 [SMILES: COCc1cc(-c2nc(-c3cnc(NCCC(=O)O)c(Cl)c3)no2)ccc1-c1ccccc1Cl] | — | — |
| 51 | 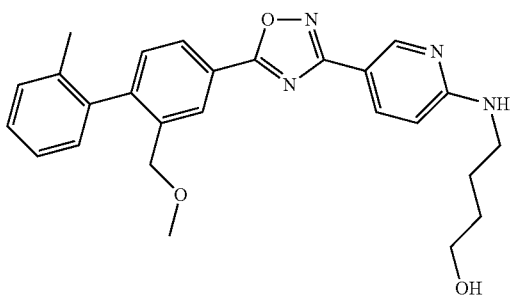 [SMILES: COCc1cc(-c2nc(-c3ccc(NCCCCO)nc3)no2)ccc1-c1ccccc1C] | — | — |
| 52 | 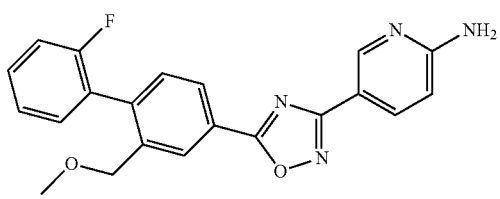 [SMILES: COCc1cc(-c2nc(-c3ccc(N)nc3)no2)ccc1-c1ccccc1F] | — | — |
| 53 | 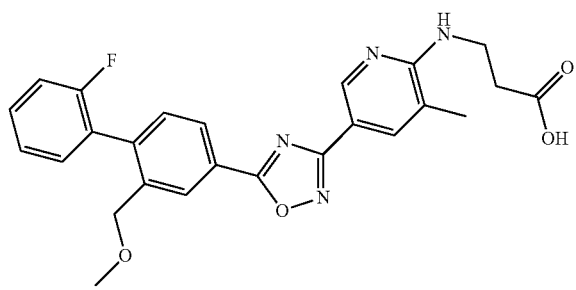 [SMILES: COCc1cc(-c2nc(-c3cnc(NCCC(=O)O)c(C)c3)no2)ccc1-c1ccccc1F] | — | — |
| 54 | 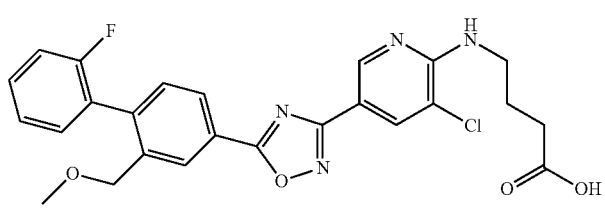 [SMILES: COCc1cc(-c2nc(-c3cnc(NCCCC(=O)O)c(Cl)c3)no2)ccc1-c1ccccc1F] | — | — |

| | | | |
|---|---|---|---|
| 55 | 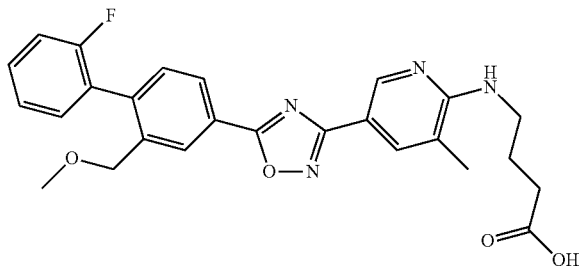 [SMILES: COCc1cc(-c2nc(-c3cnc(NCCCC(=O)O)c(C)c3)no2)ccc1-c1ccccc1F] | — | — |
| 56 | 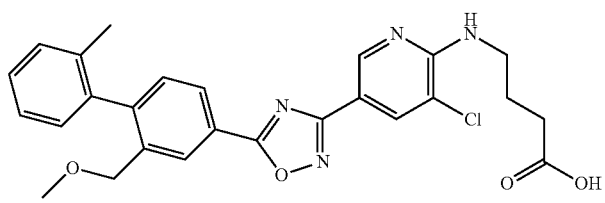 [SMILES: COCc1cc(-c2nc(-c3cnc(NCCCC(=O)O)c(Cl)c3)no2)ccc1-c1ccccc1C] | — | — |
| 57 | 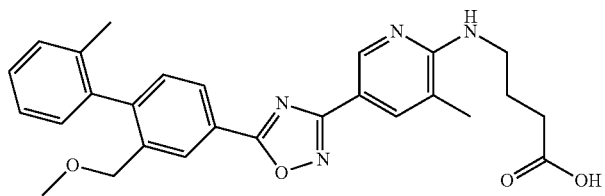 [SMILES: COCc1cc(-c2nc(-c3cnc(NCCCC(=O)O)c(C)c3)no2)ccc1-c1ccccc1C] | — | — |
| 58 | 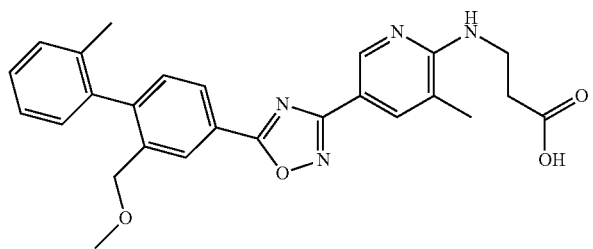 [SMILES: COCc1cc(-c2nc(-c3cnc(NCCC(=O)O)c(C)c3)no2)ccc1-c1ccccc1C] | — | — |
| 59 | 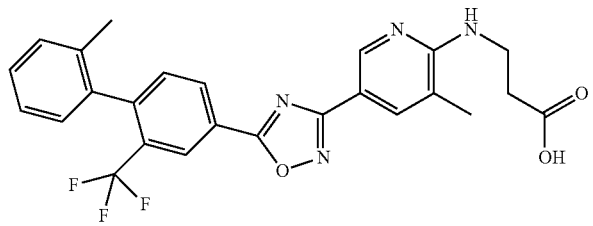 [SMILES: Cc1ccccc1-c1ccc(-c2nc(-c3cnc(NCCC(=O)O)c(C)c3)no2)cc1C(F)(F)F] | — | — |
| 60 | 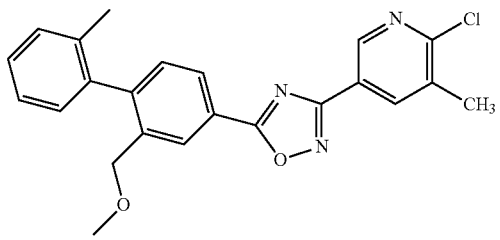 [SMILES: COCc1cc(-c2nc(-c3cnc(Cl)c(C)c3)no2)ccc1-c1ccccc1C] | — | — |

| | | | |
|---|---|---|---|
| 61 | 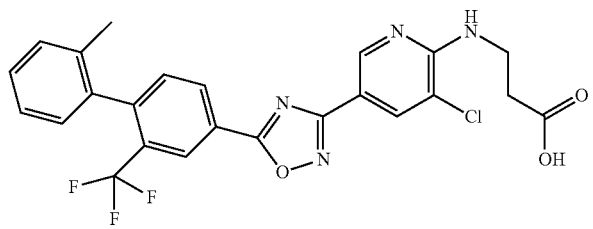 [SMILES: Cc1ccccc1-c1ccc(-c2nc(-c3cnc(NCCC(=O)O)c(Cl)c3)no2)cc1C(F)(F)F] | — | — |
| 62 | 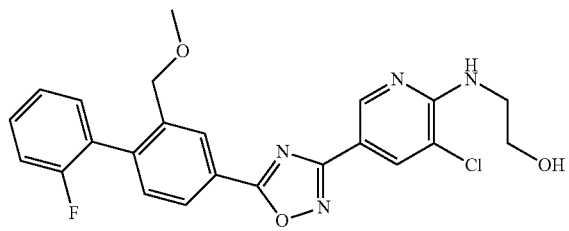 [SMILES: COCc1cc(-c2nc(-c3cnc(NCCO)c(Cl)c3)no2)ccc1-c1ccccc1F] | — | — |
| 63 | 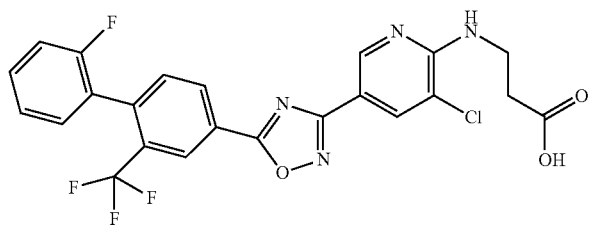 | — | — |
| 64 | 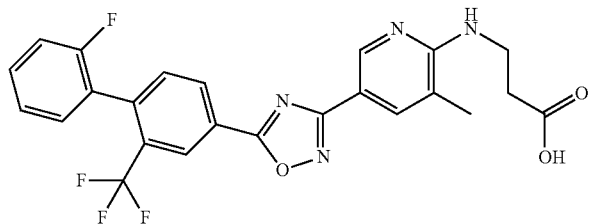 [SMILES: Cc1cc(-c2noc(-c3ccc(-c4ccccc4F)c(C(F)(F)F)c3)n2)cnc1NCCC(=O)O] | — | — |
| 65 | 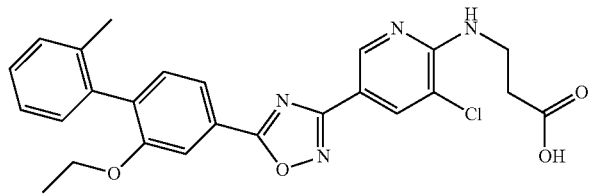 [SMILES: CCOc1cc(-c2nc(-c3cnc(NCCC(=O)O)c(Cl)c3)no2)ccc1-c1ccccc1C] | — | — |
| 66 | 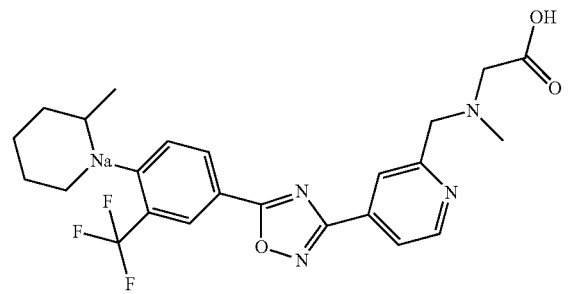 | — | — |

| | | |
|---|---|---|
| 67 | 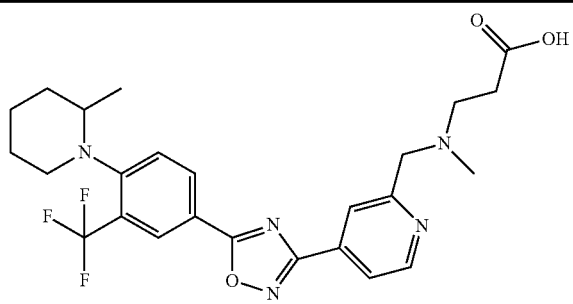 | — — |
| 68 | 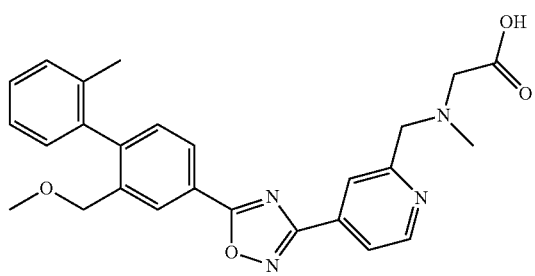 [SMILES: COCc1cc(-c2nc(-c3ccnc(CN(C)CC(=O)O)c3)no2)ccc1-c1ccccc1C] | — — |
| 69 | 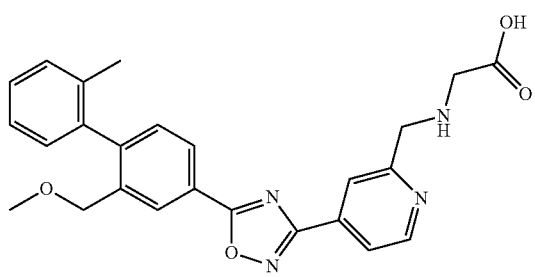 [SMILES: COCc1cc(-c2nc(-c3ccnc(CNCC(=O)O)c3)no2)ccc1-c1ccccc1C] | — — |
| 70 | 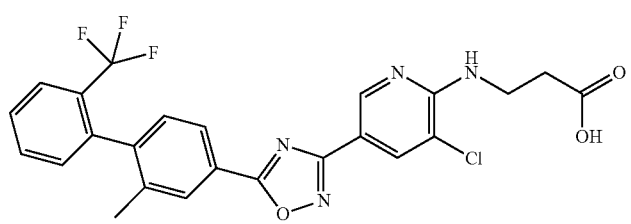 [SMILES: Cc1cc(-c2nc(-c3cnc(NCCC(=O)O)c(Cl)c3)no2)ccc1-c1ccccc1C(F)(F)F] | — — |
| 71 | 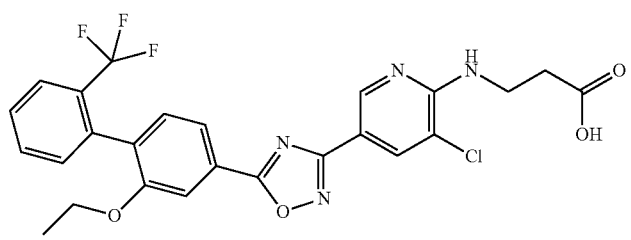 [SMILES: CCOc1cc(-c2nc(-c3cnc(NCCC(=O)O)c(Cl)c3)no2)ccc1-c1ccccc1C(F)(F)F] | — — |
| 72 | 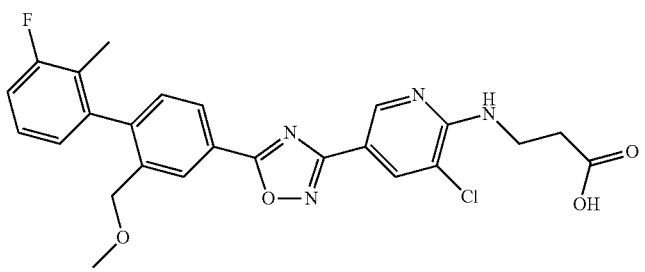 [SMILES: COCc1cc(-c2nc(-c3cnc(NCCC(=O)O)c(Cl)c3)no2)ccc1-c1cccc(F)c1C] | — — |

-continued
| | | | |
|---|---|---|---|
| 73 | 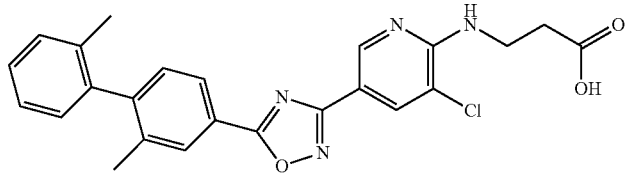 [SMILES: Cc1ccccc1-c1ccc(-c2nc(-c3cnc(NCCC(=O)O)c(Cl)c3)no2)cc1C] | — | — |
| 74 | 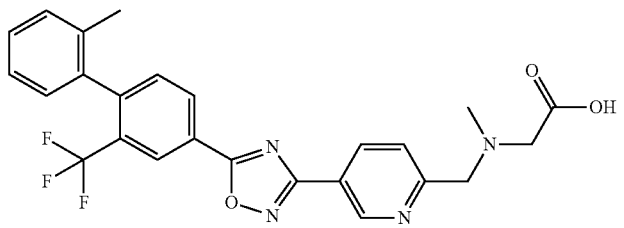 [SMILES: Cc1ccccc1-c1ccc(-c2nc(-c3ccc(CN(C)CC(=O)O)nc3)no2)cc1C(F)(F)F] | — | — |
| 75 | 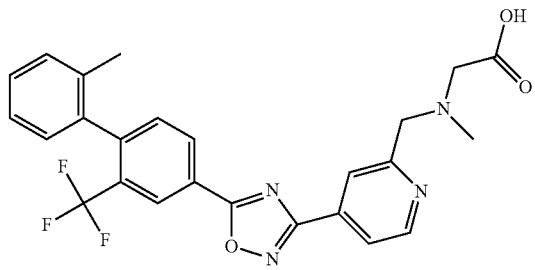 [SMILES: Cc1ccccc1-c1ccc(-c2nc(-c3ccnc(CN(C)CC(=O)O)c3)no2)cc1C(F)(F)F] | — | — |
| 76 | 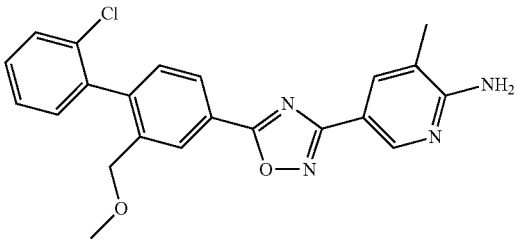 [SMILES: COCc1cc(-c2nc(-c3cnc(N)c(C)c3)no2)ccc1-c1ccccc1Cl] | — | — |
| 77 | 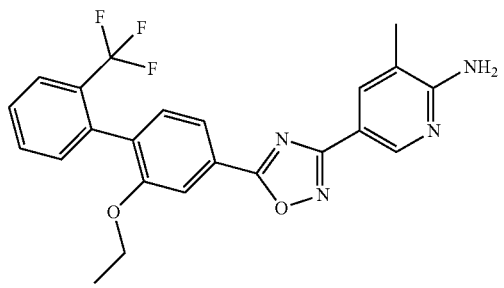 [SMILES: CCOc1cc(-c2nc(-c3cnc(N)c(C)c3)no2)ccc1-c1ccccc1C(F)(F)F] | — | — |
| 78 | 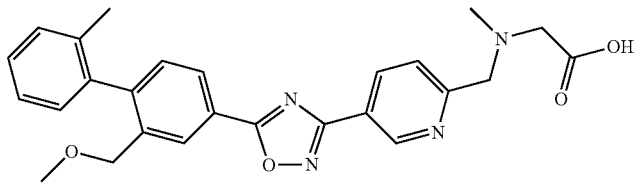 [SMILES: COCc1cc(-c2nc(-c3ccc(CN(C)CC(=O)O)nc3)no2)ccc1-c1ccccc1C] | — | — |

| | | | |
|---|---|---|---|
| 79 | 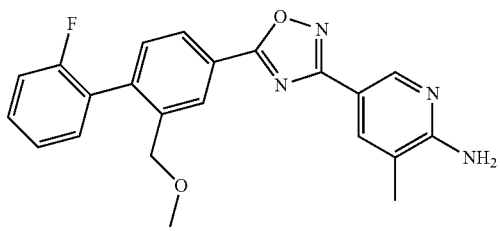 [SMILES: COCc1cc(-c2nc(-c3cnc(N)c(C)c3)no2)ccc1-c1ccccc1F] | — | — |
| 80 | 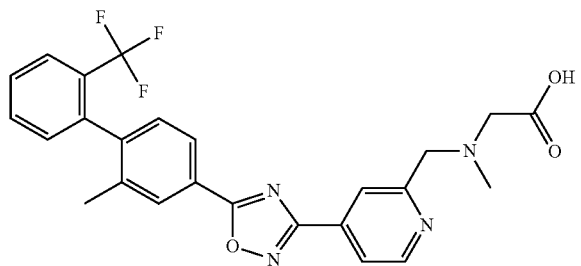 [SMILES: Cc1cc(-c2nc(-c3ccnc(CN(C)CC(=O)O)c3)no2)ccc1-c1ccccc1C(F)(F)F] | — | — |
| 81 | 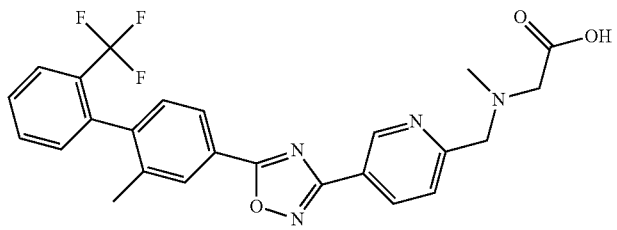 [SMILES: Cc1cc(-c2nc(-c3ccc(CN(C)CC(=O)O)nc3)no2)ccc1-c1ccccc1C(F)(F)F] | — | — |
| 82 | 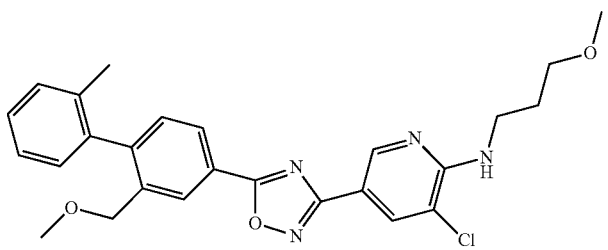 [SMILES: COCCCNc1ncc(-c2noc(-c3ccc(-c4ccccc4C)c(COC)c3)n2)cc1Cl] | — | — |
| 83 | 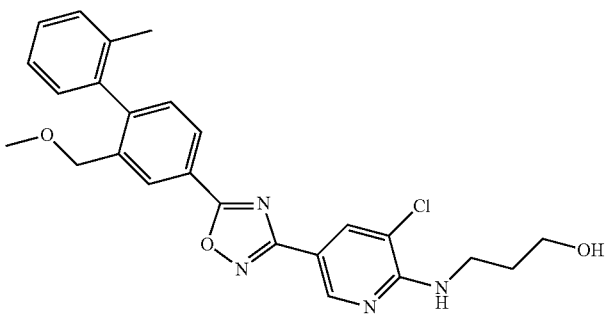 [SMILES: COCc1cc(-c2nc(-c3cnc(NCCCO)c(Cl)c3)no2)ccc1-c1ccccc1C] | — | — |

-continued

| 84 | 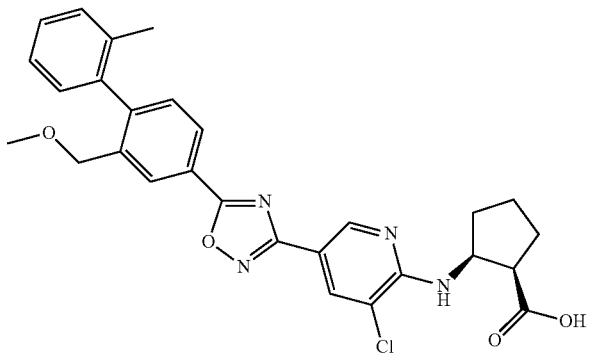 [SMILES: COCc1cc(-c2nc(-c3cnc(N[C@H]4CCC[C@H]4C(=O)O)c(Cl)c3)no2)ccc1-c1ccccc1C] | — | — |

| Ex | S1P1 binding IC50 (M) (96 well-plate) | S1P3 binding IC50 (M) (96 well-plate) | S1P1 binding IC50 (M) (384 well-plate) | S1P3 binding IC50 (M) (384 well-plate) | S1P1 Internalization EC50 (M) |
|---|---|---|---|---|---|
| 1 | — | — | — | — | — |
| 2 | 4.830E−09 | — | — | — | — |
| 3 | — | — | — | — | — |
| 4 | 1.750E−09 | 6.070E−06 | 3.200E−08 | 7.850E−06 | 3.200E−08 |
| 5 | — | — | — | — | — |
| 6 | — | — | — | — | — |
| 7 | 9.090E−09 | — | — | — | — |
| 8 | — | — | — | — | — |
| 9 | 4.290E−09 | — | — | — | — |
| 10 | — | — | — | — | — |
| 11 | — | — | 6.420E−08 | 2.970E−06 | 2.440E−07 |
| 12 | 8.840E−09 | — | — | — | — |
| 13 | — | — | — | — | — |
| 14 | 1.890E−08 | 1.650E−05 | — | — | 4.490E−08 |
| 15 | 1.040E−08 | — | — | — | 6.000E−09 |
| 16 | — | — | — | — | — |
| 17 | — | — | 2.920E−08 | — | 1.520E−07 |
| 18 | 4.330E−09 | 2.210E−05 | 1.520E−08 | — | 4.940E−08 |
| 19 | — | — | — | — | — |
| 20 | 1.030E−08 | — | — | — | — |
| 21 | 4.760E−08 | — | — | — | — |
| 22 | 1.300E−09 | — | — | — | — |
| 23 | — | — | — | — | — |
| 24 | — | — | — | — | — |
| 25 | — | — | — | — | — |
| 26 | — | — | — | — | — |
| 27 | 5.700E−09 | — | — | — | — |
| 28 | 4.540E−09 | — | — | — | — |
| 29 | — | — | — | — | — |
| 30 | — | — | — | — | — |
| 31 | — | — | — | — | — |
| 32 | 1.390E−09 | 9.400E−06 | 2.120E−08 | — | 3.880E−08 |
| 33 | 5.370E−08 | — | — | — | — |
| 34 | 5.260E−09 | — | — | — | — |
| 35 | — | — | — | — | — |
| 36 | — | — | — | — | — |
| 37 | 1.070E−09 | 2.860E−06 | 1.060E−08 | 1.500E−05 | 1.980E−08 |
| 38 | — | — | — | — | — |
| 39 | — | — | — | — | — |
| 40 | 5.490E−08 | — | — | — | 3.070E−07 |
| 41 | 6.720E−09 | — | 1.720E−08 | — | 8.420E−08 |
| 42 | 2.890E−09 | — | — | — | 4.790E−08 |
| 43 | 2.440E−09 | 1.120E−05 | 4.100E−08 | — | 3.350E−08 |
| 44 | 4.220E−09 | — | 3.030E−08 | — | 5.600E−08 |
| 45 | 2.880E−09 | 9.310E−06 | 1.400E−08 | 7.940E−06 | 2.240E−08 |
| 46 | 3.310E−09 | 7.210E−06 | 4.420E−08 | — | 5.930E−08 |
| 47 | 6.020E−09 | 2.000E−05 | — | — | 2.680E−08 |
| 48 | 3.150E−09 | 1.370E−06 | — | — | 2.870E−08 |
| 49 | 3.710E−09 | — | 2.400E−08 | — | 6.150E−08 |
| 50 | 1.580E−09 | 5.820E−06 | 1.980E−08 | 9.450E−06 | 1.730E−08 |
| 51 | 1.050E−08 | 1.790E−05 | — | 2.000E−05 | 8.530E−08 |
| 52 | 1.650E−09 | 3.620E−06 | 1.820E−08 | 3.250E−06 | 2.310E−08 |
| 53 | 6.380E−09 | 3.100E−06 | — | — | 9.920E−08 |
| 54 | 2.010E−09 | 9.320E−07 | — | — | 1.640E−08 |
| 55 | 6.020E−09 | 2.820E−06 | — | 3.390E−06 | 6.450E−08 |
| 56 | 1.710E−09 | 2.090E−06 | 4.770E−09 | 1.710E−06 | 4.030E−08 |
| 57 | 5.600E−09 | 7.440E−06 | — | 8.670E−06 | 8.140E−08 |
| 58 | 2.940E−09 | 9.300E−06 | 2.480E−08 | 5.260E−06 | 4.550E−08 |

| | | | | | |
|---|---|---|---|---|---|
| 59 | 1.040E−08 | 2.000E−05 | 4.560E−08 | — | 1.560E−07 |
| 60 | 2.830E−09 | 6.530E−06 | 4.340E−09 | 3.000E−06 | 1.950E−08 |
| 61 | 5.280E−09 | — | 9.480E−09 | — | 1.980E−07 |
| 62 | 3.100E−09 | — | 7.540E−09 | — | 9.080E−08 |
| 63 | 5.400E−09 | 3.870E−06 | 1.730E−08 | — | 5.000E−08 |
| 64 | 1.090E−08 | 9.990E−06 | 2.110E−08 | 8.320E−06 | 1.250E−07 |
| 65 | 2.070E−09 | 1.600E−06 | 7.950E−09 | 2.410E−06 | 1.610E−08 |
| 66 | 3.300E−09 | 7.440E−07 | 8.680E−09 | 1.380E−06 | 1.450E−08 |
| 67 | 1.200E−09 | 1.410E−07 | | 4.680E−07 | 1.420E−08 |
| 68 | 1.790E−09 | 8.550E−07 | 1.180E−08 | 1.080E−06 | 1.050E−08 |
| 69 | 2.600E−09 | 1.700E−07 | 3.190E−09 | 1.620E−07 | 9.200E−09 |
| 70 | — | — | 1.720E−08 | — | 9.340E−08 |
| 71 | — | 5.750E−06 | 3.400E−08 | 8.920E−06 | 2.130E−08 |
| 72 | — | — | 8.690E−09 | 3.780E−06 | 2.330E−08 |
| 73 | — | — | 1.470E−08 | — | 1.730E−07 |
| 74 | — | — | 7.830E−09 | 2.880E−06 | 1.790E−08 |
| 75 | — | — | 9.460E−09 | 2.260E−06 | 1.520E−08 |
| 76 | — | — | 2.160E−08 | — | 3.740E−08 |
| 77 | — | — | 1.490E−08 | — | 7.350E−08 |
| 78 | 3.010E−09 | 3.040E−06 | 3.500E−09 | 2.480E−06 | 9.480E−09 |
| 79 | — | — | 2.150E−08 | — | 5.870E−08 |
| 80 | — | — | 2.760E−08 | — | 9.360E−08 |
| 81 | — | — | 2.500E−08 | — | 1.700E−07 |
| 82 | — | — | 4.560E−08 | — | 1.280E−07 |
| 83 | 2.900E−09 | — | — | — | 4.670E−08 |
| 84 | 1.350E−08 | — | — | — | 4.270E−07 |

Example 98

In vivo Models Evaluating the In Vivo Efficacy of S1P Agonists

Model of S1P Agonists-Induced Lymphopenia in Mice

Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythrocytes and platelets. Compounds of Formula (I) are tested according to the above assay and have an ED50 of less than 100 mg/kg, more preferable below 50 mg/kg at 24 hours.

Model of MOG-Induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 µl of PBS) by ip route and 100 µl of an emulsion containing MOG35-55 peptide (NeoMPS, 200 µg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 µl of PBS) was done by ip route. After EAE induction, mice were weighed daily and the neurological impairment was quantified using a 15-points clinical scale assessing the paralysis (tail, hind limbs and fore limbs), the incontinency and the death.

Clinical Score:

1—Tail

Score=0 A normal mouse holds its tail erect when moving.

Score=1 If the extremity of the tail is flaccid with a tendency to fall.

Score=2 If the tail is completely flaccid and drags on the table.

2—Hind limbs

Score=0 A normal mouse has an energetic walk and doesn't drag his paws.

Score=1 Either one of the following tests is positive:
  a—Flip test: while holding the tail between thumb and index finger, flip the animal on his back and observe the time it takes to right itself. A healthy mouse will turn itself immediately. A delay suggests hind-limb weakness.
  b—Place the mouse on the wire cage top and observe as it crosses from one side to the other. If one or both limbs frequently slip between the bars we consider that there is a partial paralysis.

Score=2 Both previous tests are positive.

Score=3 One or both hind limbs show signs of paralysis but some movements are preserved; for example: the animal can grasp and hold on to the underside of the wire cage top for a short moment before letting go Score=4 When both hind legs are paralyzed and the mouse drags them when moving.

3—Fore limbs:

Score=0 A normal mouse uses his front paws actively for grasping and walking and holds his head erect.

Score=1 Walking is possible but difficult due to a weakness in one or both of the paws, for example, the front paws are considered weak when the mouse has difficulty grasping the underside of the wire top cage. Another sign of weakness is head drooping.

Score=2 When one forelimb is paralyzed (impossibility to grasp and the mouse turns around the paralyzed limb). At this time the head has also lost much of its muscle tone.

Score=3 Mouse cannot move, and food and water are unattainable.

4—Bladder:

Score=0 A normal mouse has full control of his bladder.

Score=1 A mouse is considered incontinent when his lower body is soaked with urine.

5—Death:

Score=15

The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

Example 99

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of formula (I):

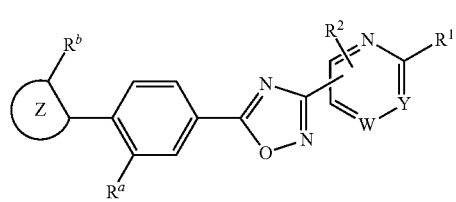

(I)

wherein:

$R^1$ denotes —$CO_2R^3$, —$CON(H)_{2-p}(A)_p$, —$N(H)(CH_2)_n CO_2R^3$, —$N(R^3)(CH_2)_n CO_2R^3$, —NH—CO-A, Hal, —$CF_3$, —$OCF_3$, —OH, —OA, —CN, or —$NO_2$, —$(CH_2)_s N(H)_{2-p}(A)_p$, —$CH(CH_3)(CH_2)_n N(H)_{2-p}(A)_p$, —$CH(R^3)(CH_2)_n N(H)_{2-p}(A)_p$, —$(CH_2)_s N(R^3)(CH_2)_n CO_2R^3$, —$(CH_2)_s NH$—CO-A, —$(CH_2)_n N(R^3)_2$, —$CH(CH_3)(CH_2)_n N(R^3)CH(CH_3)(CH_2)_n CO_2R^3$, or —$CH(R^3)(CH_2)_n N(R^3)CH(R^3)(CH_2)_n CO_2R^3$, or when in position meta or para to the oxadiazole ring, $R^1$ also denotes —$N(H)_{2-p}(A)_p$ or A, $R^2$ is H, Hal, —CN, —$NO_2$, —OH, OA, —$CO_2R^3$, —$CON(H)_{2-p}(A)_p$, —$N(H)(CH_2)_n CO_2R^3$, —NH—CO-A, —$CF_3$, or —$OCF_3$, or when in position meta or para to the oxadiazole ring, $R^2$ also denotes —$N(H)_{2-p}(A)_p$ or A, $R^a$ and $R^b$ are independently from each other A, —$CF_3$, Hal, —$CH_2$—$OR^3$, $OR^3$, —$OCF_3$, ($C_1$-$C_7$)alkyl, —$(CH_2)_n O(CH_2)_n OMe$ or $CH(CH_3)OCH_3$, W, Y are independently from each other CH, Z denotes Ar, A is branched or linear alkyl having 1 to 12 C-atoms, wherein one or more H-atoms are optionally substituted Hal, $OR^3$, CN, $CO_2R^3$ or $N(R^3)_2$ and wherein one or more non-adjacent $CH_2$-groups are optionally substituted by O, $NR^3$ or S and/or by —CH=CH— or —C≡C— groups, or A denotes a cycloalkyl or cycloalkylalkylene having 3-7 ring C atoms, Ar denotes a monocyclic or bicyclic, aromatic carbocyclic ring having 6 carbon atoms, which is unsubstituted, monosubstituted, disubstituted or trisubstituted by Hal, —$CF_3$, —$OCF_3$, —$NO_2$, —CN, perfluoroalkyl, A, OA, —OH, —$NH_2$, —COH, —$COOR^3$, —$CONH_2$, —$CON(H)_{2-q}A_q$, —$NR^3(CH_2)_n COA$, —$NR^3(CH_2)_n COOA$, —$NR^3(CH_2)_n COR^3$, —$N(H)_{2-q}A_q$, —$NHSO_2A$, —$NHSO_2$—$N(H)_{2-m}(A)_m$, —$N(H)_{1-q}A_q COA$, —$N(H)_{1-q}A_q SO_2$—$N(H)_{2-m}(A)_m$, —$N(H)_{1-q}A_q CON(H)_{2-m}(A)_m$, —COOA, —$SO_2A$, —$SO_2N(H)_{2-m}(A)_m$, or —$(CH_2)_n OR^3$, Hal is F, Cl, Br or I, $R^3$ is H or A, m is 0, 1 or 2, p is 0, 1 or 2, q is 0 or 1, s is 1, 2, 3, 4 or 5, n is 0, 1, 2, 3, 4 or 5, and pharmaceutically acceptable salts thereof.

2. The compound according to claim 1, wherein Z is selected from the following groups:

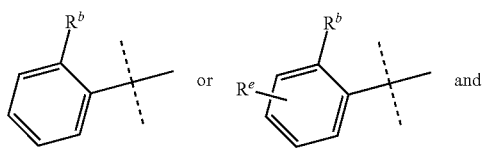

wherein $R^b$ and $R^e$ are independently from one another selected from A, OA, $OR^3$, $CF_3$, or $OCF_3$.

3. The compound according to claim 1, wherein said compound is selected from the Formulae (Ia), (Ib), (Ic), (Id), (Ih) or (Ii):

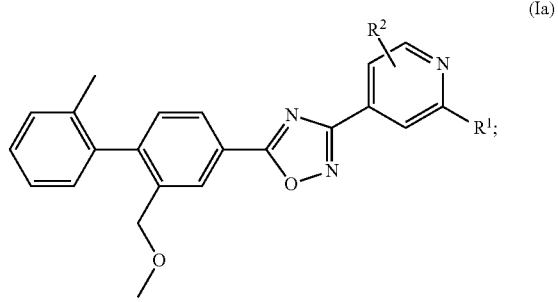

(Ia)

-continued

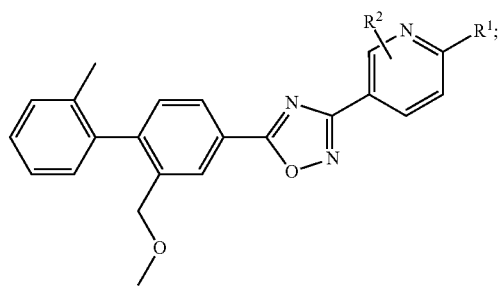
(Ib)

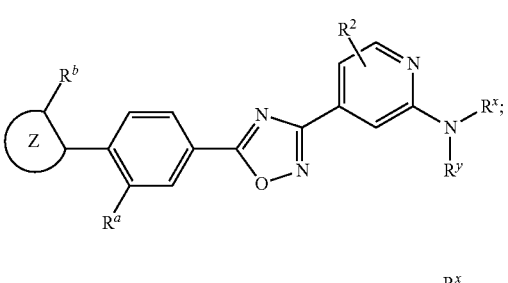
(Ic)

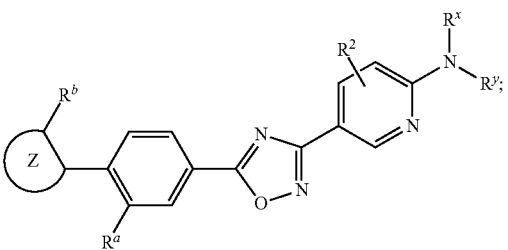
(Id)

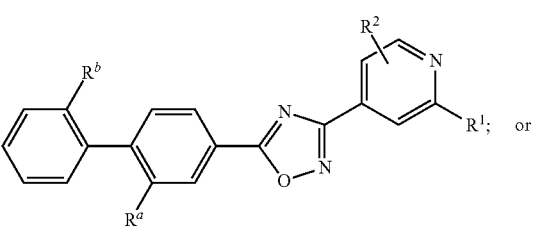
(Ih)

-continued

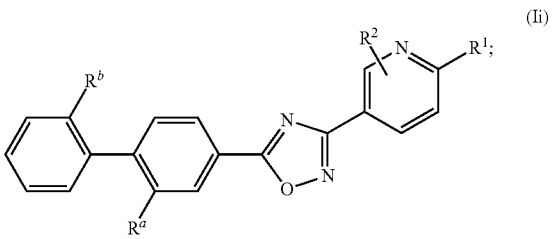
(Ii)

wherein Z, R$^a$, R$^b$, A, R$^1$ and R$^2$ are as defined in claim 1, R$^x$ and R$^y$ are independently from one another H, (CH$_2$)$_n$ CO$_2$R$^3$, A or C$_1$-C$_7$ alkyl, and wherein n is 0, 1, 2, 3, 4 or 5 and R$^3$ is H or A, and pharmaceutically acceptable salts thereof.

4. The compound according to claim 1, wherein R$^a$ is selected from:

—CH$_3$, —CH$_2$—CH$_3$, —CH$_2$—CH(CH$_3$)$_2$, —CF$_3$, —CH$_2$—CF$_3$, —CH$_2$OCH$_3$, —CH$_2$OCH$_2$CH$_3$, —OCH$_3$, —OCH$_2$CH$_3$, —CH$_2$OCF$_3$, —CH$_2$—N(CH$_3$)$_2$, —CH$_2$—N(CH$_3$)—CH$_2$CH$_3$, or —CH(CH$_3$)OCH$_3$.

5. The compound according to claim 1, wherein R$^b$ is selected from:

—CH$_3$, —CH$_2$—CH$_3$, —CH$_2$—CH(CH$_3$)$_2$, —CF$_3$, —CH$_2$—CF$_3$, —CH$_2$OCH$_3$, —CH$_2$OCH$_2$CH$_3$, F, Cl, —CH$_2$F, —CF$_2$CH$_3$, —OCF$_2$CH$_3$, —CH$_2$OCF$_3$, —CH$_2$—N(CH$_3$)$_2$, —CH$_2$—N(CH$_3$)—CH$_2$CH$_3$, or —CH(CH$_3$)OCH$_3$.

6. The compound according to claim 1, wherein said compound is selected from:

| Ex | Formula |
|---|---|
| 1 |  |
| 2 |  |

-continued
| Ex | Formula |
|---|---|
| 3 | 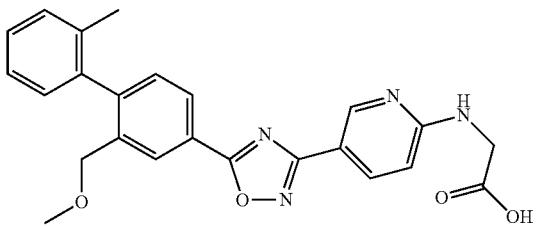 [SMILES: COCc1cc(-c2nc(-c3ccc(NCC(=O)O)nc3)no2)ccc1-c1ccccc1C] |
| 4 | 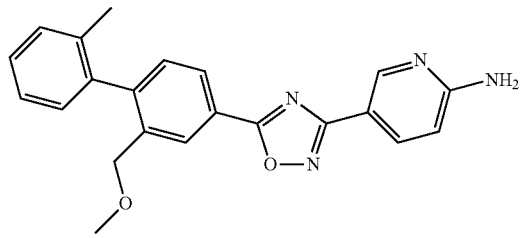 [SMILES: COCc1cc(-c2nc(-c3ccc(N)nc3)no2)ccc1-c1ccccc1C] |
| 5 | 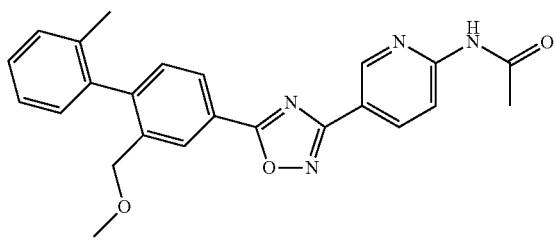 [SMILES: COCc1cc(-c2nc(-c3ccc(NC(C)=O)nc3)no2)ccc1-c1ccccc1C] |
| 6 | 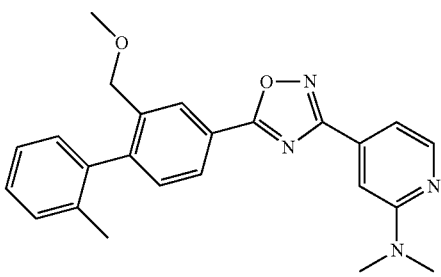 [SMILES: COCc1cc(-c2nc(-c3ccnc(N(C)C)c3)no2)ccc1-c1ccccc1C] |
| 7 | 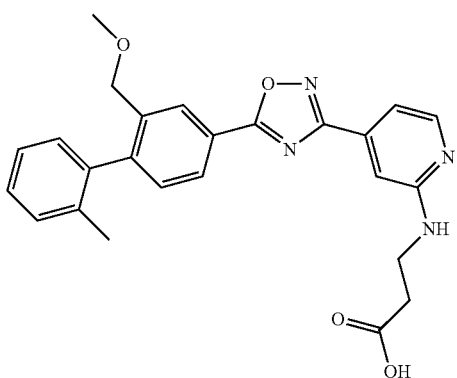 [SMILES: COCc1cc(-c2nc(-c3ccnc(NCCC(=O)O)c3)no2)ccc1-c1ccccc1C] |

-continued
| Ex | Formula |
|---|---|
| 8 | 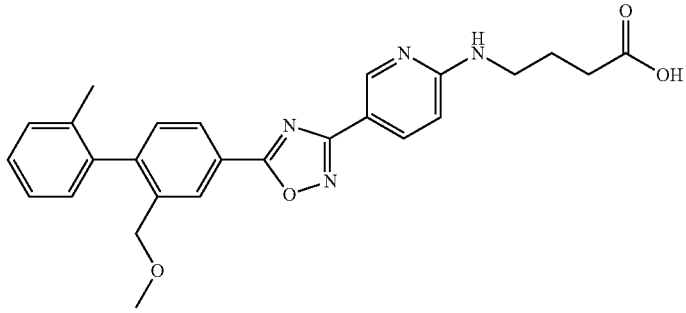 [SMILES: COCc1cc(-c2nc(-c3ccc(NCCCC(=O)O)nc3)no2)ccc1-c1ccccc1C] |
| 10 | 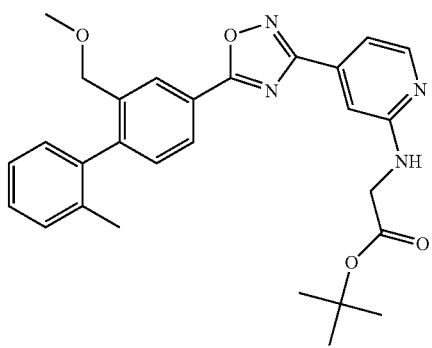 [SMILES: COCc1cc(-c2nc(-c3ccnc(NCC(=O)OC(C)(C)C)c3)no2)ccc1-c1ccccc1C] |
| 11 | 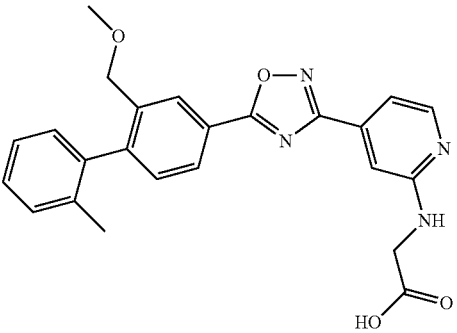 [SMILES: COCc1cc(-c2nc(-c3ccnc(NCC(=O)O)c3)no2)ccc1-c1ccccc1C] |
| 12 | 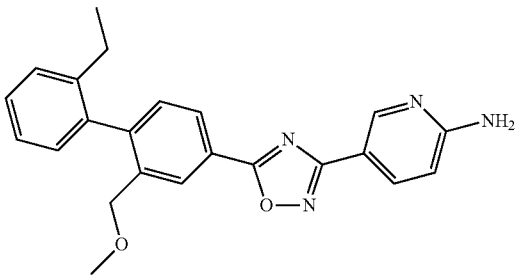 [SMILES: CCc1ccccc1-c1ccc(-c2nc(-c3ccc(N)nc3)no2)cc1COC] |
| 13 | 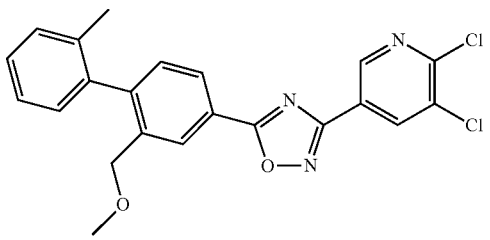 [SMILES: COCc1cc(-c2nc(-c3cnc(Cl)c(Cl)c3)no2)ccc1-c1ccccc1C] |

-continued
| Ex | Formula |
|---|---|
| 14 | 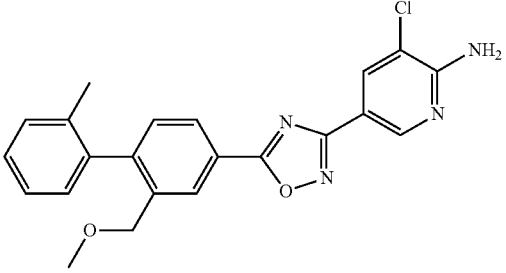 [SMILES: COCc1cc(-c2nc(-c3cnc(N)c(Cl)c3)no2)ccc1-c1ccccc1C] |
| 15 | 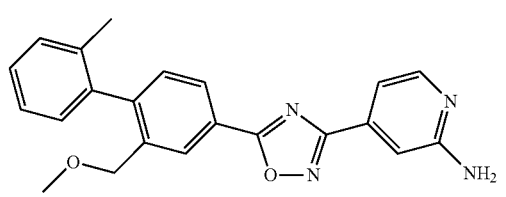 [SMILES: COCc1cc(-c2nc(-c3ccnc(N)c3)no2)ccc1-c1ccccc1C] |
| 18 | 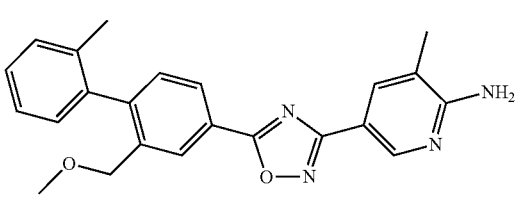 [SMILES: COCc1cc(-c2nc(-c3cnc(N)c(C)c3)no2)ccc1-c1ccccc1C] |
| 19 | 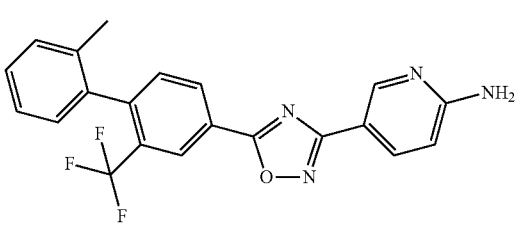 [SMILES: Cc1ccccc1-c1ccc(-c2nc(-c3ccc(N)nc3)no2)cc1C(F)(F)F] |
| 21 | 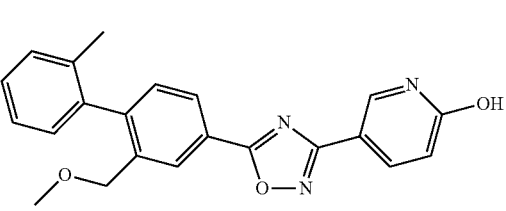 [SMILES: COCc1cc(-c2nc(-c3ccc(O)nc3)no2)ccc1-c1ccccc1C] |
| 23 | 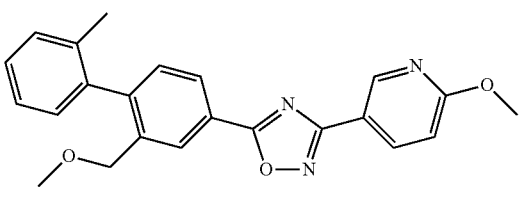 [SMILES: COCc1cc(-c2nc(-c3ccc(OC)nc3)no2)ccc1-c1ccccc1C] |
| 24 | 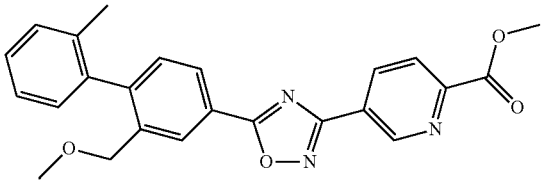 [SMILES: COCc1cc(-c2nc(-c3ccc(C(=O)OC)nc3)no2)ccc1-c1ccccc1C] |

-continued

| Ex | Formula |
|---|---|
| 25 | |
| 26 | |
| 28 | |
| 29 | |
| 30 | |
| 32 | |
| 34 | |

| Ex | Formula |
|---|---|
| 35 | 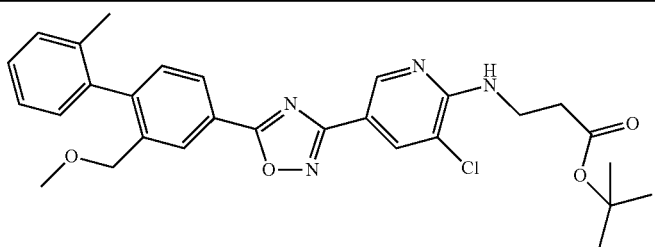 |
| 36 | 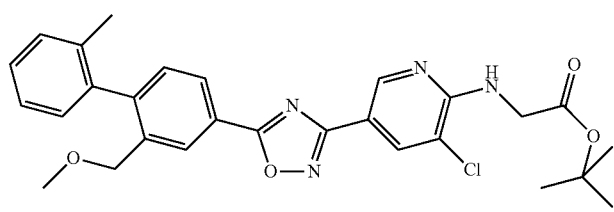 [SMILES: COCc1cc(-c2nc(-c3cnc(NCC(=O)OC(C)(C)C)c(Cl)c3)no2)ccc1-c1ccccc1C] |
| 37 | 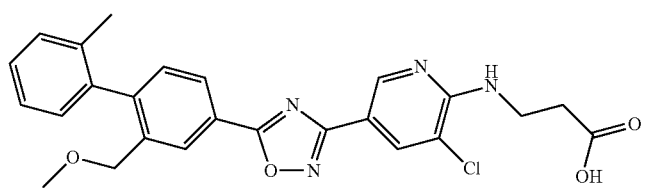 [SMILES: COCc1cc(-c2nc(-c3cnc(NCCC(=O)O)c(Cl)c3)no2)ccc1-c1ccccc1C] |
| 38 | 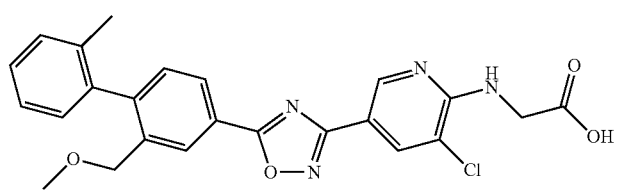 [SMILES: COCc1cc(-c2nc(-c3cnc(NCC(=O)O)c(Cl)c3)no2)ccc1-c1ccccc1C] |
| 40 | 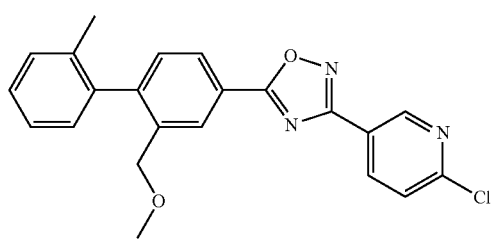 [SMILES: COCc1cc(-c2nc(-c3ccc(Cl)nc3)no2)ccc1-c1ccccc1C] |
| 41 | 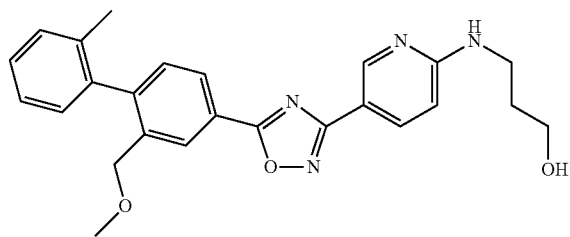 [SMILES: COCc1cc(-c2nc(-c3ccc(NCCCO)nc3)no2)ccc1-c1ccccc1C] |
| 43 | 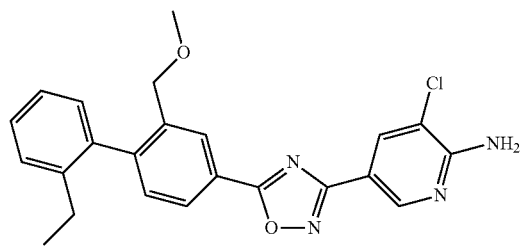 [SMILES: CCc1ccccc1-c1ccc(-c2nc(-c3cnc(N)c(Cl)c3)no2)cc1COC] |

| Ex | Formula |
|---|---|
| 44 | 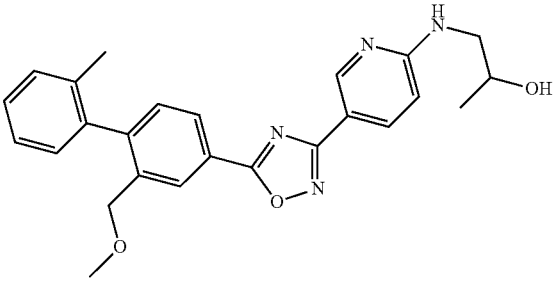 [SMILES: COCc1cc(-c2nc(-c3ccc(NCC(C)O)nc3)no2)ccc1-c1ccccc1C] |
| 45 | 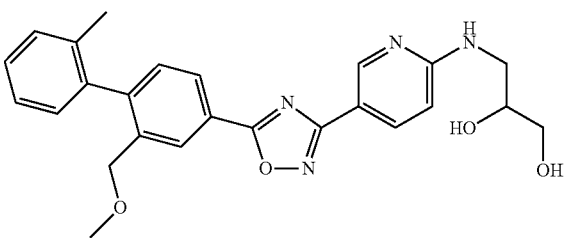 [SMILES: COCc1cc(-c2nc(-c3ccc(NCC(O)CO)nc3)no2)ccc1-c1ccccc1C] |
| 46 | 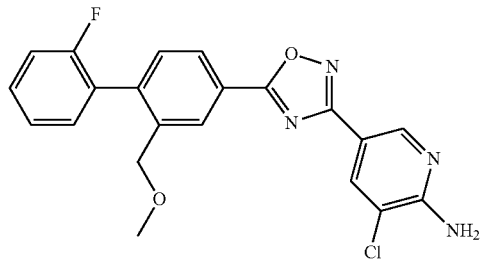 [SMILES: COCc1cc(-c2nc(-c3cnc(N)c(Cl)c3)no2)ccc1-c1ccccc1F] |
| 47 | 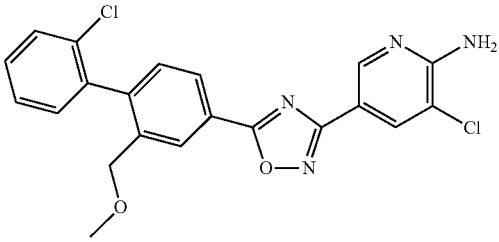 [SMILES: COCc1cc(-c2nc(-c3cnc(N)c(Cl)c3)no2)ccc1-c1ccccc1Cl] |
| 48 | 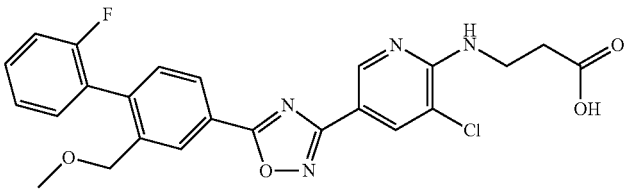 [SMILES: COCc1cc(-c2nc(-c3cnc(NCCC(=O)O)c(Cl)c3)no2)ccc1-c1ccccc1F] |
| 49 | 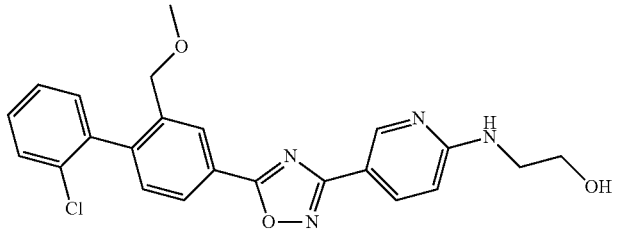 [SMILES: COCc1cc(-c2nc(-c3ccc(NCCO)nc3)no2)ccc1-c1ccccc1Cl] |

-continued
| Ex | Formula |
|---|---|
| 50 | 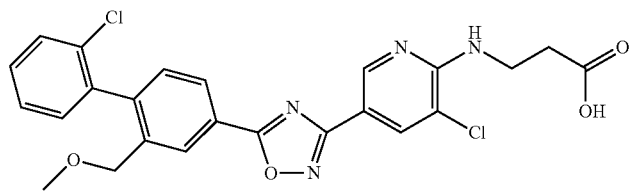 |
| 51 | 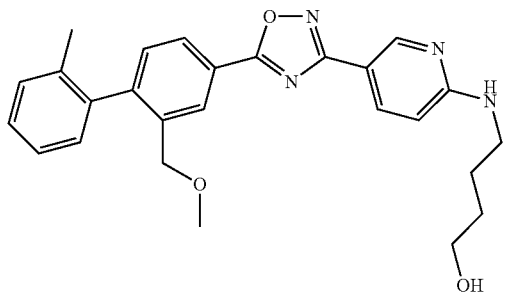 [SMILES: COCc1cc(-c2nc(-c3ccc(NCCCCO)nc3)no2)ccc1-c1ccccc1C] |
| 52 | 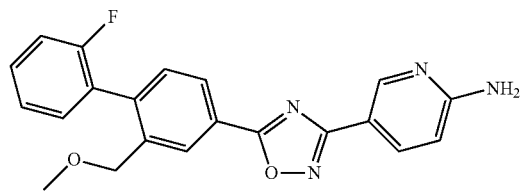 [SMILES: COCc1cc(-c2nc(-c3ccc(N)nc3)no2)ccc1-c1ccccc1F] |
| 53 | 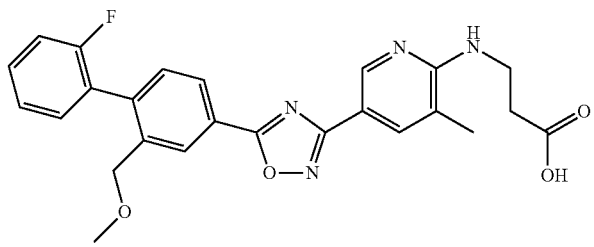 [SMILES: COCc1cc(-c2nc(-c3cnc(NCCC(=O)O)c(C)c3)no2)ccc1-c1ccccc1F] |
| 54 | 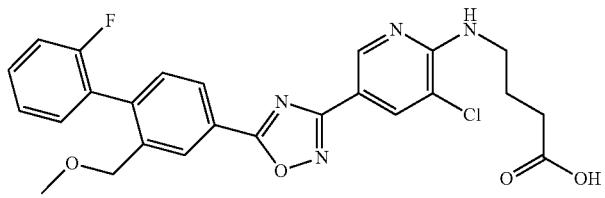 |
| 55 | 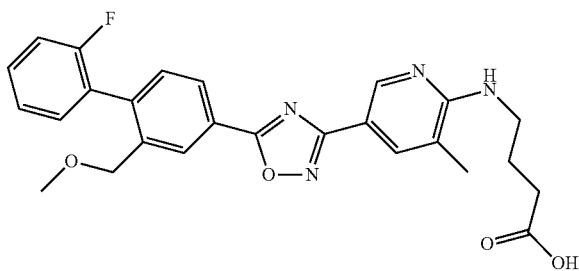 [SMILES: COCc1cc(-c2nc(-c3cnc(NCCCC(=O)O)c(C)c3)no2)ccc1-c1ccccc1F] |

-continued

| Ex | Formula |
|---|---|
| 56 | (structure) |
| 57 | (structure) |
| 58 | (structure) |
| 59 | (structure) |
| 60 | (structure) |
| 61 | (structure) |

-continued
| Ex | Formula |
|---|---|
| 62 | 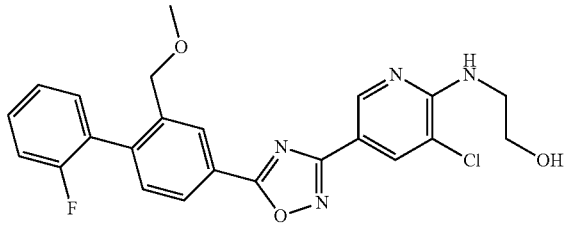 [SMILES: COCc1cc(-c2nc(-c3cnc(NCCO)c(Cl)c3)no2)ccc1-c1ccccc1F] |
| 63 | 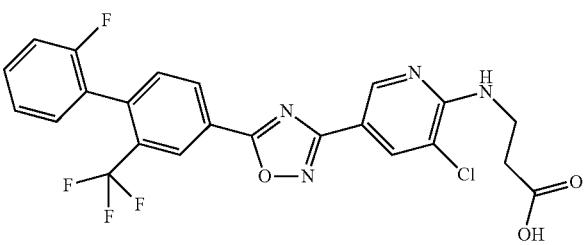 [SMILES: O=C(O)CCNc1ncc(-c2noc(-c3ccc(-c4ccccc4F)c(C(F)(F)F)c3)n2)cc1Cl] |
| 64 | 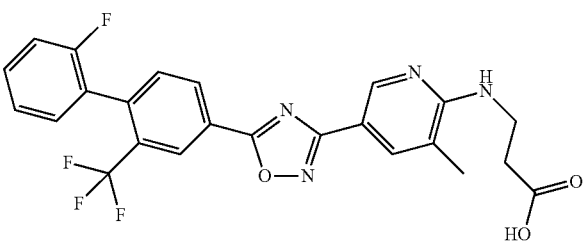 [SMILES: Cc1cc(-c2noc(-c3ccc(-c4ccccc4F)c(C(F)(F)F)c3)n2)cnc1NCCC(=O)O] |
| 65 | 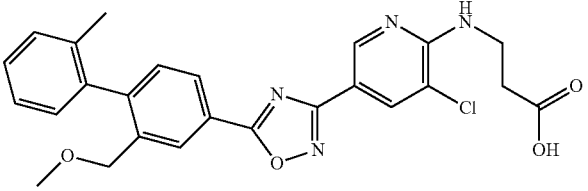 [SMILES: COCc1cc(-c2nc(-c3cnc(NCCC(=O)O)c(Cl)c3)no2)ccc1-c1ccccc1C] |
| 68 | 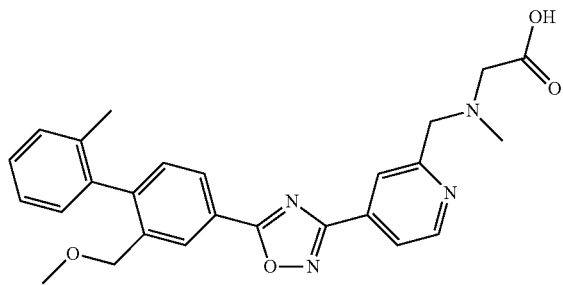 [SMILES: COCc1cc(-c2nc(-c3ccnc(CN(C)CC(=O)O)c3)no2)ccc1-c1ccccc1C] |
| 69 | 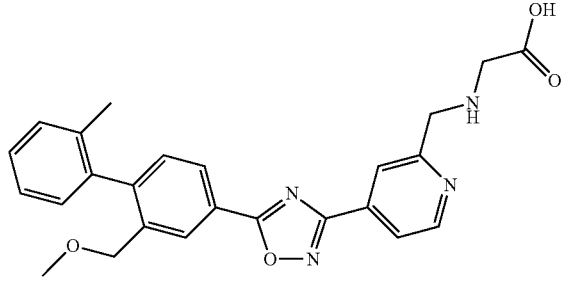 [SMILES: COCc1cc(-c2nc(-c3ccnc(CNCC(=O)O)c3)no2)ccc1-c1ccccc1C] |

| Ex | Formula |
|---|---|
| 70 | |
| 71 | |
| 72 | |
| 73 | |
| 74 | |
| 75 | |

221
-continued
| Ex | Formula |
|---|---|
| 76 | 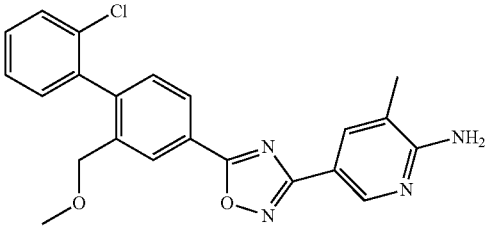 [SMILES: COCc1cc(-c2nc(-c3cnc(N)c(C)c3)no2)ccc1-c1ccccc1Cl] |
| 77 | 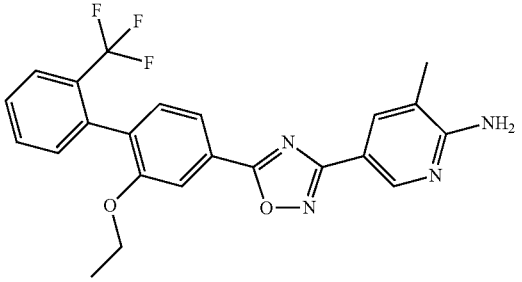 [SMILES: CCOc1cc(-c2nc(-c3cnc(N)c(C)c3)no2)ccc1-c1ccccc1C(F)(F)F] |
| 78 | 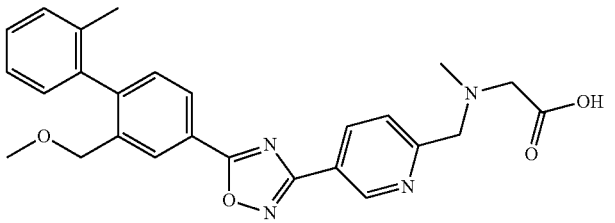 [SMILES: COCc1cc(-c2nc(-c3ccc(CN(C)CC(=O)O)nc3)no2)ccc1-c1ccccc1C] |
| 79 | 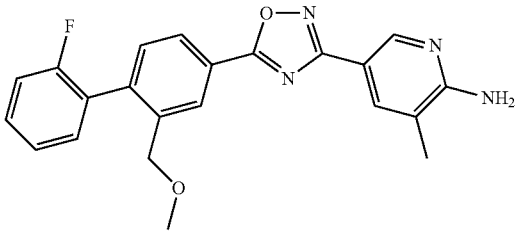 [SMILES: COCc1cc(-c2nc(-c3cnc(N)c(C)c3)no2)ccc1-c1ccccc1F] |
| 80 | 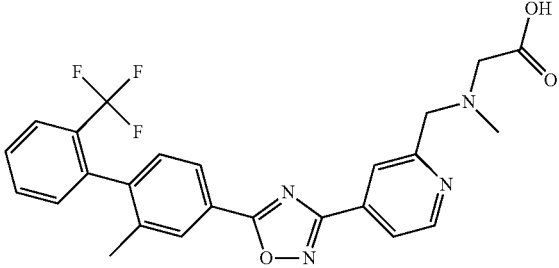 [SMILES: Cc1cc(-c2nc(-c3ccnc(CN(C)CC(=O)O)c3)no2)ccc1-c1ccccc1C(F)(F)F] |
| 81 | 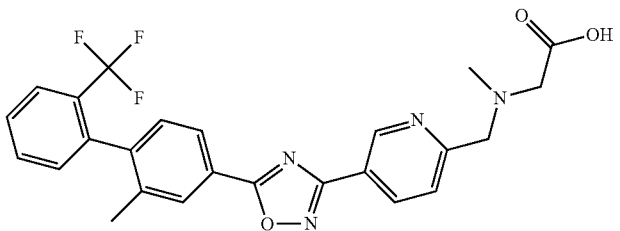 [SMILES: Cc1cc(-c2nc(-c3ccc(CN(C)CC(=O)O)nc3)no2)ccc1-c1ccccc1C(F)(F)F] |
222

| Ex | Formula |
| --- | --- |
| 82 | |
| 83 | |
| 84 | |
| 85 | |
| 86 | |
| 90 | |

| Ex | Formula |
|---|---|
| 91 | 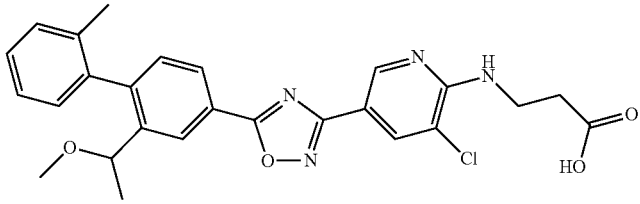 [SMILES: COC(C)c1cc(-c2nc(-c3cnc(NCCC(=O)O)c(Cl)c3)no2)ccc1-c1ccccc1C] |
| 92 | 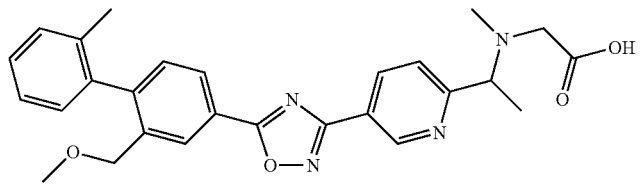 |
| 93 | 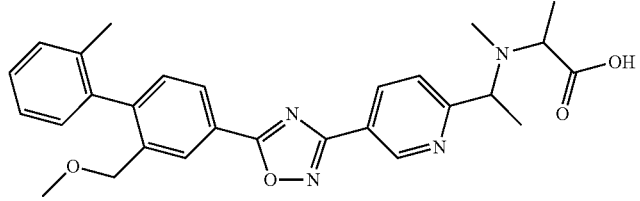 [SMILES: COCc1cc(-c2nc(-c3ccc(C(C)N(C)C(C)C(=O)O)nc3)no2)ccc1-c1ccccc1C] |
| 94 | 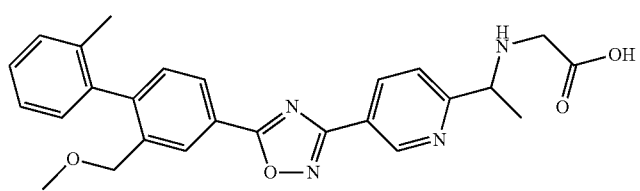 [SMILES: COCc1cc(-c2nc(-c3ccc(C(C)NCC(=O)O)nc3)no2)ccc1-c1ccccc1C] |
| 95 | 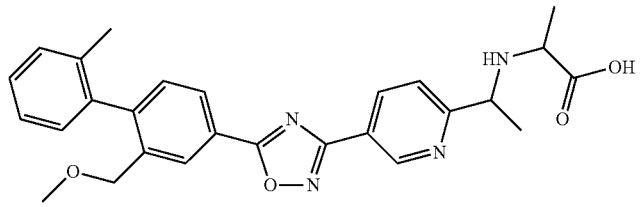 [SMILES: COCc1cc(-c2nc(-c3ccc(C(C)NC(C)C(=O)O)nc3)no2)ccc1-c1ccccc1C] |
| or 96 | 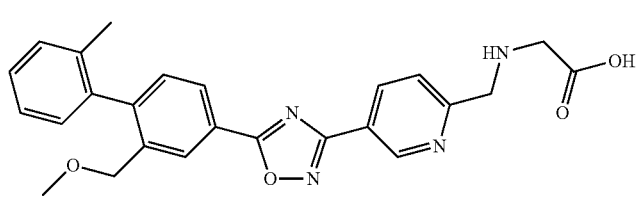 [SMILES: COCc1cc(-c2nc(-c3ccc(CNCC(=O)O)nc3)no2)ccc1-c1ccccc1C] |
and pharmaceutically acceptable salts thereof.
7. A pharmaceutical composition comprising at least one compound according to claim 1 and/or a pharmaceutically acceptable salt thereof and an excipient and/or adjuvant.
* * * * *

UNITED STATES PATENT AND TRADEMARK OFFICE
CERTIFICATE OF CORRECTION

PATENT NO. : 8,791,142 B2
APPLICATION NO. : 13/203044
DATED : July 29, 2014
INVENTOR(S) : Anna Quattropani, Patrick Gerber and Jerome Dorbais Page 1 of 5

It is certified that error appears in the above-identified patent and that said Letters Patent is hereby corrected as shown below:

In the Specification

Column 2,
Line 49, "Oyster" should read --Cyster--.

Column 15,
Lines 12-22, Formula Ia,

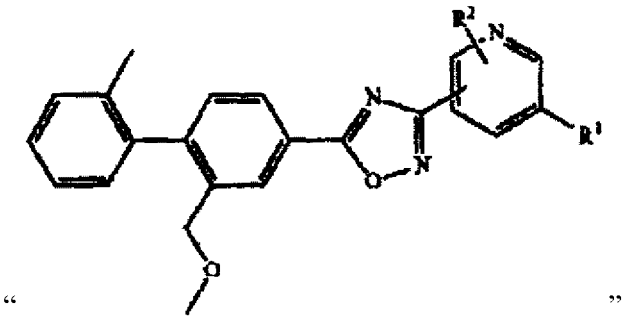

" should read

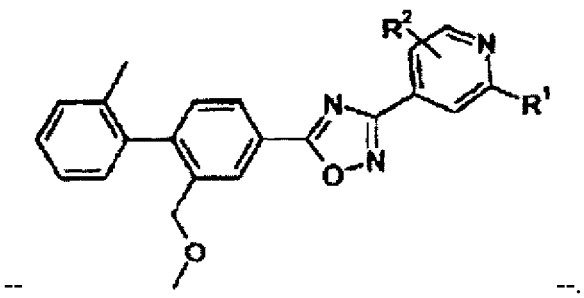

--.

Signed and Sealed this
Twelfth Day of May, 2015

Michelle K. Lee
*Director of the United States Patent and Trademark Office*

Column 15,
Lines 25-35, Formula Ib,
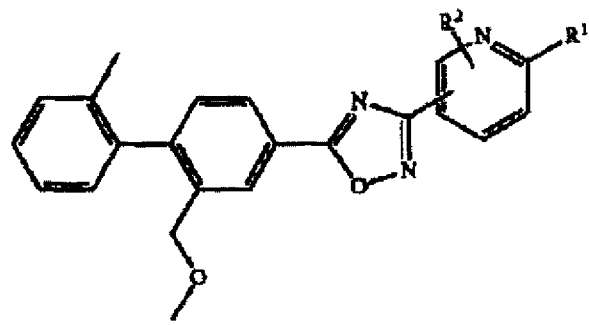
" "
should read
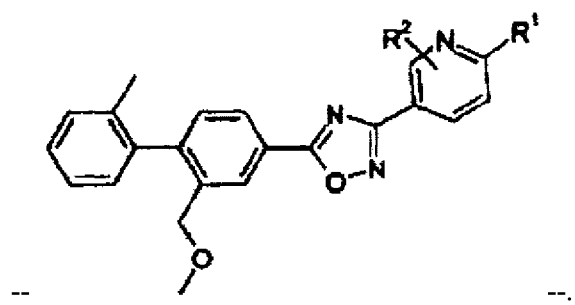
-- --.
Column 16,
Lines 35-42, Formula Ih,
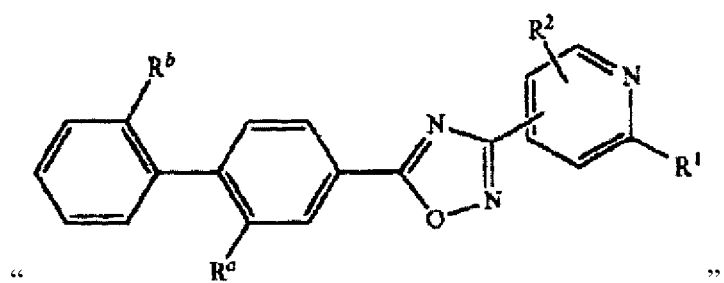
" "
should read
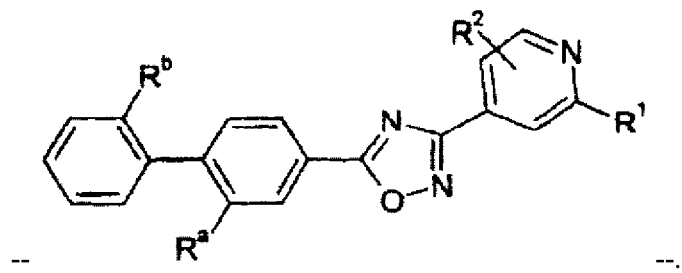
-- --.

Column 41,
Example 60,
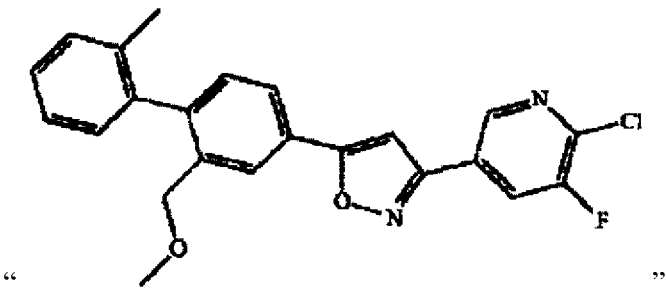
" "
should read
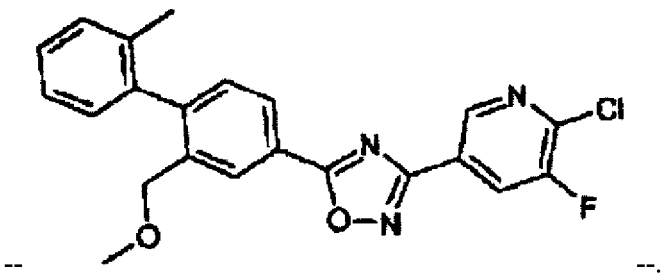
-- --.
Column 45,
Example 71,
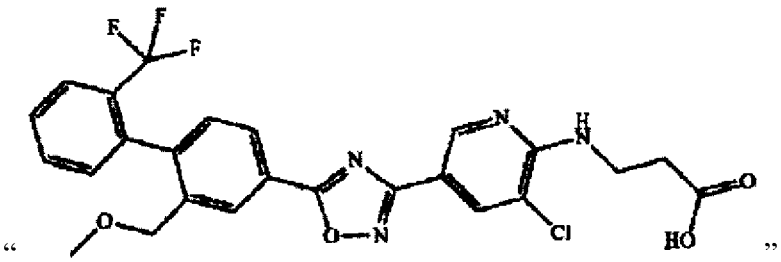
" "
should read
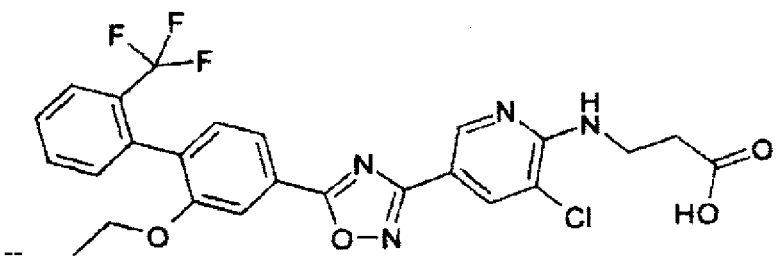
-- --.

Column 51,
Example 95,

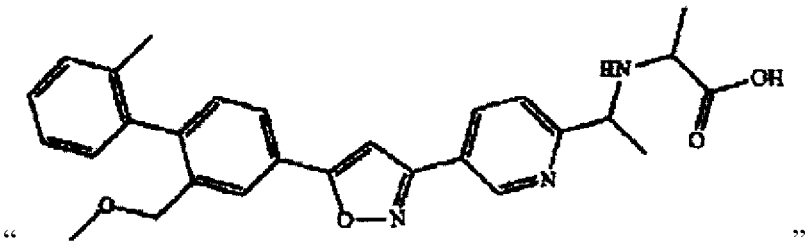

"  "

should read

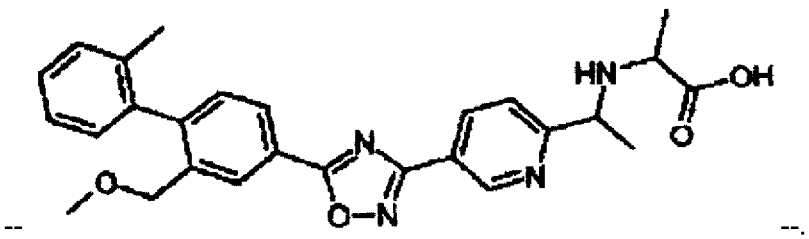

-- --.

Column 59,
Lines 5-6, "immunerogulatory abnomality," should read
--immunoregulatory abnormality,--.
Line 36, "alopecia greata," should read --alopecia areata,--.

Column 91,
Lines 49-59, "5-Chloro-W-hydroxy-6-[(2-methoxyethyl)amino]pyridine-3-
    carboximidamide" should read
        --5-Chloro-$N'$-hydroxy-6-[(2-methoxyethyl)amino]pyridine-3-
        carboximidamide--.

Column 116,
Line 35, "[C24H24N4O3-0.1C2H6O-0.1H20]" should read
    --[$C_{24}H_{24}N_4O_3$-0.1$C_2H_6O$-0.1$H_2O$]--.

Column 183,
Example 60,

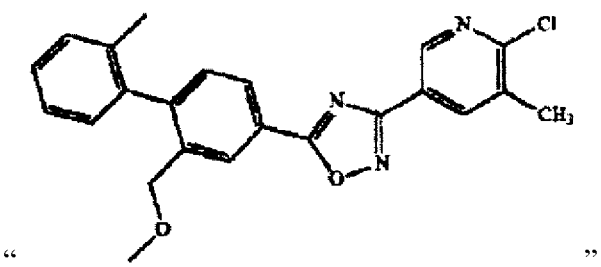

"  "

should read

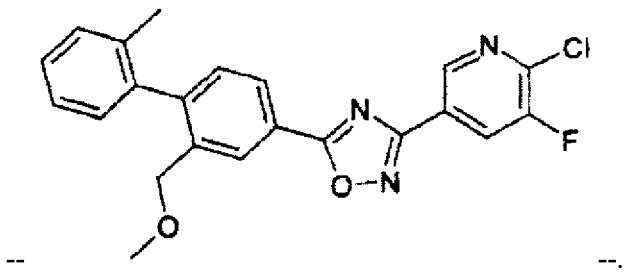

--.

Column 185,
Example 66,

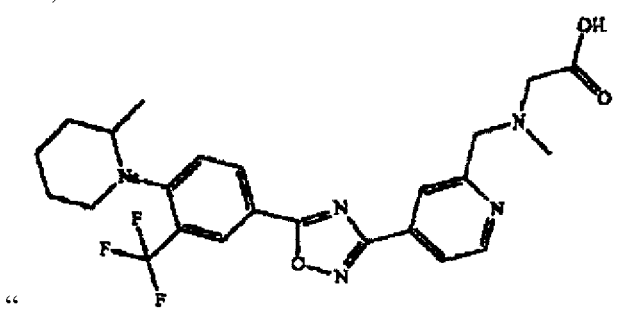

" "

should read

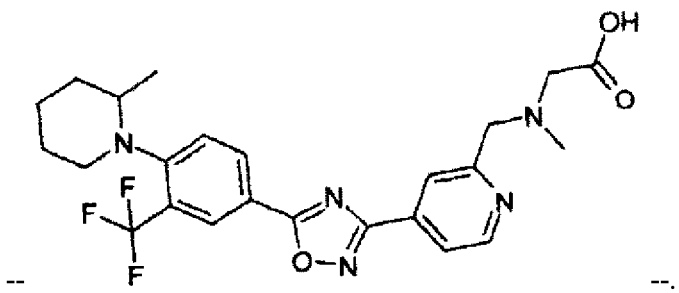

--.

In the Claims

Column 198,
Line 17, "monocyclic or bicyclic, aromatic" should read --monocyclic, aromatic--.
Line 36, "and pharmaceutically acceptable salts thereof" should read
       --and a pharmaceutically acceptable salt thereof--.

Column 200,
Line 22, "and pharmaceutically acceptable salts thereof" should read
       --and a pharmaceutically acceptable salt thereof--.

Column 225,
Line 55, "and pharmaceutically acceptable salts thereof" should read
       --and a pharmaceutically acceptable salt thereof--.